US012723057B2

(12) United States Patent
Chun et al.

(10) Patent No.: US 12,723,057 B2
(45) Date of Patent: Sep. 1, 2026

(54) ANTIVIRAL COMPOUNDS AND METHODS OF MAKING AND USING THE SAME

(71) Applicant: Gilead Sciences, Inc., Foster City, CA (US)

(72) Inventors: Byoung-Kwon Chun, Pleasanton, CA (US); Michael O. Clarke, Redwood City, CA (US); Deeba Ensan, Foster City, CA (US); Richard L. Mackman, Millbrae, CA (US); Devan Naduthambi, San Bruno, CA (US); Dustin S. Siegel, Half Moon Bay, CA (US)

(73) Assignee: Gilead Sciences, Inc., Foster City, CA (US)

( * ) Notice: Subject to any disclaimer, the term of this patent is extended or adjusted under 35 U.S.C. 154(b) by 389 days.

(21) Appl. No.: 18/174,474

(22) Filed: Feb. 24, 2023

(65) Prior Publication Data

US 2024/0199676 A1 Jun. 20, 2024

Related U.S. Application Data

(60) Provisional application No. 63/316,273, filed on Mar. 3, 2022.

(51) Int. Cl.
*C07H 7/06* (2006.01)
*A61K 31/706* (2006.01)
*A61P 31/14* (2006.01)

(52) U.S. Cl.
CPC ............. *C07H 7/06* (2013.01); *A61K 31/706* (2013.01); *A61P 31/14* (2018.01)

(58) Field of Classification Search
IPC .................................... C07H 7/06; A61P 31/14
See application file for complete search history.

(56) References Cited

U.S. PATENT DOCUMENTS

| | | | |
|---|---|---|---|
| 4,707,540 | A | 11/1987 | Manser et al. |
| 5,446,137 | A | 8/1995 | Maag et al. |
| 6,699,994 | B1 | 3/2004 | Babu et al. |
| 8,101,745 | B2 | 1/2012 | Hostetler et al. |
| 8,119,607 | B2 | 2/2012 | Francom et al. |
| 8,242,085 | B2 | 8/2012 | Babu et al. |
| 8,318,700 | B2 | 11/2012 | Hostetler et al. |
| 8,440,813 | B2 | 5/2013 | Babu et al. |
| 9,370,528 | B2 | 6/2016 | Schentag et al. |
| 9,388,208 | B2 | 7/2016 | Clarke et al. |
| 9,701,682 | B2 | 7/2017 | Clarke et al. |
| 9,724,360 | B2 | 8/2017 | Chun et al. |
| 9,777,035 | B2 | 10/2017 | Girijavallabhan et al. |
| 9,815,864 | B2 | 11/2017 | Beigelman et al. |
| 10,004,719 | B1 | 6/2018 | Hsu et al. |
| 10,059,716 | B2 | 8/2018 | Clarke et al. |
| 10,251,904 | B2 | 4/2019 | Clarke et al. |
| 10,377,761 | B2 | 8/2019 | Clarke et al. |
| 10,682,368 | B2 | 6/2020 | Perron et al. |
| 11,773,122 | B2 | 10/2023 | Lazerwith et al. |
| 11,780,844 | B2 | 10/2023 | Bartlett et al. |
| 11,814,406 | B2 | 11/2023 | Bunyan et al. |
| 11,845,755 | B2 | 12/2023 | Bartlett et al. |
| 11,851,438 | B2 | 12/2023 | Bartlett et al. |
| 11,926,645 | B2 | 3/2024 | Bunyan et al. |
| 12,180,217 | B2 | 12/2024 | Bartlett et al. |
| 12,297,226 | B2 | 5/2025 | Bunyan et al. |
| 12,448,383 | B2 | 10/2025 | Bartlett et al. |
| 2002/0035082 | A1 | 3/2002 | Grinstaff et al. |
| 2002/0188137 | A1 | 12/2002 | Dershem et al. |
| 2003/0170891 | A1 | 9/2003 | McSwiggen |
| 2003/0175950 | A1 | 9/2003 | McSwiggen |
| 2003/0199516 | A1 | 10/2003 | Moser et al. |
| 2004/0009959 | A1 | 1/2004 | Potter et al. |
| 2004/0157838 | A1 | 8/2004 | Griffith |
| 2004/0157839 | A1 | 8/2004 | Griffith |
| 2004/0214837 | A1 | 10/2004 | Griffith et al. |
| 2004/0229839 | A1 | 11/2004 | Babu et al. |
| 2004/0229840 | A1 | 11/2004 | Bhat et al. |
| 2006/0121312 | A1 | 6/2006 | Yamada et al. |
| 2006/0194144 | A1 | 8/2006 | Sooriyakumaran et al. |
| 2006/0281922 | A1 | 12/2006 | Gao et al. |
| 2007/0232635 | A1 | 10/2007 | Chelliah et al. |
| 2007/0270374 | A1 | 11/2007 | Gallop |
| 2009/0318380 | A1 | 12/2009 | Sofia et al. |
| 2009/0323011 | A1 | 12/2009 | He et al. |
| 2009/0323012 | A1 | 12/2009 | He et al. |
| 2010/0035836 | A1 | 2/2010 | Francom et al. |
| 2010/0040804 | A1 | 2/2010 | Zhang |

(Continued)

FOREIGN PATENT DOCUMENTS

| | | | |
|---|---|---|---|
| CN | 102000103 | A | 4/2011 |
| CN | 102286047 | A | 12/2011 |

(Continued)

OTHER PUBLICATIONS

Brachwitz et al. (1999) "Synthesis and Antiproliferative Potency of 9-Beta-D-Arabiofuranosyl-2-Fluoroadenine Phospholipid Adducts", Bioorganic & Medicinal Chemistry, Eslevier, Astermdam, NL, vol. 7, No. 6, pp. 1195-1200, XP001031156.
Cockerill et al. (2019) "State of the Art in Respiratory Syncytial Virus Drug Discovery and Development", Journal of Medicinal Chemistry, 62(7):3206-3227.
Colombo et al. (1985) "Asymetric Dihydroxylations via Chiral Oxazolidines", Tetrahedron Letters, 26(44):5459-5462.
Feng et al. (2014) "Inhibition of Hepatitis C Virus Replication by GS-6620, a Potent C-Nucleoside Monophosphate Prodrug", Antimicrobial Agents and Chemotherapy, 58(4):1930-1942.

(Continued)

*Primary Examiner* — Traviss C McIntosh, III

(57) ABSTRACT

Antiviral compounds and methods of using the same, singly or in combination with additional agents, and pharmaceutical compositions of said compounds for the treatment of viral infections are disclosed.

20 Claims, No Drawings

Specification includes a Sequence Listing.

(56) References Cited

U.S. PATENT DOCUMENTS

| | | | |
|---|---|---|---|
| 2010/0096603 | A1 | 4/2010 | Wang et al. |
| 2010/0184942 | A1 | 7/2010 | Chen et al. |
| 2010/0186626 | A1 | 7/2010 | Shin et al. |
| 2011/0212994 | A1 | 9/2011 | Clem et al. |
| 2011/0216273 | A1 | 9/2011 | He et al. |
| 2011/0287927 | A1 | 11/2011 | Grasset et al. |
| 2011/0319459 | A1 | 12/2011 | Gupta et al. |
| 2012/0009147 | A1 | 1/2012 | Cho et al. |
| 2012/0020921 | A1 | 1/2012 | Cho et al. |
| 2012/0035115 | A1 | 2/2012 | Manoharan et al. |
| 2012/0070411 | A1 | 3/2012 | Beigelman et al. |
| 2012/0070415 | A1 | 3/2012 | Beigelman et al. |
| 2012/0071434 | A1 | 3/2012 | Smith et al. |
| 2012/0214735 | A1 | 8/2012 | Bhuniya et al. |
| 2012/0214762 | A1 | 8/2012 | Staben et al. |
| 2012/0219568 | A1 | 8/2012 | Liu et al. |
| 2012/0264649 | A1 | 10/2012 | Bazan et al. |
| 2013/0303669 | A1 | 11/2013 | Morimoto et al. |
| 2014/0038991 | A1 | 2/2014 | Yu et al. |
| 2014/0200215 | A1 | 7/2014 | Buckman et al. |
| 2014/0309413 | A1 | 10/2014 | Rose et al. |
| 2015/0011497 | A1 | 1/2015 | Beigelman et al. |
| 2015/0051167 | A1 | 2/2015 | Wang et al. |
| 2015/0105341 | A1 | 4/2015 | Beigelman et al. |
| 2015/0252265 | A1 | 9/2015 | Archetti et al. |
| 2015/0274767 | A1 | 10/2015 | Girijavallabhan et al. |
| 2015/0366887 | A1 | 12/2015 | Blatt et al. |
| 2015/0366888 | A1 | 12/2015 | Blatt et al. |
| 2016/0024107 | A1 | 1/2016 | Clarke et al. |
| 2016/0053175 | A1 | 2/2016 | Song et al. |
| 2016/0122374 | A1 | 5/2016 | Chun et al. |
| 2016/0244668 | A1 | 8/2016 | Saito et al. |
| 2016/0257657 | A1 | 9/2016 | Wipf et al. |
| 2017/0071964 | A1 | 3/2017 | Clarke et al. |
| 2017/0186964 | A1 | 6/2017 | Cho et al. |
| 2018/0002366 | A1 | 1/2018 | Girijavallabhan et al. |
| 2018/0044369 | A1 | 2/2018 | Beigelman et al. |
| 2018/0079774 | A1 | 3/2018 | Beigelman et al. |
| 2018/0226580 | A1 | 8/2018 | Fitzgerald et al. |
| 2019/0185748 | A1 | 6/2019 | Liao |
| 2019/0185754 | A1 | 6/2019 | Archetti et al. |
| 2019/0241807 | A1 | 8/2019 | Mizusaki et al. |
| 2021/0060051 | A1 | 3/2021 | Schinazi et al. |
| 2021/0284669 | A1 | 9/2021 | Chun et al. |
| 2021/0284670 | A1 | 9/2021 | Chin et al. |
| 2021/0292348 | A1 | 9/2021 | Byun et al. |
| 2022/0143052 | A1 | 5/2022 | Lazerwith et al. |
| 2023/0212199 | A1 | 7/2023 | Chun et al. |
| 2023/0248753 | A1 | 8/2023 | Lazerwith et al. |
| 2023/0250117 | A1 | 8/2023 | Lazerwith et al. |
| 2023/0322813 | A1 | 10/2023 | Chun et al. |
| 2023/0382940 | A1 | 11/2023 | Chun et al. |
| 2024/0025932 | A1 | 1/2024 | Lazerwith et al. |
| 2024/0309028 | A1 | 9/2024 | Chun et al. |
| 2025/0084088 | A1 | 3/2025 | Ensan et al. |
| 2025/0090537 | A1 | 3/2025 | Chun et al. |
| 2025/0197410 | A1 | 6/2025 | Bartlett et al. |

FOREIGN PATENT DOCUMENTS

| | | | |
|---|---|---|---|
| CN | 102603836 | A | 7/2012 |
| CN | 103709220 | A | 4/2014 |
| CN | 104086612 | A | 10/2014 |
| CN | 105646629 | A | 6/2016 |
| CN | 105777580 | A | 7/2016 |
| CN | 106518766 | A | 3/2017 |
| CN | 106518767 | A | 3/2017 |
| CN | 106892920 | A | 6/2017 |
| CN | 107286190 | A | 10/2017 |
| CN | 108276352 | A | 7/2018 |
| CN | 109748921 | A | 5/2019 |
| CN | 109748943 | A | 5/2019 |
| CN | 109748944 | A | 5/2019 |
| CN | 110215456 | A | 9/2019 |
| CN | 110330540 | A | 10/2019 |
| CN | 110724174 | A | 1/2020 |
| CN | 110776512 | A | 2/2020 |
| CN | 111620909 | A | 9/2020 |
| CN | 113185519 | A | 7/2021 |
| CN | 113368251 | A | 9/2021 |
| CN | 113929724 | A | 1/2022 |
| DE | 2626792 | A1 | 12/1977 |
| DE | 3528753 | A1 | 2/1987 |
| DE | 4232852 | A1 | 3/1994 |
| DE | 19934799 | A1 | 2/2001 |
| DE | 10064823 | A1 | 6/2002 |
| EP | 0284952 | A2 | 10/1988 |
| EP | 0419944 | A2 | 4/1991 |
| EP | 0458214 | A1 | 11/1991 |
| EP | 0682098 | A2 | 11/1995 |
| EP | 0924265 | A2 | 6/1999 |
| EP | 1046631 | A1 | 10/2000 |
| EP | 1170353 | A2 | 1/2002 |
| EP | 1593713 | A1 | 11/2005 |
| EP | 1975718 | A2 | 10/2008 |
| EP | 1978077 | A1 | 10/2008 |
| EP | 2098226 | A1 | 9/2009 |
| EP | 2388069 | A1 | 11/2011 |
| EP | 2778169 | A1 | 9/2014 |
| EP | 2896678 | A1 | 7/2015 |
| EP | 2980182 | A1 | 2/2016 |
| FR | 2354774 | A1 | 1/1978 |
| FR | 2669639 | A1 | 5/1992 |
| JP | S6286363 | A | 4/1987 |
| JP | H03503538 | A | 8/1991 |
| JP | H0931092 | A | 2/1997 |
| JP | H09328497 | A | 12/1997 |
| JP | 2002326995 | A | 11/2002 |
| JP | 2002326996 | A | 11/2002 |
| JP | 2003246770 | A | 9/2003 |
| JP | 2004315613 | A | 11/2004 |
| JP | 2005120172 | A | 5/2005 |
| JP | 2006232875 | A | 9/2006 |
| JP | 2008007634 | A | 1/2008 |
| JP | 2009543884 | A | 12/2009 |
| JP | 2012216832 | A | 11/2012 |
| JP | 5295692 | B2 | 9/2013 |
| JP | 2014145852 | A | 8/2014 |
| JP | 2016132779 | A | 7/2016 |
| JP | 2018044028 | A | 3/2018 |
| JP | 2018203945 | A | 12/2018 |
| JP | 2020510070 | A | 4/2020 |
| KR | 20120135501 | A | 12/2012 |
| KR | 20160098975 | A | 8/2016 |
| KR | 20160110899 | A | 9/2016 |
| KR | 20160110900 | A | 9/2016 |
| KR | 20190041918 | A | 4/2019 |
| KR | 20190076339 | A | 7/2019 |
| NL | 7606413 | A | 12/1977 |
| WO | WO-8807043 | A1 | 9/1988 |
| WO | WO-9110671 | A1 | 7/1991 |
| WO | WO-9201695 | A1 | 2/1992 |
| WO | WO-9201696 | A1 | 2/1992 |
| WO | WO-9214805 | A1 | 9/1992 |
| WO | WO-9316075 | A1 | 8/1993 |
| WO | WO-9614329 | A1 | 5/1996 |
| WO | WO-9640705 | A1 | 12/1996 |
| WO | WO-9816184 | A2 | 4/1998 |
| WO | WO-9900399 | A1 | 1/1999 |
| WO | WO-9914226 | A2 | 3/1999 |
| WO | WO-9926933 | A1 | 6/1999 |
| WO | WO-9926941 | A1 | 6/1999 |
| WO | WO-9951565 | A1 | 10/1999 |
| WO | WO-9961583 | A2 | 12/1999 |
| WO | WO-0001381 | A1 | 1/2000 |
| WO | WO-0032152 | A2 | 6/2000 |
| WO | WO-0034276 | A1 | 6/2000 |
| WO | WO-0063154 | A1 | 10/2000 |
| WO | WO-0066604 | A2 | 11/2000 |
| WO | WO-0100197 | A2 | 1/2001 |
| WO | WO-0110842 | A2 | 2/2001 |
| WO | WO-0114320 | A1 | 3/2001 |
| WO | WO-0119841 | A1 | 3/2001 |
| WO | WO-0121577 | A2 | 3/2001 |

(56) References Cited

FOREIGN PATENT DOCUMENTS

| | | | |
|---|---|---|---|
| WO | WO-0123357 | A2 | 4/2001 |
| WO | WO-0147862 | A1 | 7/2001 |
| WO | WO-0164642 | A2 | 9/2001 |
| WO | WO-0177091 | A2 | 10/2001 |
| WO | WO-0207516 | A2 | 1/2002 |
| WO | WO-0234711 | A1 | 5/2002 |
| WO | WO-0234736 | A1 | 5/2002 |
| WO | WO-0239987 | A2 | 5/2002 |
| WO | WO-02062766 | A2 | 8/2002 |
| WO | WO-02094185 | A2 | 11/2002 |
| WO | WO-02100415 | A2 | 12/2002 |
| WO | WO-03039523 | A2 | 5/2003 |
| WO | WO-03041649 | A2 | 5/2003 |
| WO | WO-03049772 | A2 | 6/2003 |
| WO | WO-03088908 | A2 | 10/2003 |
| WO | WO-03090748 | A1 | 11/2003 |
| WO | WO-03091262 | A1 | 11/2003 |
| WO | WO-2004002999 | A2 | 1/2004 |
| WO | WO-2004007472 | A1 | 1/2004 |
| WO | WO-2004014312 | A2 | 2/2004 |
| WO | WO-2004037159 | A2 | 5/2004 |
| WO | WO-2004041752 | A2 | 5/2004 |
| WO | WO-2004080966 | A1 | 9/2004 |
| WO | WO-2004083177 | A2 | 9/2004 |
| WO | WO-2004083263 | A1 | 9/2004 |
| WO | WO-2004087153 | A2 | 10/2004 |
| WO | WO-2004091499 | A2 | 10/2004 |
| WO | WO-2004106356 | A1 | 12/2004 |
| WO | WO-2004110350 | A2 | 12/2004 |
| WO | WO-2005020885 | A2 | 3/2005 |
| WO | WO-2005021568 | A2 | 3/2005 |
| WO | WO-2005023771 | A1 | 3/2005 |
| WO | WO-2005025515 | A2 | 3/2005 |
| WO | WO-2005040135 | A1 | 5/2005 |
| WO | WO-2005058832 | A1 | 6/2005 |
| WO | WO-2005093476 | A1 | 10/2005 |
| WO | WO-2005095544 | A1 | 10/2005 |
| WO | WO-2005097052 | A1 | 10/2005 |
| WO | WO-2005111099 | A1 | 11/2005 |
| WO | WO-2006001463 | A1 | 1/2006 |
| WO | WO-2006006490 | A1 | 1/2006 |
| WO | WO-2006008438 | A1 | 1/2006 |
| WO | WO-2006016101 | A1 | 2/2006 |
| WO | WO-2006030193 | A1 | 3/2006 |
| WO | WO-2006038594 | A1 | 4/2006 |
| WO | WO-2006048634 | A1 | 5/2006 |
| WO | WO-2006061094 | A1 | 6/2006 |
| WO | WO-2006063717 | A2 | 6/2006 |
| WO | WO-2006066074 | A2 | 6/2006 |
| WO | WO-2006094347 | A1 | 9/2006 |
| WO | WO-2006098380 | A1 | 9/2006 |
| WO | WO-2006105440 | A2 | 10/2006 |
| WO | WO-2006110656 | A2 | 10/2006 |
| WO | WO-2006119800 | A1 | 11/2006 |
| WO | WO-2006130217 | A2 | 12/2006 |
| WO | WO-2007007588 | A1 | 1/2007 |
| WO | WO-2007011759 | A2 | 1/2007 |
| WO | WO-2007024021 | A1 | 3/2007 |
| WO | WO-2007031185 | A1 | 3/2007 |
| WO | WO-2007056143 | A2 | 5/2007 |
| WO | WO-2007056170 | A2 | 5/2007 |
| WO | WO-2007076034 | A2 | 7/2007 |
| WO | WO-2007084667 | A2 | 7/2007 |
| WO | WO-2007095188 | A2 | 8/2007 |
| WO | WO-2007125320 | A1 | 11/2007 |
| WO | WO-2007130783 | A2 | 11/2007 |
| WO | WO-2008001195 | A2 | 1/2008 |
| WO | WO-2008011557 | A2 | 1/2008 |
| WO | WO-2008012555 | A2 | 1/2008 |
| WO | WO-2008021388 | A1 | 2/2008 |
| WO | WO-2008024364 | A2 | 2/2008 |
| WO | WO-2008082601 | A2 | 7/2008 |
| WO | WO-2008092006 | A2 | 7/2008 |
| WO | WO-2008095040 | A2 | 8/2008 |
| WO | WO-2008109177 | A2 | 9/2008 |
| WO | WO-2008109180 | A2 | 9/2008 |
| WO | WO-2008109181 | A2 | 9/2008 |
| WO | WO-2008117047 | A1 | 10/2008 |
| WO | WO-2008121360 | A1 | 10/2008 |
| WO | WO-2008133966 | A1 | 11/2008 |
| WO | WO-2008151437 | A1 | 12/2008 |
| WO | WO-2009001097 | A2 | 12/2008 |
| WO | WO-2009009951 | A1 | 1/2009 |
| WO | WO-2009011228 | A1 | 1/2009 |
| WO | WO-2009011229 | A1 | 1/2009 |
| WO | WO-2009067409 | A1 | 5/2009 |
| WO | WO-2009069095 | A2 | 6/2009 |
| WO | WO-2009076593 | A1 | 6/2009 |
| WO | WO-2009076618 | A2 | 6/2009 |
| WO | WO-2009086192 | A1 | 7/2009 |
| WO | WO-2009086201 | A1 | 7/2009 |
| WO | WO-2009111653 | A2 | 9/2009 |
| WO | WO-2009132123 | A1 | 10/2009 |
| WO | WO-2009132135 | A1 | 10/2009 |
| WO | WO-2009151921 | A1 | 12/2009 |
| WO | WO-2009152095 | A2 | 12/2009 |
| WO | WO-2010001174 | A1 | 1/2010 |
| WO | WO-2010007116 | A2 | 1/2010 |
| WO | WO-2010026153 | A1 | 3/2010 |
| WO | WO-2010036407 | A2 | 4/2010 |
| WO | WO-2010060952 | A1 | 6/2010 |
| WO | WO-2010073126 | A2 | 7/2010 |
| WO | WO-2010084115 | A2 | 7/2010 |
| WO | WO-2010108135 | A1 | 9/2010 |
| WO | WO-2010108140 | A1 | 9/2010 |
| WO | WO-2010145778 | A1 | 12/2010 |
| WO | WO-2011005860 | A2 | 1/2011 |
| WO | WO-2011015037 | A1 | 2/2011 |
| WO | WO-2011016430 | A1 | 2/2011 |
| WO | WO-2011031896 | A2 | 3/2011 |
| WO | WO-2011032169 | A2 | 3/2011 |
| WO | WO-2011035231 | A1 | 3/2011 |
| WO | WO-2011035250 | A1 | 3/2011 |
| WO | WO-2011035842 | A1 | 3/2011 |
| WO | WO-2011036557 | A1 | 3/2011 |
| WO | WO-2011038207 | A1 | 3/2011 |
| WO | WO-2011057214 | A2 | 5/2011 |
| WO | WO-2011086075 | A1 | 7/2011 |
| WO | WO-2011097300 | A1 | 8/2011 |
| WO | WO-2011100131 | A2 | 8/2011 |
| WO | WO-2011109799 | A1 | 9/2011 |
| WO | WO-2011119869 | A1 | 9/2011 |
| WO | WO-2011/146401 | A1 | 11/2011 |
| WO | WO-2011150288 | A1 | 12/2011 |
| WO | WO-2011156632 | A2 | 12/2011 |
| WO | WO-2012012465 | A1 | 1/2012 |
| WO | WO-2012012776 | A1 | 1/2012 |
| WO | WO-2012031539 | A1 | 3/2012 |
| WO | WO-2012034626 | A1 | 3/2012 |
| WO | WO-2012037038 | A1 | 3/2012 |
| WO | WO-2012040124 | A1 | 3/2012 |
| WO | WO-2012040126 | A1 | 3/2012 |
| WO | WO-2012040127 | A1 | 3/2012 |
| WO | WO-2012068340 | A2 | 5/2012 |
| WO | WO-2012083048 | A2 | 6/2012 |
| WO | WO-2012087596 | A1 | 6/2012 |
| WO | WO-2012088155 | A1 | 6/2012 |
| WO | WO-2012088438 | A1 | 6/2012 |
| WO | WO-2012092471 | A2 | 7/2012 |
| WO | WO-2012121973 | A1 | 9/2012 |
| WO | WO-2012128944 | A1 | 9/2012 |
| WO | WO-2012139028 | A2 | 10/2012 |
| WO | WO-2012142075 | A1 | 10/2012 |
| WO | WO-2012142085 | A1 | 10/2012 |
| WO | WO-2012142523 | A2 | 10/2012 |
| WO | WO-2012160392 | A1 | 11/2012 |
| WO | WO-2013000855 | A1 | 1/2013 |
| WO | WO-2013007586 | A1 | 1/2013 |
| WO | WO-2013030288 | A1 | 3/2013 |
| WO | WO-2013033270 | A2 | 3/2013 |
| WO | WO-2013040492 | A2 | 3/2013 |
| WO | WO-2013040568 | A1 | 3/2013 |
| WO | WO-2013044030 | A1 | 3/2013 |
| WO | WO-2013056132 | A2 | 4/2013 |

(56) References Cited

FOREIGN PATENT DOCUMENTS

WO WO-2013072466 A1 5/2013
WO WO-2013087765 A1 6/2013
WO WO-2013090420 A2 6/2013
WO WO-2013096679 A1 6/2013
WO WO-2013096680 A1 6/2013
WO WO-2013101552 A1 7/2013
WO WO-2013135339 A2 9/2013
WO WO-2013138236 A1 9/2013
WO WO-2013142124 A1 9/2013
WO WO-2013142157 A1 9/2013
WO WO-2013142159 A1 9/2013
WO WO-2013142525 A1 9/2013
WO WO-2013147795 A1 10/2013
WO WO-2013151975 A1 10/2013
WO WO-2013182262 A1 12/2013
WO WO-2014005125 A2 1/2014
WO WO-2014008236 A1 1/2014
WO WO-2014015936 A1 1/2014
WO WO-2014026198 A1 2/2014
WO WO-2014031872 A2 2/2014
WO WO-2014035140 A2 3/2014
WO WO-2014048998 A1 4/2014
WO WO-2014057095 A1 4/2014
WO WO-2014058801 A1 4/2014
WO WO-2014059901 A1 4/2014
WO WO-2014059902 A1 4/2014
WO WO-2014090369 A1 6/2014
WO WO-2014100498 A1 6/2014
WO WO-2014100505 A1 6/2014
WO WO-2014102077 A1 7/2014
WO WO-2014124458 A1 8/2014
WO WO-2014134127 A1 9/2014
WO WO-2014134251 A1 9/2014
WO WO-2014149164 A1 9/2014
WO WO-2014160012 A2 10/2014
WO WO-2014209979 A1 12/2014
WO WO-2015003146 A1 1/2015
WO WO-2015006280 A1 1/2015
WO WO-2015016187 A1 2/2015
WO WO-2015024120 A1 2/2015
WO WO-2015031710 A1 3/2015
WO WO-2015038596 A1 3/2015
WO WO-2015046827 A1 4/2015
WO WO-2015051169 A2 4/2015
WO WO-2015061742 A2 4/2015
WO WO-2015069939 A1 5/2015
WO WO-2015089511 A2 6/2015
WO WO-2015118898 A1 8/2015
WO WO-2015120237 A2 8/2015
WO WO-2015129672 A1 9/2015
WO WO-2015/148746 A1 10/2015
WO WO-2015143712 A1 10/2015
WO WO-2015148869 A1 10/2015
WO WO-2015160251 A1 10/2015
WO WO-2015196118 A1 12/2015
WO WO-2015196128 A2 12/2015
WO WO-2015196130 A2 12/2015
WO WO-2015198915 A1 12/2015
WO WO-2015200205 A1 12/2015
WO WO-2015200219 A1 12/2015
WO WO-2016010026 A1 1/2016
WO WO-2016018697 A1 2/2016
WO WO-2016029186 A1 2/2016
WO WO-2016031406 A1 3/2016
WO WO-2016041877 A1 3/2016
WO WO-2016066582 A1 5/2016
WO WO-2016069827 A1 5/2016
WO WO-2016069975 A1 5/2016
WO WO-2016070952 A1 5/2016
WO WO-2016074762 A1 5/2016
WO WO-2016096076 A1 6/2016
WO WO-2016100441 A1 6/2016
WO WO-2016100569 A1 6/2016
WO WO-2016107664 A1 7/2016
WO WO-2016115222 A1 7/2016
WO WO-2016116124 A1 7/2016
WO WO-2016116254 A1 7/2016
WO WO-2016116508 A1 7/2016
WO WO-2016117271 A1 7/2016
WO WO-2016145142 A1 9/2016
WO WO-2016148170 A1 9/2016
WO WO-2016152340 A1 9/2016
WO WO-2016161176 A1 10/2016
WO WO-2016162644 A1 10/2016
WO WO-2016170948 A1 10/2016
WO WO-2016172631 A2 10/2016
WO WO-2016178876 A2 11/2016
WO WO-2016184361 A1 11/2016
WO WO-2016192902 A1 12/2016
WO WO-2017005673 A1 1/2017
WO WO-2017019817 A1 2/2017
WO WO-2017019822 A1 2/2017
WO WO-2017019830 A1 2/2017
WO WO-2017023894 A1 2/2017
WO WO-2017024310 A1 2/2017
WO WO-2017027646 A1 2/2017
WO WO-2017032840 A1 3/2017
WO WO-2017041893 A1 3/2017
WO WO-2017045612 A1 3/2017
WO WO-2017045615 A1 3/2017
WO WO-2017045616 A1 3/2017
WO WO-2017045740 A1 3/2017
WO WO-2017049060 A1 3/2017
WO WO-2017058807 A1 4/2017
WO WO-2017059357 A1 4/2017
WO WO-2017066781 A1 4/2017
WO WO-2017066782 A1 4/2017
WO WO-2017066791 A1 4/2017
WO WO-2017066793 A1 4/2017
WO WO-2017066797 A1 4/2017
WO WO-2017068875 A1 4/2017
WO WO-2017073931 A1 5/2017
WO WO-2017073932 A1 5/2017
WO WO-2017073933 A1 5/2017
WO WO-2017091767 A2 6/2017
WO WO-2017093214 A1 6/2017
WO WO-2017097401 A1 6/2017
WO WO-2017153186 A1 9/2017
WO WO-2017156262 A1 9/2017
WO WO-2017161028 A1 9/2017
WO WO-2017165489 A1 9/2017
WO WO-2017184668 A1 10/2017
WO WO-2017205980 A1 12/2017
WO WO-2017207993 A1 12/2017
WO WO-2018015323 A2 1/2018
WO WO-2018031818 A2 2/2018
WO WO-2018065356 A1 4/2018
WO WO-2018067615 A1 4/2018
WO WO-2018098206 A1 5/2018
WO WO-2018/119263 A1 6/2018
WO WO-2018106818 A1 6/2018
WO WO-2018106820 A1 6/2018
WO WO-2018110529 A1 6/2018
WO WO-2018116901 A1 6/2018
WO WO-2018138685 A2 8/2018
WO WO-2018169946 A1 9/2018
WO WO-2018175746 A1 9/2018
WO WO-2018183635 A1 10/2018
WO WO-2018184590 A1 10/2018
WO WO-2018189134 A1 10/2018
WO WO-2018204198 A1 11/2018
WO WO-2018208667 A1 11/2018
WO WO-2018213185 A1 11/2018
WO WO-2018218171 A1 11/2018
WO WO-2018218281 A1 12/2018
WO WO-2018222172 A1 12/2018
WO WO-2018226976 A1 12/2018
WO WO-2018237194 A1 12/2018
WO WO-2019014247 A1 1/2019
WO WO-2019018185 A1 1/2019
WO WO-2019051269 A1 3/2019
WO WO-2019052935 A1 3/2019
WO WO-2019053696 A1 * 3/2019 ............ C07H 19/23
WO WO-2019084271 A1 5/2019

(56) References Cited

FOREIGN PATENT DOCUMENTS

| | | | |
|---|---|---|---|
| WO | WO-2019086400 | A1 | 5/2019 |
| WO | WO-2019092171 | A1 | 5/2019 |
| WO | WO-2019098109 | A1 | 5/2019 |
| WO | WO-2019125974 | A1 | 6/2019 |
| WO | WO-2019129059 | A1 | 7/2019 |
| WO | WO-2019133712 | A1 | 7/2019 |
| WO | WO-2019154953 | A1 | 8/2019 |
| WO | WO-2019154956 | A1 | 8/2019 |
| WO | WO-2019173682 | A1 | 9/2019 |
| WO | WO-2019195056 | A1 | 10/2019 |
| WO | WO-2019215076 | A1 | 11/2019 |
| WO | WO-2019218797 | A1 | 11/2019 |
| WO | WO-2020032152 | A1 | 2/2020 |
| WO | WO-2020033413 | A2 | 2/2020 |
| WO | WO-2021167882 | A1 | 8/2021 |
| WO | WO-2021168004 | A1 | 8/2021 |
| WO | WO-2021168008 | A1 | 8/2021 |
| WO | WO-2021168038 | A1 | 8/2021 |
| WO | WO-2021213288 | A1 | 10/2021 |
| WO | WO-2022046631 | A1 | 3/2022 |
| WO | WO-2022047065 | A2 | 3/2022 |
| WO | WO-2023167938 | A1 | 9/2023 |
| WO | WO-2023167944 | A1 | 9/2023 |
| WO | WO-2023168254 | A1 | 9/2023 |

OTHER PUBLICATIONS

Griffon et al. (2001) "Synthesis And Antiproliferative Activity Of Some 4'-C-Hydroxymethyl-α- And -β-D-Arabino-Pentofuranosyl Pyrimidine Nucleosides", Nucleosides, Nucleotides & Nucleic Acids, 20(4-7):649-652.
Griffon et al. (2006) "Synthesis and Biological Evaluation of Some 4'-C-(Hydroxymethyl)-α- and -β-D-Arabinofuranosyl Pyrimidine and Adenine Nucleosides", Collection of Czechoslovak Chemical Communications, 71(7):1063-1087.
International Preliminary Report on Patentability dated Dec. 15, 2021 for International Application No. PCT/US2021/018169 (20 pages).
International Preliminary Report on Patentability dated Sep. 1, 2022 for International Application No. PCT/US2021/018458 (12 pages).
International Search Report-Written Opinion dated Apr. 16, 2021 for International Application No. PCT/US2021/018169 (19 pages).
International Search Report-Written Opinion dated May 18, 2021 for International Application No. PCT/US2021/018458 (17 pages).
Koshkin et al. (1998) "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 54(14):3607-3630.
Leisvuori Anna (2015) "Prodrug Strategies of Antiviral Nucleotides: Studies on Enzymatically and Thermally Removable Phosphate Protecting Groups", University of Turku, Turku, Finland, 86 pages.
Milani et al. (2007) "Nucleolipoplexes:A New Paradigm for Phospholipid Bilayer-Nucleic Acid Interactions", Journal of the American Chemical Society, Sep. 26;129(38):11664-5.
Musich et al. (1978) "Synthesis of Anthopleurine, The Alarm Pheromone from Anthopleura Elegantissima", Journal of the American Chemical Society, 100(15):4865-4872.
Overend et al. (1970) "Branched Chain Sugars Part 12 Branched Sugars Derived from Methyl 2, 3-O-Isopropylidene-β-L-erythro-Pentopyranosid-4-Ulose and a Synthesis of L-Apiose", Carbohydrate Research, 15(2):185-195.
Patil et al. (1994) "4-Aza-7,9-Dideazaadenosine, a New Cytotoxic Synthetic C-Nucleoside Analogue of Adenosine", Tetrahedron Letters, 35(30):5339-5342.
Patil et al. (1994) "Synthesis of Pyrrolo[2,1-f][1,2,4]triazine Congeners of Nucleic Acid Purines via the N-Amination of 2-Substituted Pyrroles", Journal of Heterocyclic Chemistry, 31(4):781-786.
Schooley et al. (2021) "Rethinking Remdesivir: Synthesis, Antiviral Activity, and Pharmacokinetics of Oral Lipid Prodrugs" Antimicrobal Agents and Chemotherapy, Sep. 17;65(10):e0115521.
Shrestha et al. (2011) "Synthesis and Properties of a Bridged Nucleic Acid with a Perhydro-1,2-oxazin-3-one Ring", Journal of Organic Chemistry, 76(24):9891-9899.
Timpe et al. (1975) "3-desoxyhex-2-enono-1,4-lactone aus D-hexofuran(osid)- urono-6,3-lactonen", Carbohydrate Research, 39(1):53-60.
Waga et al. (1993) "Synthesis of 4'-C-Methylnucleosides", Bioscience, Biotechnology, Biochemistry, 57(9):1433-1438.
Wenska et al. (2007) "Synthesis of Conformationally Constrained 2'-N,4'-C-Ethylene-Bridged Adenosine (aza-ENA-A)", Heterocycles, 73(1):303-324.
Youssefyeh et al. (1977) "Synthetic Routes to 4'-hydroxymethylnucleosides" Tetrahedron Letters 18(5):435-438.
International Search Report and Written Opinion dated May 12, 20232 for International Application No. PCT/US2023/063283 (16 pages).
Meanwell, N. "The Influence of Bioisosteres in Drug Design: Tactical Applications to Address Developability Problems", Tactics in Contemporary Drug Design, vol. 9, pp. 283-382, Springer, Berlin Heidelberg, Jan. 28, 2014.
Jagodzinska et al. (2008) "Assessing the Bioisosterism of the Trifluoromethyl Group with a Protease Probe", Chemmedchem Communications, Wiley-Vch, De, vol. 4, No. 1, Dec. 9, 2008, pp. 49-51.
Shuto, S. Yuki lyaku Bunshiron (Organic drug molecular theory), Second Print, Aug. 25, 2012, p. 169-171.

* cited by examiner

SEQUENCE LISTING

```
Sequence total quantity: 3
SEQ ID NO: 1            moltype = DNA  length = 22
FEATURE                 Location/Qualifiers
source                  1..22
                        mol_type = other DNA
                        organism = synthetic construct
SEQUENCE: 1
catccagcaa atacaccatc ca                                           22

SEQ ID NO: 2            moltype = DNA  length = 28
FEATURE                 Location/Qualifiers
source                  1..28
                        mol_type = other DNA
                        organism = synthetic construct
SEQUENCE: 2
ttctgcacat cataattagg agtatcaa                                     28

SEQ ID NO: 3            moltype = DNA  length = 15
FEATURE                 Location/Qualifiers
source                  1..15
                        mol_type = other DNA
                        organism = synthetic construct
SEQUENCE: 3
cggagcacag gagat                                                   15
```

ANTIVIRAL COMPOUNDS AND METHODS OF MAKING AND USING THE SAME

CROSS-REFERENCE TO RELATED APPLICATIONS

This application claims priority to U.S. Provisional Application No. 63/316,273, filed Mar. 3, 2022, which is incorporated herein in its entireties for all purposes.

SEQUENCE LISTING

The instant application contains a Sequence Listing which has been submitted electronically in .XML file format and is hereby incorporated by reference in its entirety. Said .XML copy, created on Feb. 10, 2023, is named 1394-US-NP.xml and is 3,489 bytes in size.

BACKGROUND

There is a need for compounds, pharmaceutical compositions, and methods for treating viral infections, for example, Paramyxoviridae, Pneumoviridae, Picornaviridae, Flaviviridae, Filoviridae, and Orthomyxovirus infections. Embodiments of the present disclosure can address these and other needs.

SUMMARY

Disclosed herein are, for instance, compounds of Formula I:

Formula I

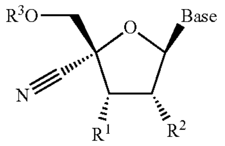

or a pharmaceutically acceptable salt thereof, wherein:

$R^1$ is OH or $OC(O)R^4$, $R^2$ is OH or $OC(O)R^5$, or $R^1$ and $R^2$ are taken together to form —OC(O)O—;

$R^3$ is H or $C(O)R^7$, or $R^1$ and $R^3$ are taken together to form —OC(O)—;

$R^4$, $R^5$, and $R^7$ are each independently $C_1$-$C_8$ alkyl, $C_3$-$C_8$ carbocyclyl, $C_6$-$C_{10}$ aryl, 4- to 6-membered heterocyclyl containing 1, 2, or 3O, or 5- to 6-membered heteroaryl containing 1, 2, or 3 heteroatoms selected from N, O, and S, wherein the alkyl, carbocyclyl, aryl, heterocyclyl, and heteroaryl of $R^4$, $R^5$, and $R^7$ are each, independently, optionally substituted with one, two or three substituents independently selected from the group consisting of halo, oxo, cyano, $N_3$, $OR^8$, $C_1$-$C_8$ alkyl, $NR^9R^{10}$, $C_3$-$C_8$ carbocyclyl, and phenyl optionally substituted with one, two, or three substituents independently selected from halo, cyano, and $C_1$-$C_6$ alkyl; and each $R^8$ is independently H, $C_1$-$C_6$ alkyl, $C_1$-$C_6$ haloalkyl, and $C_3$-$C_6$ cycloalkyl;

each $R^9$ is independently H, $C_1$-$C_6$ alkyl, $C_1$-$C_6$ haloalkyl, and $C_3$-$C_6$ cycloalkyl;

each $R^{10}$ is independently H, $C_1$-$C_6$ alkyl, $C_1$-$C_6$ haloalkyl, and $C_3$-$C_6$ cycloalkyl; and Base is

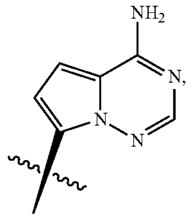
,
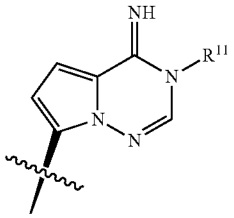
,
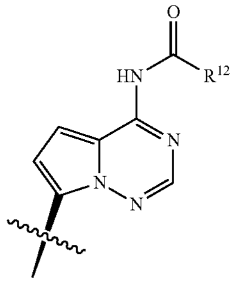
, or
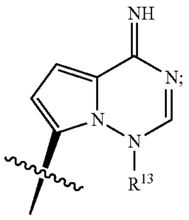

wherein $R^{11}$ is $C_1$-$C_6$ alkyl substituted with $—OP(O)(OH)_2$ or $—OC(O)R^{12}$;

$R^{12}$ is $C_1$-$C_8$ alkyl; and $R^{13}$ is $C_1$-$C_6$ alkyl substituted with $—OP(O)(OH)_2$ or $—OC(O)R^{12}$.

Also disclosed herein are compounds of sub-formulas of Formula I, such as Formulas II, III, IV, V, VI, VII, VIII, IX, X, and XI.

Disclosed herein are pharmaceutical compositions comprising a pharmaceutically effective amount of a compound disclosed herein, or a pharmaceutically acceptable salt thereof, and a pharmaceutically acceptable carrier or excipient.

Also disclosed herein are methods of treating or preventing a viral infection in a subject in need thereof, wherein the method comprises administering to the subject a compound disclosed herein, or a pharmaceutically acceptable salt thereof.

Also disclosed herein are methods of treating or preventing a viral infection in a human in need thereof, wherein the method comprises administering to the human a compound disclosed herein, or a pharmaceutically acceptable salt thereof.

The present disclosure provides a method for manufacturing a medicament for treating or preventing a viral infection in a subject in need thereof, characterized in that a compound disclosed herein, or a pharmaceutically acceptable salt thereof, is used.

The present disclosure provides a method for manufacturing a medicament for treating or preventing a viral infection in a human in need thereof, characterized in that a compound disclosed herein, or a pharmaceutically acceptable salt thereof, is used.

The present disclosure provides use of a compound disclosed herein, or a pharmaceutically acceptable salt thereof, for the manufacture of a medicament for the treatment or prevention of a viral infection in a human in need thereof.

The present disclosure provides use of a compound disclosed herein, or a pharmaceutically acceptable salt thereof, for the manufacture of a medicament for the treatment or prevention of a viral infection in a human in need thereof.

DETAILED DESCRIPTION

I. General

The disclosure relates generally to methods and compounds for treating or preventing viral infections, for example Paramyxoviridae, Pneumoviridae, Picornaviridae, Flaviviridae, Filoviridae, and Orthomyxovirus infections. The following description sets forth exemplary methods, parameters and the like. It should be recognized, however, that such description is not intended as a limitation on the scope of the present disclosure but is instead provided as a description of exemplary embodiments.

II. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, $—CONH_2$ is attached through the carbon atom. A dash at the front or end of a chemical group is a matter of convenience; chemical groups can be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

A squiggly line on a chemical group as shown below, for example,

indicates a point of attachment, i.e., it shows the broken bond by which the group is connected to another described group.

As used herein, "a compound of the disclosure" can mean a compound of any of the Formulas I-XI or a pharmaceutically acceptable salt, thereof. Similarly, the phrase "a compound of Formula (number)" means a compound of that formula and pharmaceutically acceptable salts thereof.

The prefix "$C_u$-$C_v$" indicates that the following group has from u to v carbon atoms. For example, "$C_1$-$C_8$ alkyl" indicates that the alkyl group has from 1 to 8 carbon atoms.

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), and 3,3-dimethyl-2-butyl ($—CH(CH_3)C(CH_3)_3$. Other alkyl groups include, but are not limited to, heptyl, octyl, nonyl, decyl, undecyl, dodecyl, pentadcyl, hexadecyl, heptadecyl and octadecyl.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Exemplary aryl groups include, but are not limited to, radicals derived from benzene (e.g., phenyl), naphthalene, anthracene, biphenyl, and the like.

"Carbocyclyl" or "carbocyclic ring" refers to a non-aromatic hydrocarbon ring consisting of carbon and hydrogen atoms, having from three to twenty carbon atoms, in certain embodiments having from three to fifteen carbon atoms, in certain embodiments having from three to ten carbon atoms, from three to eight carbon atoms, from three to seven carbon atoms, or from 3 to 6 carbon atoms and which is saturated or partially unsaturated and attached to the rest of the molecule by a single bond. Carbocyclic rings include, for example, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane.

"Cycloalkyl" refers to a saturated or partially saturated cyclic alkyl group having a single ring or multiple rings including fused, bridged, and spiro ring systems. As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include, but are not limited to, cyclopropyl, cyclobutyl, cyclopentyl, cyclohexyl, cycloheptyl, and cyclooctyl. Cycloalkyl groups also include partially unsaturated ring systems containing one or more double bonds, including fused ring systems with one aromatic ring and one non-aromatic ring, but not fully aromatic ring systems.

"Cyano" or "carbonitrile" refers to the group CN.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ alkyl) or 1 to 3 carbon atoms (i.e., $C_1$-$C_3$ alkyl). Examples of suitable haloalkyl groups include, but are not limited to, $—CF_3$, $—CHF_2$, $—CFH_2$, $—CH_2CF_3$, fluorochloromethyl, difluorochloromethyl, 1,1,1-trifluoroethyl and pentafluoroethyl.

"Halo" or "halogen" as used herein refers to fluoro (—F), chloro (—Cl), bromo (—Br) and iodo (—I).

"Hydroxy" refers to —OH.

"Halogen" or "halo" includes fluoro, chloro, bromo, and iodo.

"Heteroaryl" refers to an aromatic group, including groups having an aromatic tautomer or resonance structure, having a single ring, multiple rings, or multiple fused rings, with at least one heteroatom in the ring, i.e., one or more ring heteroatoms independently selected from nitrogen, oxygen, and sulfur, wherein the nitrogen or sulfur can be oxidized. Thus, the term includes rings having one or more annular O, N, S, S(O), $S(O)_2$, and N-oxide groups. The term includes rings having one or more annular C(O) groups. As used herein, heteroaryl include 5 to 20 ring atoms (i.e., 5- to 20-membered heteroaryl), 5 to 12 ring atoms (i.e., 5- to 12-membered heteroaryl), or 5 to 10 ring atoms (i.e., 5- to 10-membered heteroaryl), and 1 to 5 heteroatoms independently selected from nitrogen, oxygen, and sulfur, and oxidized forms of the heteroatoms. Examples of heteroaryl groups include, but are not limited to, pyridin-2(1H)-one, pyridazin-3(2H)-one, pyrimidin-4(3H)-one, quinolin-2(1H)-one, pyrimidinyl, purinyl, pyridyl, pyridazinyl, benzothiazolyl, and pyrazolyl. Heteroaryl does not encompass or overlap with aryl as defined above.

"Heterocycle" or "heterocyclyl" refer to a saturated or unsaturated cyclic alkyl group, with one or more ring heteroatoms independently selected from nitrogen, oxygen and sulfur. A heterocyclyl can be a single ring or multiple rings wherein the multiple rings can be fused, bridged, or spiro. As used herein, heterocyclyl has 3 to 20 ring atoms (i.e., 3 to 20 membered heterocyclyl), 3 to 12 ring atoms (i.e., 3 to 12 membered heterocyclyl), 3 to 10 ring atoms (i.e., 3 to 10 membered heterocyclyl), 3 to 8 ring atoms (i.e., 3 to 8 membered heterocyclyl), 4 to 12 ring carbon atoms (i.e., 4 to 12 membered heterocyclyl), 4 to 8 ring atoms (i.e., 4 to 8 membered heterocyclyl), or 4 to 6 ring atoms (i.e., 4 to 6 membered heterocyclyl). Examples of heterocyclyl groups include pyrrolidinyl, piperidinyl, piperazinyl, oxetanyl, dioxolanyl, azetidinyl, and morpholinyl.

The term "optionally substituted" in reference to a particular moiety of the compound disclosed herein (e.g., an optionally substituted aryl group) refers to a moiety wherein all substituents are hydrogen or wherein one or more of the hydrogens of the moiety can be replaced by the listed substituents.

Oxo" refers to the group (=O) or (O).

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, formulations, dosage forms and other materials which are useful in preparing a pharmaceutical composition that is suitable for veterinary or human pharmaceutical use.

The compounds described herein can be prepared and/or formulated as pharmaceutically acceptable salts or when appropriate as a free base. Pharmaceutically acceptable salts are non-toxic salts of a free base form of a compound that possess the desired pharmacological activity of the free base. These salts can be derived from inorganic or organic acids or bases. For example, a compound that contains a basic nitrogen can be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in REMINGTON: THE SCIENCE AND PRACTICE OF PHARMACY, $21^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom can be replaced by a deuterium atom or D, in which n is the number of hydrogen atoms in the molecule. As known in the art, the deuterium atom is a non-radioactive isotope of the hydrogen atom. Such compounds can increase resistance to metabolism, and thus can be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism," TRENDS PHARMACOL. SCI., 5(12):524-527 (1984). Such compounds are synthesized by means well known in the art, for example by employing starting materials in which one or more hydrogen atoms have been replaced by deuterium. The compounds disclosed herein can be deuterated at various positions, including (but not limited to), the following positions:

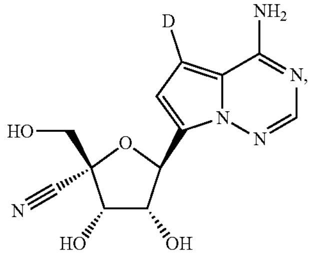

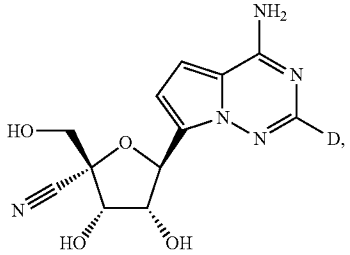

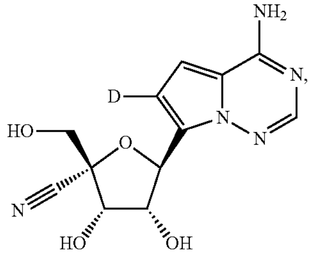

-continued

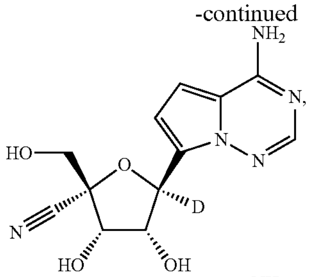

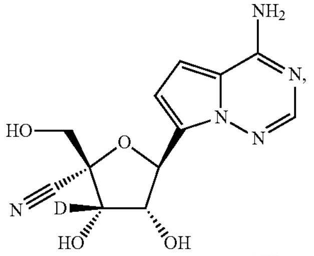

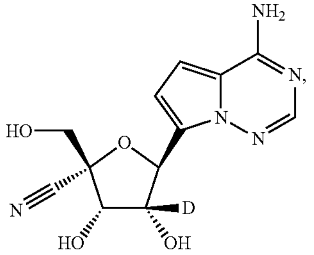

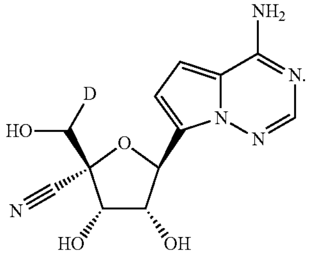

and

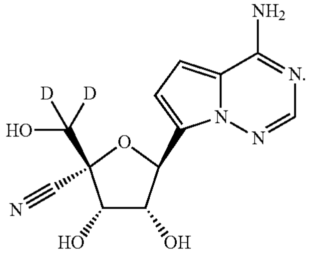

Examples of isotopes that can be incorporated into the disclosed compounds also include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$ and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula I-XI, can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)- isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

The terms "prevention" or "preventing" means any treatment of a disease or condition that causes the clinical symptoms of the disease or condition not to develop. The term "prevention" or "preventing" also encompasses the administration of a compound or composition according to the embodiments disclosed herein post-exposure of the subject to the virus but before the appearance of symptoms of the disease, and/or prior to the detection of the virus in the blood, to prevent the appearance of symptoms of the disease and/or to prevent the virus from reaching detectible levels in the blood, and the administration of a compound or composition according to the embodiments disclosed herein to prevent perinatal transmission of viral infection from mother to baby, by administration to the mother before giving birth and to the child within the first days of life.

"Racemates" refers to a mixture of enantiomers. The mixture can comprise equal or unequal amounts of each enantiomer.

"Stereoisomer" and "stereoisomers" refer to compounds that differ in the chirality of one or more stereocenters. Stereoisomers include enantiomers and diastereomers. The compounds can exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see, e.g., Chapter 4 of Advanced Organic Chemistry, 4th ed., J. March, John Wiley & Sons, New York, 1992).

A "subject" or "patient" is meant to describe a human or vertebrate animal including a dog, cat, pocket pet, marmoset, horse, cow, pig, sheep, goat, elephant, giraffe, chicken, lion, monkey, owl, rat, squirrel, slender loris, and mouse. A "pocket pet" refers to a group of vertebrate animals capable of fitting into a commodious coat pocket such as, for example, hamsters, chinchillas, ferrets, rats, guinea pigs, gerbils, rabbits and sugar gliders.

Unless defined otherwise, all technical and scientific terms used herein have the same meaning as commonly understood by one of ordinary skill in the art. A dash at the front or end of a chemical group is a matter of convenience; chemical groups can be depicted with or without one or more dashes without losing their ordinary meaning. A wavy line drawn through a line in a structure indicates a point of attachment of a group. A dashed line indicates an optional bond. Unless chemically or structurally required, no directionality is indicated or implied by the order in which a chemical group is written or the point at which it is attached to the remainder of the molecule. For instance, the group "$—SO_2CH_2—$" is equivalent to "$—CH_2SO_2—$" and both can be connected in either direction. Similarly, an "arylalkyl" group, for example, can be attached to the remainder of the molecule at either an aryl or an alkyl portion of the group. A prefix such as "$C_{u-v}$" or ($C_u$-$C_v$) indicates that the following group has from u to v carbon atoms. For example, "$C_{1-6}$alkyl" and "$C_1$-$C_6$ alkyl" both indicate that the alkyl group has from 1 to 6 carbon atoms.

Unless otherwise specified, the carbon atoms of the compounds of Formulas I-XI are intended to have a valence of four. If in some chemical structure representations, carbon atoms do not have a sufficient number of variables attached to produce a valence of four, the remaining carbon substituents needed to provide a valence of four should be assumed to be hydrogen.

The terms "treating" and "treatment" as used herein are intended to mean the administration of a compound or composition according to the embodiments disclosed herein to alleviate or eliminate symptoms of a viral infection and/or to reduce viral load in a subject.

The term "therapeutically effective amount," as used herein, is the amount of compound disclosed herein present in a formulation described herein that is needed to provide a desired level of drug in the secretions and tissues of the airways and lungs, or alternatively, in the bloodstream of a subject to be treated to give an anticipated physiological response or desired biological effect when such a formulation is administered by the chosen route of administration. The precise amount will depend upon numerous factors, for example the particular compound disclosed herein, the specific activity of the formulation, the delivery device employed, the physical characteristics of the formulation, its intended use, as well as subject considerations such as severity of the disease state, subject cooperation, etc., and can readily be determined by one skilled in the art based upon the information provided herein. The term "therapeutically effective amount" or "effective amount" also means amounts that eliminate or reduce the subject's viral burden and/or viral reservoir.

The term "adjacent carbons" as used herein refers to consecutive carbons atoms that are directly attached to each other. For example, in

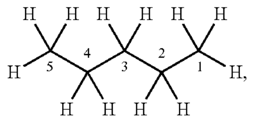

$C_1$ and $C_2$ are adjacent carbons, $C_2$ and $C_3$ are adjacent carbons, $C_3$ and $C_4$ are adjacent carbons, and $C_4$ and $C_5$ are adjacent carbons. Similarly, in

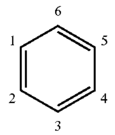

$C_1$ and $C_2$ are adjacent carbons, $C_2$ and $C_3$ are adjacent carbons, $C_3$ and $C_4$ are adjacent carbons, and $C_4$ and $C_5$ are adjacent carbons, $C_5$ and $C_6$ are adjacent carbons and $C_6$ and $C_1$ are adjacent carbons.

"Solvate" as used herein refers to the result of the interaction of a solvent and a compound. Solvates of salts of the compounds described herein are also provided. Hydrates of the compounds described herein are also provided.

"Prodrug" as used herein refers to a derivative of a drug that upon administration to the human body is converted to the parent drug according to some chemical or enzymatic pathway.

As used herein, "pharmaceutically acceptable carrier" or "pharmaceutically acceptable excipient" includes, but is not limited to, any and all solvents, dispersion media, coatings, antibacterial and antifungal agents, isotonic and absorption delaying agents, and combinations thereof. The use of pharmaceutically acceptable carriers and pharmaceutically acceptable excipients for pharmaceutically active substances is well known in the art. Except insofar as any conventional media or agent is incompatible with the active ingredient, its use in the therapeutic formulations is contemplated. Supplementary active ingredients can also be incorporated into the formulations. The carrier(s) must be "acceptable" in the sense of being compatible with the other ingredients of the formulation and physiologically innocuous to the recipient thereof.

III. Compounds

Provided herein are compounds of Formula I:

Formula I

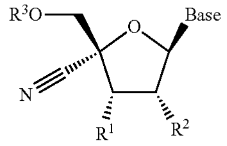

or a pharmaceutically acceptable salt thereof, wherein:

$R^1$ is OH or $OC(O)R^4$;

$R^2$ is OH or $OC(O)R^5$; or $R^1$ and $R^2$ are taken together to form —OC(O)O—;

$R^3$ is H or $C(O)R^7$, or $R^1$ and $R^3$ are taken together to form —OC(O)—;

$R^4$, $R^5$, and $R^7$ are each independently $C_1$-$C_8$ alkyl, $C_3$-$C_8$ carbocyclyl, $C_6$-$C_{10}$ aryl, 4 to 6 membered heterocyclyl containing 1, 2, or 3O, or 5 to 6 membered heteroaryl containing 1, 2, or 3 heteroatoms selected from N, O, and S;

wherein the alkyl, carbocyclyl, aryl, heterocyclyl, and heteroaryl of $R^4$, $R^5$, and $R^7$ are each, independently, optionally substituted with one, two or three substituents independently selected from the group consisting of halo, oxo, cyano, $—N_3$, $—OR^8$, $C_1$-$C_8$ alkyl, $—NR^9R^{10}$, $C_3$-$C_8$ carbocyclyl optionally substituted with $C_1$-$C_6$ alkyl, and phenyl optionally substituted with one, two, or three substituents independently selected from halo, cyano, and $C_1$-$C_6$ alkyl; and each $R^8$ is independently H, $C_1$-$C_6$ alkyl, $C_1$-$C_6$ haloalkyl, and $C_3$-$C_6$ cycloalkyl;

each $R^9$ is independently H, $C_1$-$C_6$ alkyl, $C_1$-$C_6$ haloalkyl, and $C_3$-$C_6$ cycloalkyl;

each $R^{10}$ is independently H, $C_1$-$C_6$ alkyl, $C_1$-$C_6$ haloalkyl, and $C_3$-$C_6$ cycloalkyl; and Base is,

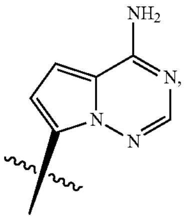 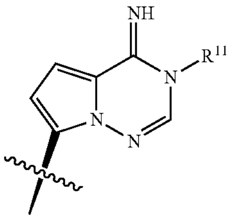 ,

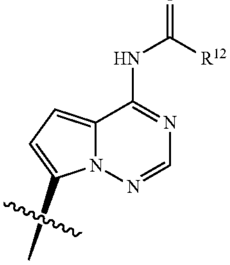 , or 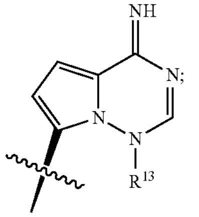

wherein $R^{11}$ is $C_1$-$C_6$ alkyl substituted with —OP(O)(OH)$_2$ or —OC(O)$R^{12}$;

$R^{12}$ is $C_1$-$C_8$ alkyl; and $R^{13}$ is $C_1$-$C_6$ alkyl substituted with —OP(O)(OH)$_2$ or —OC(O)$R^{12}$.

In some embodiments, the alkyl, carbocyclyl, aryl, heterocyclyl, and heteroaryl of $R^4$, $R^5$, and $R^7$ are each, independently, optionally substituted with one, two or three substituents independently selected from the group consisting of halo, oxo, cyano, —$N_3$, —$OR^8$, $C_1$-$C_8$ alkyl, —$NR^9R^{10}$, $C_3$-$C_8$ carbocyclyl, and phenyl optionally substituted with one, two, or three substituents independently selected from halo, cyano, and $C_1$-$C_6$ alkyl.

$R^1$ can be OH or OC(O)$R^4$. In some embodiments, $R^1$ is OH. In some embodiments, $R^1$ is OC(O)$R^4$.

$R^2$ can be OH or OC(O)$R^5$. In some embodiments, $R^2$ is OH. In some embodiments, $R^2$ is OC(O)$R^5$.

In some embodiments, $R^1$ is OH and $R^2$ is OH. In some embodiments, $R^1$ and $R^2$ are taken together to form —OC(O)—.

$R^3$ can be H or C(O)O$R^7$. In some embodiments, $R^3$ is H. In some embodiments, $R^3$ is C(O)O$R^7$. In some embodiments, $R^3$ is selected from

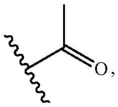 , 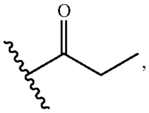 , 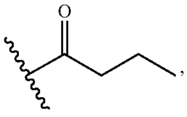 ,

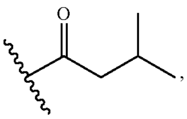 , 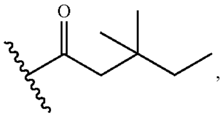 ,

-continued

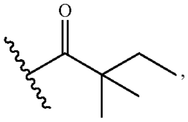 , 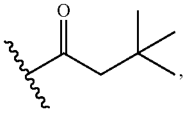 ,

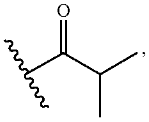 , 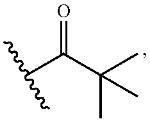 ,

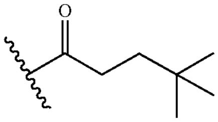 , 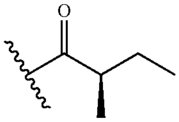 ,

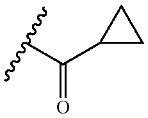 , 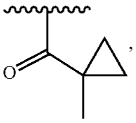 , 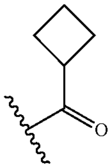 ,

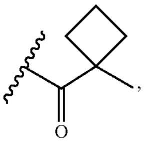 , 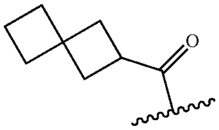 ,

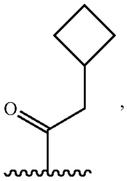 , 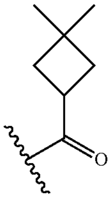 , 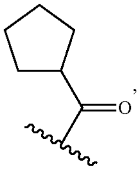 ,

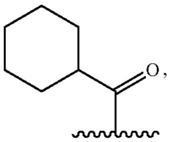 , 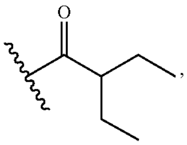 ,

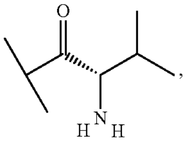 , 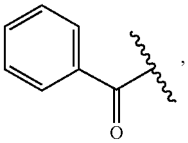 ,

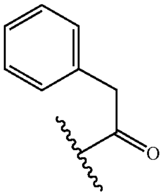 , 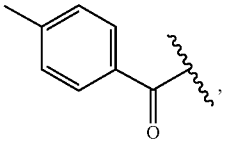 ,

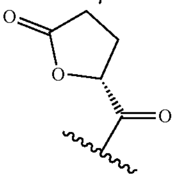 , or 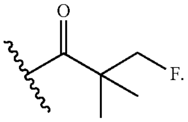

In some embodiments, $R^7$ is $C_1$-$C_6$ alkyl optionally substituted with one, two, or three substituents independently selected from halo, $C_3$-$C_6$ carbocyclyl, phenyl and $NH_2$. In some embodiments, $R^7$ is methyl, ethyl, propyl, isopropyl, isobutyl, tert-butyl, 1-ethylpropyl, 2,2-dimethylpropyl, 2,2-dimethylbutyl, 1,1-dimethylpropyl, 3,3-dimethylbutyl, 1-methylpropyl, 2-fluoro-1,1-dimethylethyl, benzyl,

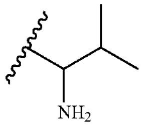, or 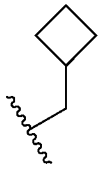.

In some embodiments, $R^7$ is $C_4$-$C_6$ alkyl. In some embodiments, $R^7$ is

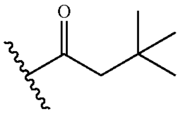.

In some embodiments, $R^7$ is $C_3$-$C_8$ carbocyclyl optionally substituted with one, two, or three substituents independently selected from $C_1$-$C_3$ alkyl. In some embodiments, $R^7$ is cyclopropyl, cyclobutyl, cyclopentyl, cyclohexyl,

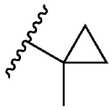, 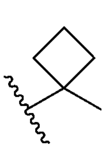, or 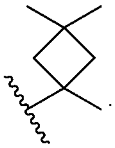.

In some embodiments, $R^7$ is phenyl optionally substituted with one, two, or three substituents independently selected from $C_1$-$C_3$ alkyl. In some embodiments, $R^7$ is phenyl optionally substituted with one, two, or three substituents independently selected from $C_1$-$C_3$ alkyl. In some embodiments, $R^7$ is 4 to 6 membered heterocyclyl containing 1, 2, or 3O, wherein the heterocyclyl of $R^7$ is optionally substituted with one, two, or three substituents independently selected from $C_1$-$C_3$ alkyl and oxo.

In some embodiments, $R^1$ and $R^3$ are taken together to form —OC(O)—

$R^4$ can be $C_1$-$C_8$ alkyl, $C_3$-$C_8$ carbocyclyl, $C_6$-$C_{10}$ aryl, 4- to 6-membered heterocyclyl containing 1, 2, or 3 O, or 5- to 6-membered heteroaryl containing 1, 2, or 3 heteroatoms selected from N, O, and S; wherein $R^4$ can be optionally substituted with one, two or three substituents independently selected from the group consisting of halo, oxo, cyano, $N_3$, $OR^8$, $C_1$-$C_8$ alkyl, $NR^9R^{10}$, $C_3$-$C_8$ carbocyclyl, and phenyl optionally substituted with one, two, or three substituents independently selected from halo, cyano, and $C_1$-$C_6$ alkyl; and $R^8$ can be H, $C_1$-$C_6$ alkyl, $C_1$-$C_6$ haloalkyl, and $C_3$-$C_6$ cycloalkyl; $R^9$ can be H, $C_1$-$C_6$ alkyl, $C_1$-$C_6$ haloalkyl, and $C_3$-$C_6$ cycloalkyl; and $R^{10}$ can be H, $C_1$-$C_6$ alkyl, $C_1$-$C_6$ haloalkyl, and $C_3$-$C_6$ cycloalkyl.

In some embodiments, $R^4$ is a $C_1$-$C_6$ (e.g., $C_1$, $C_2$, $C_3$, $C_4$, $C_5$, or $C_6$) alkyl. In some embodiments, the $C_1$-$C_6$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_6$ alkyl is $C_1$-$C_3$ alkyl. In some embodiments, the $C_1$-$C_6$ alkyl is $C_2$-$C_5$ alkyl. In some embodiments, the $C_1$-$C_6$ alkyl is $C_4$-$C_6$ alkyl.

In some embodiments, the $C_1$-$C_6$ alkyl is a branched $C_1$-$C_6$ alkyl. In some embodiments, the $C_1$-$C_6$ alkyl is an unbranched $C_1$-$C_6$ alkyl. In some embodiments, the $C_1$-$C_6$ alkyl is an unsubstituted $C_1$-$C_6$ alkyl. In some embodiments, the $C_1$-$C_6$ alkyl is a substituted $C_1$-$C_6$ alkyl. In some embodiments, the $C_1$-$C_6$ alkyl is a branched, unsubstituted $C_1$-$C_6$ alkyl. In some embodiments, the $C_1$-$C_6$ alkyl is a branched, substituted $C_1$-$C_6$ alkyl. In some embodiments, the $C_1$-$C_6$ alkyl is an unbranched, unsubstituted $C_1$-$C_6$ alkyl.

In some embodiments, $R^4$ is $C_3$-$C_8$(e.g., $C_3$, $C_4$, $C_5$, $C_6$, $C_7$, or $C_8$) carbocyclyl. In some embodiments, the $C_3$-$C_8$ carbocyclyl is saturated. In some embodiments, the $C_3$-$C_8$ carbocyclyl is partially unsaturated. Exemplary $C_3$-$C_8$ carbocyclic rings include, but are not limited to, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. In some embodiments, the $C_3$-$C_8$ carbocyclyl is unsubstituted $C_3$-$C_8$ carbocyclyl. In some embodiments, the $C_3$-$C_8$ carbocyclyl is substituted $C_3$-$C_8$ carbocyclyl. In some embodiments, the $C_3$-$C_8$ carbocyclyl is unbranched $C_3$-$C_8$ carbocyclyl. In some embodiments, the $C_3$-$C_8$ carbocyclyl is branched $C_3$-$C_8$ carbocyclyl.

In some embodiments, $R^4$ is $C_6$-$C_{10}$ aryl. In some embodiments, the $C_6$-$C_{10}$ aryl is unsubstituted $C_6$-$C_{10}$ aryl. In some embodiments, the $C_6$-$C_{10}$ aryl is substituted $C_6$-$C_{10}$ aryl. In some embodiments, the $C_6$-$C_{10}$ aryl is phenyl. In some embodiments, the $C_6$-$C_{10}$ aryl is naphthyl.

In some embodiments, $R^4$ is 4- to 6- (e.g., 4-, 5-, 6-) membered heterocyclyl containing one, two, or three O. In some embodiments, the 4- to 6-membered heterocyclyl is 4-membered heterocyclyl containing one O. In some embodiments, the 4- to 6-membered heterocyclyl is 4-membered heterocyclyl containing two O. In some embodiments, the 4- to 6-membered heterocyclyl is 4-membered heterocyclyl containing three O. In some embodiments, the 4- to 6-membered heterocyclyl is 5-membered heterocyclyl containing one O. In some embodiments, the 4- to 6-membered heterocyclyl is 5-membered heterocyclyl containing two O. In some embodiments, the 4- to 6-membered heterocyclyl is 5-membered heterocyclyl containing three O. In some embodiments, the 4- to 6-membered heterocyclyl is 6-membered heterocyclyl containing one O. In some embodiments, the 4- to 6-membered heterocyclyl is 6-membered heterocyclyl containing two O. In some embodiments, the 4- to 6-membered heterocyclyl is 6-membered heterocyclyl containing three O. In some embodiments, the 4- to 6-membered heterocyclyl is an unsubstituted 4- to 6-membered heterocyclyl. In some embodiments, the 4- to 6-membered heterocyclyl is a substituted 4- to 6-membered heterocyclyl.

In some embodiments, $R^4$ is 5- to 6-membered heteroaryl containing 1, 2, or 3 heteroatoms selected from N, O, and S. In some embodiments, the 5- to 6-membered heteroaryl is 5-membered heteroaryl containing one heteroatom selected from N, O, and S. In some embodiments, the 5- to 6-membered heteroaryl is 5-membered heteroaryl containing two heteroatoms selected from N, O, and S. In some embodiments, the 5- to 6-membered heteroaryl is 5-membered heteroaryl containing three heteroatoms selected from N, O, and S. In some embodiments, the 5- to 6-membered heteroaryl is 6-membered heteroaryl containing one heteroatom selected from N, O, and S. In some embodiments, the 5- to 6-membered heteroaryl is 6-membered heteroaryl containing two heteroatoms selected from N, O, and S. In some embodiments, the 5- to 6-membered heteroaryl is 6-membered heteroaryl containing three heteroatoms selected from N, O, and S. In some embodiments, the 5- to 6-membered heteroaryl is pyridinyl. In some embodiments, the 5- to 6-membered heteroaryl is pyrimidinyl. In some embodiments, the 5- to 6-membered heteroaryl is an unsubstituted 5- to 6-membered heteroaryl. In some embodiments, the 5- to 6-membered heteroaryl is a substituted 5- to 6-membered heteroaryl.

In some embodiments, $R^4$ is unsubstituted. In some embodiments, $R^4$ is substituted with one substituent. In some embodiments, $R^4$ is substituted with two substituents. In some embodiments, $R^4$ is substituted three substituents. In some embodiments, $R^4$ is substituted with one, two or three substituents wherein at least one substituent is halo. In some embodiments, $R^4$ is substituted with one, two or three substituents wherein at least one substituent is oxo. In some embodiments, $R^4$ is substituted with one, two or three substituents wherein at least one substituent is cyano. In some embodiments, $R^4$ is substituted with one, two or three substituents wherein at least one substituent is $N_3$. In some embodiments, $R^4$ is substituted with one, two or three substituents wherein at least one substituent is $OR^8$.

In some embodiments, $R^4$ is substituted with one, two or three substituents wherein at least one substituent is a $C_1$-$C_8$(e.g., $C_1$, $C_2$, $C_3$, $C_4$, $C_5$, $C_6$, $C_7$, or $C_8$) alkyl. In some embodiments, the $C_1$-$C_8$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_8$ alkyl is $C_1$-$C_6$ alkyl. In some embodiments, the $C_1$-$C_8$ alkyl is $C_1$-$C_3$ alkyl. In some embodiments, the $C_1$-$C_8$ alkyl is $C_2$-$C_5$ alkyl. In some embodiments, the $C_1$-$C_8$ alkyl is $C_4$-$C_5$ alkyl. In some embodiments, the $C_1$-$C_8$ alkyl is a branched $C_1$-$C_8$ alkyl. In some embodiments, the $C_1$-$C_8$ alkyl is an unbranched $C_1$-$C_8$ alkyl. In some embodiments, the $C_1$-$C_8$ alkyl is an unsubstituted $C_1$-$C_8$ alkyl. In some embodiments, the $C_1$-$C_8$ alkyl is a branched, unsubstituted $C_1$-$C_8$ alkyl. In some embodiments, the $C_1$-$C_8$ alkyl is an unbranched, unsubstituted $C_1$-$C_8$ alkyl.

In some embodiments, $R^4$ is substituted with one, two or three substituents wherein at least one substituent is $NR^9R^{10}$. In some embodiments, $R^4$ is substituted with one, two or three substituents wherein at least one substituent is $NH_2$.

In some embodiments, $R^4$ is substituted with one, two or three substituents wherein at least one substituent is $C_3$-$C_8$ (e.g., $C_3$, $C_4$, $C_5$, $C_6$, $C_7$, or $C_8$) carbocyclyl. In some embodiments, the $C_3$-$C_8$ carbocyclyl is saturated. In some embodiments, the $C_3$-$C_8$ carbocyclyl is partially unsaturated. Exemplary $C_3$-$C_8$ carbocyclic rings include, but are not limited to, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. In some embodiments, the $C_3$-$C_8$ carbocyclyl is unsubstituted $C_3$-$C_8$ carbocyclyl. In some embodiments, the $C_3$-$C_8$ carbocyclyl is substituted $C_3$-$C_8$ carbocyclyl. In some embodiments, the $C_3$-$C_8$ carbocyclyl is unbranched $C_3$-$C_8$ carbocyclyl. In some embodiments, the $C_3$-$C_8$ carbocyclyl is branched $C_3$-$C_8$ carbocyclyl.

In some embodiments, $R^4$ is substituted with one, two or three substituents wherein at least one substituent is phenyl. In some embodiments, $R^4$ is substituted with one, two or three substituents wherein at least one substituent is phenyl substituted with one, two, or three substituents independently selected from halo, cyano, and $C_1$-$C_6$ alkyl. In some embodiments, $R^4$ is substituted with one, two or three substituents wherein at least one substituent is phenyl substituted with one, two, or three substituents wherein at least one substituent is halo (e.g., fluoro, chloro, iodo, bromo). In some embodiments, $R^4$ is substituted with one, two or three substituents wherein at least one substituent is phenyl substituted with one, two, or three substituents wherein at least one substituent is cyano. In some embodiments, $R^4$ is substituted with at least one halo and at least one oxo. In some embodiments, $R^4$ is substituted with at least one halo and at least one cyano. In some embodiments, $R^4$ is substituted with at least one halo and at least one $N_3$. In some embodiments, $R^4$ is substituted with at least one halo and at least one $OR^8$. In some embodiments, $R^4$ is substituted with at least one halo and at least one $NR^9R^{10}$. In some embodiments, $R^4$ is substituted with at least one halo and at least one $C_3$-$C_8$ carbocyclyl. In some embodiments, $R^4$ is substituted with at least one halo and at least one unsubstituted phenyl. In some embodiments, $R^4$ is substituted with at least one halo and at least one phenyl substituted with one, two, or three substituents independently selected from halo, cyano, and $C_1$-$C_6$ alkyl. In some embodiments, $R^4$ is substituted with at least one oxo and at least one cyano. In some embodiments, $R^4$ is substituted with at least one oxo and at least one N3. In some embodiments, $R^4$ is substituted with at least one oxo and at least one $OR^8$. In some embodiments, $R^4$ is substituted with at least one oxo and at least one $C_1$-$C_8$ alkyl. In some embodiments, $R^4$ is substituted with at least one oxo and at least one $NR^9R^{10}$. In some embodiments, $R^4$ is substituted with at least one oxo and at least one $C_3$-$C_8$ carbocyclyl. In some embodiments, $R^4$ is substituted with at least one oxo and at least one unsubstituted phenyl. In some embodiments, $R^4$ is substituted with at least one oxo and at least one phenyl substituted with one, two, or three substituents independently selected from halo, cyano, and $C_1$-$C_6$ alkyl. In some embodiments, $R^4$ is substituted with at least one cyano and at least one $N_3$. In some embodiments, $R^4$ is substituted with at least one $N_3$ and at least one $OR^8$. In some embodiments, $R^4$ is substituted with at least one cyano and at least one $C_1$-$C_8$ alkyl. In some embodiments, $R^4$ is substituted with at least one cyano and at least one $NR^9R^{10}$. In some embodiments, $R^4$ is substituted with at least one cyano and at least one $C_3$-$C_8$ carbocyclyl. In some embodiments, $R^4$ is substituted with at least one cyano and at least one unsubstituted phenyl. In some embodiments, $R^4$ is substituted with at least one cyano and at least one phenyl substituted with one, two, or three substituents independently selected from halo, cyano, and $C_1$-$C_6$ alkyl. In some embodiments, $R^4$ is substituted with at least one $N_3$ and at least one $OR^8$. In some embodiments, $R^4$ is substituted with at least one $N_3$ and at least one $C_1$-$C_8$ alkyl. In some embodiments, $R^4$ is substituted with at least one $N_3$ and at least one $NR^9R^{10}$. In some embodiments, $R^4$ is substituted with at least one $N_3$ and at least one $C_3$-$C_8$ carbocyclyl. In some embodiments, $R^4$ is substituted with at least one $N_3$ and at least one unsubstituted phenyl. In some embodiments, $R^4$ is substituted with at least one $N_3$ and at least one phenyl substituted with one, two, or three substituents independently selected from halo, cyano, and $C_1$-$C_6$ alkyl. In some embodiments, $R^4$ is substituted with at least one $OR^8$ and at least one $C_1$-$C_8$ alkyl. In some embodiments, $R^4$ is substituted with at least one $OR^8$ and at least one $NR^9R^{10}$. In some embodiments, $R^4$ is substituted with at least one $OR^8$ and at least one $C_3$-$C_8$ carbocyclyl. In some embodiments, $R^4$ is substituted with at least one $OR^8$ and at least one unsubstituted phenyl. In some embodiments, $R^4$ is substituted with at least one $OR^8$ and at least one phenyl substituted with one, two, or three substituents independently selected from halo, cyano, and $C_1$-$C_6$ alkyl. In some embodiments, $R^4$ is substituted with at least one $C_1$-$C_8$ alkyl and at least one $NR^9R^{10}$. In some embodiments, $R^4$ is substituted with at least one $C_1$-$C_8$ alkyl and at least one $C_3$-$C_8$ carbocyclyl. In some embodiments, $R^4$ is substituted with at least one $C_1$-$C_8$ alkyl and at least one unsubstituted phenyl. In some embodiments, $R^4$ is substituted with at least one $C_1$-$C_8$ alkyl and at least one phenyl substituted with one, two, or three substituents independently selected from halo, cyano, and $C_1$-$C_6$ alkyl. In some embodiments, $R^4$ is substituted with at least one $C_3$-$C_8$ carbocyclyl and at least one unsubstituted phenyl. In some embodiments, $R^4$ is substituted with at least one $C_3$-$C_8$ carbocyclyl and at least one phenyl substituted with one, two, or three substituents independently selected from halo, cyano, and $C_1$-$C_6$ alkyl.

$R^5$ can be $C_1$-$C_8$ alkyl, $C_3$-$C_8$ carbocyclyl, $C_6$-$C_{10}$ aryl, 4 to 6 membered heterocyclyl containing 1, 2, or 3 O, or 5 to 6 membered heteroaryl containing 1, 2, or 3 heteroatoms selected from N, O, and S; wherein $R^5$ can be optionally substituted with one, two or three substituents independently selected from the group consisting of halo, oxo, cyano, —$N_3$, —$OR^8$, $C_1$-$C_8$ alkyl, —$NR^9R^{10}$, $C_3$-$C_8$ carbocyclyl, and phenyl optionally substituted with one, two, or three substituents independently selected from halo, cyano, and $C_1$-$C_6$ alkyl; and $R^8$ can be H, $C_1$-$C_6$ alkyl, $C_1$-$C_6$ haloalkyl, and $C_3$-$C_6$ cycloalkyl; $R^9$ can be H, $C_1$-$C_6$ alkyl, $C_1$-$C_6$ haloalkyl, and $C_3$-$C_6$ cycloalkyl; and $R^{10}$ can be H, $C_1$-$C_6$ alkyl, $C_1$-$C_6$ haloalkyl, and $C_3$-$C_6$ cycloalkyl.

In some embodiments, $R^5$ is a $C_1$-$C_6$ (e.g., $C_1$, $C_2$, $C_3$, $C_4$, $C_5$, or $C_6$) alkyl. In some embodiments, the $C_1$-$C_6$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_6$ alkyl is $C_1$-$C_3$ alkyl. In some embodiments, the $C_1$-$C_6$ alkyl is $C_2$-$C_5$ alkyl. In some embodiments, the $C_1$-$C_6$ alkyl is $C_4$-$C_6$ alkyl. In some embodiments, the $C_1$-$C_6$ alkyl is a branched $C_1$-$C_6$ alkyl. In some embodiments, the $C_1$-$C_6$ alkyl is an unbranched $C_1$-$C_6$ alkyl. In some embodiments, the $C_1$-$C_6$ alkyl is an unsubstituted $C_1$-$C_6$ alkyl. In some embodiments, the $C_1$-$C_6$ alkyl is a substituted $C_1$-$C_6$ alkyl. In some embodiments, the $C_1$-$C_6$ alkyl is a branched, unsubstituted $C_1$-$C_6$ alkyl. In some embodiments, the $C_1$-$C_6$ alkyl is a branched, substituted $C_1$-$C_6$ alkyl. In some embodiments, the $C_1$-$C_6$ alkyl is an unbranched, unsubstituted $C_1$-$C_6$ alkyl.

In some embodiments, $R^5$ is $C_3$-$C_8$ (e.g., $C_3$, $C_4$, $C_5$, $C_6$, $C_7$, or $C_8$) carbocyclyl. In some embodiments, the $C_3$-$C_8$ carbocyclyl is saturated. In some embodiments, the $C_3$-$C_8$ carbocyclyl is partially unsaturated. Exemplary $C_3$-$C_8$ carbocyclic rings include, but are not limited to, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. In some embodiments, the $C_3$-$C_8$ carbocyclyl is unsubstituted $C_3$-$C_8$ carbocyclyl. In some embodiments, the $C_3$-$C_8$ carbocyclyl is substituted $C_3$-$C_8$ carbocyclyl. In some embodiments, the $C_3$-$C_8$ carbocyclyl is unbranched $C_3$-$C_8$ carbocyclyl. In some embodiments, the $C_3$-$C_8$ carbocyclyl is branched $C_3$-$C_8$ carbocyclyl.

In some embodiments, $R^5$ is $C_6$-$C_{10}$ aryl. In some embodiments, the $C_6$-$C_{10}$ aryl is $C_6$ aryl (e.g., phenyl) or $C_{10}$ aryl (e.g., naphthyl). In some embodiments, the $C_6$-$C_{10}$ aryl is unsubstituted $C_6$-$C_{10}$ aryl. In some embodiments, the $C_6$-$C_{10}$ aryl is substituted $C_6$-$C_{10}$ aryl. In some embodiments, the $C_6$-$C_{10}$ aryl is phenyl. In some embodiments, the $C_6$-$C_{10}$ aryl is naphthyl.

In some embodiments, $R^5$ is 4- to 6- (e.g., 4-, 5-, 6-) membered heterocyclyl containing one, two, or three O. In some embodiments, the 4- to 6-membered heterocyclyl is 4-membered heterocyclyl containing one O. In some embodiments, the 4- to 6-membered heterocyclyl is 4-membered heterocyclyl containing two O. In some embodiments, the 4- to 6-membered heterocyclyl is 4-membered heterocyclyl containing three O. In some embodiments, the 4- to 6-membered heterocyclyl is 5-membered heterocyclyl containing one O. In some embodiments, the 4- to 6-membered heterocyclyl is 5-membered heterocyclyl containing two O. In some embodiments, the 4- to 6-membered heterocyclyl is 5-membered heterocyclyl containing three O. In some embodiments, the 4- to 6-membered heterocyclyl is 6-membered heterocyclyl containing one O. In some embodiments, the 4- to 6-membered heterocyclyl is 6-membered heterocyclyl containing two O. In some embodiments, the 4- to 6-membered heterocyclyl is 6-membered heterocyclyl containing three O. In some embodiments, the 4- to 6-membered heterocyclyl is an unsubstituted 4- to 6-membered heterocyclyl. In some embodiments, the 4- to 6-membered heterocyclyl is a substituted 4- to 6-membered heterocyclyl.

In some embodiments, $R^5$ is 5- to 6-membered heteroaryl containing 1, 2, or 3 heteroatoms selected from N, O, and S. In some embodiments, the 5- to 6-membered heteroaryl is 5-membered heteroaryl containing one heteroatom selected from N, O, and S. In some embodiments, the 5- to 6-membered heteroaryl is 5-membered heteroaryl containing two heteroatoms selected from N, O, and S. In some embodiments, the 5- to 6-membered heteroaryl is 5-membered heteroaryl containing three heteroatoms selected from N, O, and S. In some embodiments, the 5- to 6-membered heteroaryl is 6-membered heteroaryl containing one heteroatom selected from N, O, and S. In some embodiments, the 5- to 6-membered heteroaryl is 6-membered heteroaryl containing two heteroatoms selected from N, O, and S. In some embodiments, the 5- to 6-membered heteroaryl is 6-membered heteroaryl containing three heteroatoms selected from N, O, and S. In some embodiments, the 5- to 6-membered heteroaryl is pyridinyl. In some embodiments, the 5- to 6-membered heteroaryl is pyrimidinyl. In some embodiments, the 5- to 6-membered heteroaryl is an unsubstituted 5- to 6-membered heteroaryl. In some embodiments, the 5- to 6-membered heteroaryl is a substituted 5- to 6-membered heteroaryl.

In some embodiments, $R^5$ is unsubstituted. In some embodiments, $R^5$ is substituted with one substituent. In some embodiments, $R^5$ is substituted with two substituents. In some embodiments, $R^5$ is substituted three substituents. In some embodiments, $R^5$ is substituted with one, two or three substituents wherein at least one substituent is halo. In some embodiments, $R^5$ is substituted with one, two or three substituents wherein at least one substituent is oxo. In some embodiments, $R^5$ is substituted with one, two or three substituents wherein at least one substituent is cyano. In some embodiments, $R^5$ is substituted with one, two or three substituents wherein at least one substituent is $N_3$. In some embodiments, $R^5$ is substituted with one, two or three substituents wherein at least one substituent is $OR^8$.

In some embodiments, $R^5$ is substituted with one, two or three substituents wherein at least one substituent is a $C_1$-$C_8$(e.g., $C_1$, $C_2$, $C_3$, $C_4$, $C_5$, $C_6$, $C_7$, or $C_8$) alkyl. In some embodiments, the $C_1$-$C_8$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_8$ alkyl is $C_1$-$C_6$ alkyl. In some embodiments, the $C_1$-$C_8$ alkyl is $C_1$-$C_3$ alkyl. In some embodiments, the $C_1$-$C_8$ alkyl is $C_2$-$C_5$ alkyl. In some embodiments, the $C_1$-$C_8$ alkyl is $C_4$-$C_5$ alkyl. In some embodiments, the $C_1$-$C_8$ alkyl is a branched $C_1$-$C_8$ alkyl. In some embodiments, the $C_1$-$C_8$ alkyl is an unbranched $C_1$-$C_8$ alkyl. In some embodiments, the $C_1$-$C_8$ alkyl is an unsubstituted $C_1$-$C_8$ alkyl. In some embodiments, the $C_1$-$C_8$ alkyl is a branched, unsubstituted $C_1$-$C_8$ alkyl. In some embodiments, the $C_1$-$C_8$ alkyl is an unbranched, unsubstituted $C_1$-$C_8$ alkyl.

In some embodiments, $R^5$ is substituted with one, two or three substituents wherein at least one substituent is $NR^9R^{10}$. In some embodiments, $R^5$ is substituted with one, two or three substituents wherein at least one substituent is $NH_2$.

In some embodiments, $R^5$ is substituted with one, two or three substituents wherein at least one substituent is $C_3$-$C_8$ (e.g., $C_3$, $C_4$, $C_5$, $C_6$, $C_7$, or $C_8$) carbocyclyl. In some embodiments, the $C_3$-$C_8$ carbocyclyl is saturated. In some embodiments, the $C_3$-$C_8$ carbocyclyl is partially unsaturated. Exemplary $C_3$-$C_8$ carbocyclic rings include, but are not limited to, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. In some embodiments, the $C_3$-$C_8$ carbocyclyl is unsubstituted $C_3$-$C_8$ carbocyclyl. In some embodiments, the $C_3$-$C_8$ carbocyclyl is substituted $C_3$-$C_8$ carbocyclyl. In some embodiments, the $C_3$-$C_8$ carbocyclyl is unbranched $C_3$-$C_8$ carbocyclyl. In some embodiments, the $C_3$-$C_8$ carbocyclyl is branched $C_3$-$C_8$ carbocyclyl.

In some embodiments, $R^5$ is substituted with one, two or three substituents wherein at least one substituent is phenyl. In some embodiments, $R^5$ is substituted with one, two or three substituents wherein at least one substituent is phenyl substituted with one, two, or three substituents independently selected from halo, cyano, and $C_1$-$C_6$ alkyl. In some embodiments, $R^5$ is substituted with one, two or three substituents wherein at least one substituent is phenyl substituted with one, two, or three substituents wherein at least one substituent is halo (e.g., fluoro, chloro, iodo, bromo). In some embodiments, $R^5$ is substituted with one, two or three substituents wherein at least one substituent is phenyl substituted with one, two, or three substituents wherein at least one substituent is cyano. In some embodiments, $R^5$ is substituted with at least one halo and at least one oxo. In some embodiments, $R^5$ is substituted with at least one halo and at least one cyano. In some embodiments, $R^5$ is substituted with at least one halo and at least one $N_3$. In some embodiments, $R^5$ is substituted with at least one halo and at least one $OR^8$. In some embodiments, $R^5$ is substituted with at least one halo and at least one $NR^9R^{10}$. In some embodiments, $R^5$ is substituted with at least one halo and at least one $C_3$-$C_8$ carbocyclyl. In some embodiments, $R^5$ is substituted with at least one halo and at least one unsubstituted phenyl. In some embodiments, $R^5$ is substituted with at least one halo and at least one phenyl substituted with one, two, or three substituents independently selected from halo, cyano, and $C_1$-$C_6$ alkyl. In some embodiments, $R^5$ is substituted with at least one oxo and at least one cyano. In some embodiments, $R^5$ is substituted with at least one oxo and at least one N3. In some embodiments, $R^5$ is substituted with at least one oxo and at least one $OR^8$. In some embodiments, $R^5$ is substituted with at least one oxo and at least one $C_1$-$C_8$ alkyl. In some embodiments, $R^5$ is substituted with at least one oxo and at least one $NR^9R^{10}$. In some embodiments, $R^5$ is substituted with at least one oxo and at least one $C_3$-$C_8$ carbocyclyl. In some embodiments, $R^5$ is substituted with at least one oxo and at least one unsubstituted phenyl. In some embodiments, $R^5$ is substituted with at least one oxo and at least one phenyl substituted with one, two, or three substituents independently selected from halo, cyano, and $C_1$-$C_6$ alkyl. In some embodiments, $R^5$ is substituted with at least one cyano and at least one $N_3$. In some embodiments, $R^5$ is substituted with at least one $N_3$ and at least one $OR^8$. In some embodiments, $R^5$ is substituted with at least one cyano and at least one $C_1$-$C_8$ alkyl. In some embodiments, $R^5$ is substituted with at least one cyano and at least one $NR^9R^{10}$. In some embodiments, $R^5$ is substituted with at least one cyano and at least one $C_3$-$C_8$ carbocyclyl. In some embodiments, $R^5$ is substituted with at least one cyano and at least one unsubstituted phenyl. In some embodiments, $R^5$ is substituted with at least one cyano and at least one phenyl substituted with one, two, or three substituents independently selected from halo, cyano, and $C_1$-$C_6$ alkyl. In some embodiments, $R^5$ is substituted with at least one $N_3$ and at least one $OR^8$. In some embodiments, $R^5$ is substituted with at least one $N_3$ and at least one $C_1$-$C_8$ alkyl. In some embodiments, $R^5$ is substituted with at least one $N_3$ and at least one $NR^9R^{10}$. In some embodiments, $R^5$ is substituted with at least one $N_3$ and at least one $C_3$-$C_8$ carbocyclyl. In some embodiments, $R^5$ is substituted with at least one $N_3$ and at least one unsubstituted phenyl. In some embodiments, $R^5$ is substituted with at least one $N_3$ and at least one phenyl substituted with one, two, or three substituents independently selected from halo, cyano, and $C_1$-$C_6$ alkyl. In some embodiments, $R^5$ is substituted with at least one $OR^8$ and at least one $C_1$-$C_8$ alkyl. In some embodiments, $R^5$ is substituted with at least one $OR^8$ and at least one $NR^9R^{10}$. In some embodiments, $R^5$ is substituted with at least one $OR^8$ and at least one $C_3$-$C_8$ carbocyclyl. In some embodiments, $R^5$ is substituted with at least one $OR^8$ and at least one unsubstituted phenyl. In some embodiments, $R^5$ is substituted with at least one $OR^8$ and at least one phenyl substituted with one, two, or three substituents independently selected from halo, cyano, and $C_1$-$C_6$ alkyl. In some embodiments, $R^5$ is substituted with at least one $C_1$-$C_8$ alkyl and at least one $NR^9R^{10}$. In some embodiments, $R^5$ is substituted with at least one $C_1$-$C_8$ alkyl and at least one $C_3$-$C_8$ carbocyclyl. In some embodiments, $R^5$ is substituted with at least one $C_1$-$C_8$ alkyl and at least one unsubstituted phenyl. In some embodiments, $R^5$ is substituted with at least one $C_1$-$C_8$ alkyl and at least one phenyl substituted with one, two, or three substituents independently selected from halo, cyano, and $C_1$-$C_6$ alkyl. In some embodiments, $R^5$ is substituted with at least one $C_3$-$C_8$ carbocyclyl and at least one unsubstituted phenyl. In some embodiments, $R^5$ is substituted with at least one $C_3$-$C_8$ carbocyclyl and at least one phenyl substituted with one, two, or three substituents independently selected from halo, cyano, and $C_1$-$C_6$ alkyl.

$R^7$ can be $C_1$-$C_8$ alkyl, $C_3$-$C_8$ carbocyclyl, $C_6$-$C_{10}$ aryl, 4 to 6 membered heterocyclyl containing 1, 2, or 3 O, or 5 to 6 membered heteroaryl containing 1, 2, or 3 heteroatoms selected from N, O, and S; wherein $R^7$ can be optionally substituted with one, two or three substituents independently selected from the group consisting of halo, oxo, cyano, —$N_3$, —$OR^8$, $C_1$-$C_8$ alkyl, —$NR^9R^{10}$, $C_3$-$C_8$ carbocyclyl, and phenyl optionally substituted with one, two, or three substituents independently selected from halo, cyano, and $C_1$-$C_6$ alkyl; and $R^8$ can be H, $C_1$-$C_6$ alkyl, $C_1$-$C_6$ haloalkyl, and $C_3$-$C_6$ cycloalkyl; $R^9$ can be H, $C_1$-$C_6$ alkyl, $C_1$-$C_6$ haloalkyl, and $C_3$-$C_6$ cycloalkyl; and $R^{10}$ can be H, $C_1$-$C_6$ alkyl, $C_1$-$C_6$ haloalkyl, and $C_3$-$C_6$ cycloalkyl.

In some embodiments, $R^7$ is a $C_1$-$C_6$ (e.g., $C_1$, $C_2$, $C_3$, $C_4$, $C_5$, or $C_6$) alkyl. In some embodiments, the $C_1$-$C_6$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_6$ alkyl is $C_1$-$C_3$ alkyl. In some embodiments, the $C_1$-$C_6$ alkyl is $C_2$-$C_5$ alkyl. In some embodiments, the $C_1$-$C_6$ alkyl is $C_4$-$C_6$ alkyl. In some embodiments, the $C_1$-$C_6$ alkyl is a branched $C_1$-$C_6$ alkyl. In some embodiments, the $C_1$-$C_6$ alkyl is an unbranched $C_1$-$C_6$ alkyl. In some embodiments, the $C_1$-$C_6$ alkyl is an unsubstituted $C_1$-$C_6$ alkyl. In some embodiments, the $C_1$-$C_6$ alkyl is a substituted $C_1$-$C_6$ alkyl. In some embodiments, the $C_1$-$C_6$ alkyl is a branched, unsubstituted $C_1$-$C_6$ alkyl. In some embodiments, the $C_1$-$C_6$ alkyl is a branched, substituted $C_1$-$C_6$ alkyl. In some embodiments, the $C_1$-$C_6$ alkyl is an unbranched, unsubstituted $C_1$-$C_6$ alkyl.

In some embodiments, $R^7$ is $C_3$-$C_8$(e.g., $C_3$, $C_4$, $C_5$, $C_6$, $C_7$, or $C_8$) carbocyclyl. In some embodiments, the $C_3$-$C_8$ carbocyclyl is saturated. In some embodiments, the $C_3$-$C_8$ carbocyclyl is partially unsaturated. Exemplary $C_3$-$C_8$ carbocyclic rings include, but are not limited to, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. In some embodiments, the $C_3$-$C_8$ carbocyclyl is unsubstituted $C_3$-$C_8$ carbocyclyl. In some embodiments, the $C_3$-$C_8$ carbocyclyl is substituted $C_3$-$C_8$ carbocyclyl. In some embodiments, the $C_3$-$C_8$ carbocyclyl is unbranched $C_3$-$C_8$ carbocyclyl. In some embodiments, the $C_3$-$C_8$ carbocyclyl is branched $C_3$-$C_8$ carbocyclyl.

In some embodiments, $R^7$ is $C_6$-$C_{10}$ aryl. In some embodiments, the $C_6$-$C_{10}$ aryl is $C_6$ aryl (e.g., phenyl) or $C_{10}$ aryl (e.g., naphthyl). In some embodiments, the $C_6$-$C_{10}$ aryl is unsubstituted $C_6$-$C_{10}$ aryl. In some embodiments, the $C_6$-$C_{10}$ aryl is substituted $C_6$-$C_{10}$ aryl. In some embodiments, the $C_6$-$C_{10}$ aryl is phenyl. In some embodiments, the $C_6$-$C_{10}$ aryl is naphthyl.

In some embodiments, $R^7$ is 4- to 6- (e.g., 4-, 5-, 6-) membered heterocyclyl containing one, two, or three O. In some embodiments, the 4- to 6-membered heterocyclyl is 4-membered heterocyclyl containing one O. In some embodiments, the 4- to 6-membered heterocyclyl is 4-membered heterocyclyl containing two O. In some embodiments, the 4- to 6-membered heterocyclyl is 4-membered heterocyclyl containing three O. In some embodiments, the 4- to 6-membered heterocyclyl is 5-membered heterocyclyl containing one O. In some embodiments, the 4- to 6-membered heterocyclyl is 5-membered heterocyclyl containing two O. In some embodiments, the 4- to 6-membered heterocyclyl is 5-membered heterocyclyl containing three O. In some embodiments, the 4- to 6-membered heterocyclyl is 6-membered heterocyclyl containing one O. In some embodiments, the 4- to 6-membered heterocyclyl is 6-membered heterocyclyl containing two O. In some embodiments, the 4- to 6-membered heterocyclyl is 6-membered heterocyclyl containing three O. In some embodiments, the 4- to 6-membered heterocyclyl is an unsubstituted 4- to 6-membered heterocyclyl. In some embodiments, the 4- to 6-membered heterocyclyl is a substituted 4- to 6-membered heterocyclyl.

In some embodiments, $R^7$ is 5- to 6-membered heteroaryl containing 1, 2, or 3 heteroatoms selected from N, O, and S. In some embodiments, the 5- to 6-membered heteroaryl is 5-membered heteroaryl containing one heteroatom selected from N, O, and S. In some embodiments, the 5- to 6-membered heteroaryl is 5-membered heteroaryl containing two heteroatoms selected from N, O, and S. In some embodiments, the 5- to 6-membered heteroaryl is 5-membered heteroaryl containing three heteroatoms selected from N, O, and S. In some embodiments, the 5- to 6-membered heteroaryl is 6-membered heteroaryl containing one heteroatom selected from N, O, and S. In some embodiments, the 5- to 6-membered heteroaryl is 6-membered heteroaryl containing two heteroatoms selected from N, O, and S. In some embodiments, the 5- to 6-membered heteroaryl is 6-membered heteroaryl containing three heteroatoms selected from N, O, and S. In some embodiments, the 5- to 6-membered heteroaryl is pyridinyl. In some embodiments, the 5- to 6-membered heteroaryl is pyrimidinyl. In some embodiments, the 5- to 6-membered heteroaryl is an unsubstituted 5- to 6-membered heteroaryl. In some embodiments, the 5- to 6-membered heteroaryl is a substituted 5- to 6-membered heteroaryl.

In some embodiments, $R^7$ is unsubstituted. In some embodiments, $R^7$ is substituted with one substituent. In some embodiments, $R^7$ is substituted with two substituents. In some embodiments, $R^7$ is substituted three substituents. In some embodiments, $R^7$ is substituted with one, two or three substituents wherein at least one substituent is halo. In some embodiments, $R^7$ is substituted with one, two or three substituents wherein at least one substituent is oxo. In some embodiments, $R^7$ is substituted with one, two or three substituents wherein at least one substituent is cyano. In some embodiments, $R^7$ is substituted with one, two or three substituents wherein at least one substituent is $N_3$. In some embodiments, $R^7$ is substituted with one, two or three substituents wherein at least one substituent is $OR^8$.

In some embodiments, $R^7$ is substituted with one, two or three substituents wherein at least one substituent is a $C_1$-$C_8$ (e.g., $C_1$, $C_2$, $C_3$, $C_4$, $C_5$, $C_6$, $C_7$, or $C_8$) alkyl. In some embodiments, the $C_1$-$C_8$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_8$ alkyl is $C_1$-$C_6$ alkyl. In some embodiments, the $C_1$-$C_8$ alkyl is $C_1$-$C_3$ alkyl. In some embodiments, the $C_1$-$C_8$ alkyl is $C_2$-$C_5$ alkyl. In some embodiments, the $C_1$-$C_8$ alkyl is $C_4$-$C_5$ alkyl. In some embodiments, the $C_1$-$C_8$ alkyl is a branched $C_1$-$C_8$ alkyl. In some embodiments, the $C_1$-$C_8$ alkyl is an unbranched $C_1$-$C_8$ alkyl. In some embodiments, the $C_1$-$C_8$ alkyl is an unsubstituted $C_1$-$C_8$ alkyl. In some embodiments, the $C_1$-$C_8$ alkyl is a branched, unsubstituted $C_1$-$C_8$ alkyl. In some embodiments, the $C_1$-$C_8$ alkyl is a branched, substituted $C_1$-$C_8$ alkyl. In some embodiments, the $C_1$-$C_8$ alkyl is an unbranched, unsubstituted $C_1$-$C_8$ alkyl.

In some embodiments, $R^7$ is substituted with one, two or three substituents wherein at least one substituent is $NR^9R^{10}$. In some embodiments, $R^7$ is substituted with one, two or three substituents wherein at least one substituent is $NH_2$.

In some embodiments, $R^7$ is substituted with one, two or three substituents wherein at least one substituent is $C_3$-$C_8$ (e.g., $C_3$, $C_4$, $C_5$, $C_6$, $C_7$, or $C_8$) carbocyclyl. In some embodiments, the $C_3$-$C_8$ carbocyclyl is saturated. In some embodiments, the $C_3$-$C_8$ carbocyclyl is partially unsaturated. Exemplary $C_3$-$C_8$ carbocyclic rings include, but are not limited to, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane. In some embodiments, the $C_3$-$C_8$ carbocyclyl is unsubstituted $C_3$-$C_8$ carbocyclyl. In some embodiments, the $C_3$-$C_8$ carbocyclyl is substituted $C_3$-$C_8$ carbocyclyl. In some embodiments, the $C_3$-$C_8$ carbocyclyl is unbranched $C_3$-$C_8$ carbocyclyl. In some embodiments, the $C_3$-$C_8$ carbocyclyl is branched $C_3$-$C_8$ carbocyclyl.

In some embodiments, $R^7$ is substituted with one, two or three substituents wherein at least one substituent is phenyl. In some embodiments, $R^7$ is substituted with one, two or three substituents wherein at least one substituent is phenyl substituted with one, two, or three substituents independently selected from halo, cyano, and $C_1$-$C_6$ alkyl. In some embodiments, $R^7$ is substituted with one, two or three substituents wherein at least one substituent is phenyl substituted with one, two, or three substituents wherein at least one substituent is halo (e.g., fluoro, chloro, iodo, bromo). In some embodiments, $R^7$ is substituted with one, two or three substituents wherein at least one substituent is phenyl substituted with one, two, or three substituents wherein at least one substituent is cyano. In some embodiments, $R^7$ is substituted with at least one halo and at least one oxo. In some embodiments, $R^7$ is substituted with at least one halo and at least one cyano. In some embodiments, $R^7$ is substituted with at least one halo and at least one $N_3$. In some embodiments, $R^7$ is substituted with at least one halo and at least one $OR^8$. In some embodiments, $R^7$ is substituted with at least one halo and at least one $NR^9R^{10}$. In some embodiments, $R^7$ is substituted with at least one halo and at least one $C_3$-$C_8$ carbocyclyl. In some embodiments, $R^7$ is substituted with at least one halo and at least one unsubstituted phenyl. In some embodiments, $R^7$ is substituted with at least one halo and at least one phenyl substituted with one, two, or three substituents independently selected from halo, cyano, and $C_1$-$C_6$ alkyl. In some embodiments, $R^7$ is substituted with at least one oxo and at least one cyano. In some embodiments, $R^7$ is substituted with at least one oxo and at least one $N_3$. In some embodiments, $R^7$ is substituted with at least one oxo and at least one $OR^8$. In some embodiments, $R^7$ is substituted with at least one oxo and at least one $C_1$-$C_8$ alkyl. In some embodiments, $R^7$ is substituted with at least one oxo and at least one $NR^9R^{10}$. In some embodiments, $R^7$ is substituted with at least one oxo and at least one $C_3$-$C_8$ carbocyclyl. In some embodiments, $R^7$ is substituted with at least one oxo and at least one unsubstituted phenyl. In some embodiments, $R^7$ is substituted with at least one oxo and at least one phenyl substituted with one, two, or three substituents independently selected from halo, cyano, and $C_1$-$C_6$ alkyl. In some embodiments, $R^7$ is substituted with at least one cyano and at least one $N_3$. In some embodiments, $R^7$ is substituted with at least one $N_3$ and at least one $OR^8$. In some embodiments, $R^7$ is substituted with at least one cyano and at least one $C_1$-$C_8$ alkyl. In some embodiments, $R^7$ is substituted with at least one cyano and at least one $NR^9R^{10}$. In some embodiments, $R^7$ is substituted with at least one cyano and at least one $C_3$-$C_8$ carbocyclyl. In some embodiments, $R^7$ is substituted with at least one cyano and at least one unsubstituted phenyl. In some embodiments, $R^7$ is substituted with at least one cyano and at least one phenyl substituted with one, two, or three substituents independently selected from halo, cyano, and $C_1$-$C_6$ alkyl. In some embodiments, $R^7$ is substituted with at least one $N_3$ and at least one $OR^8$. In some embodiments, $R^7$ is substituted with at least one $N_3$ and at least one $C_1$-$C_8$ alkyl. In some embodiments, $R^7$ is substituted with at least one $N_3$ and at least one $NR^9R^{10}$. In some embodiments, $R^7$ is substituted with at least one $N_3$ and at least one $C_3$-$C_8$ carbocyclyl. In some embodiments, $R^7$ is substituted with at least one $N_3$ and at least one unsubstituted phenyl. In some embodiments, $R^7$ is substituted with at least one $N_3$ and at least one phenyl substituted with one, two, or three substituents independently selected from halo, cyano, and $C_1$-$C_6$ alkyl. In some embodiments, $R^7$ is substituted with at least one $OR^8$ and at least one $C_1$-$C_8$ alkyl. In some embodiments, $R^7$ is substituted with at least one $OR^8$ and at least one $NR^9R^{10}$. In some embodiments, $R^7$ is substituted with at least one $OR^8$ and at least one $C_3$-$C_8$ carbocyclyl. In some embodiments, $R^7$ is substituted with at least one $OR^8$ and at least one unsubstituted phenyl. In some embodiments, $R^7$ is substituted with at least one $OR^8$ and at least one phenyl substituted with one, two, or three substituents independently selected from halo, cyano, and $C_1$-$C_6$ alkyl. In some embodiments, $R^7$ is substituted with at least one $C_1$-$C_8$ alkyl and at least one $NR^9R^{10}$. In some embodiments, $R^7$ is substituted with at least one $C_1$-$C_8$ alkyl and at least one $C_3$-$C_8$ carbocyclyl. In some embodiments, $R^7$ is substituted with at least one $C_1$-$C_8$ alkyl and at least one unsubstituted phenyl. In some embodiments, $R^7$ is substituted with at least one $C_1$-$C_8$ alkyl and at least one phenyl substituted with one, two, or three substituents independently selected from halo, cyano, and $C_1$-$C_6$ alkyl. In some embodiments, $R^7$ is substituted with at least one $C_3$-$C_8$ carbocyclyl and at least one unsubstituted phenyl. In some embodiments, $R^7$ is substituted with at least one $C_3$-$C_8$ carbocyclyl and at least one phenyl substituted with one, two, or three substituents independently selected from halo, cyano, and $C_1$-$C_6$ alkyl.

Each $R^8$ can be independently H, $C_1$-$C_6$ alkyl, $C_1$-$C_6$ haloalkyl, and $C_3$-$C_6$ cycloalkyl. In some embodiments, at least one $R^8$ is H. In some embodiments, at least one $R^8$ is $C_1$-$C_6$ (e.g., $C_1$, $C_2$, $C_3$, $C_4$, $C_5$, or $C_6$) alkyl, for instance, methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, at least one $R^8$ is $C_1$-$C_3$ alkyl. In some embodiments, at least one $R^8$ is $C_2$-$C_5$ alkyl. In some embodiments, at least one $R^8$ is $C_4$-$C_6$ alkyl. In some embodiments, at least one $R^8$ is a branched $C_1$-$C_6$ alkyl. In some embodiments, $R^8$ is an unbranched $C_1$-$C_6$ alkyl. In some embodiments, at least one $R^1$ is an unsubstituted $C_1$-$C_6$ alkyl. In some embodiments, at least one $R^8$ is a branched, unsubstituted $C_1$-$C_6$ alkyl. In some embodiments, at least one $R^8$ is an unbranched, unsubstituted $C_1$-$C_6$ alkyl.

In some embodiments, at least one $R^8$ is $C_1$-$C_6$ (e.g., $C_1$, $C_2$, $C_3$, $C_4$, $C_5$, or $C_6$) haloalkyl, wherein a $C_1$-$C_6$ alkyl is substituted with at least one halo (e.g., fluoro, iodo, chloro, or bromo). Exemplary $C_1$-$C_6$ haloalkyl include halomethyl, haloethyl, halo-n-propyl, haloisopropyl, halo-n-butyl, halo-isobutyl, halo-s-butyl, halo-t-butyl, halo-n-pentyl, halo-2-pentyl, halo-3-pentyl, halo-2-methyl-2-butyl, halo-3-methyl-2-butyl, halo-3-methyl-1-butyl, halo-2-methyl-1-butyl, halo-1-hexyl, halo-2-hexyl, halo-3-hexyl, halo-2-methyl-2-pentyl, halo-3-methyl-2-pentyl, halo-4-methyl-2-pentyl, halo-3-methyl-3-pentyl, halo-2-methyl-3-pentyl, halo-2,3-dimethyl-2-butyl, or halo-3,3-dimethyl-2-butyl. In some embodiments, the $C_1$-$C_6$ haloalkyl contains at least one (e.g., one, two, three, four, or five) halo. In some embodiments, the $C_1$-$C_6$ haloalkyl contains at least one fluoro. In some embodiments, the $C_1$-$C_6$ haloalkyl contains at least one chloro. In some embodiments, the $C_1$-$C_6$ haloalkyl contains at least one iodo. In some embodiments, the $C_1$-$C_6$ haloalkyl contains at least one bromo. In some embodiments, the $C_1$-$C_6$ haloalkyl contains at least one fluoro and at least one chloro. In some embodiments, the $C_1$-$C_6$ haloalkyl contains at least one fluoro and at least one iodo. In some embodiments, the $C_1$-$C_6$ haloalkyl contains at least one fluoro and at least one bromo. In some embodiments, the $C_1$-$C_6$ haloalkyl contains at least one chloro and at least one iodo. In some embodiments, the $C_1$-$C_6$ haloalkyl contains at least one chloro and at least one bromo. In some embodiments, the $C_1$-$C_6$ haloalkyl contains at least one iodo and at least one bromo. Examples of suitable $C_1$-$C_6$ haloalkyl groups include, but are not limited to, —$CF_3$, —$CHF_2$, —$CFH_2$, —$CH_2CF_3$, fluorochloromethyl, difluorochloromethyl, 1,1,1-trifluoroethyl and pentafluoroethyl.

In some embodiments, at least one $R^8$ is $C_3$-$C_6$ (e.g., $C_3$, $C_4$, $C_5$, or $C_6$) cycloalkyl. In some embodiments, $R^8$ is a $C_3$ cycloalkyl, $C_4$ cycloalkyl, $C_5$ cycloalkyl, or $C_6$ cycloalkyl. In some embodiments, the $C_3$-$C_{10}$ cycloalkyl is saturated. In some embodiments, the $C_3$-$C_6$ cycloalkyl is partially saturated. In some embodiments, the $C_3$-$C_6$ cycloalkyl includes partially unsaturated ring systems containing at least (e.g., one, two) double bonds. In some embodiments, $R^8$ is cyclopropyl, cyclobutyl, cyclopentyl, or cyclohexyl.

Each $R^9$ can be independently H, $C_1$-$C_6$ alkyl, $C_1$-$C_6$ haloalkyl, and $C_3$-$C_6$ cycloalkyl. In some embodiments, at least one $R^9$ is H. In some embodiments, at least one $R^9$ is $C_1$-$C_6$ (e.g., $C_1$, $C_2$, $C_3$, $C_4$, $C_5$, or $C_6$) alkyl, for instance, methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, at least one $R^9$ is $C_1$-$C_3$ alkyl. In some embodiments, at least one $R^9$ is $C_2$-$C_5$ alkyl. In some embodiments, at least one $R^9$ is $C_4$-$C_6$ alkyl. In some embodiments, at least one $R^9$ is a branched $C_1$-$C_6$ alkyl. In some embodiments, $R^9$ is an unbranched $C_1$-$C_6$ alkyl. In some embodiments, at least one $R^9$ is an unsubstituted $C_1$-$C_6$ alkyl. In some embodiments, at least one $R^9$ is a branched, unsubstituted $C_1$-$C_6$ alkyl. In some embodiments, at least one $R^9$ is an unbranched, unsubstituted $C_1$-$C_6$ alkyl.

In some embodiments, at least one $R^9$ is $C_1$-$C_6$ (e.g., $C_1$, $C_2$, $C_3$, $C_4$, $C_5$, or $C_6$) haloalkyl, wherein a $C_1$-$C_6$ alkyl is substituted with at least one halo (e.g., fluoro, iodo, chloro, or bromo). Exemplary $C_1$-$C_6$ haloalkyl include halomethyl, haloethyl, halo-n-propyl, haloisopropyl, halo-n-butyl, halo-isobutyl, halo-s-butyl, halo-t-butyl, halo-n-pentyl, halo-2-pentyl, halo-3-pentyl, halo-2-methyl-2-butyl, halo-3-methyl-2-butyl, halo-3-methyl-1-butyl, halo-2-methyl-1-butyl, halo-1-hexyl, halo-2-hexyl, halo-3-hexyl, halo-2-methyl-2-pentyl, halo-3-methyl-2-pentyl, halo-4-methyl-2-pentyl, halo-3-methyl-3-pentyl, halo-2-methyl-3-pentyl, halo-2,3-dimethyl-2-butyl, or halo-3,3-dimethyl-2-butyl. In some embodiments, the $C_1$-$C_6$ haloalkyl contains at least one (e.g., one, two, three, four, or five) halo. In some embodiments, the $C_1$-$C_6$ haloalkyl contains at least one fluoro. In some embodiments, the $C_1$-$C_6$ haloalkyl contains at least one chloro. In some embodiments, the $C_1$-$C_6$ haloalkyl contains at least one iodo. In some embodiments, the $C_1$-$C_6$ haloalkyl contains at least one bromo. In some embodiments, the $C_1$-$C_6$ haloalkyl contains at least one fluoro and at least one chloro. In some embodiments, the $C_1$-$C_6$ haloalkyl contains at least one fluoro and at least one iodo. In some embodiments, the $C_1$-$C_6$ haloalkyl contains at least one fluoro and at least one bromo. In some embodiments, the $C_1$-$C_6$ haloalkyl contains at least one chloro and at least one iodo. In some embodiments, the $C_1$-$C_6$ haloalkyl contains at least one chloro and at least one bromo. In some embodiments, the $C_1$-$C_6$ haloalkyl contains at least one iodo and at least one bromo. Examples of suitable $C_1$-$C_6$ haloalkyl groups include, but are not limited to, —$CF_3$, —$CHF_2$, —$CFH_2$, —$CH_2CF_3$, fluorochloromethyl, difluorochloromethyl, 1,1,1-trifluoroethyl and pentafluoroethyl.

In some embodiments, at least one $R^9$ is $C_3$-$C_6$ (e.g., $C_3$, $C_4$, $C_5$, or $C_6$) cycloalkyl. In some embodiments, $R^9$ is a $C_3$ cycloalkyl, $C_4$ cycloalkyl, $C_5$ cycloalkyl, or $C_6$ cycloalkyl. In some embodiments, the $C_3$-$C_{10}$ cycloalkyl is saturated. In some embodiments, the $C_3$-$C_6$ cycloalkyl is partially saturated. In some embodiments, the $C_3$-$C_6$ cycloalkyl includes partially unsaturated ring systems containing at least (e.g., one, two) double bonds. In some embodiments, $R^9$ is cyclopropyl, cyclobutyl, cyclopentyl, or cyclohexyl.

Each $R^{10}$ can be independently H, $C_1$-$C_6$ alkyl, $C_1$-$C_6$ haloalkyl, and $C_3$-$C_6$ cycloalkyl. In some embodiments, at least one $R^{10}$ is H. In some embodiments, at least one $R^{10}$ is $C_1$-$C_6$ (e.g., $C_1$, $C_2$, $C_3$, $C_4$, $C_5$, or $C_6$) alkyl, for instance, methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, at least one $R^{10}$ is $C_1$-$C_3$ alkyl. In some embodiments, at least one $R^{10}$ is $C_2$-$C_5$ alkyl. In some embodiments, at least one $R^{10}$ is $C_4$-$C_6$ alkyl. In some embodiments, at least one $R^{10}$ is a branched $C_1$-$C_6$ alkyl. In some embodiments, $R^{10}$ is an unbranched $C_1$-$C_6$ alkyl. In some embodiments, at least one $R^{10}$ is an unsubstituted $C_1$-$C_6$ alkyl. In some embodiments, at least one $R^{10}$ is a branched, unsubstituted $C_1$-$C_6$ alkyl. In some embodiments, at least one $R^{10}$ is an unbranched, unsubstituted $C_1$-$C_6$ alkyl.

In some embodiments, at least one $R^{10}$ is $C_1$-$C_6$ (e.g., $C_1$, $C_2$, $C_3$, $C_4$, $C_5$, or $C_6$) haloalkyl, wherein a $C_1$-$C_6$ alkyl is substituted with at least one halo (e.g., fluoro, iodo, chloro, or bromo). Exemplary $C_1$-$C_6$ haloalkyl include halomethyl, haloethyl, halo-n-propyl, haloisopropyl, halo-n-butyl, halo-isobutyl, halo-s-butyl, halo-t-butyl, halo-n-pentyl, halo-2-pentyl, halo-3-pentyl, halo-2-methyl-2-butyl, halo-3-methyl-2-butyl, halo-3-methyl-1-butyl, halo-2-methyl-1-butyl, halo-1-hexyl, halo-2-hexyl, halo-3-hexyl, halo-2-methyl-2-pentyl, halo-3-methyl-2-pentyl, halo-4-methyl-2-pentyl, halo-3-methyl-3-pentyl, halo-2-methyl-3-pentyl, halo-2,3-dimethyl-2-butyl, or halo-3,3-dimethyl-2-butyl. In some embodiments, the $C_1$-$C_6$ haloalkyl contains at least one (e.g., one, two, three, four, or five) halo. In some embodiments, the $C_1$-$C_6$ haloalkyl contains at least one fluoro. In some embodiments, the $C_1$-$C_6$ haloalkyl contains at least one chloro. In some embodiments, the $C_1$-$C_6$ haloalkyl contains at least one iodo. In some embodiments, the $C_1$-$C_6$ haloalkyl contains at least one bromo. In some embodiments, the $C_1$-$C_6$ haloalkyl contains at least one fluoro and at least one chloro. In some embodiments, the $C_1$-$C_6$ haloalkyl contains at least one fluoro and at least one iodo. In some embodiments, the $C_1$-$C_6$ haloalkyl contains at least one fluoro and at least one bromo. In some embodiments, the $C_1$-$C_6$ haloalkyl contains at least one chloro and at least one iodo. In some embodiments, the $C_1$-$C_6$ haloalkyl contains at least one chloro and at least one bromo. In some embodiments, the $C_1$-$C_6$ haloalkyl contains at least one iodo and at least one bromo. Examples of suitable $C_1$-$C_6$ haloalkyl groups include, but are not limited to, $-CF_3$, $-CHF_2$, $-CFH_2$, $-CH_2CF_3$, fluorochloromethyl, difluorochloromethyl, 1,1,1-trifluoroethyl and pentafluoroethyl.

In some embodiments, at least one $R^{10}$ is $C_3$-$C_6$ (e.g., $C_3$, $C_4$, $C_5$, or $C_6$) cycloalkyl. In some embodiments, $R^{10}$ is a $C_3$ cycloalkyl, $C_4$ cycloalkyl, $C_5$ cycloalkyl, or $C_6$ cycloalkyl. In some embodiments, the $C_3$-$C_{10}$ cycloalkyl is saturated. In some embodiments, the $C_3$-$C_6$ cycloalkyl is partially saturated. In some embodiments, the $C_3$-$C_6$ cycloalkyl includes partially unsaturated ring systems containing at least (e.g., one, two) double bonds. In some embodiments, $R^{10}$ is cyclopropyl, cyclobutyl, cyclopentyl, or cyclohexyl.

Base can be

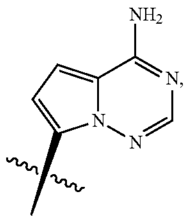

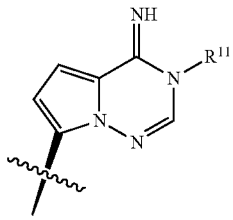

,

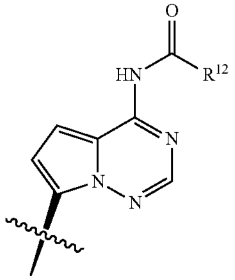

, or

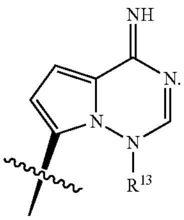

In some embodiments, Base is

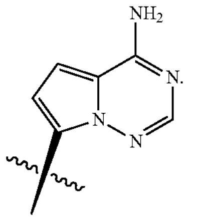

In some embodiments, Base is

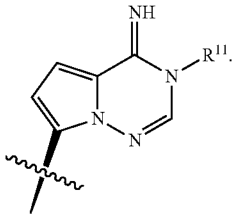

In some embodiments, Base is

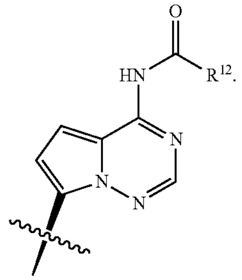

In some embodiments, Base is

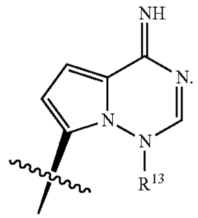

Base is

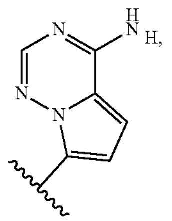

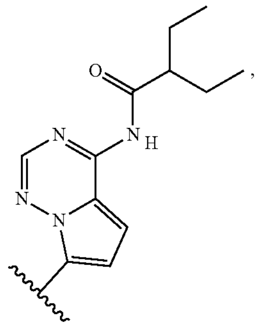

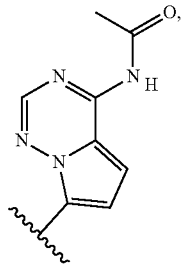

-continued

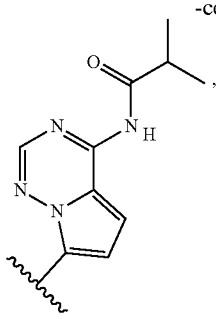

,

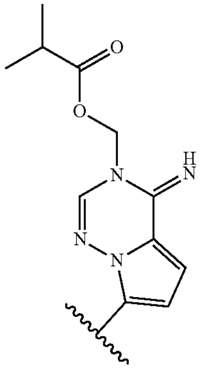

, or

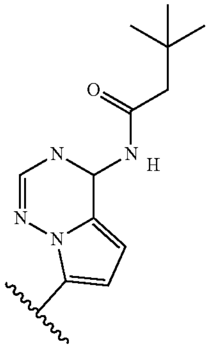

.

$R^{11}$ can be $C_1$-$C_6$ (e.g., $C_1$, $C_2$, $C_3$, $C_4$, $C_5$, or $C_6$) alkyl substituted with —OP(O)$(OH)_2$ or —OC(O)$R^{12}$. In some embodiments, the $C_1$-$C_6$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_6$ alkyl is $C_1$-$C_3$ alkyl. In some embodiments, the $C_1$-$C_6$ alkyl is $C_2$-$C_5$ alkyl. In some embodiments, the $C_1$-$C_6$ alkyl is $C_4$-$C_6$ alkyl. In some embodiments, the $C_1$-$C_6$ alkyl is a branched $C_1$-$C_6$ alkyl. In some embodiments, the $C_1$-$C_6$ alkyl is an unbranched $C_1$-$C_6$ alkyl. In some embodiments, the $C_1$-$C_6$ alkyl is a substituted $C_1$-$C_6$ alkyl. In some embodiments, the $C_1$-$C_6$ alkyl is a branched, substituted $C_1$-$C_6$ alkyl. In some embodiments, the $C_1$-$C_6$ alkyl is an unbranched, substituted $C_1$-$C_6$ alkyl. In some embodiments, the t$C_1$-$C_6$ alkyl is substituted with —OP(O)$(OH)_2$. In some embodiments, the $C_1$-$C_6$ alkyl is substituted with —OC(O)$R^{12}$.

$R^{12}$ can be $C_1$-$C_8$ alkyl or $C_1$-$C_8$ alkoxy. In some embodiments, $R^{12}$ is $C_1$-$C_8$ (e.g., $C_1$, $C_2$, $C_3$, $C_4$, $C_5$, $C_6$, $C_7$, or $C_8$) alkyl. In some embodiments, the $C_1$-$C_8$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_8$ alkyl is $C_1$-$C_6$ alkyl. In some embodiments, the $C_1$-$C_8$ alkyl is $C_1$-$C_3$ alkyl. In some embodiments, the $C_1$-$C_8$ alkyl is $C_2$-$C_5$ alkyl. In some embodiments, the $C_1$-$C_8$ alkyl is $C_4$-$C_8$ alkyl. In some embodiments, the $C_1$-$C_8$ alkyl is a branched $C_1$-$C_8$ alkyl. In some embodiments, the $C_1$-$C_8$ alkyl is an unbranched $C_1$-$C_8$ alkyl. In some embodiments, the $C_1$-$C_8$ alkyl is an unsubstituted $C_1$-$C_8$ alkyl. In some embodiments, the $C_1$-$C_8$ alkyl is a branched, unsubstituted $C_1$-$C_8$ alkyl. In some embodiments, the $C_1$-$C_8$ alkyl is an unbranched, unsubstituted $C_1$-$C_8$ alkyl.

In some embodiments, $R^{12}$ is $C_1$-$C_8$ (e.g., $C_1$, $C_2$, $C_3$, $C_4$, $C_5$, $C_6$, $C_7$, or $C_8$) alkoxy. The alkyl portion of an alkoxy group can have 1, 2, 3, 4, 5, or 6 carbon atoms (i.e., $C_1$-$C_6$ alkoxy) or 1, 2, or 3 carbon atoms (i.e., $C_1$-$C_3$ alkoxy). Examples of suitable alkoxy groups include, but are not limited to, methoxy (—O—$CH_3$ or —OMe), ethoxy (—$OCH_2CH_3$ or -OEt), isopropoxy (—O—$CH(CH_3)_2$), t-butoxy (—O—$C(CH_3)_3$ or -OtBu) and the like. Other examples of suitable alkoxy groups include, but are not limited to, sec-butoxy, tert-butoxy, pentoxy, and hexoxy.

$R^{13}$ can be $C_1$-$C_6$ (e.g., $C_1$, $C_2$, $C_3$, $C_4$, $C_5$, or $C_6$) alkyl substituted with —OP(O)$(OH)_2$ or —OC(O)$R^{12}$. In some embodiments, the $C_1$-$C_6$ alkyl is methyl, ethyl, -n-propyl, isopropyl, -n-butyl, isobutyl, -s-butyl, -t-butyl, -n-pentyl, -2-pentyl, -3-pentyl, -2-methyl-2-butyl, -3-methyl-2-butyl, -3-methyl-1-butyl, -2-methyl-1-butyl, -1-hexyl, -2-hexyl, -3-hexyl, -2-methyl-2-pentyl, -3-methyl-2-pentyl, -4-methyl-2-pentyl, -3-methyl-3-pentyl, -2-methyl-3-pentyl, -2,3-dimethyl-2-butyl, or -3,3-dimethyl-2-butyl. In some embodiments, the $C_1$-$C_6$ alkyl is $C_1$-$C_3$ alkyl. In some embodiments, the $C_1$-$C_6$ alkyl is $C_2$-$C_5$ alkyl. In some embodiments, the $C_1$-$C_6$ alkyl is $C_4$-$C_6$ alkyl. In some embodiments, the $C_1$-$C_6$ alkyl is a branched $C_1$-$C_6$ alkyl. In some embodiments, the $C_1$-$C_6$ alkyl is an unbranched $C_1$-$C_6$ alkyl. In some embodiments, the $C_1$-$C_6$ alkyl is a substituted $C_1$-$C_6$ alkyl. In some embodiments, the $C_1$-$C_6$ alkyl is a branched, substituted $C_1$-$C_6$ alkyl. In some embodiments, the $C_1$-$C_6$ alkyl is an unbranched, substituted $C_1$-$C_6$ alkyl. In some embodiments, the t$C_1$-$C_6$ alkyl is substituted with —OP(O)$(OH)_2$. In some embodiments, the $C_1$-$C_6$ alkyl is substituted with —OC(O)$R^{12}$.

In some embodiments, $R^1$ is OH or OC(O)$R^4$, $R^2$ is OH or OC(O)$R^5$, $R^3$ is H or C(O)$R^7$, $R^4$ is $C_1$-$C_8$ alkyl, $R^5$ is $C_1$-$C_8$ alkyl, $R^7$ is $C_1$-$C_8$ alkyl, $C_3$-$C_8$ carbocyclyl, $C_6$-$C_{10}$ aryl, 4 to 6 membered heterocyclyl containing one O, wherein $R^7$ is optionally substituted with one or two substituents independently selected from the group consisting of halo, oxo, $C_1$-$C_8$ alkyl, $NH_2$, $C_3$-$C_8$ carbocyclyl, and phenyl; Base is

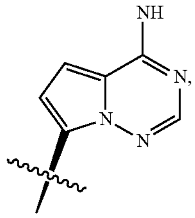

-continued

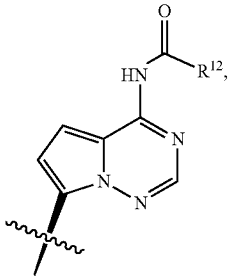

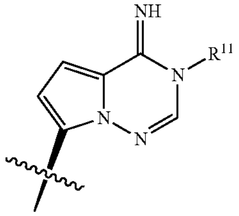

or

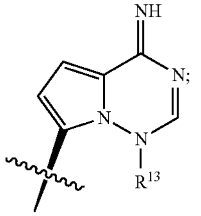

wherein $R^{11}$ is $C_1$-$C_6$ alkyl substituted with $OC(O)R^{12}$; $R^{12}$ is $C_1$-$C_8$ alkyl; and $R^{13}$ is $C_1$-$C_6$ alkyl substituted with $—OP(O)(OH)_2$ or $—OC(O)R^{12}$.

In some embodiments, $R^1$ is OH and $R^2$ is OH. In some embodiments, $R^1$ is OH and $R^2$ is $OC(O)R^5$. In some embodiments, $R^1$ is OH, $R^2$ is $OC(O)R^5$, and $R^5$ is $C_1$-$C_8$ alkyl. In some embodiments, $R^2$ is OH and $R^1$ is $OC(O)R^4$. In some embodiments, $R^2$ is OH, $R^1$ is $OC(O)R^4$, and $R^4$ is $C_1$-$C_8$ alkyl. In some embodiments, $R^1$ is $OC(O)R^4$ and $R^2$ is $OC(O)R^5$. In some embodiments, $R^1$ is $OC(O)R^4$, $R^2$ is $OC(O)R^5$, and $R^4$ is $C_1$-$C_8$ alkyl. In some embodiments, $R^1$ is $OC(O)R^4$, $R^2$ is $OC(O)R^5$, and $R^5$ is $C_1$-$C_8$ alkyl. In some embodiments, $R^1$ is $OC(O)R^4$, $R^2$ is $OC(O)R^5$, $R^4$ is $C_1$-$C_8$ alkyl, and $R^5$ is $C_1$-$C_8$ alkyl. In some embodiments, $R^1$ is OH, $R^2$ is $OC(O)R^5$, and $R^5$ is $C_1$-$C_3$ alkyl (e.g., methyl, isopropyl). In some embodiments, $R^2$ is OH, $R^1$ is $OC(O)R^4$, and $R^4$ is $C_1$-$C_3$ alky (e.g., methyl, isopropyl). In some embodiments, $R^1$ is $OC(O)R^4$, $R^2$ is $OC(O)R^5$, and $R^4$ is $C_1$-$C_3$ alkyl (e.g., methyl, isopropyl). In some embodiments, $R^1$ is $OC(O)R^4$, $R^2$ is $OC(O)R^5$, and $R^5$ is $C_1$-$C_3$ alkyl (e.g., methyl, isopropyl). In some embodiments, $R^1$ is $OC(O)R^4$, $R^2$ is $OC(O)R^5$, $R^4$ is $C_1$-$C_3$ alkyl (e.g., methyl, isopropyl), and $R^5$ is $C_1$-$C_3$ alkyl (e.g., methyl, isopropyl).

In some embodiments, $R^1$ is OH and $R^3$ is H. In some embodiments, $R^1$ is OH and $R^3$ is $C(O)R^7$, wherein $R^7$ is $C_1$-$C_8$ alkyl. In some embodiments, $R^1$ is OH and $R^3$ is $C(O)R^7$, wherein $R^7$ is $C_1$-$C_6$ alkyl. In some embodiments, $R^1$ is OH and $R^3$ is $C(O)R^7$, wherein $R^7$ is $C_1$-$C_3$ alkyl. In some embodiments, $R^1$ is OH and $R^3$ is $C(O)R^7$, wherein $R^7$ is $C_1$-$C_8$ alkyl substituted with one $NH_2$. In some embodiments, $R^1$ is OH and $R^3$ is $C(O)R^7$, wherein $R^7$ is $C_1$-$C_6$ alkyl substituted with one $NH_2$. In some embodiments, $R^1$ is OH and $R^3$ is $C(O)R^7$, wherein $R^7$ is $C_4$-$C_6$ alkyl substituted with one $NH_2$. In some embodiments, $R^1$ is OH and $R^3$ is $C(O)R^7$, wherein $R^7$ is $C_1$-$C_8$ alkyl substituted with one halo. In some embodiments, $R^1$ is OH and $R^3$ is $C(O)R^7$, wherein $R^7$ is $C_1$-$C_6$ alkyl substituted with one fluoro. In some embodiments, $R^1$ is $OC(O)R^4$ and $R^3$ is $C(O)R^7$, wherein $R^7$ is $C_4$-$C_6$ alkyl substituted with one fluoro. In some embodiments, $R^1$ is $OC(O)R^4$ and $R^3$ is $C(O)R^7$, wherein $R^7$ is $C_1$-$C_8$ alkyl. In some embodiments, $R^1$ is $OC(O)R^4$ and $R^3$ is $C(O)R^7$, wherein $R^7$ is $C_1$-$C_6$ alkyl. In some embodiments, $R^1$ is $OC(O)R^4$ and $R^3$ is $C(O)R^7$, wherein $R^7$ is $C_1$-$C_3$ alkyl. In some embodiments, $R^1$ is $OC(O)R^4$ and $R^3$ is $C(O)R^7$, wherein $R^7$ is $C_1$-$C_8$ alkyl substituted with $C_3$-$C_8$ carbocycle. In some embodiments, $R^1$ is $OC(O)R^4$ and $R^3$ is $C(O)R^7$, wherein $R^7$ is $C_1$-$C_6$ alkyl substituted with $C_3$-$C_8$ carbocycle. In some embodiments, $R^1$ is $OC(O)R^4$ and $R^3$ is $C(O)R^7$, wherein $R^7$ is $C_1$-$C_6$ alkyl substituted with spiro[3,3]heptyl. In some embodiments, $R^1$ is $OC(O)R^4$ and $R^3$ is $C(O)R^7$, wherein $R^7$ is $C_1$-$C_3$ alkyl substituted with $C_3$-$C_8$ carbocycle. In some embodiments, $R^1$ is $OC(O)R^4$ and $R^3$ is $C(O)R^7$, wherein $R^7$ is $C_1$-$C_3$ alkyl substituted with cyclobutyl. In some embodiments, $R^1$ is $OC(O)R^4$ and $R^3$ is $C(O)R^7$, wherein $R^7$ is $C_1$-$C_3$ alkyl substituted with cyclobutyl substituted with methyl. In some embodiments, $R^1$ is $OC(O)R^4$ and $R^3$ is $C(O)R^7$, wherein $R^7$ is $C_1$-$C_8$ alkyl substituted with phenyl. In some embodiments, $R^1$ is $OC(O)R^4$, $R^3$ is $C(O)R^7$, $R^4$ is $C_1$-$C_8$ alkyl, and $R^7$ is $C_1$-$C_8$ alkyl. In some embodiments, $R^1$ is $OC(O)R^4$, $R^3$ is $C(O)R^7$, $R^4$ is $C_1$-$C_6$ alkyl, and $R^7$ is $C_1$-$C_6$ alkyl. In some embodiments, $R^1$ is $OC(O)R^4$, $R^3$ is $C(O)R^7$, $R^4$ is $C_1$-$C_3$ alkyl, and $R^7$ is $C_1$-$C_3$ alkyl. In some embodiments, $R^1$ is OH and $R^3$ is $C(O)R^7$, wherein $R^7$ is $C_6$-$C_{10}$ aryl. In some embodiments, $R^1$ is OH and $R^3$ is $C(O)R^7$, wherein $R^7$ is phenyl. In some embodiments, $R^1$ is OH and $R^3$ is $C(O)R^7$, wherein $R^7$ is $C_6$-$C_{10}$ aryl substituted with one $C_1$-$C_8$ alkyl. In some embodiments, $R^1$ is OH and $R^3$ is $C(O)R^7$, wherein $R^7$ is phenyl substituted with methyl. In some embodiments, $R^1$ is OH and $R^3$ is $C(O)R^7$, wherein $R^7$ is $C_3$-$C_8$ carbocyclyl. In some embodiments, $R^1$ is OH and $R^3$ is $C(O)R^7$, wherein $R^7$ is cyclohexyl. In some embodiments, $R^1$ is OH and $R^3$ is $C(O)R^7$, wherein $R^7$ is cycloheptyl. In some embodiments, $R^1$ is OH and $R^3$ is $C(O)R^7$, wherein $R^7$ is cyclobutyl. In some embodiments, $R^1$ is OH and $R^3$ is $C(O)R^7$, wherein $R^7$ is cyclobutyl substituted with one or two $C_1$-$C_8$ alkyl. In some embodiments, $R^1$ is OH and $R^3$ is $C(O)R^7$, wherein $R^7$ is cyclobutyl substituted with two $C_1$-$C_8$ alkyl. In some embodiments, $R^1$ is OH and $R^3$ is $C(O)R^7$, wherein $R^7$ is cyclobutyl substituted with two $C_1$-$C_6$ alkyl. In some embodiments, $R^1$ is OH and $R^3$ is $C(O)R^7$, wherein $R^7$ is cyclobutyl substituted with two $C_1$-$C_3$ alkyl. In some embodiments, $R^1$ is OH and $R^3$ is $C(O)R^7$, wherein $R^7$ is cyclobutyl substituted with two methyl. In some embodiments, $R^1$ is OH and $R^3$ is $C(O)R^7$, wherein $R^7$ is cyclopropyl. In some embodiments, $R^1$ is OH and $R^3$ is $C(O)R^7$, wherein $R^7$ is 4- to 6-membered heterocyclyl. In some embodiments, $R^1$ is OH and $R^3$ is $C(O)R^7$, wherein $R^7$ is 4- to 6-membered heterocyclyl containing one O. In some embodiments, $R^1$ is OH and $R^3$ is $C(O)R^7$, wherein $R^7$ is 4- to 6-membered heterocyclyl containing one O, wherein $R^7$ is substituted with oxo.

In some embodiments, $R^2$ is OH and $R^3$ is H. In some embodiments, $R^2$ is OH and $R^3$ is $C(O)R^7$, wherein $R^7$ is $C_1$-$C_8$ alkyl. In some embodiments, $R^2$ is OH and $R^3$ is $C(O)R^7$, wherein $R^7$ is $C_1$-$C_6$ alkyl. In some embodiments, $R^2$ is OH and $R^3$ is $C(O)R^7$, wherein $R^7$ is $C_1$-$C_3$ alkyl. In some embodiments, $R^2$ is OH and $R^3$ is $C(O)R^7$, wherein $R^7$ is $C_1$-$C_8$ alkyl substituted with one $NH_2$. In some embodiments, $R^2$ is OH and $R^3$ is $C(O)R^7$, wherein $R^7$ is $C_1$-$C_6$ alkyl substituted with one $NH_2$. In some embodiments, $R^2$ is OH and $R^3$ is $C(O)R^7$, wherein $R^7$ is $C_4$-$C_6$ alkyl substituted with one $NH_2$. In some embodiments, $R^2$ is OH and $R^3$ is $C(O)R^7$, wherein $R^7$ is $C_1$-$C_8$ alkyl substituted with one halo. In some embodiments, $R^2$ is OH and $R^3$ is $C(O)R^7$, wherein $R^7$ is $C_1$-$C_6$ alkyl substituted with one fluoro. In some embodiments, $R^2$ is $OC(O)R^4$ and $R^3$ is $C(O)R^7$, wherein $R^7$ is $C_4$-$C_6$ alkyl substituted with one fluoro. In some embodiments, $R^2$ is $OC(O)R^4$ and $R^3$ is $C(O)R^7$, wherein $R^7$ is $C_1$-$C_8$ alkyl. In some embodiments, $R^2$ is $OC(O)R^4$ and $R^3$ is $C(O)R^7$, wherein $R^7$ is $C_1$-$C_6$ alkyl. In some embodiments, $R^2$ is $OC(O)R^4$ and $R^3$ is $C(O)R^7$, wherein $R^7$ is $C_1$-$C_3$ alkyl. In some embodiments, $R^2$ is $OC(O)R^4$ and $R^3$ is $C(O)R^7$, wherein $R^7$ is $C_1$-$C_8$ alkyl substituted with $C_3$-$C_8$ carbocycle. In some embodiments, $R^2$ is $OC(O)R^4$ and $R^3$ is $C(O)R^7$, wherein $R^7$ is $C_1$-$C_6$ alkyl substituted with $C_3$-$C_8$ carbocycle. In some embodiments, $R^2$ is $OC(O)R^4$ and $R^3$ is $C(O)R^7$, wherein $R^7$ is $C_1$-$C_6$ alkyl substituted with spiro[3,3]heptyl. In some embodiments, $R^2$ is $OC(O)R^4$ and $R^3$ is $C(O)R^7$, wherein $R^7$ is $C_1$-$C_3$ alkyl substituted with $C_3$-$C_8$ carbocycle. In some embodiments, $R^2$ is $OC(O)R^4$ and $R^3$ is $C(O)R^7$, wherein $R^7$ is $C_1$-$C_3$ alkyl substituted with cyclobutyl. In some embodiments, $R^2$ is $OC(O)R^4$ and $R^3$ is $C(O)R^7$, wherein $R^7$ is $C_1$-$C_3$ alkyl substituted with cyclobutyl substituted with methyl. In some embodiments, $R^2$ is $OC(O)R^4$ and $R^3$ is $C(O)R^7$, wherein $R^7$ is $C_1$-$C_8$ alkyl substituted with phenyl. In some embodiments, $R^2$ is $OC(O)R^4$, $R^3$ is $C(O)R^7$, $R^4$ is $C_1$-$C_8$ alkyl, and $R^7$ is $C_1$-$C_8$ alkyl. In some embodiments, $R^2$ is $OC(O)R^4$, $R^3$ is $C(O)R^7$, $R^4$ is $C_1$-$C_6$ alkyl, and $R^7$ is $C_1$-$C_6$ alkyl. In some embodiments, $R^2$ is $OC(O)R^4$, $R^3$ is $C(O)R^7$, $R^4$ is $C_1$-$C_3$ alkyl, and $R^7$ is $C_1$-$C_3$ alkyl. In some embodiments, $R^2$ is OH and $R^3$ is $C(O)R^7$, wherein $R^7$ is $C_6$-$C_{10}$ aryl. In some embodiments, $R^2$ is OH and $R^3$ is $C(O)R^7$, wherein $R^7$ is phenyl. In some embodiments, $R^2$ is OH and $R^3$ is $C(O)R^7$, wherein $R^7$ is $C_6$-$C_{10}$ aryl substituted with one $C_1$-$C_8$ alkyl. In some embodiments, $R^2$ is OH and $R^3$ is $C(O)R^7$, wherein $R^7$ is phenyl substituted with methyl. In some embodiments, $R^2$ is OH and $R^3$ is $C(O)R^7$, wherein $R^7$ is $C_3$-$C_8$ carbocyclyl. In some embodiments, $R^2$ is OH and $R^3$ is $C(O)R^7$, wherein $R^7$ is cyclohexyl. In some embodiments, $R^2$ is OH and $R^3$ is $C(O)R^7$, wherein $R^7$ is cycloheptyl. In some embodiments, $R^2$ is OH and $R^3$ is $C(O)R^7$, wherein $R^7$ is cyclobutyl. In some embodiments, $R^2$ is OH and $R^3$ is $C(O)R^7$, wherein $R^7$ is cyclobutyl substituted with one or two $C_1$-$C_8$ alkyl. In some embodiments, $R^2$ is OH and $R^3$ is $C(O)R^7$, wherein $R^7$ is cyclobutyl substituted with two $C_1$-$C_8$ alkyl. In some embodiments, $R^2$ is OH and $R^3$ is $C(O)R^7$, wherein $R^7$ is cyclobutyl substituted with two $C_1$-$C_6$ alkyl. In some embodiments, $R^2$ is OH and $R^3$ is $C(O)R^7$, wherein $R^7$ is cyclobutyl substituted with two $C_1$-$C_3$ alkyl. In some embodiments, $R^2$ is OH and $R^3$ is $C(O)R^7$, wherein $R^7$ is cyclobutyl substituted with two methyl. In some embodiments, $R^2$ is OH and $R^3$ is $C(O)R^7$, wherein $R^7$ is cyclopropyl. In some embodiments, $R^2$ is OH and $R^3$ is $C(O)R^7$, wherein $R^7$ is 4- to 6-membered heterocyclyl. In some embodiments, $R^2$ is OH and $R^3$ is $C(O)R^7$, wherein $R^7$ is 4- to 6-membered heterocyclyl containing one O. In some embodiments, $R^1$ is OH and $R^3$ is $C(O)R^7$, wherein $R^7$ is 4- to 6-membered heterocyclyl containing one O, wherein $R^7$ is substituted with oxo.

In some embodiments, $R^1$ is OH and Base is

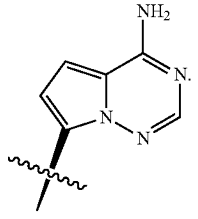

In some embodiments, $R^1$ is $OC(O)R^4$ and Base

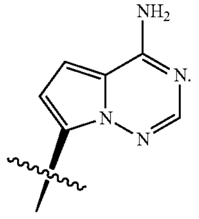

In some embodiments, $R^1$ is $OC(O)R^4$, $R^4$ is $C_1$-$C_8$ alkyl, and Base is

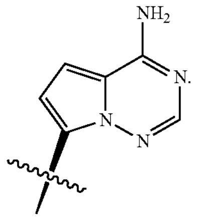

In some embodiments, $R^1$ is $OC(O)R^4$, $R^4$ is $C_1$-$C_6$ alkyl, and Base is

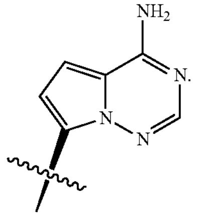

In some embodiments, $R^1$ is $OC(O)R^4$, $R^4$ is $C_1$-$C_3$ alkyl, and Base is

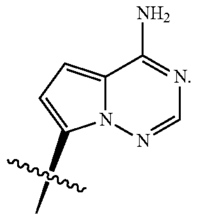

In some embodiments, $R^1$ is $OC(O)R^4$, $R^4$ is isopropyl or methyl, and Base is

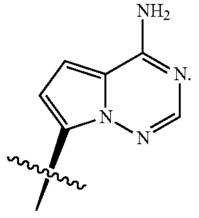

some embodiments, $R^1$ is OH and Base is

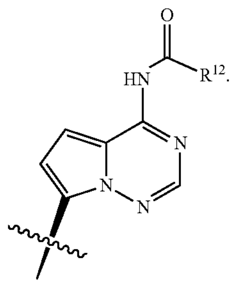

In some embodiments, $R^1$ is $OC(O)R^4$ and Base is

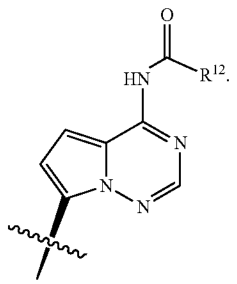

In some embodiments, $R^1$ is $OC(O)R^4$, $R^4$ is $C_1$-$C_8$ alkyl, and Base is

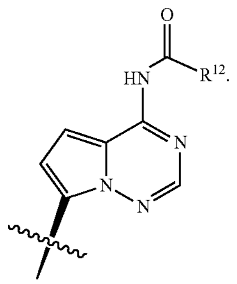

In some embodiments, $R^1$ is $OC(O)R^4$, $R^4$ is $C_1$-$C_6$ alkyl, and Base is

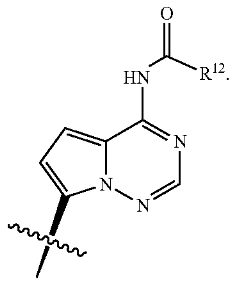

In some embodiments, $R^1$ is $OC(O)R^4$, $R^4$ is $C_1$-$C_3$ alkyl, and Base is

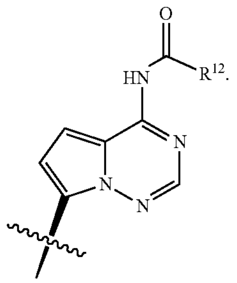

In some embodiments, $R^1$ is OH and Base is

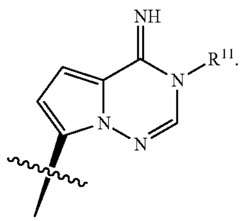

In some embodiments, $R^1$ is OH and Base is

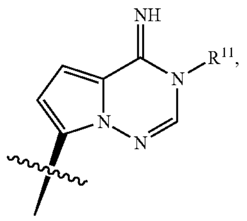

wherein $R^{11}$ is $C_1$-$C_6$ alkyl. In some embodiments, $R^1$ is OH and Base is

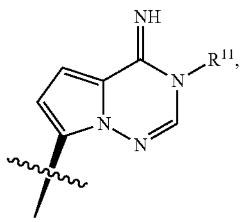

wherein $R^{11}$ is $C_1$-$C_6$ alkyl substituted with $OC(O)R^{12}$. In some embodiments, $R^1$ is OH and Base is

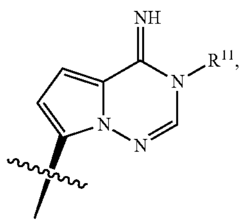

wherein $R^{11}$ is $C_1$-$C_6$ alkyl substituted with $OC(O)R^{12}$ and $R^{12}$ is $C_1$-$C_3$ alkyl. In some embodiments, $R^1$ is OH or $OC(O)R^4$ and $R^4$ is $C_1$-$C_8$ alkyl, and Base is

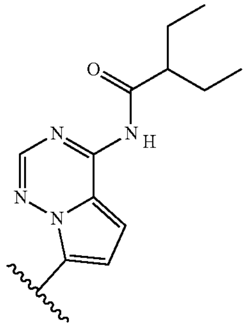
,
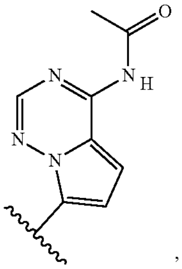
,
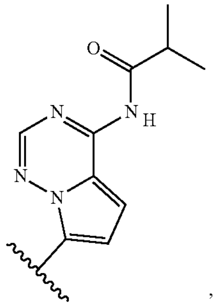
,
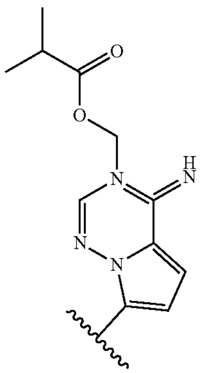
, or
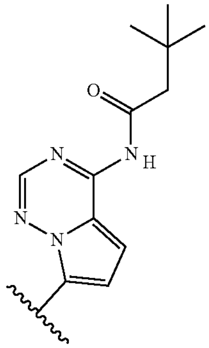
.

In some embodiments, $R^2$ is OH and Base is

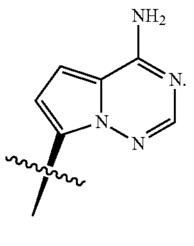

In some embodiments, $R^2$ is $OC(O)R^5$ and Base is

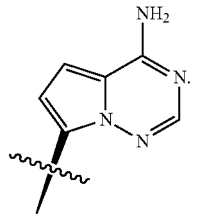

In some embodiments, $R^2$ is $OC(O)R^5$, $R^5$ is $C_1$-$C_8$ alkyl, and Base is

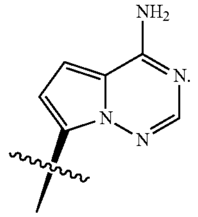

In some embodiments, $R^2$ is $OC(O)R^5$, $R^5$ is $C_1$-$C_6$ alkyl, and Base is

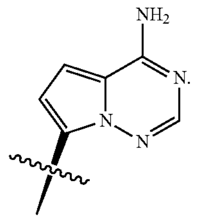

In some embodiments, $R^2$ is $OC(O)R^5$, $R^5$ is $C_1$-$C_3$ alkyl, and Base is

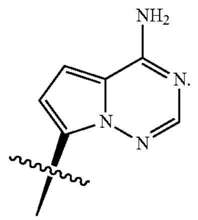

In some embodiments, $R^2$ is $OC(O)R^5$, $R^5$ is isopropyl or methyl, and Base is

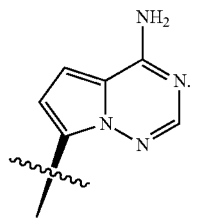

In some embodiments, $R^2$ is OH and Base is

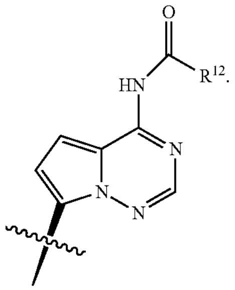

In some embodiments, $R^2$ is $OC(O)R^5$ and Base is

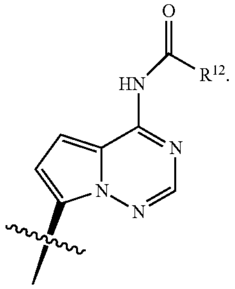

In some embodiments, $R^2$ is $OC(O)R^5$, $R^5$ is $C_1$-$C_8$ alkyl, and Base is

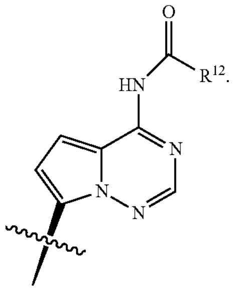

In some embodiments, $R^2$ is $OC(O)R^5$, $R^5$ is $C_1$-$C_6$ alkyl, and Base is

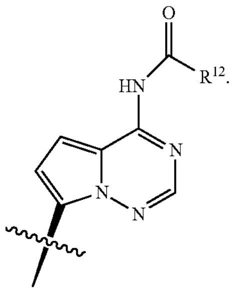

In some embodiments, $R^2$ is $OC(O)R^5$, $R^5$ is $C_1$-$C_3$ alkyl, and Base is

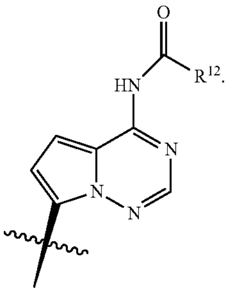
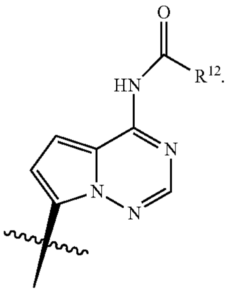

In some embodiments, $R^2$ is OH and Base is

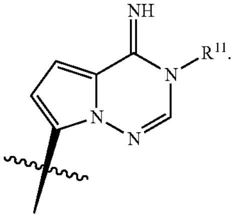

In some embodiments, $R^2$ is OH and Base is

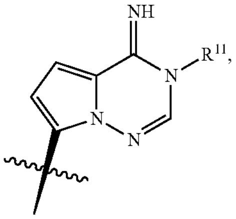

wherein $R^{11}$ is $C_1$-$C_6$ alkyl. In some embodiments, $R^2$ is OH and Base is

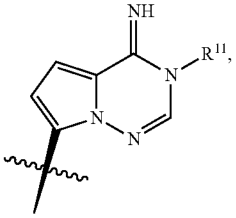

wherein $R^{11}$ is $C_1$-$C_6$ alkyl substituted with $OC(O)R^{12}$. In some embodiments, $R^2$ is OH and Base is

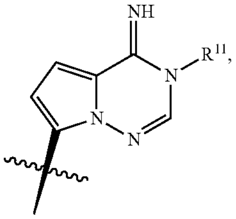

wherein $R^{11}$ is $C_1$-$C_6$ alkyl substituted with $OC(O)R^{12}$ and $R^{12}$ is $C_1$-$C_3$ alkyl. In some embodiments, $R^2$ is OH or $OC(O)R^5$ and $R^5$ is $C_1$-$C_8$ alkyl, and Base is

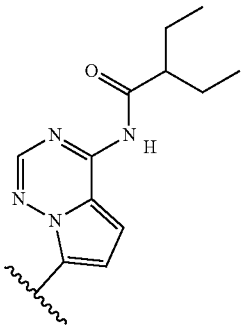
,
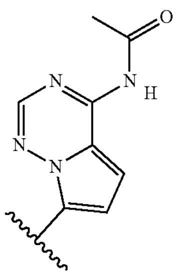
,
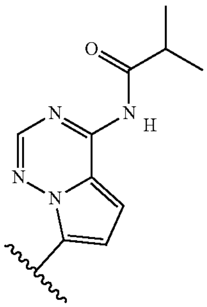
,
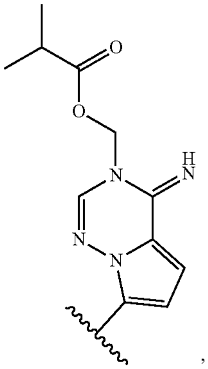
, or
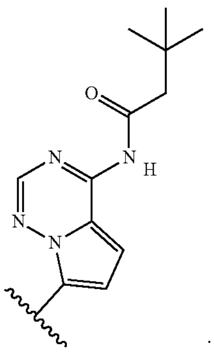
.

In some embodiments, the compound of Formula I is not

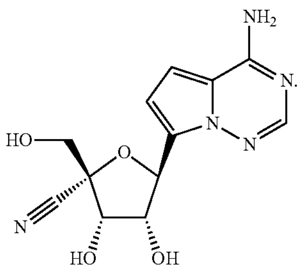 [SMILES: N#C[C@]1(CO)O[C@@H](c2ccc3c(N)ncnn23)[C@H](O)[C@@H]1O]

In some embodiments, the compounds and pharmaceutically acceptable salts of Formula I include the compounds in Table 1 and the pharmaceutically acceptable salts thereof.

TABLE 1

| Some Compounds of Formula I |
|---|
| 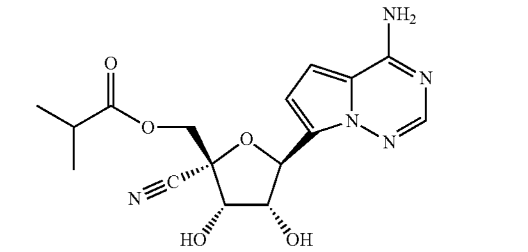 [SMILES: CC(C)C(=O)OC[C@@]1(C#N)O[C@@H](c2ccc3c(N)ncnn23)[C@H](O)[C@@H]1O] |
| 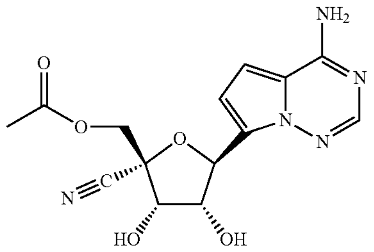 [SMILES: CC(=O)OC[C@@]1(C#N)O[C@@H](c2ccc3c(N)ncnn23)[C@H](O)[C@@H]1O] |
| 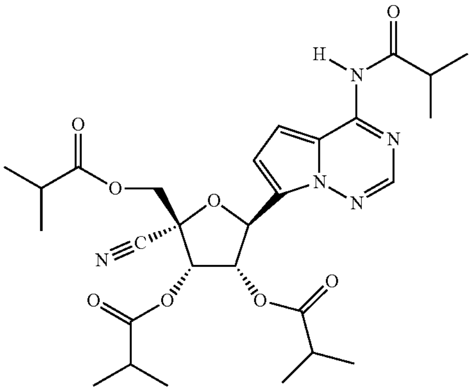 [SMILES: CC(C)C(=O)Nc1ncnn2c([C@@H]3O[C@](C#N)(COC(=O)C(C)C)[C@@H](OC(=O)C(C)C)[C@H]3OC(=O)C(C)C)ccc12] |
| 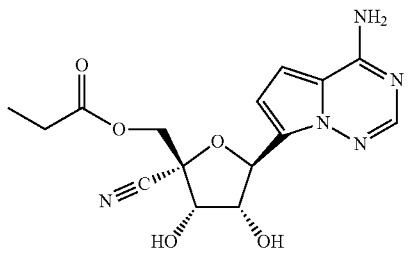 [SMILES: CCC(=O)OC[C@@]1(C#N)O[C@@H](c2ccc3c(N)ncnn23)[C@H](O)[C@@H]1O] |
| 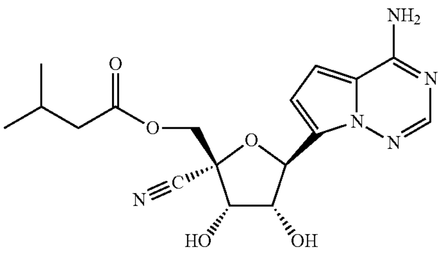 [SMILES: CC(C)CC(=O)OC[C@@]1(C#N)O[C@@H](c2ccc3c(N)ncnn23)[C@H](O)[C@@H]1O] |

TABLE 1-continued
| Some Compounds of Formula I |
| --- |
| 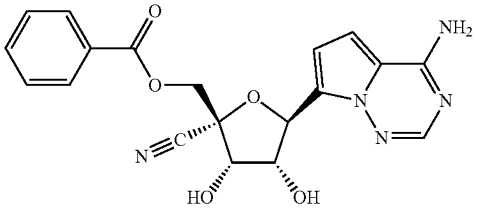 [SMILES: N#C[C@]1(COC(=O)c2ccccc2)O[C@@H](c2ccc3c(N)ncnn23)[C@H](O)[C@@H]1O] |
| 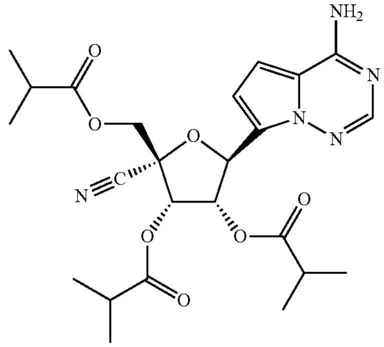 [SMILES: CC(C)C(=O)OC[C@@]1(C#N)O[C@@H](c2ccc3c(N)ncnn23)[C@H](OC(=O)C(C)C)[C@@H]1OC(=O)C(C)C] |
| 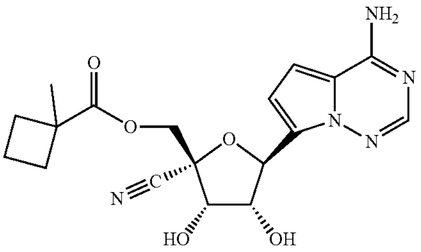 [SMILES: CC1(C(=O)OC[C@@]2(C#N)O[C@@H](c3ccc4c(N)ncnn34)[C@H](O)[C@@H]2O)CCC1] |
| 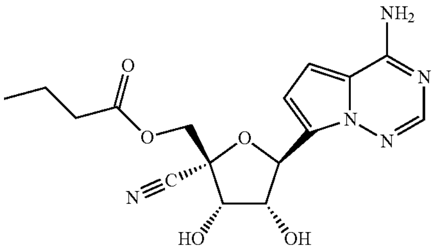 [SMILES: CCCC(=O)OC[C@@]1(C#N)O[C@@H](c2ccc3c(N)ncnn23)[C@H](O)[C@@H]1O] |
| 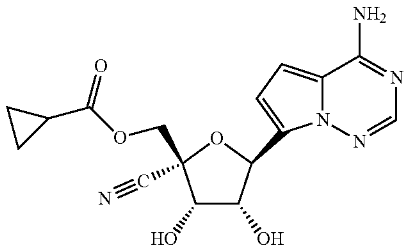 [SMILES: N#C[C@]1(COC(=O)C2CC2)O[C@@H](c2ccc3c(N)ncnn23)[C@H](O)[C@@H]1O] |
| 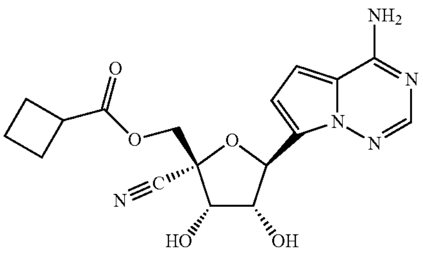 [SMILES: N#C[C@]1(COC(=O)C2CCC2)O[C@@H](c2ccc3c(N)ncnn23)[C@H](O)[C@@H]1O] |
TABLE 1-continued
| Some Compounds of Formula I |
| --- |
| 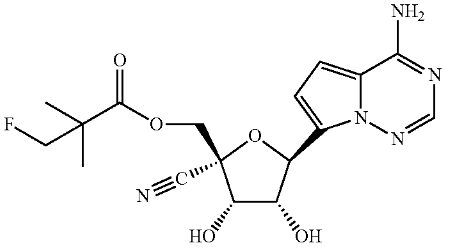 [SMILES: CC(C)(CF)C(=O)OC[C@@]1(C#N)O[C@@H](c2ccc3c(N)ncnn23)[C@H](O)[C@@H]1O] |
| 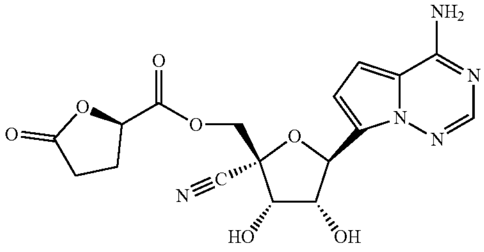 [SMILES: N#C[C@]1(COC(=O)[C@H]2CCC(=O)O2)O[C@@H](c2ccc3c(N)ncnn23)[C@H](O)[C@@H]1O] |
| 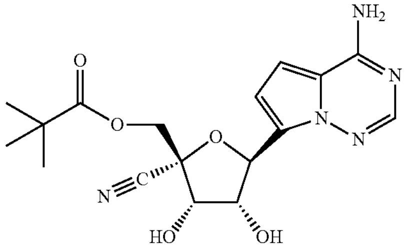 [SMILES: CC(C)(C)C(=O)OC[C@@]1(C#N)O[C@@H](c2ccc3c(N)ncnn23)[C@H](O)[C@@H]1O] |
| 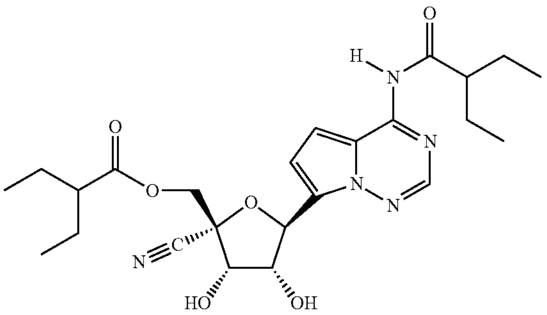 [SMILES: CCC(CC)C(=O)Nc1ncnn2c([C@@H]3O[C@](C#N)(COC(=O)C(CC)CC)[C@@H](O)[C@H]3O)ccc12] |
| 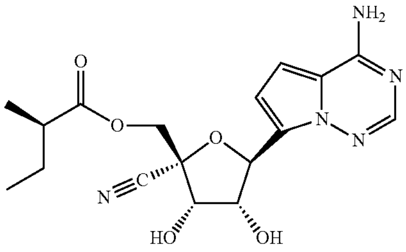 [SMILES: CC[C@@H](C)C(=O)OC[C@@]1(C#N)O[C@@H](c2ccc3c(N)ncnn23)[C@H](O)[C@@H]1O] |
| 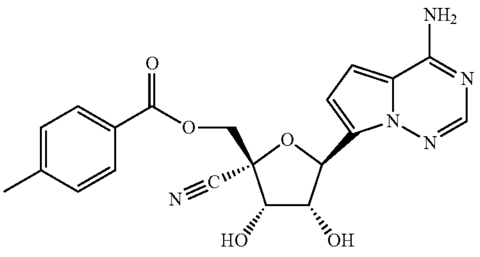 [SMILES: Cc1ccc(C(=O)OC[C@@]2(C#N)O[C@@H](c3ccc4c(N)ncnn34)[C@H](O)[C@@H]2O)cc1] |

TABLE 1-continued
| Some Compounds of Formula I |
|---|
| 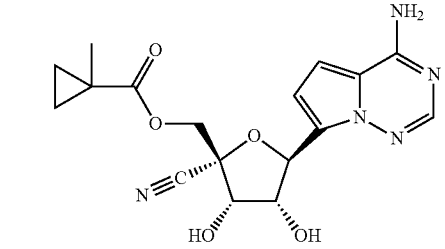 [SMILES: CC1(C(=O)OC[C@@]2(C#N)O[C@@H](c3ccc4c(N)ncnn34)[C@H](O)[C@@H]2O)CC1] |
| 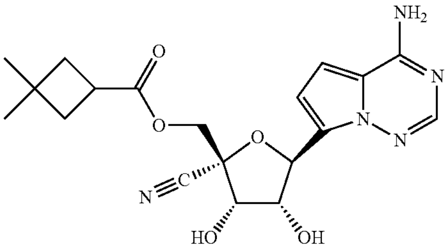 [SMILES: CC1(C)CC(C(=O)OC[C@@]2(C#N)O[C@@H](c3ccc4c(N)ncnn34)[C@H](O)[C@@H]2O)C1] |
| 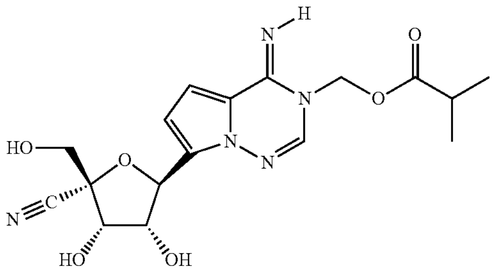 [SMILES: [H]/N=c1/c2ccc([C@@H]3O[C@](C#N)(CO)[C@@H](O)[C@H]3O)n2ncn1COC(=O)C(C)C] |
| 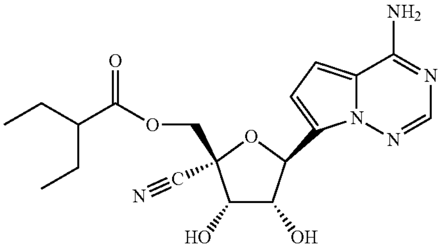 [SMILES: CCC(CC)C(=O)OC[C@@]1(C#N)O[C@@H](c2ccc3c(N)ncnn23)[C@H](O)[C@@H]1O] |
| 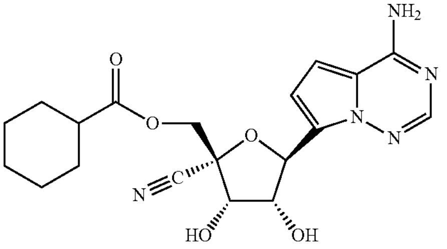 [SMILES: N#C[C@]1(COC(=O)C2CCCCC2)O[C@@H](c2ccc3c(N)ncnn23)[C@H](O)[C@@H]1O] |
| 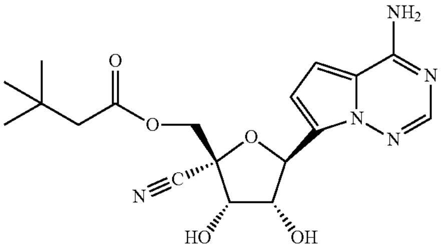 [SMILES: CC(C)(C)CC(=O)OC[C@@]1(C#N)O[C@@H](c2ccc3c(N)ncnn23)[C@H](O)[C@@H]1O] |
TABLE 1-continued
| Some Compounds of Formula I |
|---|
| 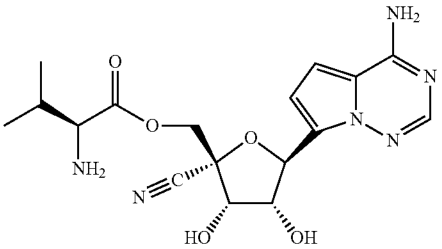 [SMILES: CC(C)[C@H](N)C(=O)OC[C@@]1(C#N)O[C@@H](c2ccc3c(N)ncnn23)[C@H](O)[C@@H]1O] |
| 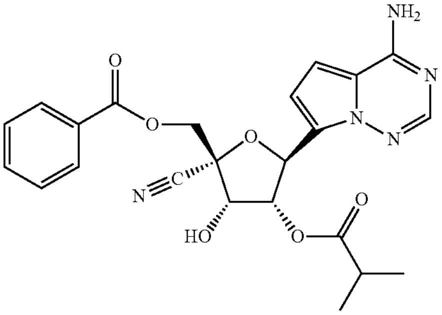 [SMILES: CC(C)C(=O)O[C@H]1[C@H](c2ccc3c(N)ncnn23)O[C@](C#N)(COC(=O)c2ccccc2)[C@H]1O] |
| 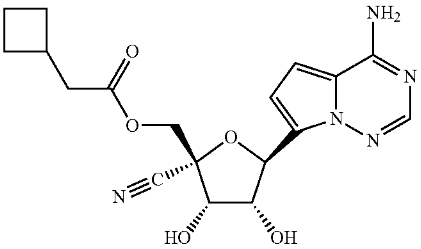 [SMILES: N#C[C@]1(COC(=O)CC2CCC2)O[C@@H](c2ccc3c(N)ncnn23)[C@H](O)[C@@H]1O] |
| 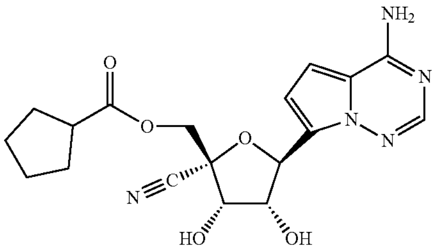 [SMILES: N#C[C@]1(COC(=O)C2CCCC2)O[C@@H](c2ccc3c(N)ncnn23)[C@H](O)[C@@H]1O] |
| 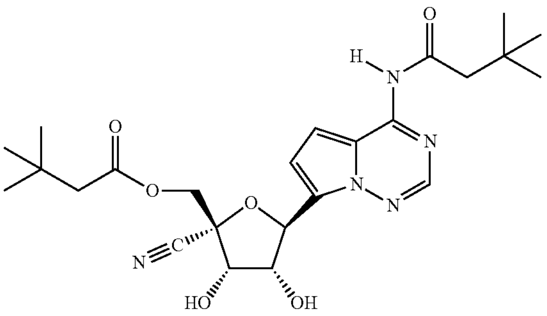 [SMILES: CC(C)(C)CC(=O)Nc1ncnn2c([C@@H]3O[C@](C#N)(COC(=O)CC(C)(C)C)[C@@H](O)[C@H]3O)ccc12] |

TABLE 1-continued

| Some Compounds of Formula I |
|---|
| 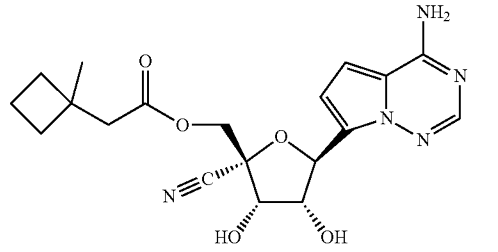 [SMILES: CC1(CC(=O)OC[C@@]2(C#N)O[C@@H](c3ccc4c(N)ncnn34)[C@H](O)[C@@H]2O)CCC1] |
| 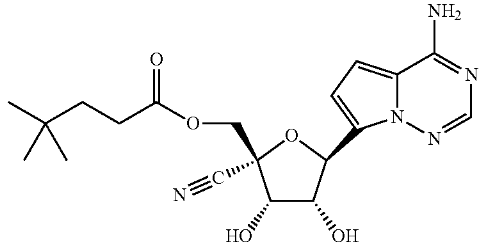 [SMILES: CC(C)(C)CCC(=O)OC[C@@]1(C#N)O[C@@H](c2ccc3c(N)ncnn23)[C@H](O)[C@@H]1O] |
| 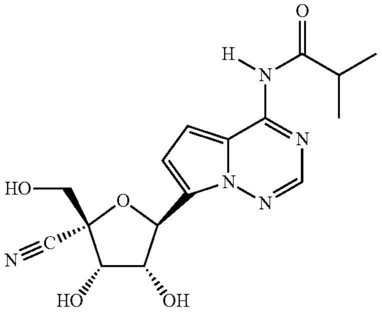 [SMILES: CC(C)C(=O)Nc1ncnn2c([C@@H]3O[C@](C#N)(CO)[C@@H](O)[C@H]3O)ccc12] |
| 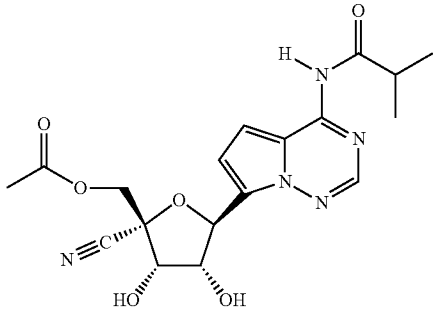 [SMILES: CC(=O)OC[C@@]1(C#N)O[C@@H](c2ccc3c(NC(=O)C(C)C)ncnn23)[C@H](O)[C@@H]1O] |
| 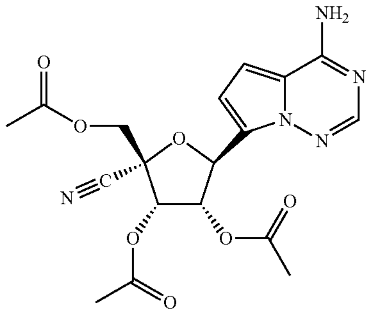 [SMILES: CC(=O)OC[C@@]1(C#N)O[C@@H](c2ccc3c(N)ncnn23)[C@H](OC(C)=O)[C@@H]1OC(C)=O] |

TABLE 1-continued

| Some Compounds of Formula I |
|---|
| 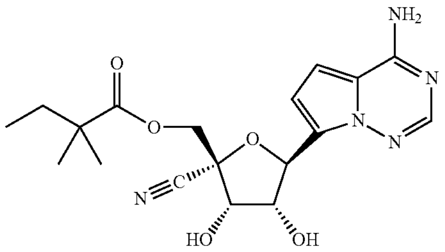 [SMILES: CCC(C)(C)C(=O)OC[C@@]1(C#N)O[C@@H](c2ccc3c(N)ncnn23)[C@H](O)[C@@H]1O] |
| 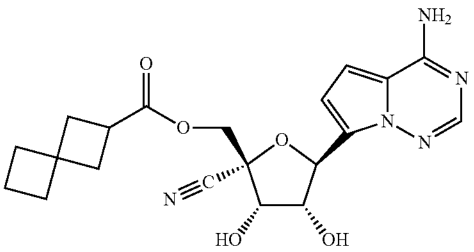 [SMILES: N#C[C@]1(COC(=O)C2CC3(CCC3)C2)O[C@@H](c2ccc3c(N)ncnn23)[C@H](O)[C@@H]1O] |
| 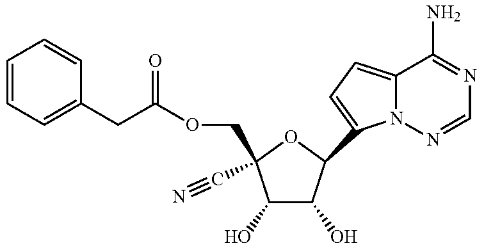 [SMILES: N#C[C@]1(COC(=O)Cc2ccccc2)O[C@@H](c2ccc3c(N)ncnn23)[C@H](O)[C@@H]1O] |

In some embodiments, the compound of Formula I has a Formula IL:

Formula II

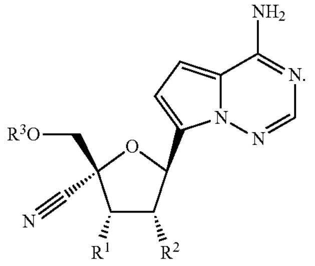

The compounds and pharmaceutically acceptable salts of Formula II are disclosed herein and the description of the substituents and compounds of Formula I apply to Formula II as relevant.

In some embodiments, the compounds and pharmaceutically acceptable salts of Formula II include the compounds in Table 2 and the pharmaceutically acceptable salts thereof.

TABLE 2
| Some Compounds of Formula II |
| --- |
| 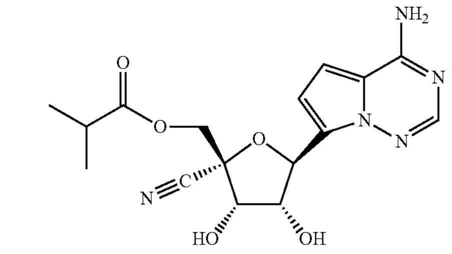 [SMILES: CC(C)C(=O)OC[C@@]1(C#N)O[C@@H](c2ccc3c(N)ncnn23)[C@H](O)[C@@H]1O] |
| 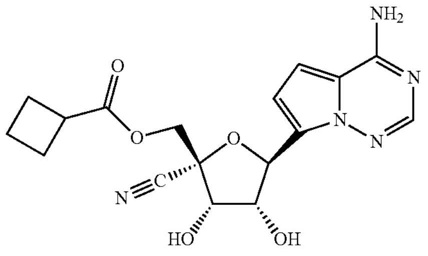 [SMILES: N#C[C@]1(COC(=O)C2CCC2)O[C@@H](c2ccc3c(N)ncnn23)[C@H](O)[C@@H]1O] |
| 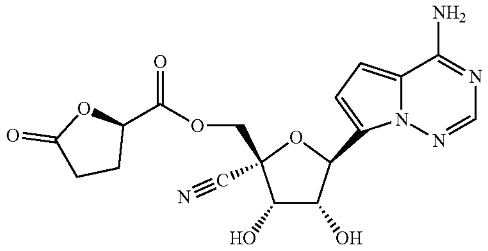 [SMILES: N#C[C@]1(COC(=O)[C@H]2CCC(=O)O2)O[C@@H](c2ccc3c(N)ncnn23)[C@H](O)[C@@H]1O] |
| 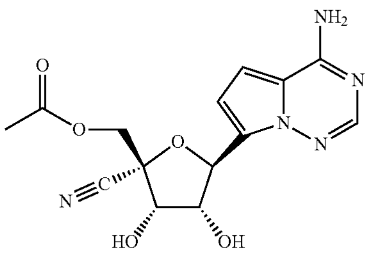 [SMILES: CC(=O)OC[C@@]1(C#N)O[C@@H](c2ccc3c(N)ncnn23)[C@H](O)[C@@H]1O] |
| 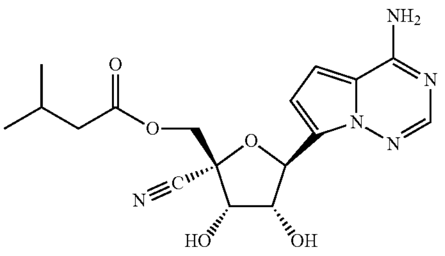 [SMILES: CC(C)CC(=O)OC[C@@]1(C#N)O[C@@H](c2ccc3c(N)ncnn23)[C@H](O)[C@@H]1O] |
| 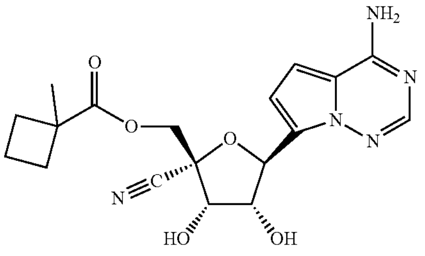 [SMILES: CC1(C(=O)OC[C@@]2(C#N)O[C@@H](c3ccc4c(N)ncnn34)[C@H](O)[C@@H]2O)CCC1] |
TABLE 2-continued
| Some Compounds of Formula II |
| --- |
| 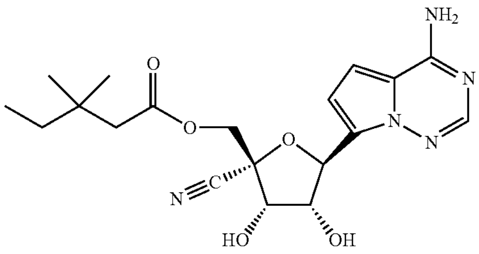 [SMILES: CCC(C)(C)CC(=O)OC[C@@]1(C#N)O[C@@H](c2ccc3c(N)ncnn23)[C@H](O)[C@@H]1O] |
| 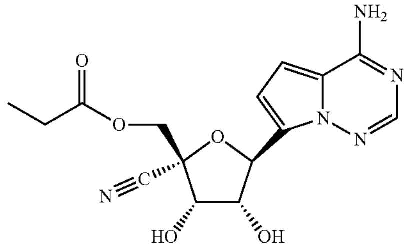 [SMILES: CCC(=O)OC[C@@]1(C#N)O[C@@H](c2ccc3c(N)ncnn23)[C@H](O)[C@@H]1O] |
| 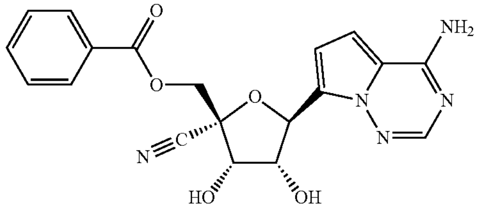 [SMILES: N#C[C@]1(COC(=O)c2ccccc2)O[C@@H](c2ccc3c(N)ncnn23)[C@H](O)[C@@H]1O] |
| 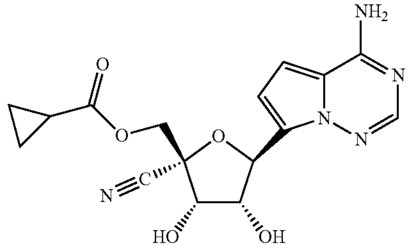 [SMILES: N#C[C@]1(COC(=O)C2CC2)O[C@@H](c2ccc3c(N)ncnn23)[C@H](O)[C@@H]1O] |
| 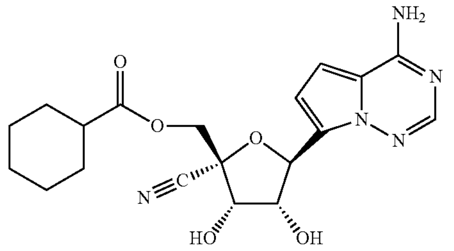 [SMILES: N#C[C@]1(COC(=O)C2CCCCC2)O[C@@H](c2ccc3c(N)ncnn23)[C@H](O)[C@@H]1O] |
| 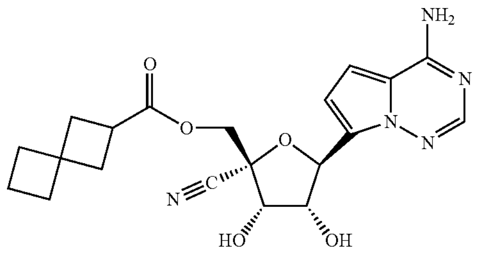 [SMILES: N#C[C@]1(COC(=O)C2CC3(CCC3)C2)O[C@@H](c2ccc3c(N)ncnn23)[C@H](O)[C@@H]1O] |

TABLE 2-continued
Some Compounds of Formula II
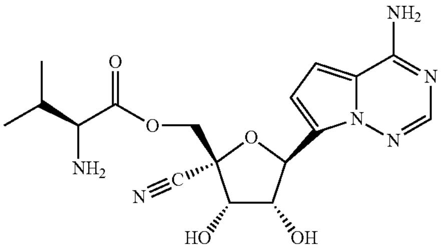 [SMILES: CC(C)[C@H](N)C(=O)OC[C@@]1(C#N)O[C@@H](c2ccc3c(N)ncnn23)[C@H](O)[C@@H]1O]
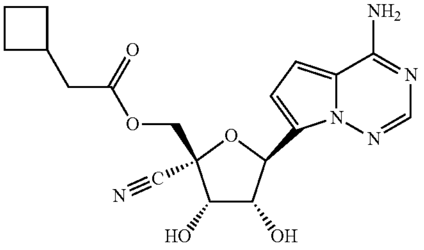 [SMILES: N#C[C@]1(COC(=O)CC2CCC2)O[C@@H](c2ccc3c(N)ncnn23)[C@H](O)[C@@H]1O]
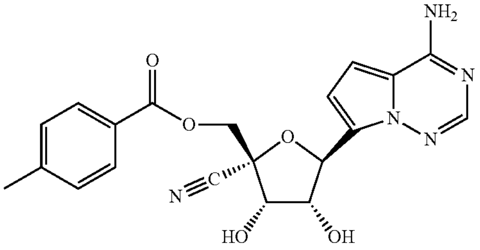 [SMILES: Cc1ccc(C(=O)OC[C@@]2(C#N)O[C@@H](c3ccc4c(N)ncnn34)[C@H](O)[C@@H]2O)cc1]
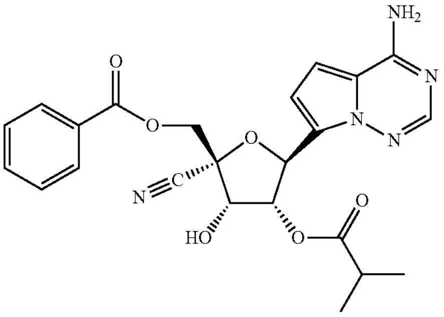 [SMILES: CC(C)C(=O)O[C@H]1[C@H](c2ccc3c(N)ncnn23)O[C@](C#N)(COC(=O)c2ccccc2)[C@H]1O]
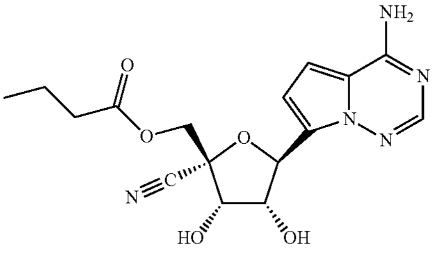 [SMILES: CCCC(=O)OC[C@@]1(C#N)O[C@@H](c2ccc3c(N)ncnn23)[C@H](O)[C@@H]1O]
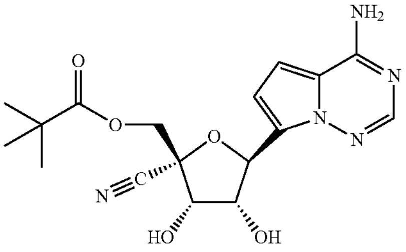 [SMILES: CC(C)(C)C(=O)OC[C@@]1(C#N)O[C@@H](c2ccc3c(N)ncnn23)[C@H](O)[C@@H]1O]
TABLE 2-continued
Some Compounds of Formula II
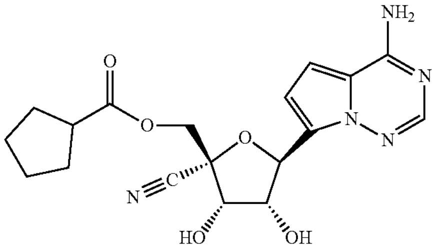 [SMILES: N#C[C@]1(COC(=O)C2CCCC2)O[C@@H](c2ccc3c(N)ncnn23)[C@H](O)[C@@H]1O]
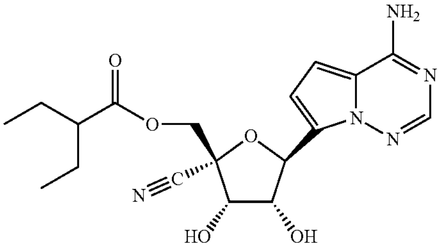 [SMILES: CCC(CC)C(=O)OC[C@@]1(C#N)O[C@@H](c2ccc3c(N)ncnn23)[C@H](O)[C@@H]1O]
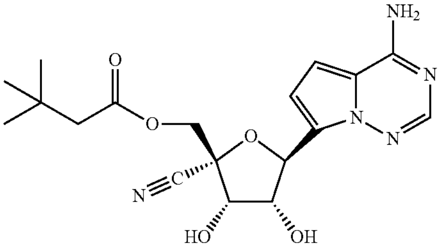 [SMILES: CC(C)(C)CC(=O)OC[C@@]1(C#N)O[C@@H](c2ccc3c(N)ncnn23)[C@H](O)[C@@H]1O]
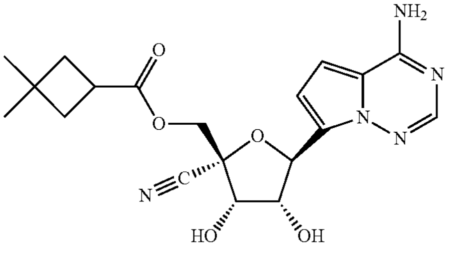 [SMILES: CC1(C)CC(C(=O)OC[C@@]2(C#N)O[C@@H](c3ccc4c(N)ncnn34)[C@H](O)[C@@H]2O)C1]
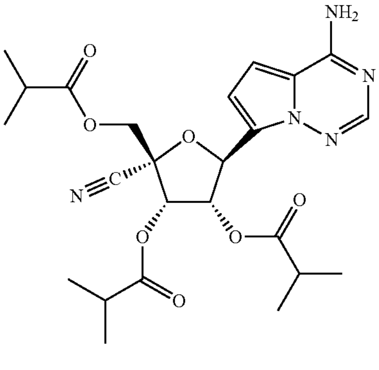 [SMILES: CC(C)C(=O)OC[C@@]1(C#N)O[C@@H](c2ccc3c(N)ncnn23)[C@H](OC(=O)C(C)C)[C@@H]1OC(=O)C(C)C]

TABLE 2-continued

Some Compounds of Formula II

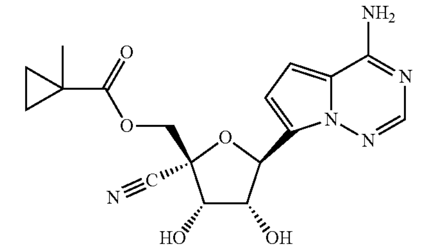 [SMILES: CC1(C(=O)OC[C@@]2(C#N)O[C@@H](c3ccc4c(N)ncnn34)[C@H](O)[C@@H]2O)CC1]

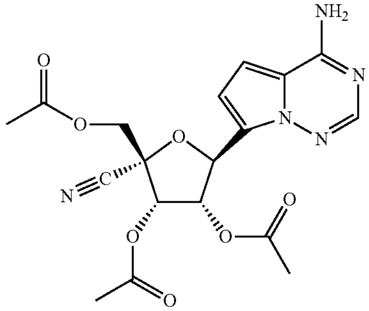 [SMILES: CC(=O)OC[C@@]1(C#N)O[C@@H](c2ccc3c(N)ncnn23)[C@H](OC(C)=O)[C@@H]1OC(C)=O]

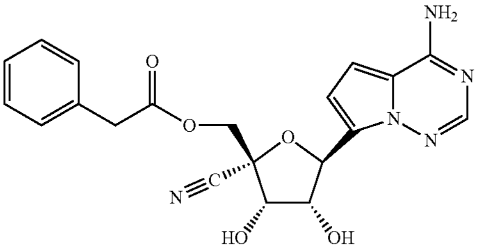 [SMILES: N#C[C@]1(COC(=O)Cc2ccccc2)O[C@@H](c2ccc3c(N)ncnn23)[C@H](O)[C@@H]1O]

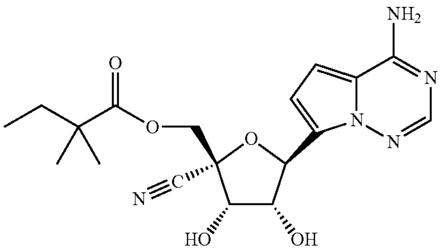 [SMILES: CCC(C)(C)C(=O)OC[C@@]1(C#N)O[C@@H](c2ccc3c(N)ncnn23)[C@H](O)[C@@H]1O]

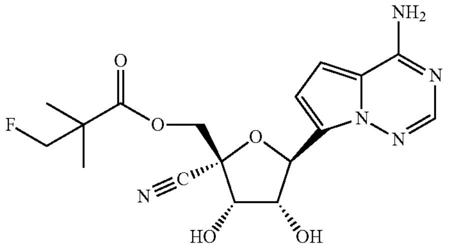 [SMILES: CC(C)(CF)C(=O)OC[C@@]1(C#N)O[C@@H](c2ccc3c(N)ncnn23)[C@H](O)[C@@H]1O]

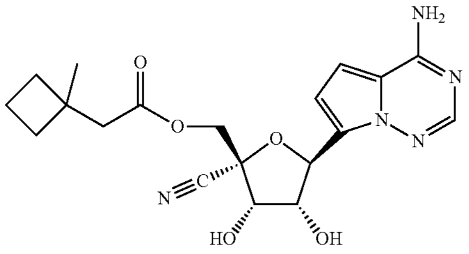 [SMILES: CC1(CC(=O)OC[C@@]2(C#N)O[C@@H](c3ccc4c(N)ncnn34)[C@H](O)[C@@H]2O)CCC1]

TABLE 2-continued

Some Compounds of Formula II

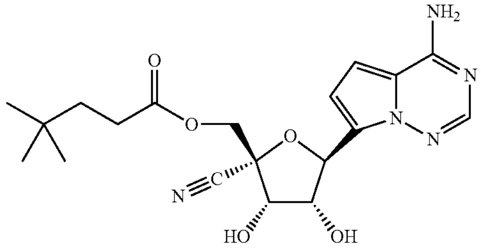 [SMILES: CC(C)(C)CCC(=O)OC[C@@]1(C#N)O[C@@H](c2ccc3c(N)ncnn23)[C@H](O)[C@@H]1O]

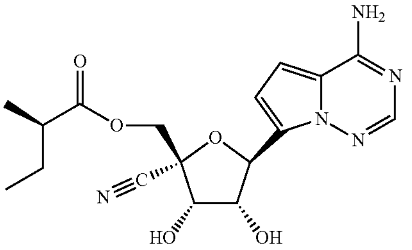 [SMILES: CC[C@@H](C)C(=O)OC[C@@]1(C#N)O[C@@H](c2ccc3c(N)ncnn23)[C@H](O)[C@@H]1O]

In some embodiments, the compound of Formula I or II has a Formula III:

Formula III

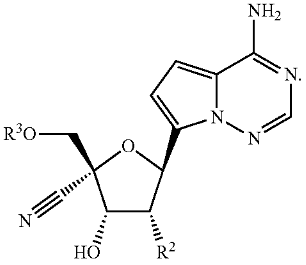

The compounds and pharmaceutically acceptable salts of Formula III are disclosed herein and the description of the substituents and compounds of Formula I apply to Formula III as relevant.

In some embodiments, the compounds and pharmaceutically acceptable salts of Formula III include the compounds in Table 3 and the pharmaceutically acceptable salts thereof

TABLE 3

Some Compounds of Formula III

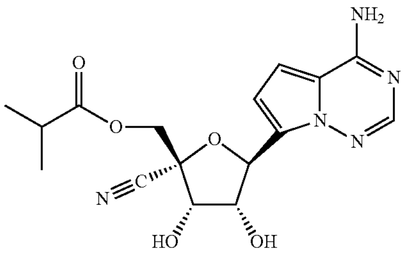 [SMILES: CC(C)C(=O)OC[C@@]1(C#N)O[C@@H](c2ccc3c(N)ncnn23)[C@H](O)[C@@H]1O]

TABLE 3-continued
| Some Compounds of Formula III |
|---|
| 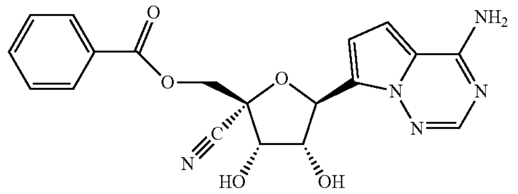 [SMILES: N#C[C@]1(COC(=O)c2ccccc2)O[C@@H](c2ccc3c(N)ncnn23)[C@H](O)[C@@H]1O] |
| 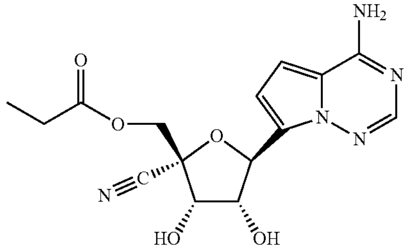 [SMILES: CCC(=O)OC[C@@]1(C#N)O[C@@H](c2ccc3c(N)ncnn23)[C@H](O)[C@@H]1O] |
| 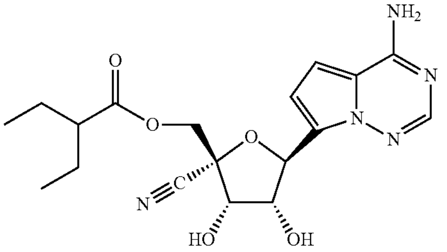 [SMILES: CCC(CC)C(=O)OC[C@@]1(C#N)O[C@@H](c2ccc3c(N)ncnn23)[C@H](O)[C@@H]1O] |
| 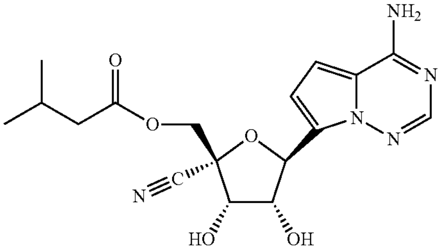 [SMILES: CC(C)CC(=O)OC[C@@]1(C#N)O[C@@H](c2ccc3c(N)ncnn23)[C@H](O)[C@@H]1O] |
| 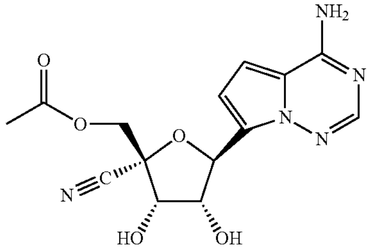 [SMILES: CC(=O)OC[C@@]1(C#N)O[C@@H](c2ccc3c(N)ncnn23)[C@H](O)[C@@H]1O] |
| 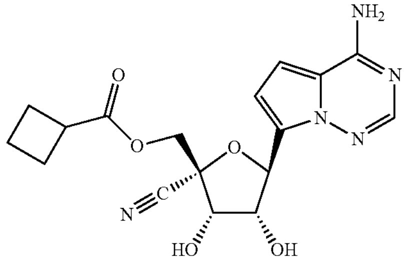 [SMILES: N#C[C@]1(COC(=O)C2CCC2)O[C@@H](c2ccc3c(N)ncnn23)[C@H](O)[C@@H]1O] |
TABLE 3-continued
| Some Compounds of Formula III |
|---|
| 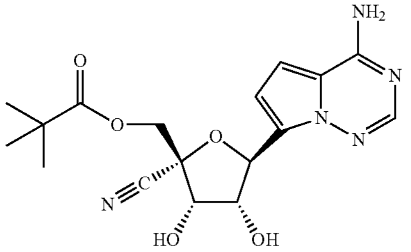 [SMILES: CC(C)(C)C(=O)OC[C@@]1(C#N)O[C@@H](c2ccc3c(N)ncnn23)[C@H](O)[C@@H]1O] |
| 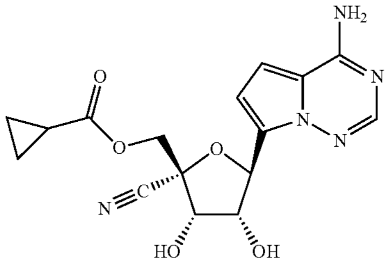 [SMILES: N#C[C@]1(COC(=O)C2CC2)O[C@@H](c2ccc3c(N)ncnn23)[C@H](O)[C@@H]1O] |
| 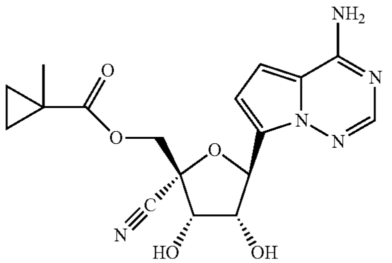 [SMILES: CC1(C(=O)OC[C@@]2(C#N)O[C@@H](c3ccc4c(N)ncnn34)[C@H](O)[C@@H]2O)CC1] |
| 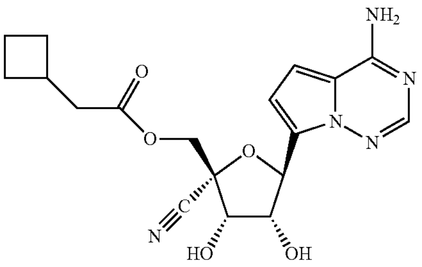 [SMILES: N#C[C@]1(COC(=O)CC2CCC2)O[C@@H](c2ccc3c(N)ncnn23)[C@H](O)[C@@H]1O] |
| 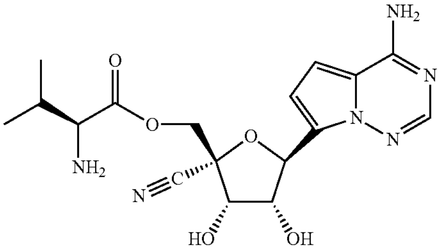 [SMILES: CC(C)[C@H](N)C(=O)OC[C@@]1(C#N)O[C@@H](c2ccc3c(N)ncnn23)[C@H](O)[C@@H]1O] |
| 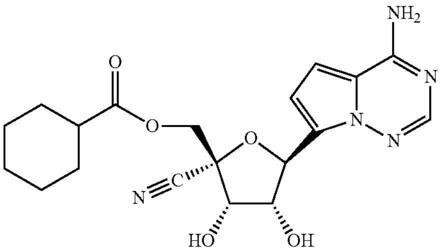 [SMILES: N#C[C@]1(COC(=O)C2CCCCC2)O[C@@H](c2ccc3c(N)ncnn23)[C@H](O)[C@@H]1O] |

TABLE 3-continued
Some Compounds of Formula III
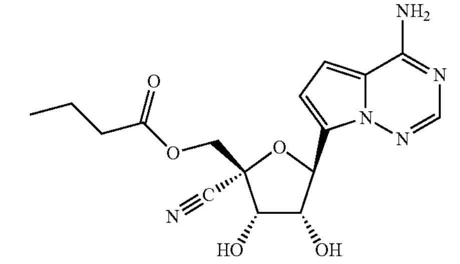 [SMILES: CCCC(=O)OC[C@@]1(C#N)O[C@@H](c2ccc3c(N)ncnn23)[C@H](O)[C@@H]1O]
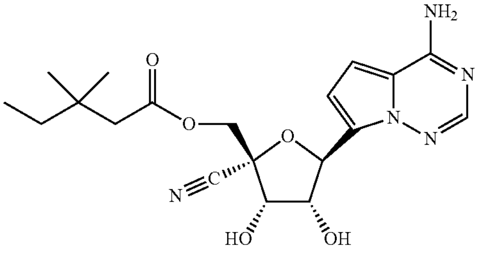 [SMILES: CCC(C)(C)CC(=O)OC[C@@]1(C#N)O[C@@H](c2ccc3c(N)ncnn23)[C@H](O)[C@@H]1O]
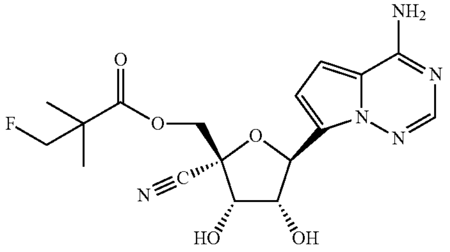 [SMILES: CC(C)(CF)C(=O)OC[C@@]1(C#N)O[C@@H](c2ccc3c(N)ncnn23)[C@H](O)[C@@H]1O]
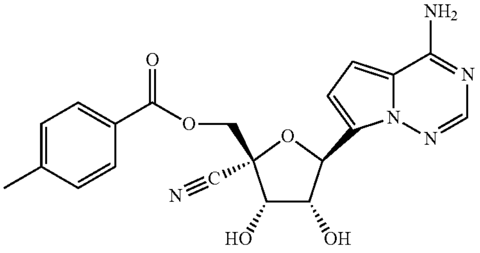 [SMILES: Cc1ccc(C(=O)OC[C@@]2(C#N)O[C@@H](c3ccc4c(N)ncnn34)[C@H](O)[C@@H]2O)cc1]
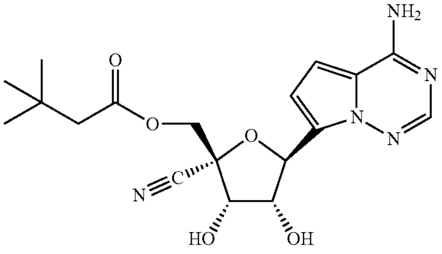 [SMILES: CC(C)(C)CC(=O)OC[C@@]1(C#N)O[C@@H](c2ccc3c(N)ncnn23)[C@H](O)[C@@H]1O]
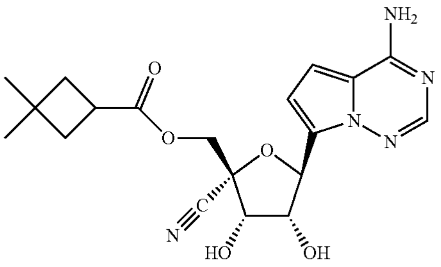 [SMILES: CC1(C)CC(C(=O)OC[C@@]2(C#N)O[C@@H](c3ccc4c(N)ncnn34)[C@H](O)[C@@H]2O)C1]
TABLE 3-continued
Some Compounds of Formula III
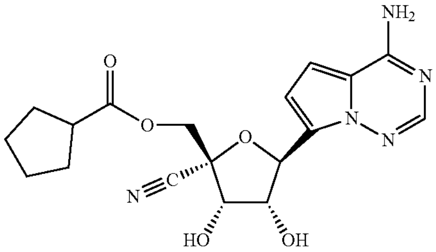 [SMILES: N#C[C@]1(COC(=O)C2CCCC2)O[C@@H](c2ccc3c(N)ncnn23)[C@H](O)[C@@H]1O]
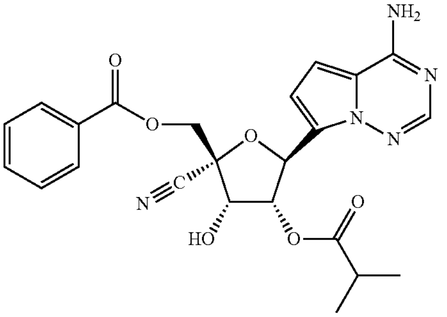 [SMILES: CC(C)C(=O)O[C@H]1[C@H](c2ccc3c(N)ncnn23)O[C@](C#N)(COC(=O)c2ccccc2)[C@H]1O]
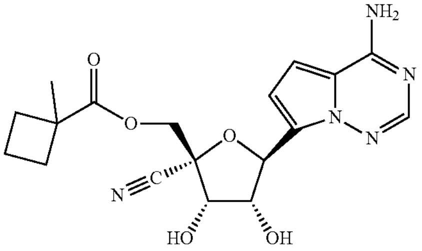 [SMILES: CC1(C(=O)OC[C@@]2(C#N)O[C@@H](c3ccc4c(N)ncnn34)[C@H](O)[C@@H]2O)CCC1]
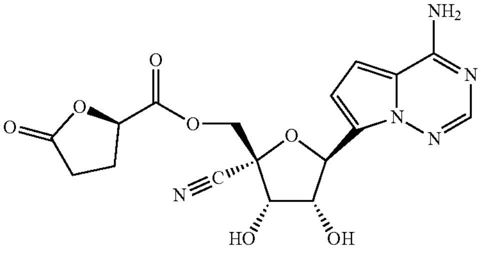 [SMILES: N#C[C@]1(COC(=O)[C@H]2CCC(=O)O2)O[C@@H](c2ccc3c(N)ncnn23)[C@H](O)[C@@H]1O]
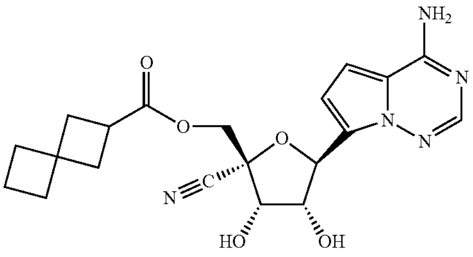 [SMILES: N#C[C@]1(COC(=O)C2CC3(CCC3)C2)O[C@@H](c2ccc3c(N)ncnn23)[C@H](O)[C@@H]1O]

TABLE 3-continued

| Some Compounds of Formula III |
| --- |
| 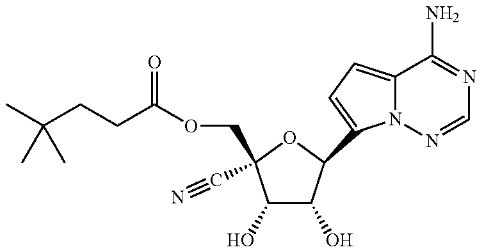 [SMILES: CC(C)(C)CCC(=O)OC[C@@]1(C#N)O[C@@H](c2ccc3c(N)ncnn23)[C@H](O)[C@@H]1O] |
| 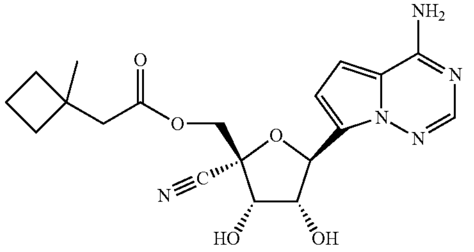 [SMILES: CC1(CC(=O)OC[C@@]2(C#N)O[C@@H](c3ccc4c(N)ncnn34)[C@H](O)[C@@H]2O)CCC1] |
| 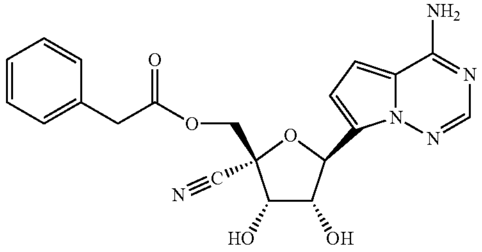 [SMILES: N#C[C@]1(COC(=O)Cc2ccccc2)O[C@@H](c2ccc3c(N)ncnn23)[C@H](O)[C@@H]1O] |
| 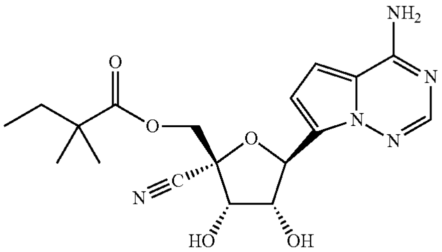 [SMILES: CCC(C)(C)C(=O)OC[C@@]1(C#N)O[C@@H](c2ccc3c(N)ncnn23)[C@H](O)[C@@H]1O] |
| 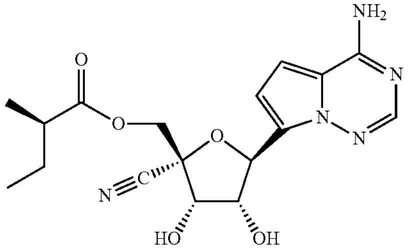 [SMILES: CC[C@@H](C)C(=O)OC[C@@]1(C#N)O[C@@H](c2ccc3c(N)ncnn23)[C@H](O)[C@@H]1O] |

In some embodiments, the compound of Formula I or II has a Formula IV:

Formula IV

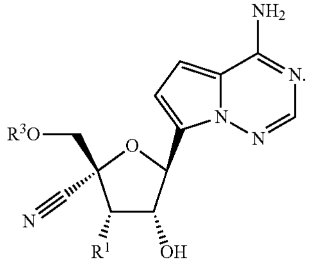

The compounds and pharmaceutically acceptable salts of Formula IV are disclosed herein and the description of the substituents and compounds of Formula I apply to Formula IV as relevant.

In some embodiments, the compounds and pharmaceutically acceptable salts of Formula IV include the compounds in Table 4 and the pharmaceutically acceptable salts thereof.

TABLE 4

| Some Compounds of Formula IV |
| --- |
| 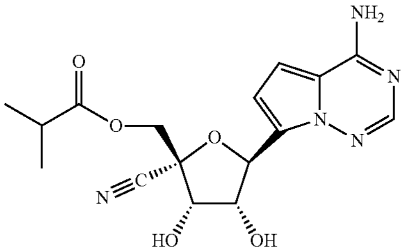 [SMILES: CC(C)C(=O)OC[C@@]1(C#N)O[C@@H](c2ccc3c(N)ncnn23)[C@H](O)[C@@H]1O] |
| 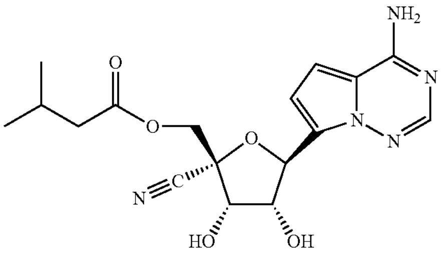 [SMILES: CC(C)CC(=O)OC[C@@]1(C#N)O[C@@H](c2ccc3c(N)ncnn23)[C@H](O)[C@@H]1O] |
| 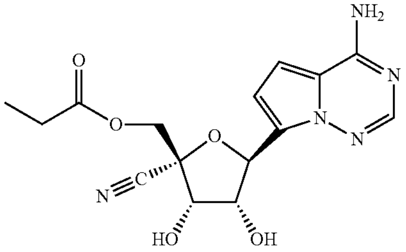 [SMILES: CCC(=O)OC[C@@]1(C#N)O[C@@H](c2ccc3c(N)ncnn23)[C@H](O)[C@@H]1O] |
| 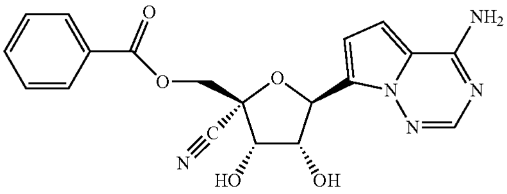 [SMILES: N#C[C@]1(COC(=O)c2ccccc2)O[C@@H](c2ccc3c(N)ncnn23)[C@H](O)[C@@H]1O] |

TABLE 4-continued
| Some Compounds of Formula IV |
| --- |
| 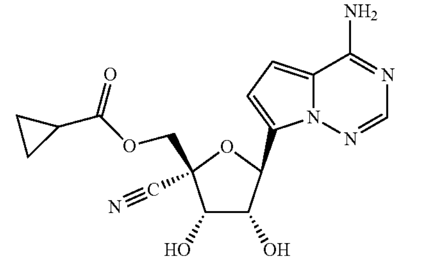 [SMILES: N#C[C@]1(COC(=O)C2CC2)O[C@@H](c2ccc3c(N)ncnn23)[C@H](O)[C@@H]1O] |
| 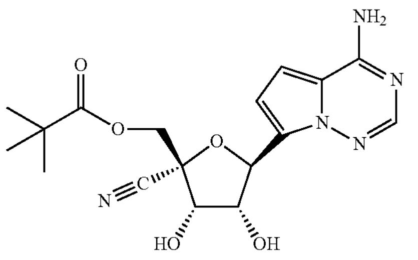 [SMILES: CC(C)(C)C(=O)OC[C@@]1(C#N)O[C@@H](c2ccc3c(N)ncnn23)[C@H](O)[C@@H]1O] |
| 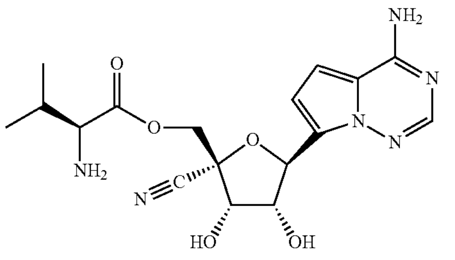 [SMILES: CC(C)[C@H](N)C(=O)OC[C@@]1(C#N)O[C@@H](c2ccc3c(N)ncnn23)[C@H](O)[C@@H]1O] |
| 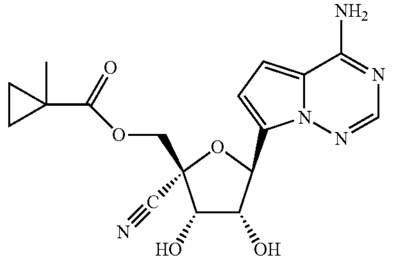 [SMILES: CC1(C(=O)OC[C@@]2(C#N)O[C@@H](c3ccc4c(N)ncnn34)[C@H](O)[C@@H]2O)CC1] |
| 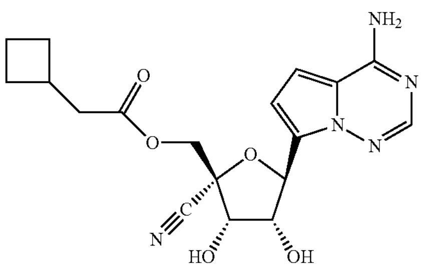 [SMILES: N#C[C@]1(COC(=O)CC2CCC2)O[C@@H](c2ccc3c(N)ncnn23)[C@H](O)[C@@H]1O] |
| 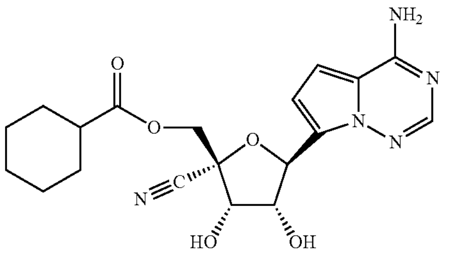 [SMILES: N#C[C@]1(COC(=O)C2CCCCC2)O[C@@H](c2ccc3c(N)ncnn23)[C@H](O)[C@@H]1O] |
TABLE 4-continued
| Some Compounds of Formula IV |
| --- |
| 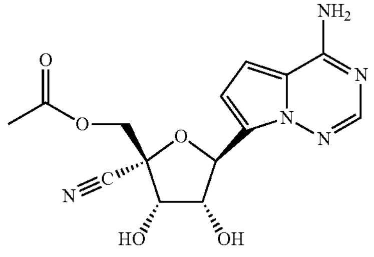 [SMILES: CC(=O)OC[C@@]1(C#N)O[C@@H](c2ccc3c(N)ncnn23)[C@H](O)[C@@H]1O] |
| 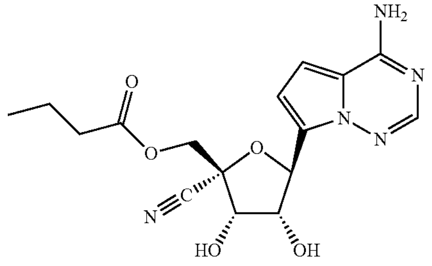 [SMILES: CCCC(=O)OC[C@@]1(C#N)O[C@@H](c2ccc3c(N)ncnn23)[C@H](O)[C@@H]1O] |
| 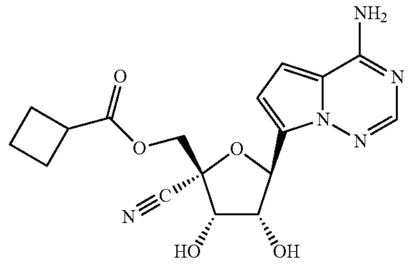 [SMILES: N#C[C@]1(COC(=O)C2CCC2)O[C@@H](c2ccc3c(N)ncnn23)[C@H](O)[C@@H]1O] |
| 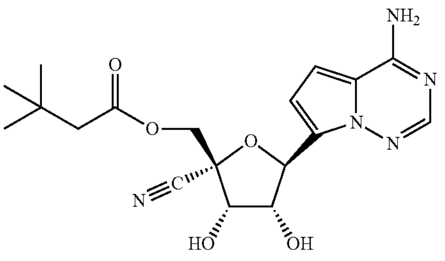 [SMILES: CC(C)(C)CC(=O)OC[C@@]1(C#N)O[C@@H](c2ccc3c(N)ncnn23)[C@H](O)[C@@H]1O] |
| 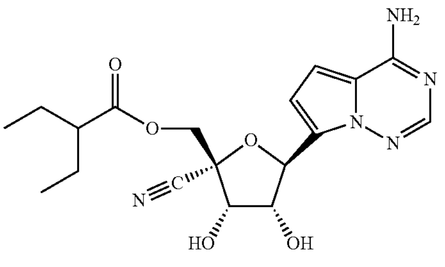 [SMILES: CCC(CC)C(=O)OC[C@@]1(C#N)O[C@@H](c2ccc3c(N)ncnn23)[C@H](O)[C@@H]1O] |
| 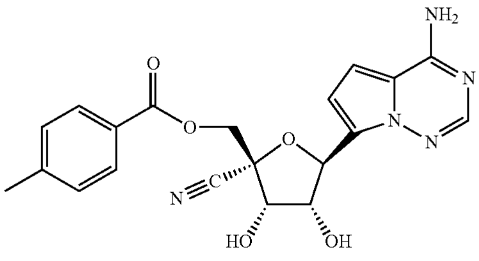 [SMILES: Cc1ccc(C(=O)OC[C@@]2(C#N)O[C@@H](c3ccc4c(N)ncnn34)[C@H](O)[C@@H]2O)cc1] |

TABLE 4-continued
| Some Compounds of Formula IV |
|---|
| 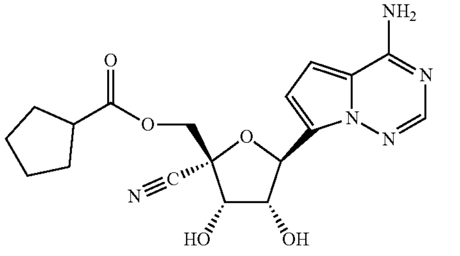 [SMILES: N#C[C@]1(COC(=O)C2CCCC2)O[C@@H](c2ccc3c(N)ncnn23)[C@H](O)[C@@H]1O] |
| 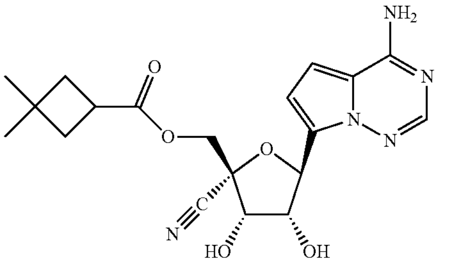 [SMILES: CC1(C)CC(C(=O)OC[C@@]2(C#N)O[C@@H](c3ccc4c(N)ncnn34)[C@H](O)[C@@H]2O)C1] |
| 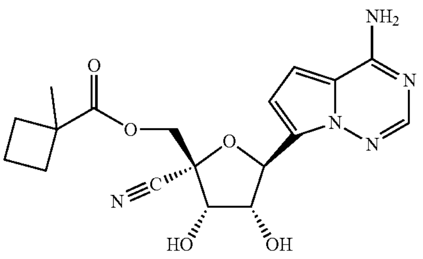 [SMILES: CC1(C(=O)OC[C@@]2(C#N)O[C@@H](c3ccc4c(N)ncnn34)[C@H](O)[C@@H]2O)CCC1] |
| 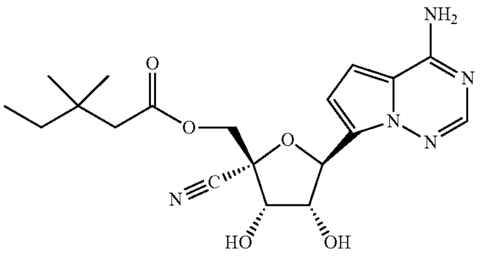 [SMILES: CCC(C)(C)CC(=O)OC[C@@]1(C#N)O[C@@H](c2ccc3c(N)ncnn23)[C@H](O)[C@@H]1O] |
| 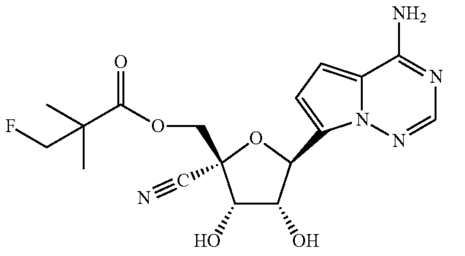 [SMILES: CC(C)(CF)C(=O)OC[C@@]1(C#N)O[C@@H](c2ccc3c(N)ncnn23)[C@H](O)[C@@H]1O] |
| 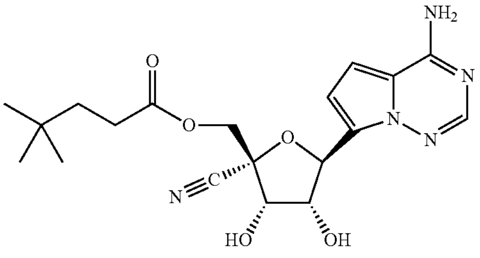 [SMILES: CC(C)(C)CCC(=O)OC[C@@]1(C#N)O[C@@H](c2ccc3c(N)ncnn23)[C@H](O)[C@@H]1O] |
TABLE 4-continued
| Some Compounds of Formula IV |
|---|
| 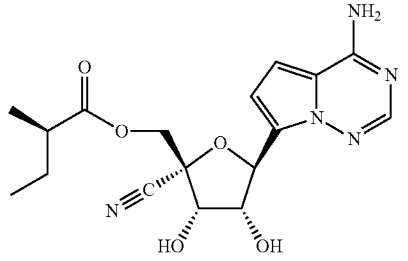 [SMILES: CC[C@@H](C)C(=O)OC[C@@]1(C#N)O[C@@H](c2ccc3c(N)ncnn23)[C@H](O)[C@@H]1O] |
| 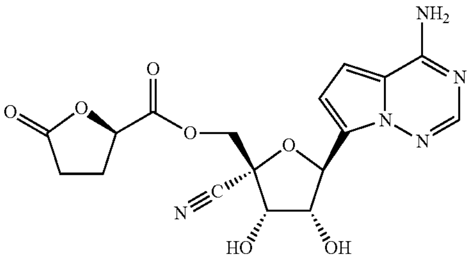 [SMILES: N#C[C@]1(COC(=O)[C@H]2CCC(=O)O2)O[C@@H](c2ccc3c(N)ncnn23)[C@H](O)[C@@H]1O] |
| 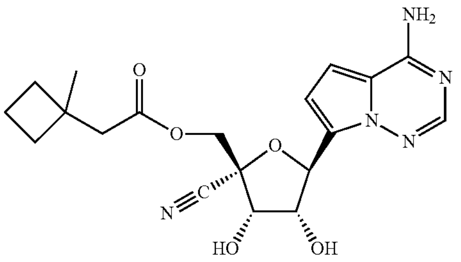 [SMILES: CC1(CC(=O)OC[C@@]2(C#N)O[C@@H](c3ccc4c(N)ncnn34)[C@H](O)[C@@H]2O)CCC1] |
| 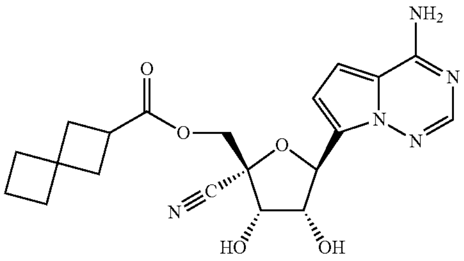 [SMILES: N#C[C@]1(COC(=O)C2CC3(CCC3)C2)O[C@@H](c2ccc3c(N)ncnn23)[C@H](O)[C@@H]1O] |
| 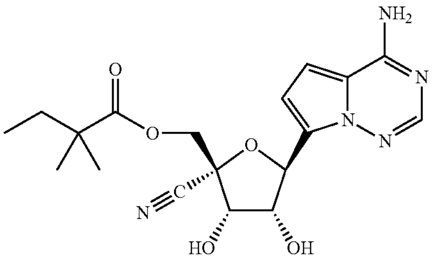 [SMILES: CCC(C)(C)C(=O)OC[C@@]1(C#N)O[C@@H](c2ccc3c(N)ncnn23)[C@H](O)[C@@H]1O] |
| 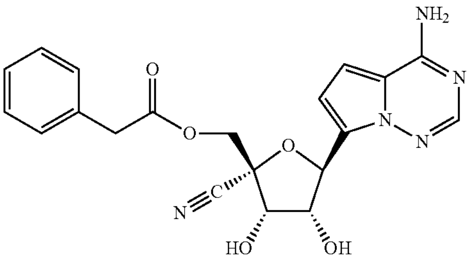 [SMILES: N#C[C@]1(COC(=O)Cc2ccccc2)O[C@@H](c2ccc3c(N)ncnn23)[C@H](O)[C@@H]1O] |

In some embodiments, the compound of Formula I, II, III, or IV has a Formula V:

Formula V

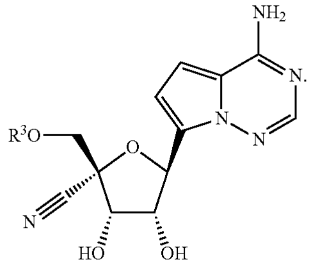

The compounds and pharmaceutically acceptable salts of Formula V are disclosed herein and the description of the substituents and compounds of Formula I apply to Formula V as relevant.

In some embodiments, the compounds and pharmaceutically acceptable salts of Formula V include the compounds in Table 5 and the pharmaceutically acceptable salts thereof.

TABLE 5

| Some Compounds of Formula V |
| --- |
| 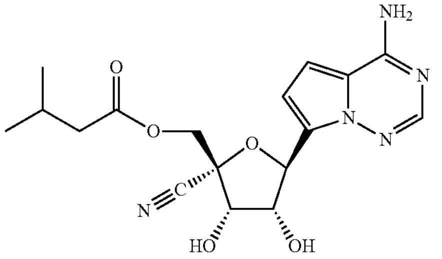 [SMILES: CC(C)CC(=O)OC[C@@]1(C#N)O[C@@H](c2ccc3c(N)ncnn23)[C@H](O)[C@@H]1O] |
| 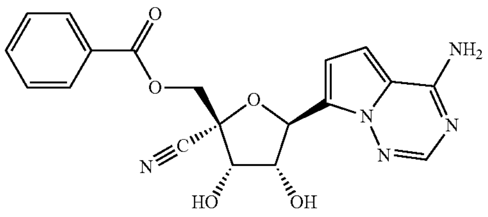 [SMILES: N#C[C@]1(COC(=O)c2ccccc2)O[C@@H](c2ccc3c(N)ncnn23)[C@H](O)[C@@H]1O] |
| 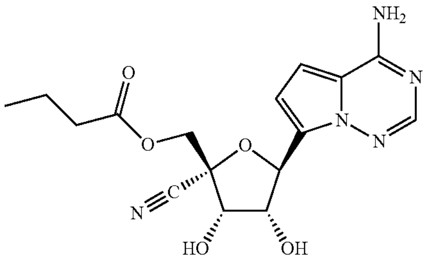 [SMILES: CCCC(=O)OC[C@@]1(C#N)O[C@@H](c2ccc3c(N)ncnn23)[C@H](O)[C@@H]1O] |

TABLE 5-continued

| Some Compounds of Formula V |
| --- |
| 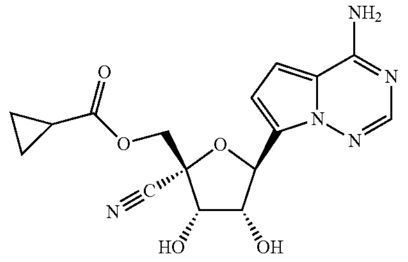 [SMILES: N#C[C@]1(COC(=O)C2CC2)O[C@@H](c2ccc3c(N)ncnn23)[C@H](O)[C@@H]1O] |
| 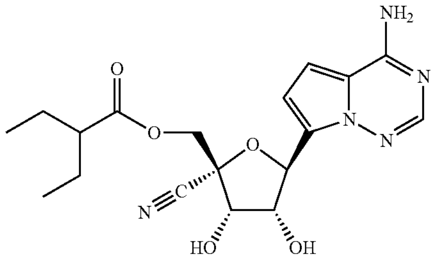 [SMILES: CCC(CC)C(=O)OC[C@@]1(C#N)O[C@@H](c2ccc3c(N)ncnn23)[C@H](O)[C@@H]1O] |
| 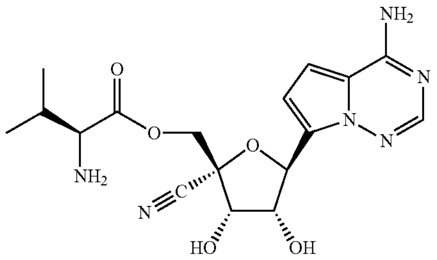 [SMILES: CC(C)[C@H](N)C(=O)OC[C@@]1(C#N)O[C@@H](c2ccc3c(N)ncnn23)[C@H](O)[C@@H]1O] |
| 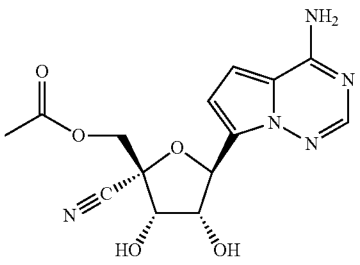 [SMILES: CC(=O)OC[C@@]1(C#N)O[C@@H](c2ccc3c(N)ncnn23)[C@H](O)[C@@H]1O] |
| 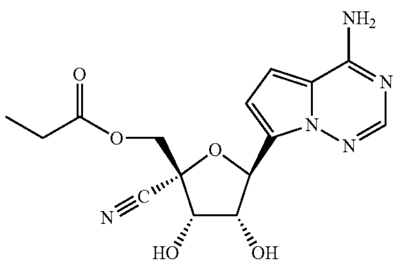 [SMILES: CCC(=O)OC[C@@]1(C#N)O[C@@H](c2ccc3c(N)ncnn23)[C@H](O)[C@@H]1O] |
| 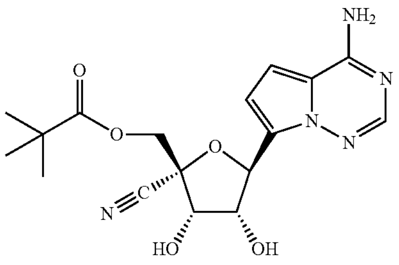 [SMILES: CC(C)(C)C(=O)OC[C@@]1(C#N)O[C@@H](c2ccc3c(N)ncnn23)[C@H](O)[C@@H]1O] |

TABLE 5-continued
| Some Compounds of Formula V |
|---|
| 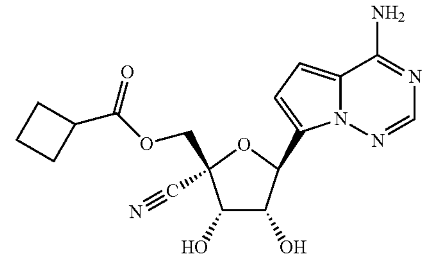 [SMILES: N#C[C@]1(COC(=O)C2CCC2)O[C@@H](c2ccc3c(N)ncnn23)[C@H](O)[C@@H]1O] |
| 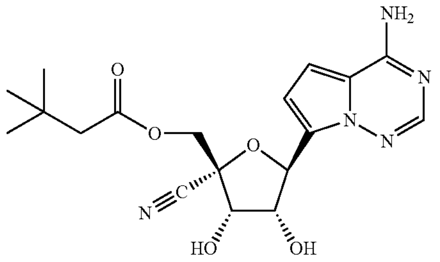 [SMILES: CC(C)(C)CC(=O)OC[C@@]1(C#N)O[C@@H](c2ccc3c(N)ncnn23)[C@H](O)[C@@H]1O] |
| 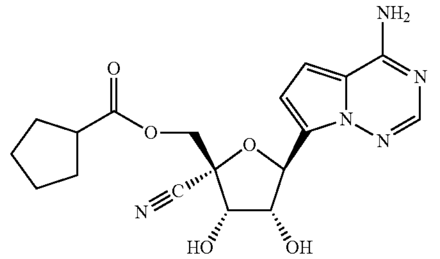 [SMILES: N#C[C@]1(COC(=O)C2CCCC2)O[C@@H](c2ccc3c(N)ncnn23)[C@H](O)[C@@H]1O] |
| 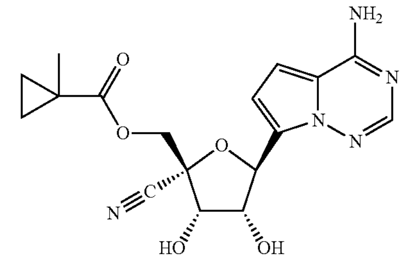 [SMILES: CC1(C(=O)OC[C@@]2(C#N)O[C@@H](c3ccc4c(N)ncnn34)[C@H](O)[C@@H]2O)CC1] |
| 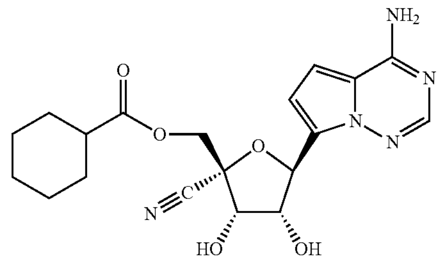 [SMILES: N#C[C@]1(COC(=O)C2CCCCC2)O[C@@H](c2ccc3c(N)ncnn23)[C@H](O)[C@@H]1O] |
| 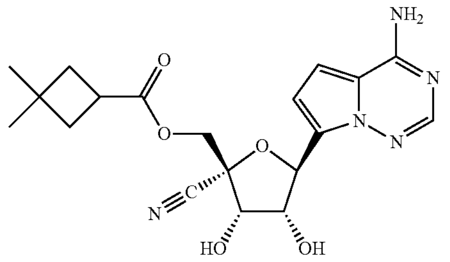 [SMILES: CC1(C)CC(C(=O)OC[C@@]2(C#N)O[C@@H](c3ccc4c(N)ncnn34)[C@H](O)[C@@H]2O)C1] |
TABLE 5-continued
| Some Compounds of Formula V |
|---|
| 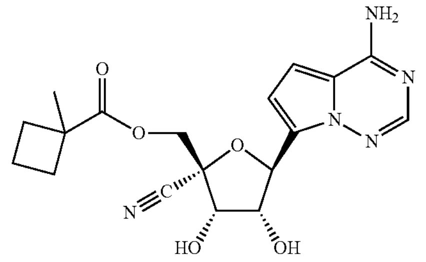 [SMILES: CC1(C(=O)OC[C@@]2(C#N)O[C@@H](c3ccc4c(N)ncnn34)[C@H](O)[C@@H]2O)CCC1] |
| 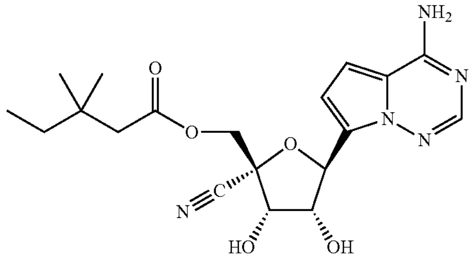 [SMILES: CCC(C)(C)CC(=O)OC[C@@]1(C#N)O[C@@H](c2ccc3c(N)ncnn23)[C@H](O)[C@@H]1O] |
| 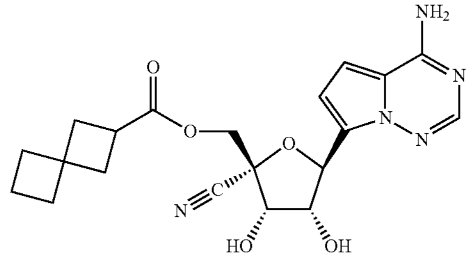 [SMILES: N#C[C@]1(COC(=O)C2CC3(CCC3)C2)O[C@@H](c2ccc3c(N)ncnn23)[C@H](O)[C@@H]1O] |
| 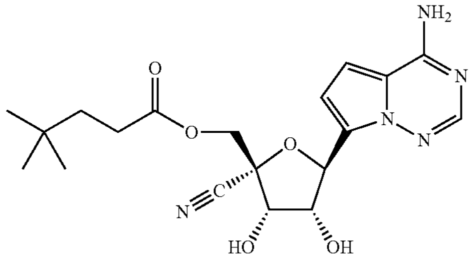 [SMILES: CC(C)(C)CCC(=O)OC[C@@]1(C#N)O[C@@H](c2ccc3c(N)ncnn23)[C@H](O)[C@@H]1O] |
| 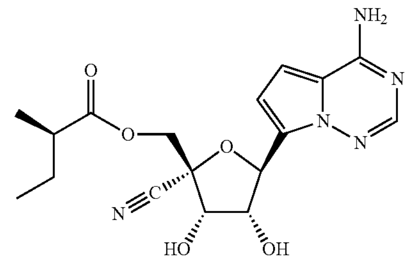 [SMILES: CC[C@@H](C)C(=O)OC[C@@]1(C#N)O[C@@H](c2ccc3c(N)ncnn23)[C@H](O)[C@@H]1O] |
| 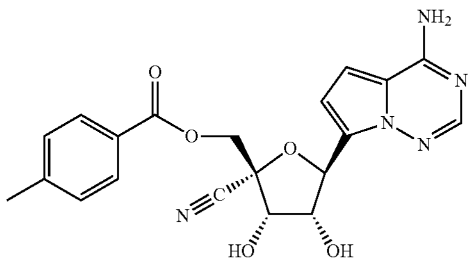 [SMILES: Cc1ccc(C(=O)OC[C@@]2(C#N)O[C@@H](c3ccc4c(N)ncnn34)[C@H](O)[C@@H]2O)cc1] |

TABLE 5-continued

| Some Compounds of Formula V |
| --- |
| 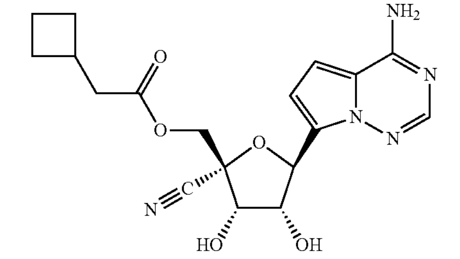 [SMILES: N#C[C@]1(COC(=O)CC2CCC2)O[C@@H](c2ccc3c(N)ncnn23)[C@H](O)[C@@H]1O] |
| 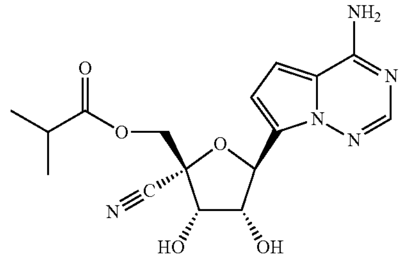 [SMILES: CC(C)C(=O)OC[C@@]1(C#N)O[C@@H](c2ccc3c(N)ncnn23)[C@H](O)[C@@H]1O] |
| 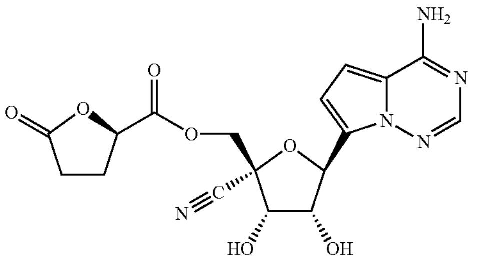 [SMILES: N#C[C@]1(COC(=O)[C@H]2CCC(=O)O2)O[C@@H](c2ccc3c(N)ncnn23)[C@H](O)[C@@H]1O] |
| 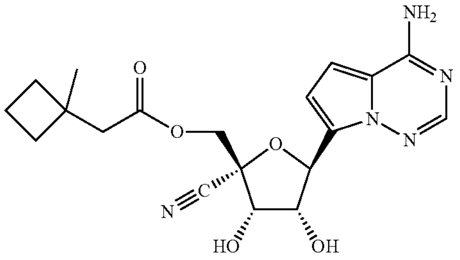 [SMILES: CC1(CC(=O)OC[C@@]2(C#N)O[C@@H](c3ccc4c(N)ncnn34)[C@H](O)[C@@H]2O)CCC1] |
| 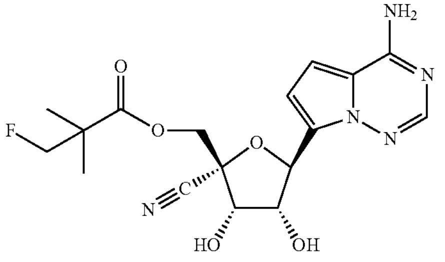 [SMILES: CC(C)(CF)C(=O)OC[C@@]1(C#N)O[C@@H](c2ccc3c(N)ncnn23)[C@H](O)[C@@H]1O] |
| 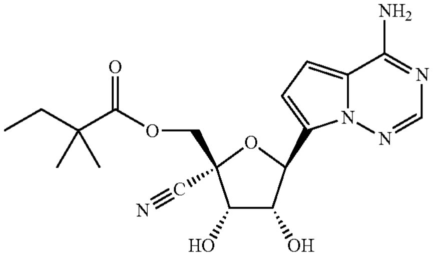 [SMILES: CCC(C)(C)C(=O)OC[C@@]1(C#N)O[C@@H](c2ccc3c(N)ncnn23)[C@H](O)[C@@H]1O] |

TABLE 5-continued

| Some Compounds of Formula V |
| --- |
| 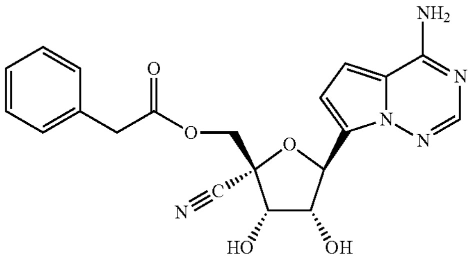 [SMILES: N#C[C@]1(COC(=O)Cc2ccccc2)O[C@@H](c2ccc3c(N)ncnn23)[C@H](O)[C@@H]1O] |

In some embodiments, the compound of Formula I or II has a Formula VI:

Formula VI

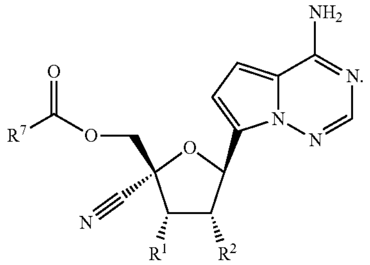

The compounds and pharmaceutically acceptable salts of Formula VI are disclosed herein and the description of the substituents and compounds of Formula I apply to Formula VI as relevant. In some embodiments, the compounds and pharmaceutically acceptable salts of Formula VI include the compounds in Table 6 and the pharmaceutically acceptable salts thereof.

TABLE 6

| Some Compounds of Formula VI |
| --- |
| 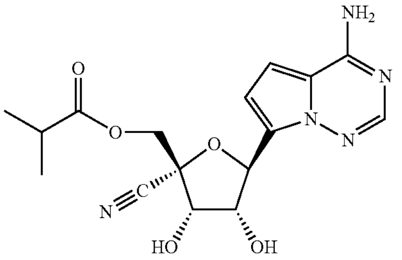 [SMILES: CC(C)C(=O)OC[C@@]1(C#N)O[C@@H](c2ccc3c(N)ncnn23)[C@H](O)[C@@H]1O] |
| 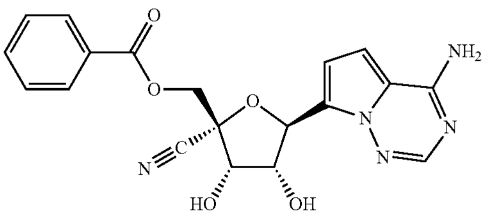 [SMILES: N#C[C@]1(COC(=O)c2ccccc2)O[C@@H](c2ccc3c(N)ncnn23)[C@H](O)[C@@H]1O] |

TABLE 6-continued
| Some Compounds of Formula VI |
| --- |
| 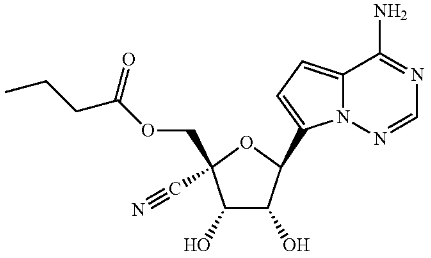 [SMILES: CCCC(=O)OC[C@@]1(C#N)O[C@@H](c2ccc3c(N)ncnn23)[C@H](O)[C@@H]1O] |
| 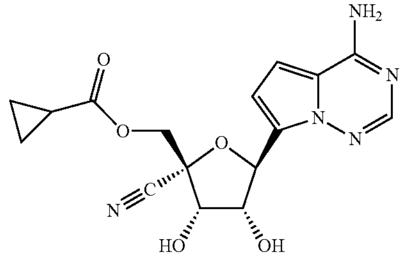 [SMILES: N#C[C@]1(COC(=O)C2CC2)O[C@@H](c2ccc3c(N)ncnn23)[C@H](O)[C@@H]1O] |
| 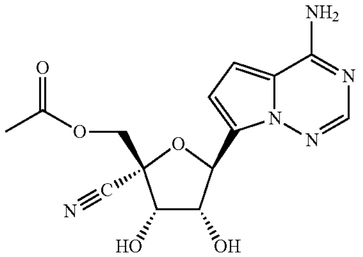 [SMILES: CC(=O)OC[C@@]1(C#N)O[C@@H](c2ccc3c(N)ncnn23)[C@H](O)[C@@H]1O] |
| 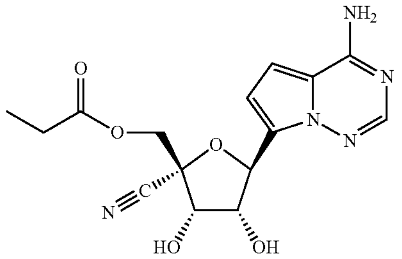 [SMILES: CCC(=O)OC[C@@]1(C#N)O[C@@H](c2ccc3c(N)ncnn23)[C@H](O)[C@@H]1O] |
| 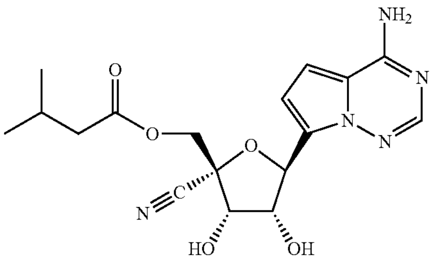 [SMILES: CC(C)CC(=O)OC[C@@]1(C#N)O[C@@H](c2ccc3c(N)ncnn23)[C@H](O)[C@@H]1O] |
| 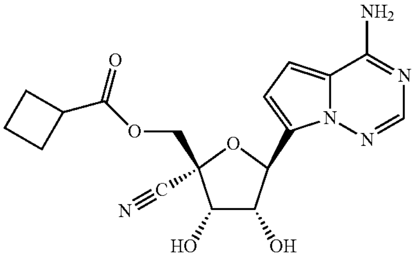 [SMILES: N#C[C@]1(COC(=O)C2CCC2)O[C@@H](c2ccc3c(N)ncnn23)[C@H](O)[C@@H]1O] |
TABLE 6-continued
| Some Compounds of Formula VI |
| --- |
| 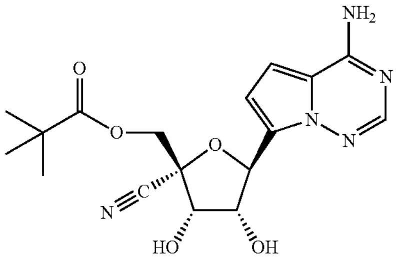 [SMILES: CC(C)(C)C(=O)OC[C@@]1(C#N)O[C@@H](c2ccc3c(N)ncnn23)[C@H](O)[C@@H]1O] |
| 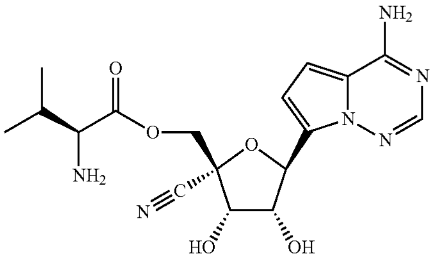 [SMILES: CC(C)[C@H](N)C(=O)OC[C@@]1(C#N)O[C@@H](c2ccc3c(N)ncnn23)[C@H](O)[C@@H]1O] |
| 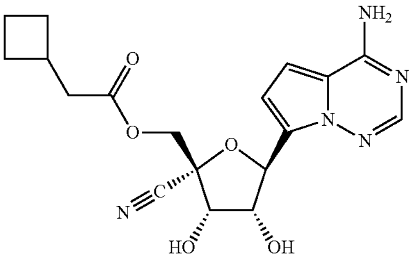 [SMILES: N#C[C@]1(COC(=O)CC2CCC2)O[C@@H](c2ccc3c(N)ncnn23)[C@H](O)[C@@H]1O] |
| 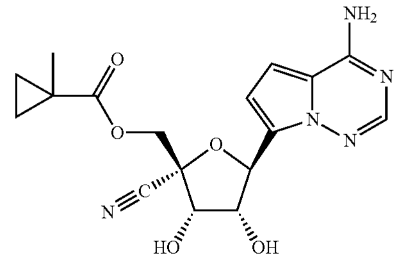 [SMILES: CC1(C(=O)OC[C@@]2(C#N)O[C@@H](c3ccc4c(N)ncnn34)[C@H](O)[C@@H]2O)CC1] |
| 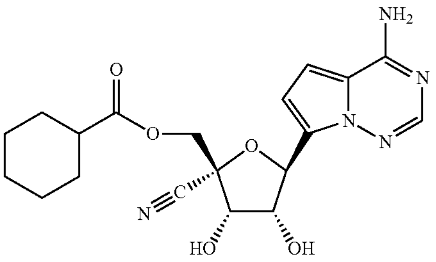 [SMILES: N#C[C@]1(COC(=O)C2CCCCC2)O[C@@H](c2ccc3c(N)ncnn23)[C@H](O)[C@@H]1O] |

TABLE 6-continued
| Some Compounds of Formula VI |
| --- |
| 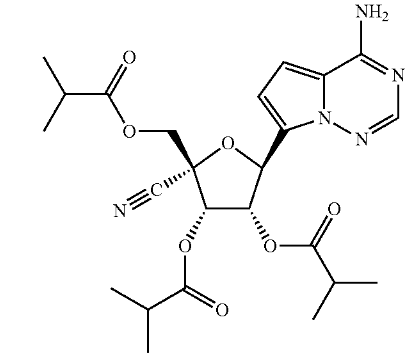 [SMILES: CC(C)C(=O)OC[C@@]1(C#N)O[C@@H](c2ccc3c(N)ncnn23)[C@H](OC(=O)C(C)C)[C@@H]1OC(=O)C(C)C] |
| 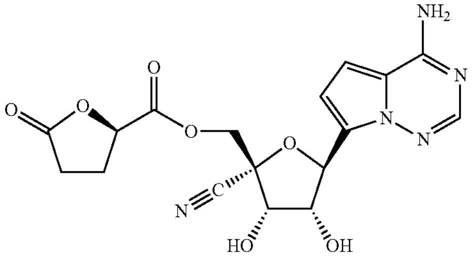 [SMILES: N#C[C@]1(COC(=O)[C@H]2CCC(=O)O2)O[C@@H](c2ccc3c(N)ncnn23)[C@H](O)[C@@H]1O] |
| 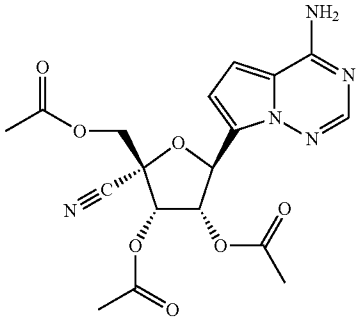 [SMILES: CC(=O)OC[C@@]1(C#N)O[C@@H](c2ccc3c(N)ncnn23)[C@H](OC(C)=O)[C@@H]1OC(C)=O] |
| 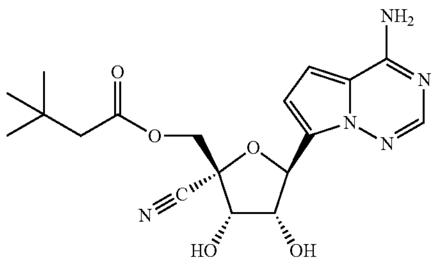 [SMILES: CC(C)(C)CC(=O)OC[C@@]1(C#N)O[C@@H](c2ccc3c(N)ncnn23)[C@H](O)[C@@H]1O] |
| 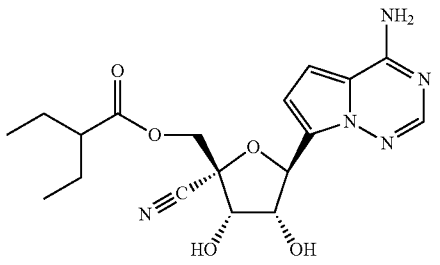 [SMILES: CCC(CC)C(=O)OC[C@@]1(C#N)O[C@@H](c2ccc3c(N)ncnn23)[C@H](O)[C@@H]1O] |
TABLE 6-continued
| Some Compounds of Formula VI |
| --- |
| 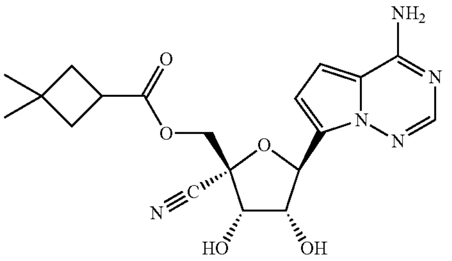 [SMILES: CC1(C)CC(C(=O)OC[C@@]2(C#N)O[C@@H](c3ccc4c(N)ncnn34)[C@H](O)[C@@H]2O)C1] |
| 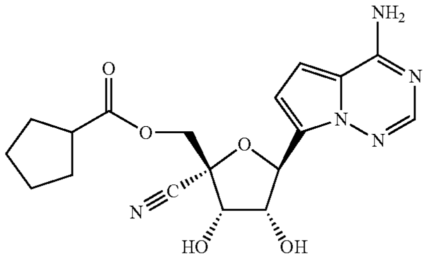 [SMILES: N#C[C@]1(COC(=O)C2CCCC2)O[C@@H](c2ccc3c(N)ncnn23)[C@H](O)[C@@H]1O] |
| 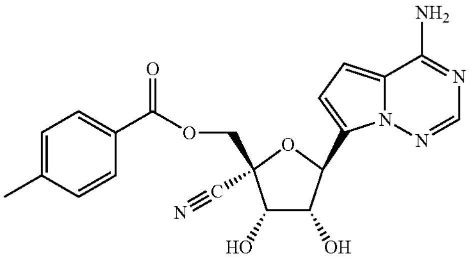 [SMILES: Cc1ccc(C(=O)OC[C@@]2(C#N)O[C@@H](c3ccc4c(N)ncnn34)[C@H](O)[C@@H]2O)cc1] |
| 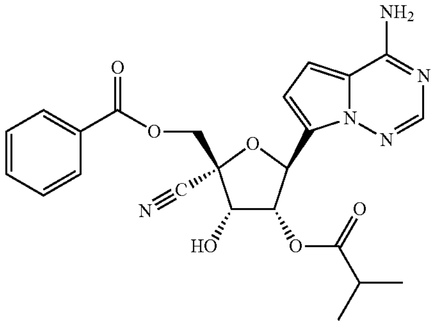 [SMILES: CC(C)C(=O)O[C@H]1[C@H](c2ccc3c(N)ncnn23)O[C@](C#N)(COC(=O)c2ccccc2)[C@H]1O] |
| 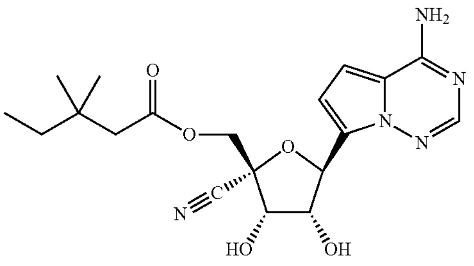 [SMILES: CCC(C)(C)CC(=O)OC[C@@]1(C#N)O[C@@H](c2ccc3c(N)ncnn23)[C@H](O)[C@@H]1O] |

TABLE 6-continued

| Some Compounds of Formula VI |
|---|
| 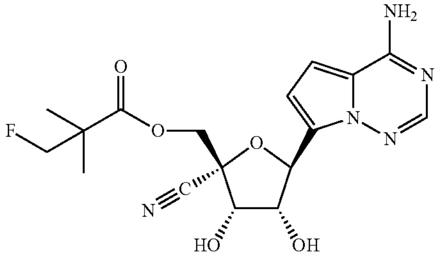 [SMILES: CC(C)(CF)C(=O)OC[C@@]1(C#N)O[C@@H](c2ccc3c(N)ncnn23)[C@H](O)[C@@H]1O] |
| 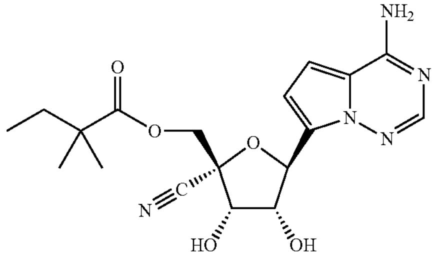 [SMILES: CCC(C)(C)C(=O)OC[C@@]1(C#N)O[C@@H](c2ccc3c(N)ncnn23)[C@H](O)[C@@H]1O] |
| 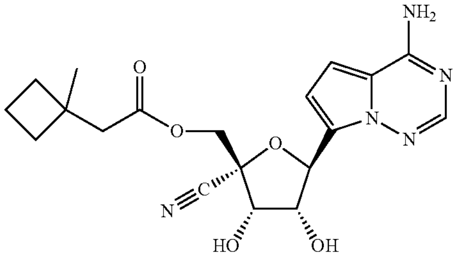 [SMILES: CC1(CC(=O)OC[C@@]2(C#N)O[C@@H](c3ccc4c(N)ncnn34)[C@H](O)[C@@H]2O)CCC1] |
| 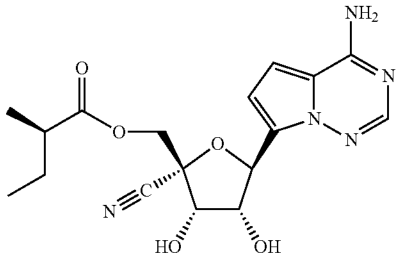 [SMILES: CC[C@@H](C)C(=O)OC[C@@]1(C#N)O[C@@H](c2ccc3c(N)ncnn23)[C@H](O)[C@@H]1O] |
| 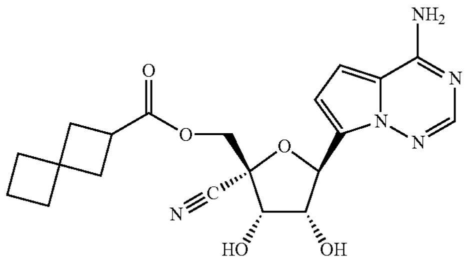 [SMILES: N#C[C@]1(COC(=O)C2CC3(CCC3)C2)O[C@@H](c2ccc3c(N)ncnn23)[C@H](O)[C@@H]1O] |
| 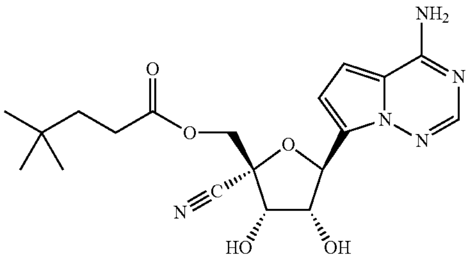 [SMILES: CC(C)(C)CCC(=O)OC[C@@]1(C#N)O[C@@H](c2ccc3c(N)ncnn23)[C@H](O)[C@@H]1O] |

TABLE 6-continued

| Some Compounds of Formula VI |
|---|
| 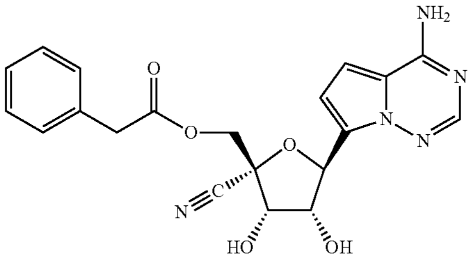 [SMILES: N#C[C@]1(COC(=O)Cc2ccccc2)O[C@@H](c2ccc3c(N)ncnn23)[C@H](O)[C@@H]1O] |

In some embodiments, the compound of Formula I has a Formula VII:

Formula VII

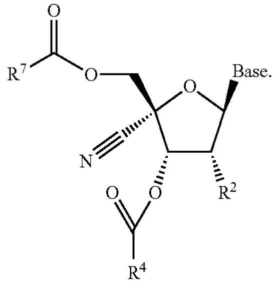

The compounds and pharmaceutically acceptable salts of Formula VII are disclosed herein and the description of the substituents and compounds of Formula I apply to Formula VII as relevant.

In some embodiments, the compounds and pharmaceutically acceptable salts of Formula VII include the compounds in Table 7 and the pharmaceutically acceptable salts thereof.

TABLE 7

| Some Compounds of Formula VII |
|---|
| 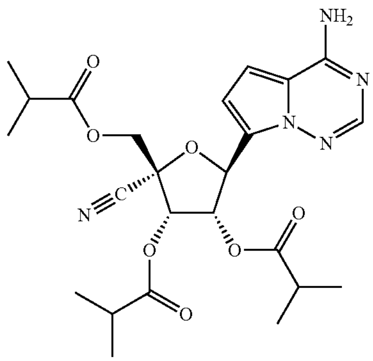 [SMILES: CC(C)C(=O)OC[C@@]1(C#N)O[C@@H](c2ccc3c(N)ncnn23)[C@H](OC(=O)C(C)C)[C@@H]1OC(=O)C(C)C] |

TABLE 7-continued

| Some Compounds of Formula VII |
| --- |
| 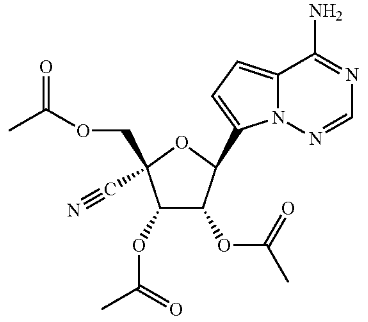 [SMILES: CC(=O)OC[C@@]1(C#N)O[C@@H](c2ccc3c(N)ncnn23)[C@H](OC(C)=O)[C@@H]1OC(C)=O] |
| 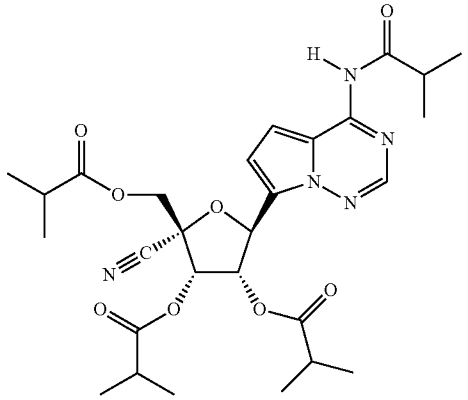 [SMILES: CC(C)C(=O)Nc1ncnn2c([C@@H]3O[C@](C#N)(COC(=O)C(C)C)[C@@H](OC(=O)C(C)C)[C@H]3OC(=O)C(C)C)ccc12] |

In some embodiments, the compound of Formula I has a Formula VIII:

Formula VIII

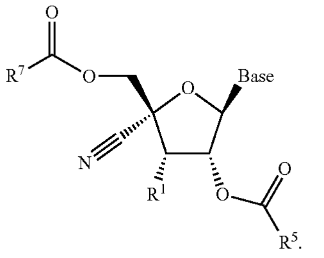

The compounds and pharmaceutically acceptable salts of Formula VIII are disclosed herein and the description of the substituents and compounds of Formula I apply to Formula VIII as relevant.

In some embodiments, the compounds and pharmaceutically acceptable salts of Formula VIII include the compounds in Table 8 and the pharmaceutically acceptable salts thereof.

TABLE 8

| Some Compounds of Formula VIII |
| --- |
| 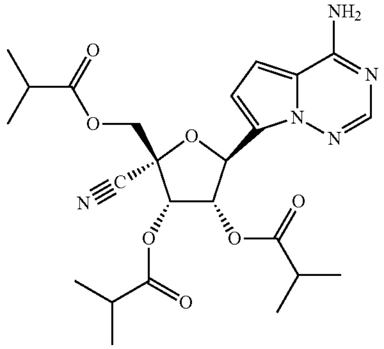 [SMILES: CC(C)C(=O)OC[C@@]1(CN)O[C@@H](c2ccc3c(N)ncnn23)[C@H](OC(=O)C(C)C)[C@@H]1OC(=O)C(C)C] |
| 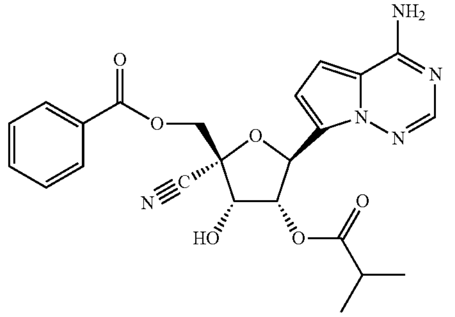 [SMILES: CC(C)C(=O)O[C@H]1[C@H](c2ccc3c(N)ncnn23)O[C@](CN)(COC(=O)c2ccccc2)[C@H]1O] |
| 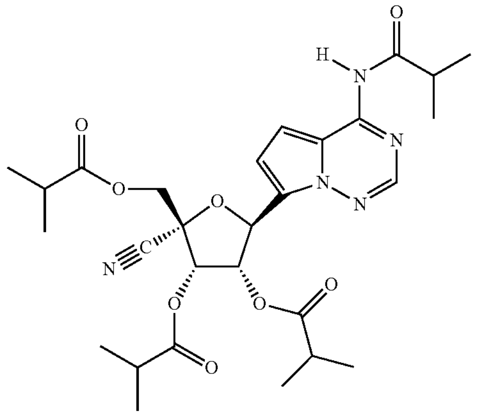 [SMILES: CC(C)C(=O)Nc1ncnn2c([C@@H]3O[C@](CN)(COC(=O)C(C)C)[C@@H](OC(=O)C(C)C)[C@H]3OC(=O)C(C)C)ccc12] |
| 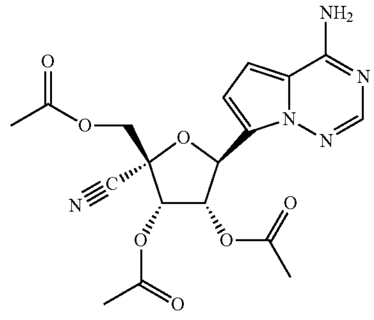 [SMILES: CC(=O)OC[C@@]1(CN)O[C@@H](c2ccc3c(N)ncnn23)[C@H](OC(C)=O)[C@@H]1OC(C)=O] |

In some embodiments, the compound of Formula I, VII, or VIII has a Formula IX:

Formula IX

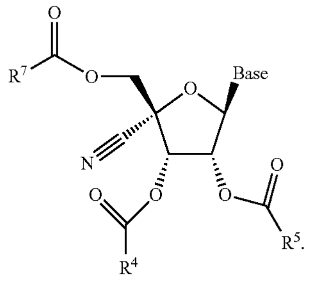

The compounds and pharmaceutically acceptable salts of Formula IX are disclosed herein and the description of the substituents and compounds of Formula I apply to Formula IX as relevant.

In some embodiments, the compounds and pharmaceutically acceptable salts of Formula IX include the compounds in Table 9 and the pharmaceutically acceptable salts thereof.

TABLE 9

| Some Compounds of Formula IX |
|---|
| 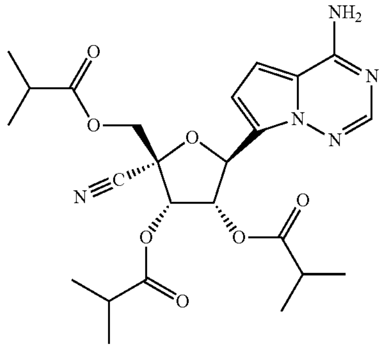 [SMILES: CC(C)C(=O)OC[C@@]1(C#N)O[C@@H](c2ccc3c(N)ncnn23)[C@H](OC(=O)C(C)C)[C@@H]1OC(=O)C(C)C] |
| 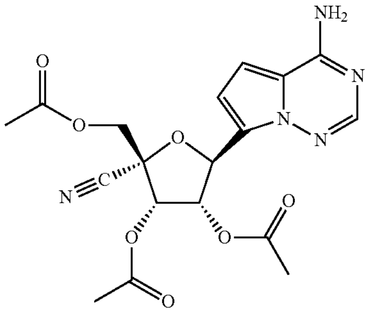 [SMILES: CC(=O)OC[C@@]1(C#N)O[C@@H](c2ccc3c(N)ncnn23)[C@H](OC(C)=O)[C@@H]1OC(C)=O] |

TABLE 9-continued

| Some Compounds of Formula IX |
|---|
| 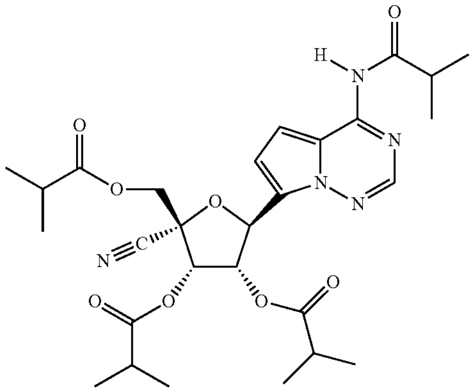 [SMILES: CC(C)C(=O)Nc1ncnn2c([C@@H]3O[C@](C#N)(COC(=O)C(C)C)[C@@H](OC(=O)C(C)C)[C@H]3OC(=O)C(C)C)ccc12] |

In some embodiments, the compound of Formula I has a Formula X:

Formula X

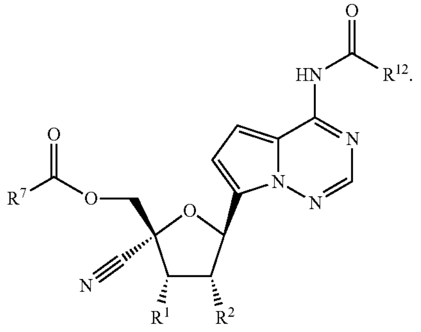

The compounds and pharmaceutically acceptable salts of Formula X are disclosed herein and the description of the substituents and compounds of Formula I apply to Formula X as relevant. In some embodiments, the compounds and pharmaceutically acceptable salts of Formula X include the compounds in Table 10 and the pharmaceutically acceptable salts thereof.

TABLE 10

| Some Compounds of Formula X |
|---|
| 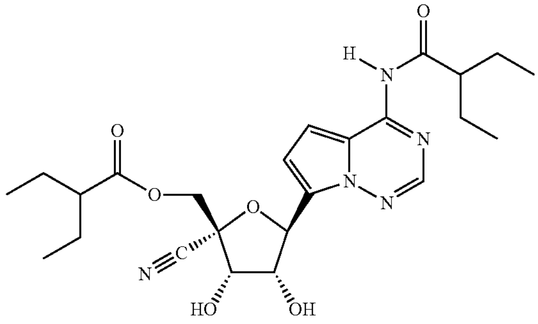 [SMILES: CCC(CC)C(=O)Nc1ncnn2c([C@@H]3O[C@](C#N)(COC(=O)C(CC)CC)[C@@H](O)[C@H]3O)ccc12] |

TABLE 10-continued

| Some Compounds of Formula X |
| --- |
| 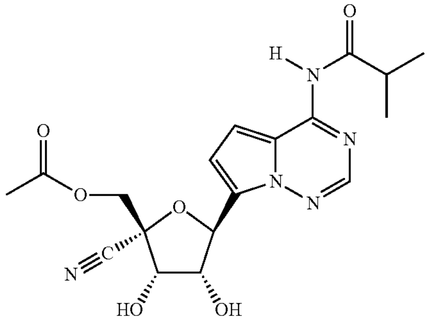 [SMILES: CC(=O)OC[C@@]1(C#N)O[C@@H](c2ccc3c(NC(=O)C(C)C)ncnn23)[C@H](O)[C@@H]1O] |
| 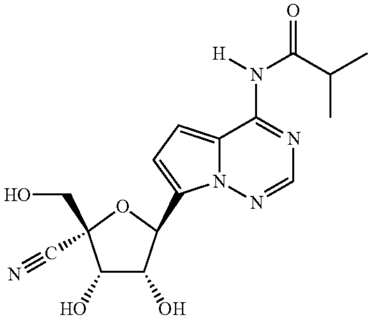 [SMILES: CC(C)C(=O)Nc1ncnn2c([C@@H]3O[C@](C#N)(CO)[C@@H](O)[C@H]3O)ccc12] |
| 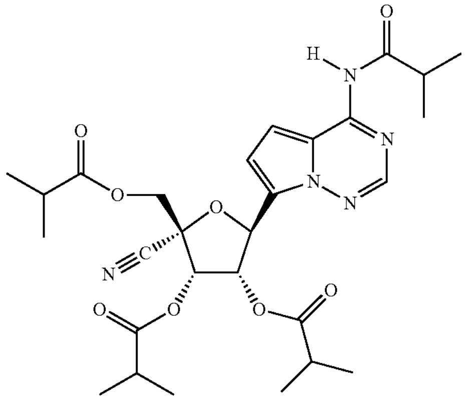 [SMILES: CC(C)C(=O)Nc1ncnn2c([C@@H]3O[C@](C#N)(COC(=O)C(C)C)[C@@H](OC(=O)C(C)C)[C@H]3OC(=O)C(C)C)ccc12] |
| 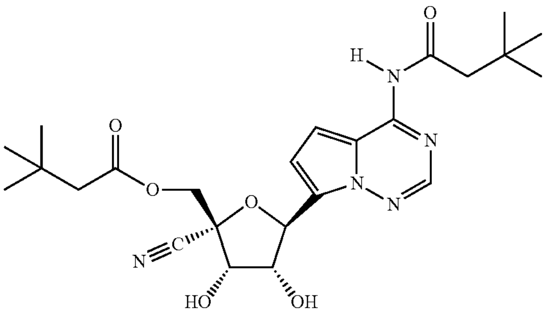 [SMILES: CC(C)(C)CC(=O)Nc1ncnn2c([C@@H]3O[C@](C#N)(COC(=O)CC(C)(C)C)[C@@H](O)[C@H]3O)ccc12] |

In some embodiments, the compound of Formula I has a Formula XI:

Formula XI

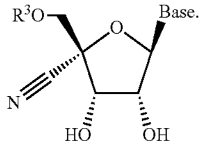

The compounds and pharmaceutically acceptable salts of Formula XI are disclosed herein and the description of the substituents and compounds of Formula I apply to Formula XI as relevant.

In some embodiments, the compounds and pharmaceutically acceptable salts of Formula XI include the compounds in Table 11 and the pharmaceutically acceptable salts thereof.

TABLE 11

| Some Compounds of Formula XI |
| --- |
| 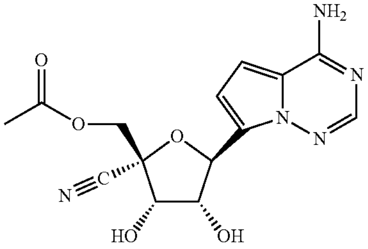 [SMILES: CC(=O)OC[C@@]1(C#N)O[C@@H](c2ccc3c(N)ncnn23)[C@H](O)[C@@H]1O] |
| 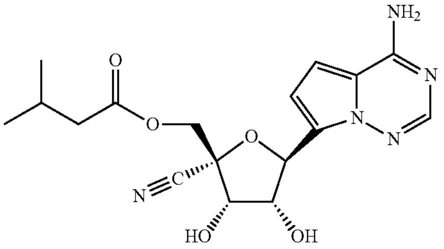 [SMILES: CC(C)CC(=O)OC[C@@]1(C#N)O[C@@H](c2ccc3c(N)ncnn23)[C@H](O)[C@@H]1O] |
| 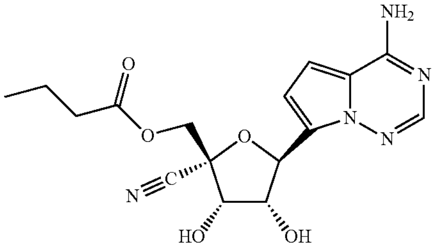 [SMILES: CCCC(=O)OC[C@@]1(C#N)O[C@@H](c2ccc3c(N)ncnn23)[C@H](O)[C@@H]1O] |
| 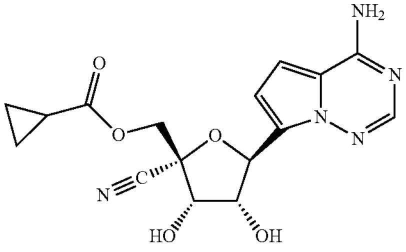 [SMILES: N#C[C@]1(COC(=O)C2CC2)O[C@@H](c2ccc3c(N)ncnn23)[C@H](O)[C@@H]1O] |

TABLE 11-continued
| Some Compounds of Formula XI |
| --- |
| 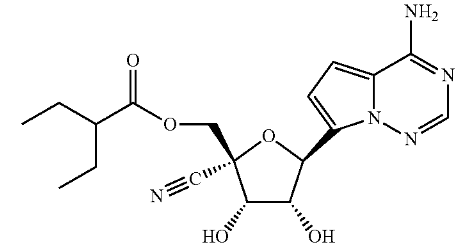 [SMILES: CCC(CC)C(=O)OC[C@@]1(C#N)O[C@@H](c2ccc3c(N)ncnn23)[C@H](O)[C@@H]1O] |
| 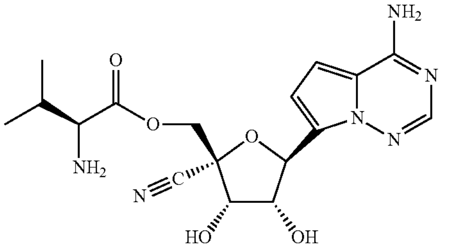 [SMILES: CC(C)[C@H](N)C(=O)OC[C@@]1(C#N)O[C@@H](c2ccc3c(N)ncnn23)[C@H](O)[C@@H]1O] |
| 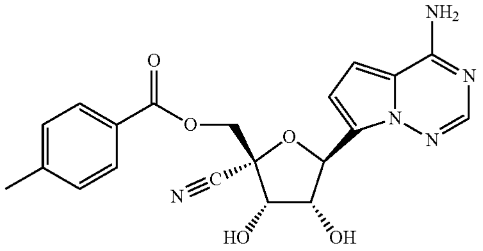 [SMILES: Cc1ccc(C(=O)OC[C@@]2(C#N)O[C@@H](c3ccc4c(N)ncnn34)[C@H](O)[C@@H]2O)cc1] |
| 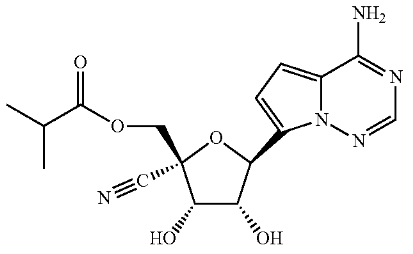 [SMILES: CC(C)C(=O)OC[C@@]1(C#N)O[C@@H](c2ccc3c(N)ncnn23)[C@H](O)[C@@H]1O] |
| 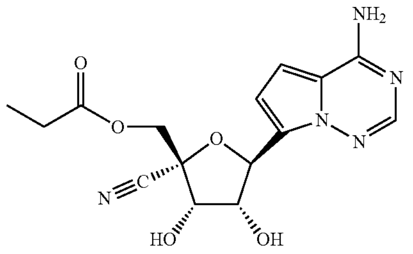 [SMILES: CCC(=O)OC[C@@]1(C#N)O[C@@H](c2ccc3c(N)ncnn23)[C@H](O)[C@@H]1O] |
| 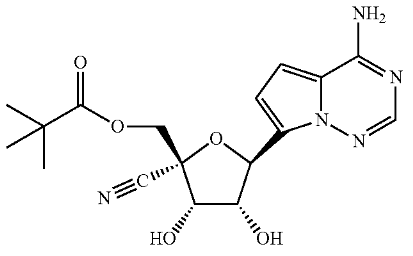 [SMILES: CC(C)(C)C(=O)OC[C@@]1(C#N)O[C@@H](c2ccc3c(N)ncnn23)[C@H](O)[C@@H]1O] |
TABLE 11-continued
| Some Compounds of Formula XI |
| --- |
| 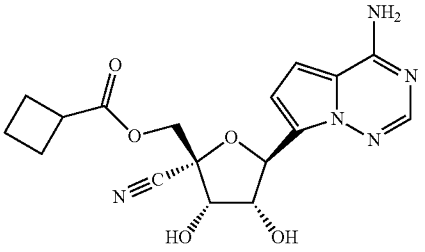 [SMILES: N#C[C@]1(COC(=O)C2CCC2)O[C@@H](c2ccc3c(N)ncnn23)[C@H](O)[C@@H]1O] |
| 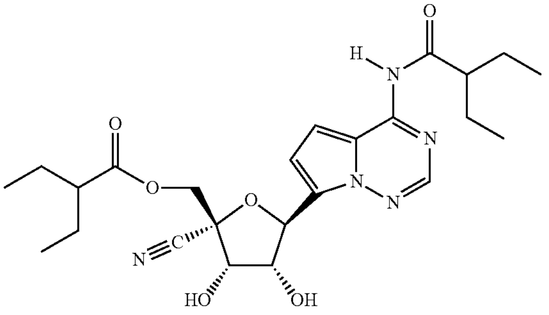 [SMILES: CCC(CC)C(=O)Nc1ncnn2c([C@@H]3O[C@](C#N)(COC(=O)C(CC)CC)[C@@H](O)[C@H]3O)ccc12] |
| 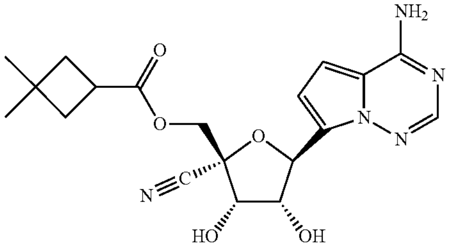 [SMILES: CC1(C)CC(C(=O)OC[C@@]2(C#N)O[C@@H](c3ccc4c(N)ncnn34)[C@H](O)[C@@H]2O)C1] |
| 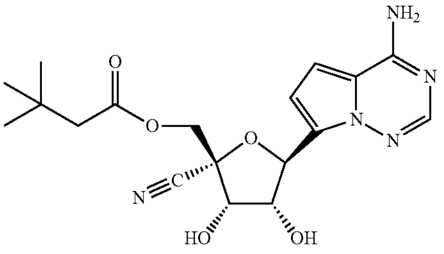 [SMILES: CC(C)(C)CC(=O)OC[C@@]1(C#N)O[C@@H](c2ccc3c(N)ncnn23)[C@H](O)[C@@H]1O] |
| 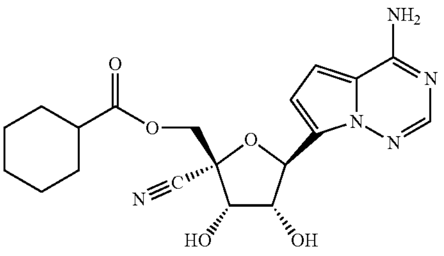 [SMILES: N#C[C@]1(COC(=O)C2CCCCC2)O[C@@H](c2ccc3c(N)ncnn23)[C@H](O)[C@@H]1O] |
| 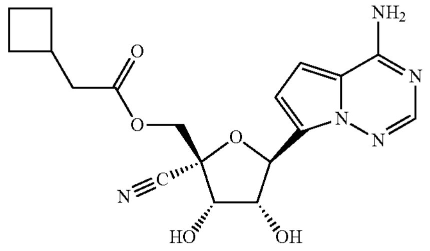 [SMILES: N#C[C@]1(COC(=O)CC2CCC2)O[C@@H](c2ccc3c(N)ncnn23)[C@H](O)[C@@H]1O] |

TABLE 11-continued
Some Compounds of Formula XI
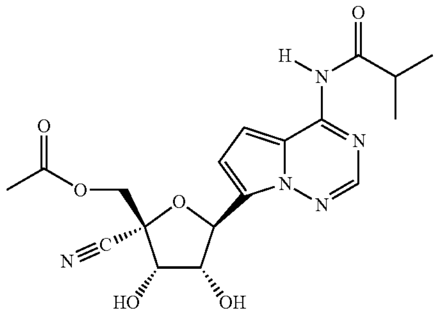 [SMILES: CC(=O)OC[C@@]1(C#N)O[C@@H](c2ccc3c(NC(=O)C(C)C)ncnn23)[C@H](O)[C@@H]1O]
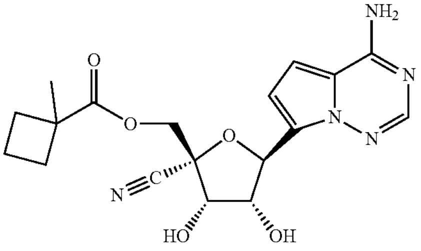 [SMILES: CC1(C(=O)OC[C@@]2(C#N)O[C@@H](c3ccc4c(N)ncnn34)[C@H](O)[C@@H]2O)CCC1]
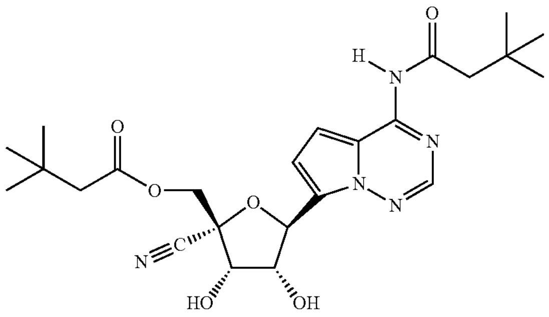 [SMILES: CC(C)(C)CC(=O)Nc1ncnn2c([C@@H]3O[C@](C#N)(COC(=O)CC(C)(C)C)[C@@H](O)[C@H]3O)ccc12]
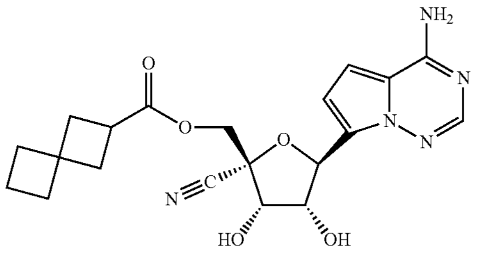 [SMILES: N#C[C@]1(COC(=O)C2CC3(CCC3)C2)O[C@@H](c2ccc3c(N)ncnn23)[C@H](O)[C@@H]1O]
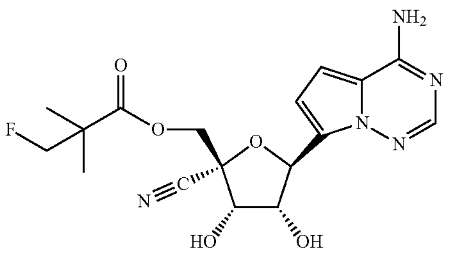 [SMILES: CC(C)(CF)C(=O)OC[C@@]1(C#N)O[C@@H](c2ccc3c(N)ncnn23)[C@H](O)[C@@H]1O]
TABLE 11-continued
Some Compounds of Formula XI
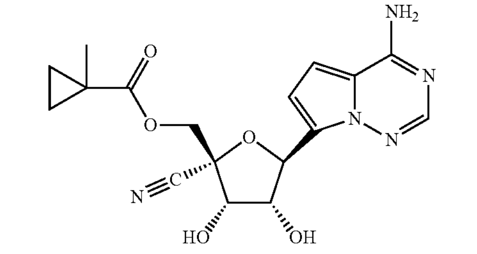 [SMILES: CC1(C(=O)OC[C@@]2(C#N)O[C@@H](c3ccc4c(N)ncnn34)[C@H](O)[C@@H]2O)CC1]
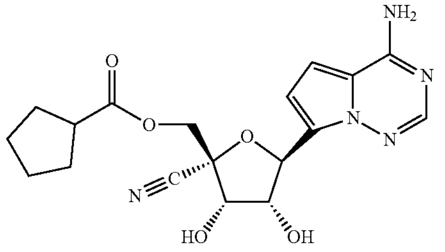 [SMILES: N#C[C@]1(COC(=O)C2CCCC2)O[C@@H](c2ccc3c(N)ncnn23)[C@H](O)[C@@H]1O]
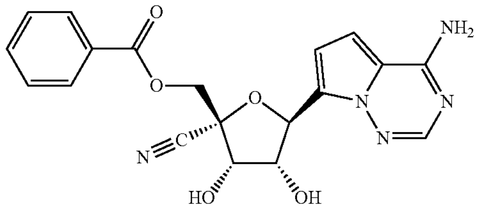 [SMILES: N#C[C@]1(COC(=O)c2ccccc2)O[C@@H](c2ccc3c(N)ncnn23)[C@H](O)[C@@H]1O]
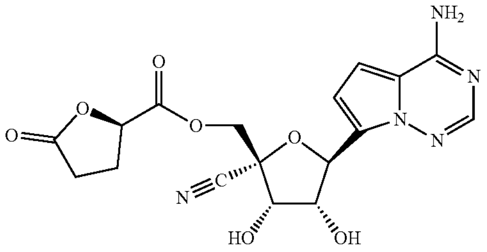 [SMILES: N#C[C@]1(COC(=O)[C@H]2CCC(=O)O2)O[C@@H](c2ccc3c(N)ncnn23)[C@H](O)[C@@H]1O]
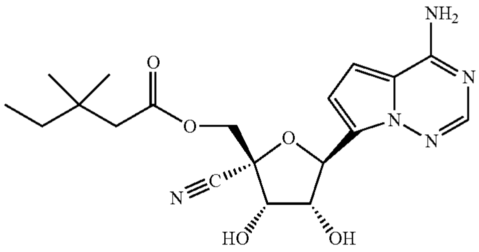 [SMILES: CCC(C)(C)CC(=O)OC[C@@]1(C#N)O[C@@H](c2ccc3c(N)ncnn23)[C@H](O)[C@@H]1O]
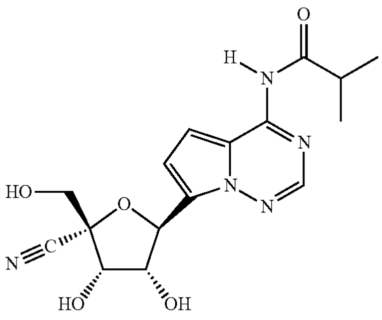 [SMILES: CC(C)C(=O)Nc1ncnn2c([C@@H]3O[C@](C#N)(CO)[C@@H](O)[C@H]3O)ccc12]

TABLE 11-continued

| Some Compounds of Formula XI |
|---|
| 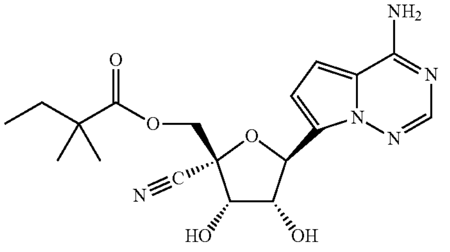 [SMILES: CCC(C)(C)C(=O)OC[C@@]1(C#N)O[C@@H](c2ccc3c(N)ncnn23)[C@H](O)[C@@H]1O] |
| 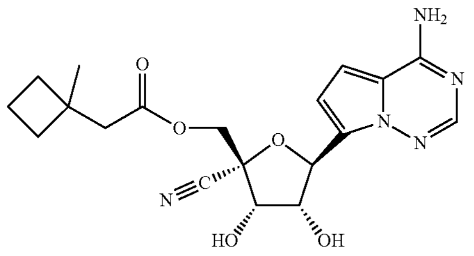 [SMILES: CC1(CC(=O)OC[C@@]2(C#N)O[C@@H](c3ccc4c(N)ncnn34)[C@H](O)[C@@H]2O)CCC1] |
| 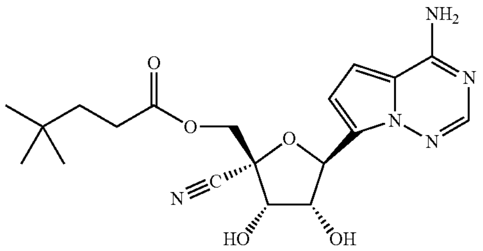 [SMILES: CC(C)(C)CCC(=O)OC[C@@]1(C#N)O[C@@H](c2ccc3c(N)ncnn23)[C@H](O)[C@@H]1O] |
| 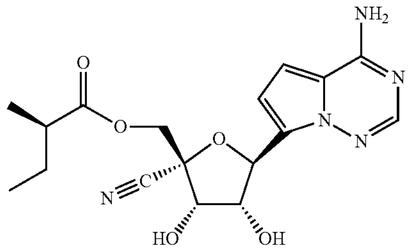 [SMILES: CC[C@@H](C)C(=O)OC[C@@]1(C#N)O[C@@H](c2ccc3c(N)ncnn23)[C@H](O)[C@@H]1O] |
| 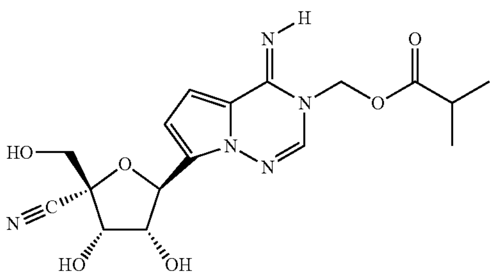 [SMILES: [H]/N=c1/c2ccc([C@@H]3O[C@](C#N)(CO)[C@@H](O)[C@H]3O)n2ncn1COC(=O)C(C)C] |
| 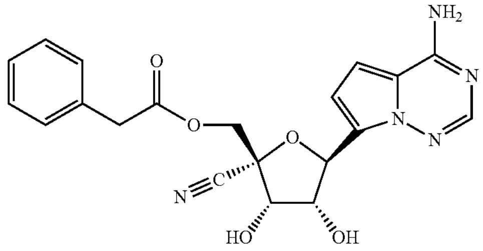 [SMILES: N#C[C@]1(COC(=O)Cc2ccccc2)O[C@@H](c2ccc3c(N)ncnn23)[C@H](O)[C@@H]1O] |

One of skill in the art is aware that each and every embodiment of a group (e.g., $R^1$) disclosed herein may be combined with any other embodiment of each of the remaining groups (e.g., $R^2$, $R^3$, etc.) to generate a complete compound of Formula (I), (II), (III), (IV), (V), (VI), (VII), (VIII), (IX), (X), or (XI), or any Formula described herein or a pharmaceutically acceptable salt, stereoisomer, mixture of stereoisomers, or tautomer thereof, each of which is deemed within the ambit of the present disclosure.

In some embodiments, the compounds and pharmaceutically acceptable salts of Formula I include the compounds in Table 1, or the pharmaceutically acceptable salts thereof. In some embodiments, the compounds disclosed herein include compounds in Table 1 IA, or the pharmaceutically acceptable salts thereof.

TABLE 11A

| Some compounds disclosed herein | |
|---|---|
| COMPOUND # | STRUCTURE |
| 1 | 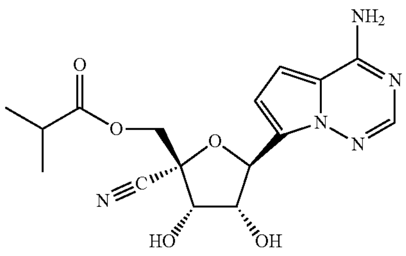 [SMILES: CC(C)C(=O)OC[C@@]1(C#N)O[C@@H](c2ccc3c(N)ncnn23)[C@H](O)[C@@H]1O] |

TABLE 11A-continued
| Some compounds disclosed herein | |
|---|---|
| COMPOUND # | STRUCTURE |
| 2 | 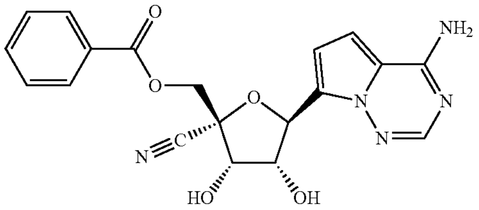 [SMILES: N#C[C@]1(COC(=O)c2ccccc2)O[C@@H](c2ccc3c(N)ncnn23)[C@H](O)[C@@H]1O] |
| 3 | 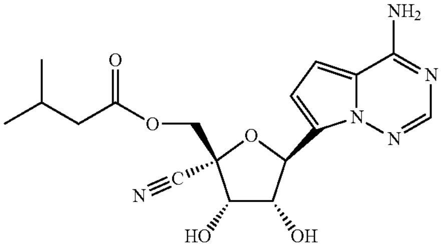 [SMILES: CC(C)CC(=O)OC[C@@]1(C#N)O[C@@H](c2ccc3c(N)ncnn23)[C@H](O)[C@@H]1O] |
| 4 | 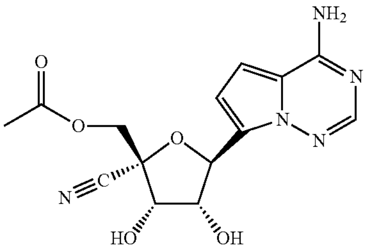 [SMILES: CC(=O)OC[C@@]1(C#N)O[C@@H](c2ccc3c(N)ncnn23)[C@H](O)[C@@H]1O] |
| 5 | 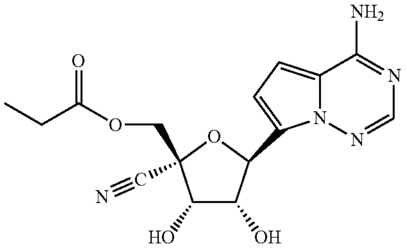 [SMILES: CCC(=O)OC[C@@]1(C#N)O[C@@H](c2ccc3c(N)ncnn23)[C@H](O)[C@@H]1O] |
| 6 | 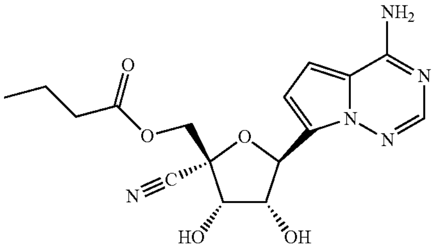 [SMILES: CCCC(=O)OC[C@@]1(C#N)O[C@@H](c2ccc3c(N)ncnn23)[C@H](O)[C@@H]1O] |
| 7 | 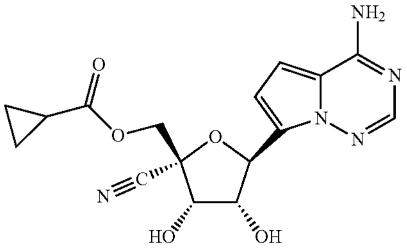 [SMILES: N#C[C@]1(COC(=O)C2CC2)O[C@@H](c2ccc3c(N)ncnn23)[C@H](O)[C@@H]1O] |

TABLE 11A-continued
| Some compounds disclosed herein | |
|---|---|
| COMPOUND # | STRUCTURE |
| 8 | 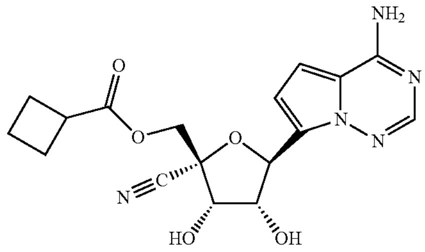 [SMILES: N#C[C@]1(COC(=O)C2CCC2)O[C@@H](c2ccc3c(N)ncnn23)[C@H](O)[C@@H]1O] |
| 9 | 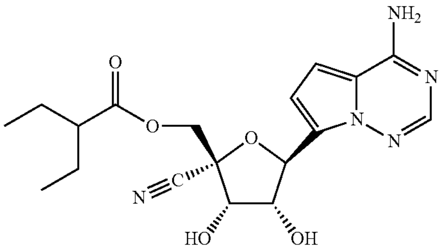 [SMILES: CCC(CC)C(=O)OC[C@@]1(C#N)O[C@@H](c2ccc3c(N)ncnn23)[C@H](O)[C@@H]1O] |
| 10 | 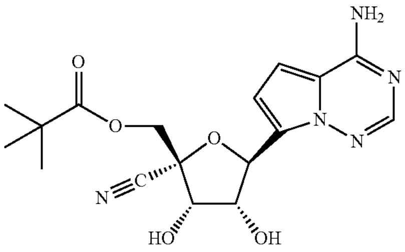 [SMILES: CC(C)(C)C(=O)OC[C@@]1(C#N)O[C@@H](c2ccc3c(N)ncnn23)[C@H](O)[C@@H]1O] |
| 11 | 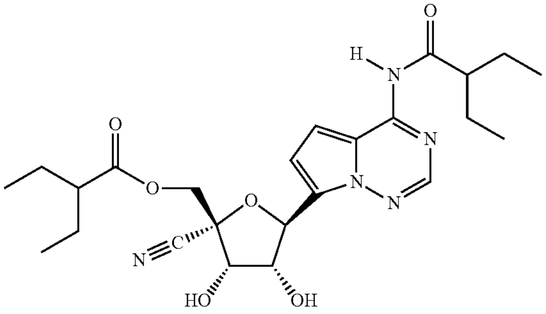 [SMILES: CCC(CC)C(=O)Nc1ncnn2c([C@@H]3O[C@](C#N)(COC(=O)C(CC)CC)[C@@H](O)[C@H]3O)ccc12] |
| 12 | 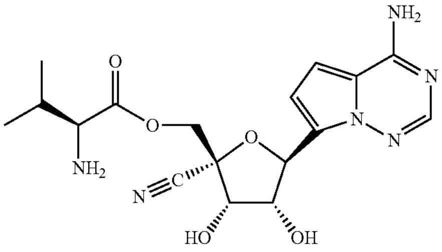 [SMILES: CC(C)[C@H](N)C(=O)OC[C@@]1(C#N)O[C@@H](c2ccc3c(N)ncnn23)[C@H](O)[C@@H]1O] |

TABLE 11A-continued
| Some compounds disclosed herein | |
|---|---|
| COMPOUND # | STRUCTURE |
| 13 | 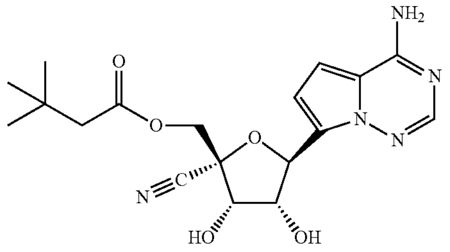 [SMILES: CC(C)(C)CC(=O)OC[C@@]1(C#N)O[C@@H](c2ccc3c(N)ncnn23)[C@H](O)[C@@H]1O] |
| 14 | 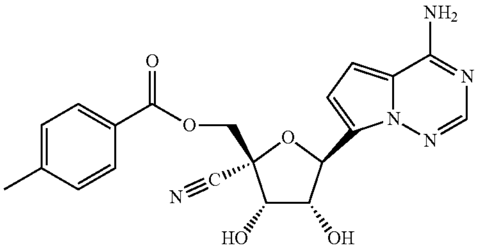 [SMILES: Cc1ccc(C(=O)OC[C@@]2(C#N)O[C@@H](c3ccc4c(N)ncnn34)[C@H](O)[C@@H]2O)cc1] |
| 15 | 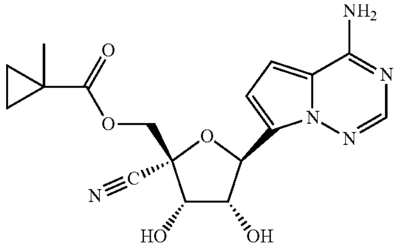 [SMILES: CC1(C(=O)OC[C@@]2(C#N)O[C@@H](c3ccc4c(N)ncnn34)[C@H](O)[C@@H]2O)CC1] |
| 16 | 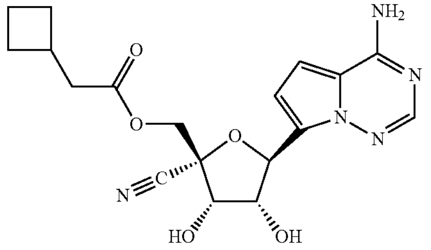 [SMILES: N#C[C@]1(COC(=O)CC2CCC2)O[C@@H](c2ccc3c(N)ncnn23)[C@H](O)[C@@H]1O] |
| 17 | 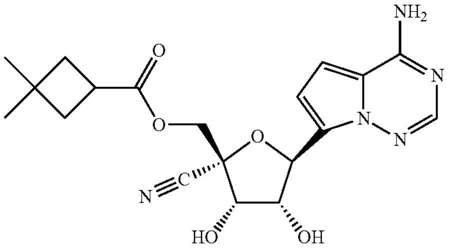 [SMILES: CC1(C)CC(C(=O)OC[C@@]2(C#N)O[C@@H](c3ccc4c(N)ncnn34)[C@H](O)[C@@H]2O)C1] |
| 18 | 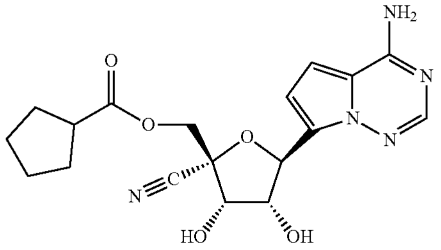 [SMILES: N#C[C@]1(COC(=O)C2CCCC2)O[C@@H](c2ccc3c(N)ncnn23)[C@H](O)[C@@H]1O] |

TABLE 11A-continued
| Some compounds disclosed herein | |
|---|---|
| COMPOUND # | STRUCTURE |
| 19 | 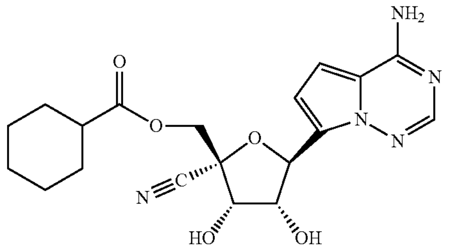 [SMILES: N#C[C@]1(COC(=O)C2CCCCC2)O[C@@H](c2ccc3c(N)ncnn23)[C@H](O)[C@@H]1O] |
| 20 | 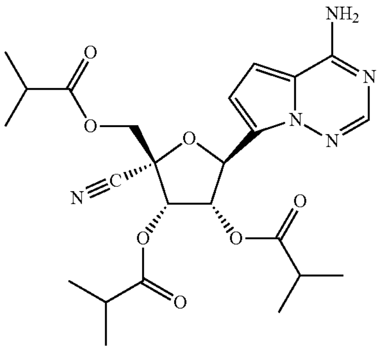 [SMILES: CC(C)C(=O)OC[C@@]1(C#N)O[C@@H](c2ccc3c(N)ncnn23)[C@H](OC(=O)C(C)C)[C@@H]1OC(=O)C(C)C] |
| 21 | 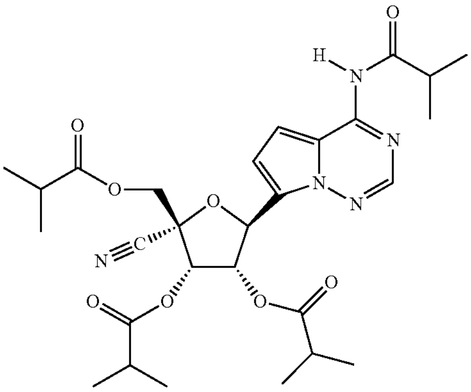 [SMILES: CC(C)C(=O)Nc1ncnn2c([C@@H]3O[C@](C#N)(COC(=O)C(C)C)[C@@H](OC(=O)C(C)C)[C@H]3OC(=O)C(C)C)ccc12] |
| 22 | 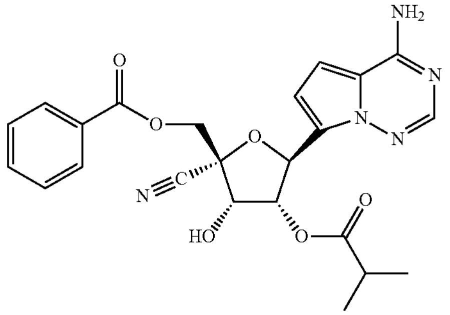 [SMILES: CC(C)C(=O)O[C@H]1[C@H](c2ccc3c(N)ncnn23)O[C@](C#N)(COC(=O)c2ccccc2)[C@H]1O] |

TABLE 11A-continued
| Some compounds disclosed herein | |
|---|---|
| COMPOUND # | STRUCTURE |
| 23 | 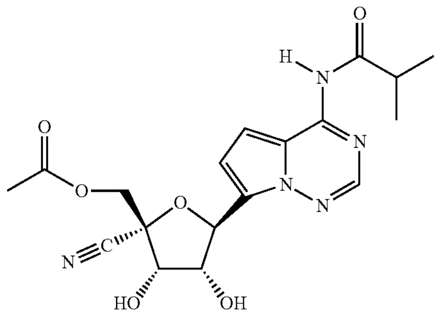 [SMILES: CC(=O)OC[C@@]1(C#N)O[C@@H](c2ccc3c(NC(=O)C(C)C)ncnn23)[C@H](O)[C@@H]1O] |
| 24 | 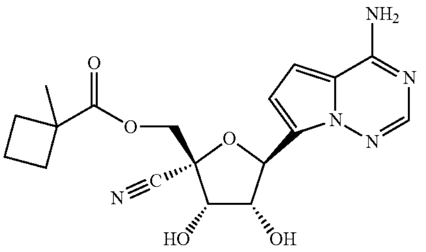 [SMILES: CC1(C(=O)OC[C@@]2(C#N)O[C@@H](c3ccc4c(N)ncnn34)[C@H](O)[C@@H]2O)CCC1] |
| 25 | 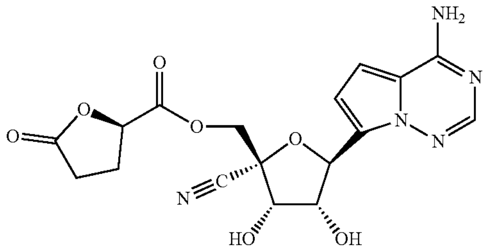 [SMILES: N#C[C@]1(COC(=O)[C@H]2CCC(=O)O2)O[C@@H](c2ccc3c(N)ncnn23)[C@H](O)[C@@H]1O] |
| 26 | 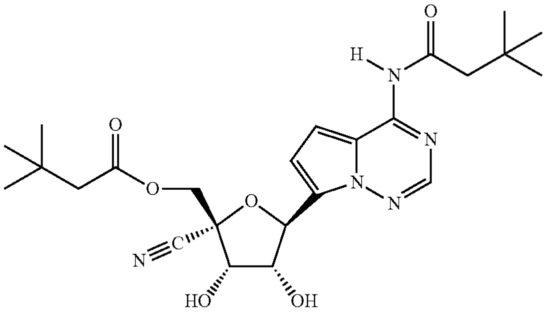 [SMILES: CC(C)(C)CC(=O)Nc1ncnn2c([C@@H]3O[C@](C#N)(COC(=O)CC(C)(C)C)[C@@H](O)[C@H]3O)ccc12] |
| 27 | 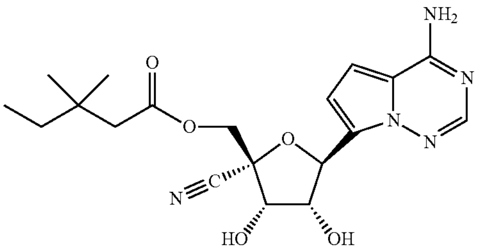 [SMILES: CCC(C)(C)CC(=O)OC[C@@]1(C#N)O[C@@H](c2ccc3c(N)ncnn23)[C@H](O)[C@@H]1O] |

TABLE 11A-continued
| Some compounds disclosed herein | |
|---|---|
| COMPOUND # | STRUCTURE |
| 28 | 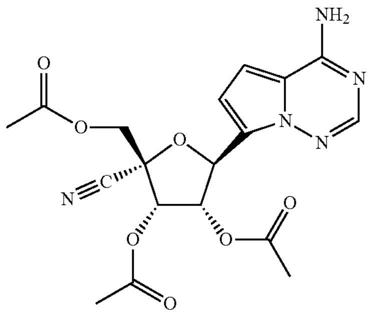 [SMILES: CC(=O)OC[C@@]1(C#N)O[C@@H](c2ccc3c(N)ncnn23)[C@H](OC(C)=O)[C@@H]1OC(C)=O] |
| 29 | 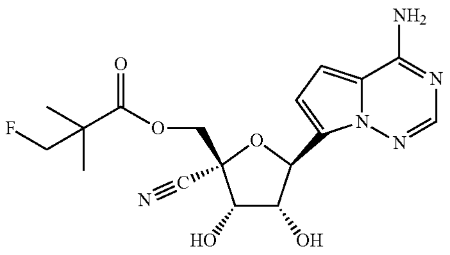 [SMILES: CC(C)(CF)C(=O)OC[C@@]1(C#N)O[C@@H](c2ccc3c(N)ncnn23)[C@H](O)[C@@H]1O] |
| 30 | 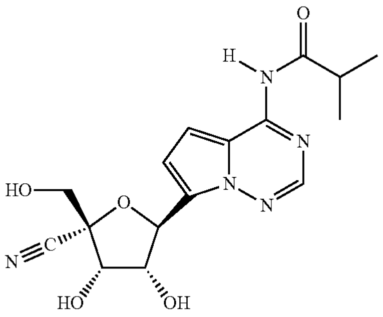 [SMILES: CC(C)C(=O)Nc1ncnn2c([C@@H]3O[C@](C#N)(CO)[C@@H](O)[C@H]3O)ccc12] |
| 31 | 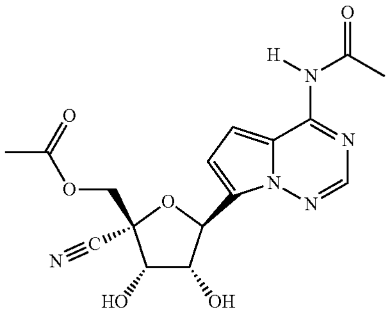 [SMILES: CC(=O)Nc1ncnn2c([C@@H]3O[C@](C#N)(COC(C)=O)[C@@H](O)[C@H]3O)ccc12] |
| 32 | 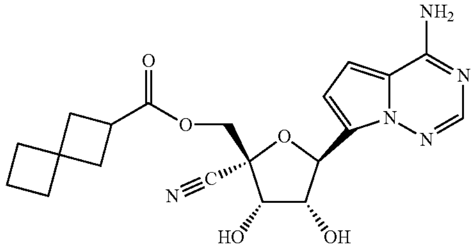 [SMILES: N#C[C@]1(COC(=O)C2CC3(CCC3)C2)O[C@@H](c2ccc3c(N)ncnn23)[C@H](O)[C@@H]1O] |

TABLE 11A-continued
| Some compounds disclosed herein | |
|---|---|
| COMPOUND # | STRUCTURE |
| 33 | 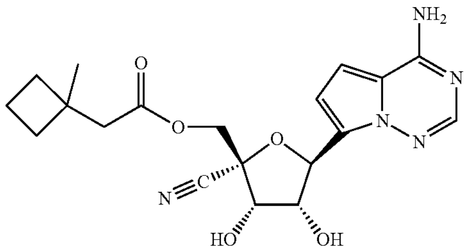 [SMILES: CC1(CC(=O)OC[C@@]2(C#N)O[C@@H](c3ccc4c(N)ncnn34)[C@H](O)[C@@H]2O)CCC1] |
| 34 | 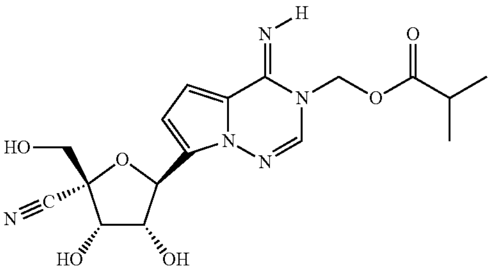 [SMILES: [H]/N=c1/c2ccc([C@@H]3O[C@](C#N)(CO)[C@@H](O)[C@H]3O)n2ncn1COC(=O)C(C)C] |
| 35 | 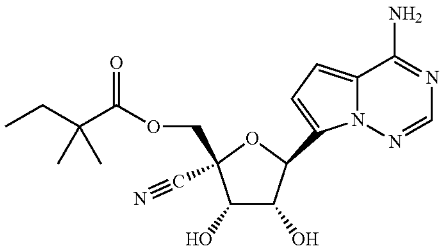 [SMILES: CCC(C)(C)C(=O)OC[C@@]1(C#N)O[C@@H](c2ccc3c(N)ncnn23)[C@H](O)[C@@H]1O] |
| 36 | 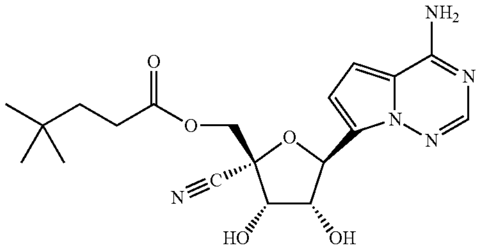 [SMILES: CC(C)(C)CCC(=O)OC[C@@]1(C#N)O[C@@H](c2ccc3c(N)ncnn23)[C@H](O)[C@@H]1O] |
| 37 | 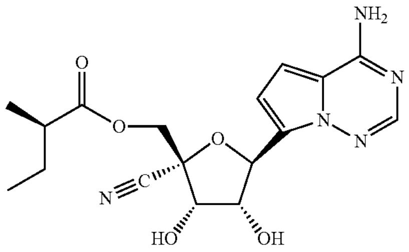 [SMILES: CC[C@@H](C)C(=O)OC[C@@]1(C#N)O[C@@H](c2ccc3c(N)ncnn23)[C@H](O)[C@@H]1O] |
| 38 | 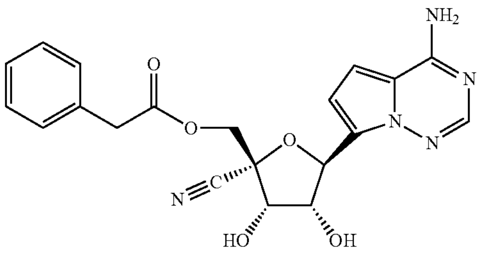 [SMILES: N#C[C@]1(COC(=O)Cc2ccccc2)O[C@@H](c2ccc3c(N)ncnn23)[C@H](O)[C@@H]1O] |

Also falling within the scope herein are the in vivo metabolic products of the compounds described herein. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabelled (e.g., $^{14}C$ or $^{3}H$) compound, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies. The conversion products, so long as they are not otherwise found in vivo, are useful in diagnostic assays for therapeutic dosing of the compounds even if they possess no HSV antiviral activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug (i.e., Compound 0 below) after overcoming biological barriers to oral delivery.

IV. Pharmaceutical Compositions

Also disclosed herein are pharmaceutical compositions comprising a pharmaceutically effective amount of a compound of the present disclosure (e.g., a compound of Formulas I to Formula XI), or a pharmaceutically acceptable salt thereof, and a pharmaceutically acceptable carrier or excipient. Also provided herein is a pharmaceutical composition comprising a pharmaceutically effective amount of a compound of the present disclosure, or a pharmaceutically acceptable salt thereof, and a pharmaceutically acceptable carrier or excipient.

The compounds disclosed herein can be formulated with conventional carriers and excipients. Tablets can contain, for instance, excipients, glidants, fillers, binders, or a combination thereof. Aqueous formulations are prepared in sterile form, and when intended for delivery by other than oral administration generally will be isotonic. Exemplary excipients include, but are not limited to, those set forth in the "HANDBOOK OF PHARMACEUTICAL EXCIPIENTS" (1986). Excipients can include, for example, ascorbic acid and other antioxidants, chelating agents such as EDTA, carbohydrates such as dextran, hydroxyalkylcellulose, hydroxyalkylmethylcellulose, stearic acid, and combinations thereof. In some embodiments, the formulation is basic. In some embodiments, the formulation is acidic. In some embodiments, the formulation has a neutral pH. In some embodiments, the pH of the formulations is from 2 to 11 (e.g., 2, 3, 4, 5, 6, 7, 8, 9, 10, 11, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 4-11, 5-6, 5-7, 5-8, 5-9, 5-10, 5-11, 6-7, 6-8, 6-9, 6-10, 6-11, 7-8, 7-9, 7-10, 7-11, 8-9, 8-10, 8-11, 9-10, or 9-11).

In some embodiments, the compounds disclosed herein have pharmacokinetic properties (e.g., oral bioavailability) suitable for oral administration of the compounds. Formulations suitable for oral administration can, for instance, be presented as discrete units such as capsules, cachets or tablets, each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient can also be administered, for instance, as a bolus, electuary, or paste.

A tablet can be made by compression or molding, optionally with one or more accessory ingredients. Compressed tablets can be prepared by compressing in a suitable machine the active ingredient in a free-flowing form such as, for instance, a powder or granules, optionally mixed with a binder, lubricant, inert diluent, preservative, surface active, dispersing agent, or a combination thereof. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

For infections of the eye or other external tissues (e.g., mouth and skin), the formulations can be applied as a topical ointment or cream containing the active ingredient(s) in an amount of, for example, 0.075 to 20% w/w (including active ingredient(s) in a range from 0.1% to 20% in increments of 0.1% w/w such as 0.6% w/w, 0.7% w/w, etc.), from 0.2% to 15% w/w, or from 0.5% to 10% w/w. When formulated in an ointment, the active ingredients can be employed in some embodiments with either a paraffinic or a water-miscible ointment base. Alternatively, the active ingredients can be formulated in a cream with an oil-in-water cream base.

In some embodiments, the aqueous phase of the cream base can include, for example, from 30% to 90% (e.g., 35%, 40%, 45%, 50%, 55%, 60%, 65%, 70%, 75%, 80%, 85%) w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. In some embodiments, the cream base can include, for instance, a compound that enhances absorption or penetration of the active ingredient through the skin or other affected areas. Examples of such dermal penetration enhancers include, but are not limited to, dimethyl sulfoxide and related analogs. In some embodiments, the cream or emulsion does not include water.

The oily phase of the emulsions can be constituted from known ingredients in a known manner. In some embodiments, the phase comprises merely an emulsifier (otherwise known as an emulgent). In some embodiments, the phase comprises a mixture of at least one emulsifier with a fat, an oil, or a combination thereof. In some embodiments, a hydrophilic emulsifier is included together with a lipophilic emulsifier that acts as a stabilizer. Together, the emulsifier(s) with or without stabilizer(s) can make up the so-called emulsifying wax, and the wax together with the oil and fat make up the so-called emulsifying ointment base that can form the oily dispersed phase of the cream formulations.

Emulgents and emulsion stabilizers suitable for use in the formulation can include, but are not limited to, TWEEN® 60, TWEEN® 80, SPAN® 80, cetostearyl alcohol, benzyl alcohol, myristyl alcohol, glyceryl mono-stearate, sodium lauryl sulfate, and combinations thereof.

The choice of suitable oils or fats for the formulation can be based on achieving the desired cosmetic properties. In some embodiments, the cream can be a non-greasy, non-staining, and washable product with suitable consistency to avoid leakage from tubes or other containers. In some embodiments, esters can be included, such as, for example, straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate, a blend of branched chain esters known as CRODAMOL® CAP, or a combination thereof. In some embodiments, high melting point lipids such as white soft paraffin and/or liquid paraffin or other mineral oils can be included.

In some embodiments, the compounds disclosed herein are administered alone. In some embodiments, the compounds disclosed herein are administered in pharmaceutical compositions. In some embodiments, the pharmaceutical compositions are for veterinary use. In some embodiments, the pharmaceutical compositions are for human use. In some embodiments, the pharmaceutical compositions disclosed herein include at least one additional therapeutic agent.

Pharmaceutical compositions disclosed herein can be in any form suitable for the intended method of administration. The pharmaceutical compositions disclosed herein can be presented in unit dosage form and can be prepared by any of the methods well known in the art of pharmacy. Exemplary techniques and formulations can be found, for instance, in REMINGTON'S PHARMACEUTICAL SCIENCES (Mack Publishing Co., Easton, PA). Such methods can include the step of bringing into association a compound disclosed herein with the carrier that constitutes one or more accessory ingredients. In general, the formulations can be prepared by uniformly and intimately bringing into association the active ingredient with liquid carriers or finely divided solid carriers or both, and then, if necessary, shaping the product.

When used for oral use for example, tablets, troches, lozenges, aqueous or oil suspensions, dispersible powders or granules, emulsions, hard or soft capsules, solutions, syrups or elixirs can be prepared. Formulations intended for oral use can be prepared according to any method known to the art for the manufacture of pharmaceutical compositions and such formulations can contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

Formulations for oral use can be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin, or olive oil.

Aqueous suspensions can contain the active materials in admixture with excipients suitable for the manufacture of aqueous suspensions. Such excipients can include, for instance, a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain, for example, one or more preservatives such as ethyl or n-propyl p-hydroxy-benzoate, one or more coloring agents, one or more flavoring agents, one or more sweetening agents (such as sucrose or saccharin), or combinations thereof. Further non-limiting examples of suspending agents include cyclodextrin. In some embodiments, the suspending agent is sulfobutyl ether beta-cyclodextrin (SEB-beta-CD), for example CAPTISOL®.

Oil suspensions can be formulated by suspending the active ingredient in a vegetable oil (e.g., arachis oil, olive oil, sesame oil, coconut oil, or a combination thereof), a mineral oil such as liquid paraffin, or a combination thereof. The oral suspensions can contain, for instance, a thickening agent, such as beeswax, hard paraffin, cetyl alcohol, or a combination thereof. In some embodiments, sweetening agents, such as those set forth above, and/or flavoring agents, are added to provide a palatable oral preparation. In some embodiments, the formulations disclosed herein are preserved by the addition of an antioxidant such as ascorbic acid.

Dispersible powders and granules suitable for preparation of an aqueous suspension by the addition of water can provide the active ingredient in admixture with a dispersing or wetting agent, a suspending agent, a preservative, and combinations thereof. Suitable dispersing or wetting agents and suspending agents are exemplified by those disclosed above. Additional excipients, for example sweetening, flavoring and coloring agents, can also be present.

The pharmaceutical compositions can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion can also contain sweetening and flavoring agents. Syrups and elixirs can be formulated with sweetening agents, such as for instance, glycerol, sorbitol or sucrose.

Such formulations can also contain, for instance, a demulcent, a preservative, a flavoring, a coloring agent, or a combination thereof.

The pharmaceutical compositions can be in the form of a sterile injectable or intravenous preparation, such as a sterile injectable aqueous or oleaginous suspension. This suspension can be formulated according to the known art using those suitable dispersing or wetting agents and suspending agents which have been mentioned above. The sterile injectable or intravenous preparation can also be a sterile injectable solution or suspension in a non-toxic parenterally acceptable diluent or solvent, such as a solution in 1,3-butane-diol or prepared as a lyophilized powder. Among the acceptable vehicles and solvents that can be employed are water, Ringer's solution and isotonic sodium chloride solution. In addition, sterile fixed oils can be employed as a solvent or suspending medium. For this purpose, any bland fixed oil can be employed including synthetic mono- or diglycerides. In addition, fatty acids such as oleic acid can likewise be used in the preparation of injectables. Among the acceptable vehicles and solvents that can be employed include, but are not limited to, water, Ringer's solution isotonic sodium chloride solution, and hypertonic sodium chloride solution.

The amount of active ingredient that can be combined with the carrier material to produce a single dosage form will vary depending upon the host treated and the particular mode of administration. For example, a time-release formulation intended for oral administration to humans can contain approximately 1 mg to 2000 mg of active material compounded with an appropriate and convenient amount of carrier material, which can vary from 5% to 95% of the total formulations (weight:weight). For example, a time-release formulation intended for oral administration to humans can contain approximately 1 mg to 1000 mg of active material compounded with an appropriate and convenient amount of carrier material, which can vary from 5% to 95% of the total formulations (weight:weight). The pharmaceutical composition can be prepared to provide easily measurable amounts for administration. For example, an aqueous solution intended for intravenous infusion can contain from 3 μg to 500 μg of the active ingredient per milliliter of solution in order that infusion of a suitable volume at a rate of 30 mL/hr can occur.

Formulations suitable for topical administration to the eye also include eye drops wherein the active ingredient is dissolved or suspended in a suitable carrier, especially an aqueous solvent for the active ingredient. In some embodiments, the compounds disclosed herein are included in the pharmaceutical compositions disclosed herein in a concentration of 0.5% to 20% (e.g., 0.5% to 10%, 1.5% w/w).

Formulations suitable for topical administration in the mouth include lozenges can comprise an active ingredient (i.e., a compound disclosed herein and/or additional therapeutic agents) in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for vaginal administration can be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions that can contain anti-oxidants, buffers, bacteriostats and solutes that render the formulation isotonic with the blood of the intended recipient; and aqueous and non-aqueous sterile suspensions that can include suspending agents and thickening agents.

The formulations can be presented in unit-dose or multi-dose containers, for example, sealed ampoules and vials, and can be stored in a freeze-dried (lyophilized) condition requiring only the addition of the sterile liquid carrier, for example water for injection, immediately before use. Extemporaneous injection solutions and suspensions are prepared from sterile powders, granules and tablets of the kind previously described. Preferred unit-dosage formulations are those containing a daily dose or unit daily sub-dose, as herein above recited, or an appropriate fraction thereof, of the active ingredient.

It should be understood that in addition to the ingredients particularly mentioned above the formulations can include other agents conventional in the art having regard to the type of formulation in question, for example those suitable for oral administration can include flavoring agents.

Further provided are veterinary formulations comprising a compound disclosed herein together with a veterinary carrier therefor.

Veterinary carriers are materials useful for the purpose of administering the formulation and can be solid, liquid or gaseous materials which are otherwise inert or acceptable in the veterinary art and are compatible with the active ingredient. These veterinary formulations can be administered orally, parenterally, or by any other desired route.

Compounds herein are used to provide controlled release pharmaceutical compositions containing as active ingredient one or more of the compounds ("controlled release formulations") in which the release of the active ingredient can be controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical composition, and will be determined by the clinician using conventional dose escalation studies. In some embodiments, the effective dose is from 0.0001 to 100 mg/kg body weight per day; for instance, from 10 to 30 mg/kg body weight per day; from 15 to 25 mg/kg body weight per day; from 10 to 15 mg/kg body weight per day; or from 20 to 30 mg/kg body weight per day. For example, the daily candidate dose for an adult human of approximately 70 kg body weight can range from 1 mg to 2000 mg (e.g., from 5 mg to 500 mg, from 500 mg to 1000 mg, from 1000 mg to 1500 mg, from 1500 mg to 2000 mg), and can take the form of single or multiple doses. For example, the daily candidate dose for an adult human of approximately 70 kg body weight can range from 1 mg to 1000 mg (e.g., from 5 mg to 500 mg), and can take the form of single or multiple doses.

V. Kits

Also provided herein are kits that includes a compound disclosed herein or a pharmaceutically acceptable salt thereof. In some embodiments the kits described herein can comprise a label and/or instructions for use of the compound in the treatment of a disease or condition in a subject (e.g., human) in need thereof. In some embodiments, the disease or condition is viral infection.

In some embodiments, the kit can also comprise one or more additional therapeutic agents and/or instructions for use of additional therapeutic agents in combination with the compound disclosed herein in the treatment of the disease or condition in a subject (e.g., human) in need thereof.

In some embodiments, the kits provided herein comprise individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units can include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit can contain a single dosage unit and in others multiple dosage units are present, such as the number of dosage units required for a specified regimen or period.

Also provided are articles of manufacture that include a compound disclosed herein, or a pharmaceutically acceptable salt, stereoisomer, mixture of stereoisomers or tautomer thereof, and a container. In some embodiments, the container of the article of manufacture is a vial, jar, ampoule, preloaded syringe, blister package, tin, can, bottle, box, an intravenous bag, an inhaler, or a nebulizer.

VI. Administration

One or more compounds of the disclosure are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. It will be appreciated that the route can vary with for example the condition of the recipient.

In the methods of the present disclosure for the treatment of a viral infection, the compounds of the present disclosure can be administered at any time to a subject who can come into contact with the virus or is already suffering from the viral infection. In some embodiments, the compounds of the present disclosure can be administered prophylactically to subjects coming into contact with subjects suffering from the viral infection or at risk of coming into contact with humans suffering from the viral infection, e.g., healthcare providers. In some embodiments, administration of the compounds of the present disclosure can be to subjects testing positive for the viral infection but not yet showing symptoms of the viral infection. In the methods of the present disclosure for the treatment of a viral infection, the compounds of the present disclosure can be administered at any time to a human who can come into contact with the virus or is already suffering from the viral infection. In some embodiments, the compounds of the present disclosure can be administered prophylactically to humans coming into contact with humans suffering from the viral infection or at risk of coming into contact with humans suffering from the viral infection, e.g., healthcare providers. In some embodiments, administration of the compounds of the present disclosure can be to humans testing positive for the viral infection but not yet showing symptoms of the viral infection. In some embodiments, administration of the compounds of the present disclosure can be to humans upon commencement of symptoms of the viral infection.

In some embodiments, the methods disclosed herein comprise event driven administration of the compound disclosed herein, or a pharmaceutically acceptable salt thereof, to the subject.

As used herein, the terms "event driven" or "event driven administration" refer to administration of a compound of Formula I-XI, or a pharmaceutically acceptable salt thereof, (1) before an event (e.g., 2 hours, 1 day, 2 days, 5 day, or 7 or more days before the event) that would expose the subject to the virus (or that would otherwise increase the subject's risk of acquiring the viral infection); and/or (2) during an event (or more than one recurring event) that would expose the subject to the virus (or that would otherwise increase the subject's risk of acquiring the viral infection); and/or (3) after an event (or after the final event in a series of recurring events) that would expose the subject to the virus (or that would otherwise increase the subject's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the subject to the virus or that would otherwise increase the subject's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, a compound disclosed herein, or a pharmaceutically acceptable salt thereof, is administered before exposure of the subject to the virus.

In some embodiments, a compound disclosed herein, or a pharmaceutically acceptable salt thereof, is administered before and after exposure of the subject to the virus.

In some embodiments, a compound disclosed herein, or a pharmaceutically acceptable salt thereof, is administered after exposure of the subject to the virus.

An example of event driven dosing regimen includes administration of a compound disclosed herein, or a pharmaceutically acceptable salt thereof, within 24 to 2 hours before the virus, followed by administration of a compound disclosed herein, or a pharmaceutically acceptable salt, every 24 hours during the period of exposure, followed by a further administration of a compound disclosed herein, or a pharmaceutically acceptable salt thereof, after the last exposure, and one last administration of a compound disclosed herein, or a pharmaceutically acceptable salt thereof, 24 hours later.

A further example of an event driven dosing regimen includes administration of the compound of any one of Formulas I-XI, or a pharmaceutically acceptable salt thereof, within 24 hours before the viral exposure, then daily administration during the period of exposure, followed by a last administration approximately 24 hours later after the last exposure (which can be an increased dose, such as a double dose).

Effective dose of active ingredient depends at least on the nature of the condition being treated, toxicity, whether the compound is being used prophylactically or against an active viral infection, the method of delivery, and the pharmaceutical composition, and will be determined by the clinician using conventional dose escalation studies. It can be expected to be from 0.0001 mg/kg to 100 mg/kg body weight per day (e.g., from 0.01 mg/kg to 10 mg/kg body weight per day; from 0.01 mg/kg to 5 mg/kg body weight per day; from 0.05 mg/kg to 0.5 mg/kg body weight per day). In some embodiments, the daily candidate dose for an adult human of approximately 70 kg body weight is from 1 mg to 4000 mg (e.g., 5 mg to 500 mg, 500 mg to 1000 mg, 1000 mg to 1500 mg, 1500 mg to 2000 mg, 2000 mg to 3000 mg, 3000 mg to 4000 mg) and can take the form of single or multiple doses (e.g., 2 doses per day, 3 doses per day). For example, the daily candidate dose for an adult human of approximately 70 kg body weight can range from 1 mg to 1000 mg (e.g., from 5 mg to 500 mg) and can take the form of single or multiple doses.

Any suitable period of time for administration of the compounds of the present disclosure is contemplated. For example, administration can be for from 1 day to 100 days, including 2, 3, 4, 5, 6, 7, 8, 9, 10, 15, 20, 25, 30, 40, 50, 60, 70, 80, or 90 days. The administration can also be for from 1 week to 15 weeks, including 1, 2, 3, 4, 5, 6, 7, 8, 9, 10, 11, 12, 13, 14, or 15 weeks. Longer periods of administration are also contemplated.

In some embodiments, the compounds disclosed herein are administered once daily. In some embodiments, the compounds disclosed herein are administered twice daily. In some embodiments, the compounds disclosed herein are administered once every alternate day. In some embodiments, the compounds disclosed herein are administered once a week. In some embodiments, the compounds disclosed herein are administered twice a week.

In some embodiments, one or more compounds disclosed herein are administered once daily. The once daily dose can be administered for as long as required, for example for up to 5 days, up to 7 days, up to 10 days, up to 15 days, up to 20 days, up to 25 days, up to a month or longer. In some embodiments, the once daily dose is administered for up to 20 days, up to 15 days, up to 14 days, up to 13 days, up to 12 days, up to 10 days, up to 8 days, up to 6 days, up to 4 days, up to 3 days, up to 2 days, or for one day.

In some embodiments, the one or more compounds disclosed herein are dosed once daily, for 6 to 12 days, for example for 8-10 days. In some embodiments, the one or more compounds are administered once daily for 9 days. In some embodiments, the one or more compounds are administered once daily for 10 days. In some embodiments 50-150 mg of one or more compounds disclosed herein is administered once daily for 5 to 12 days, for e.g., for 5 days, 6 days, 7 days, 8 days, 9 days, 10 days, 11 days, or 12 days. In some embodiments 100 mg of one or more compounds disclosed herein is administered once daily for 5 to 12 days, for e.g., for 5 days, 6 days, 7 days, 8 days, 9 days, 10 days, 11 days, or 12 days. In some embodiments 500-2000 mg (e.g., 500-1000 mg, 1000-1500 mg) of one or more compounds disclosed herein is administered once daily for 5 to 12 days, for e.g., for 5 days, 6 days, 7 days, 8 days, 9 days, 10 days, 11 days, or 12 days.

In some embodiments, one or more compounds disclosed herein are administered twice daily. The twice daily dose can be administered for as long as required, for example for up to 5 days, up to 7 days, up to 10 days, up to 15 days, up to 20 days, up to 25 days, up to a month or longer. In some embodiments, the twice daily dose is administered for up to 20 days, up to 15 days, up to 14 days, up to 13 days, up to 12 days, up to 10 days, up to 8 days, up to 6 days, up to 4 days, up to 3 days, up to 2 days, or for one day.

In some embodiments, the one or more compounds disclosed herein are dosed twice daily, for 6 to 12 days, for example for 8-10 days. In some embodiments, the one or more compounds are administered twice daily for 9 days. In some embodiments, the one or more compounds are administered twice daily for 10 days. In some embodiments 1-2000 mg of one or more compounds disclosed herein is administered twice daily for 5 to 12 days, for e.g., for 5 days, 6 days, 7 days, 8 days, 9 days, 10 days, 11 days, or 12 days. In some embodiments 500-2000 mg (e.g., 500-1000 mg, 1000-1500 mg, 1500-2000 mg) of one or more compounds disclosed herein is administered twice daily for 5 to 12 days, for e.g., for 5 days, 6 days, 7 days, 8 days, 9 days, 10 days, 11 days, or 12 days.

VII. Methods of Use

The present disclosure also provides a method of treating or preventing a viral infection in a subject (e.g., human) in need thereof, the method comprising administering to the subject a compound described herein.

In some embodiments, the present disclosure provides a method of treating a viral infection in a subject (e.g., human) in need thereof, the method comprising administering to a subject in need thereof a compound described herein.

In some embodiments, the present disclosure provides for methods of treating or preventing a viral infection in a subject (e.g., human) in need thereof, the method comprising administering to the subject a compound disclosed herein and at least one additional active therapeutic or prophylactic agent.

In some embodiments, the present disclosure provides for methods of treating a viral infection in a subject (e.g., human) in need thereof, the method comprising administering to the subject a compound disclosed herein, and at least one additional active therapeutic agent.

In some embodiments, the present disclosure provides for methods of inhibiting a viral polymerase in a cell, the methods comprising contacting the cell infected a virus with a compound disclosed herein, whereby the viral polymerase is inhibited.

In some embodiments, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

A. Paramyxoviridae

In some embodiments, the viral infection is a Paramyxoviridae virus infection. As such, in some embodiments, the present disclosure provides methods for treating a Paramyxoviridae infection in a subject (e.g., a human) in need thereof, the method comprising administering to the subject a compound disclosed herein. In some embodiments, the Paramyxoviridae virus includes a BSL4 pathogen. Paramyxoviridae viruses include, but are not limited to, Nipah virus, Hendra virus, measles, mumps, and parainfluenza virus.

In some embodiments, the present disclosure provides a method for manufacturing a medicament for treating a Paramyxoviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of Paramyxoviridae virus infection.

In some embodiments, the present disclosure provides a compound of the present disclosure, or a pharmaceutically acceptable salt thereof, for use in the treatment of a Paramyxoviridae virus infection in a subject (e.g., human) in need thereof.

B. Pneumoviridae

In some embodiments, the viral infection is a Pneumoviridae virus infection. In some embodiments, the present disclosure provides a method of treating a Pneumoviridae virus infection in a subject (e.g., human) in need thereof, the method comprising administering to the human a therapeutically effective amount of a compound of the present disclosure, or a pharmaceutically acceptable salt thereof. Pneumoviridae viruses include, but are not limited to, respiratory syncytial virus (RSV) and human metapneumovirus. In some embodiments, the Pneumoviridae virus infection is a respiratory syncytial virus (RSV) infection. In some embodiments, the Pneumoviridae virus infection is human metapneumovirus infection.

In some embodiments, the present disclosure provides a method for manufacturing a medicament for treating a Pneumoviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides a method for manufacturing a medicament for treating a Pneumoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Pneumoviridae virus infection. In some embodiments, the Pneumoviridae virus infection is a respiratory syncytial virus infection. In some embodiments, the Pneumoviridae virus infection is human metapneumovirus infection.

In some embodiments, the present disclosure provides a compound of the present disclosure, or a pharmaceutically acceptable salt thereof, for use in the treatment of a Pneumoviridae virus infection in a human in need thereof. In some embodiments, the Pneumoviridae virus infection is a respiratory syncytial virus (RSV) infection. In some embodiments, the Pneumoviridae virus infection is human metapneumovirus infection.

In certain embodiments, the present disclosure provides methods for treating an RSV infection, comprising administering to a subject (e.g., a human) infected with respiratory syncytial virus a therapeutically effective amount a compound of the present disclosure or a pharmaceutically acceptable salt thereof. In some embodiments, the human is suffering from a chronic respiratory syncytial viral infection. In some embodiments, the human is acutely infected with RSV.

In certain embodiments, a method of inhibiting RSV replication is provided, comprising administering a compound of the present disclosure, or a pharmaceutically acceptable salt thereof, to a subject (e.g., a human).

In certain embodiments, the present disclosure provides a method for reducing the viral load associated with RSV infection, wherein the method comprises administering to a subject (e.g., a human) infected with RSV a therapeutically effective amount of a compound of the present disclosure, or a pharmaceutically acceptable salt thereof, wherein the therapeutically effective amount is sufficient to reduce the RSV viral load in the subject.

As described more fully herein, compounds of the present disclosure can be administered with one or more additional therapeutic agent(s) to a subject (e.g., a human) infected with RSV.

The additional therapeutic agent(s) can be administered to the infected subject (e.g., a human) at the same time as a compound of the present disclosure or before or after administration of a compound of the present disclosure.

In certain embodiments, a compound of the present disclosure, or a pharmaceutically acceptable salt thereof, for use in treating or preventing an RSV infection is provided. In certain embodiments, a compound of the present disclosure (e.g., a compound of Formula I through Formula XI), or a pharmaceutically acceptable salt thereof, for the manufacture of a medicament for treating or preventing an RSV infection is provided.

In some embodiments, a method of inhibiting RSV replication is provided, wherein the method comprises administering to a subject (e.g., human) in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

C. Picornaviridae

In some embodiments, the viral infection is a Picornaviridae virus infection. In some embodiments, the present disclosure provides a method of treating a Picornaviridae virus infection in a human in need thereof, the method comprising administering to the subject (e.g., human) a therapeutically effective amount of a compound of the present disclosure, or a pharmaceutically acceptable salt thereof. Picornaviridae viruses are enteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection. In some embodiments, the Picornaviridae virus infection is enterovirus infection. In some embodiments, the Picornaviridae virus infection is selected from the group consisting of Coxsackie A virus infection, Coxsackie A virus infection, enterovirus D68 infection, enterovirus B69 infection, enterovirus D70 infection, enterovirus A71 infection, and poliovirus infection. In some embodiments, the Picornaviridae virus is foot and mouth disease virus (FMDV).

In some embodiments, the present disclosure provides a method for manufacturing a medicament for treating a Picornaviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of a Picornaviridae virus infection. In some embodiments, the Picornaviridae virus infection is human rhinovirus infection.

In some embodiments, the present disclosure provides a compound of the present disclosure, or a pharmaceutically acceptable salt thereof, for use in the treatment of a Picornaviridae virus infection in a subject (e.g., human) in need thereof. In some embodiments, the Picornaviridae virus infection is human rhinovirus infection.

D. Flaviviridae

In some embodiments, the viral infection is a Flaviviridae virus infection. In some embodiments, the present disclosure provides a method of treating a Flaviviridae virus infection in a subject (e.g., human) in need thereof, the method comprising administering to the subject (e.g., human) a therapeutically effective amount of a compound of the present disclosure, or a pharmaceutically acceptable salt thereof. Representative Flaviviridae viruses include, but are not limited to, dengue, Yellow fever, West Nile, Zika, Japanese encephalitis virus, tick-borne encephalitis virus (TBEV), and Hepatitis C (HCV). In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Japanese encephalitis virus infection. In some embodiments, the Flaviviridae virus infection is a tick-borne encephalitis virus (TBEV) infection. In some embodiments, the Flaviviridae virus infection is a Hepatitis C virus infection. In some embodiments, the Flaviviridae virus infection is bovine viral diarrhea virus (BVDV). In some embodiments, the Flaviviridae virus infection is swine fever virus (SFV).

In some embodiments, the present disclosure provides a method for manufacturing a medicament for treating a Flaviviridae virus infection in a subject (e.g., human) in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a subject (e.g., human) of a Flaviviridae virus infection. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection.

In some embodiments, the present disclosure provides a compound of the present disclosure, or a pharmaceutically acceptable salt thereof, for use in the treatment of a Flaviviridae virus infection in a human in need thereof. In some embodiments, the Flaviviridae virus infection is a dengue virus infection. In some embodiments, the Flaviviridae virus infection is a Yellow fever virus infection. In some embodiments, the Flaviviridae virus infection is a West Nile virus infection. In some embodiments, the Flaviviridae virus infection is a Zika virus infection. In some embodiments, the Flaviviridae virus infection is a Hepatitis C virus infection.

E. Filoviridae

In some embodiments, the viral infection is a Filoviridae virus infection. In some embodiments, the present disclosure provides a method of treating a Filoviridae virus infection in a subject (e.g., human) in need thereof, the method comprising administering to the subject (e.g., human) a therapeutically effective amount of a compound of the present disclosure, or a pharmaceutically acceptable salt thereof. Representative Filoviridae viruses include, but are not limited to, ebola (variants Zaire, Bundibugio, Sudan, Tai forest, or Reston) and marburg. In some embodiments, the Filoviridae virus infection is an ebola virus infection. In some embodiments, the Filoviridae virus infection is a marburg virus infection.

In some embodiments, the present disclosure provides a method for manufacturing a medicament for treating a Filoviridae virus infection in a human in need thereof, characterized in that the compound of the present disclosure, or a pharmaceutically acceptable salt thereof, is used. In some embodiments, the present disclosure provides use of a compound of the present disclosure, or a pharmaceutically acceptable salt thereof, for the manufacture of a medicament for the treatment in a human of a Filoviridae virus infection. In some embodiments, the Filoviridae virus infection is an ebola virus infection.

In some embodiments, the present disclosure provides a compound of the present disclosure, or a pharmaceutically acceptable salt thereof, for use in the treatment of a Filoviridae virus infection in a subject (e.g., human) in need thereof. In some embodiments, the Filoviridae virus infection is an ebola virus infection. In some embodiments, the Filoviridae virus infection is a marburg virus infection.

VIII. Combination Therapy

The compounds described herein can also be used in combination with one or more additional therapeutic agents or prophylactic agents. As such, also provided herein are methods for treatment of viral infections in a subject in need thereof, wherein the methods comprise administering to the subject a compound disclosed herein and a therapeutically effective amount of one or more additional therapeutic or prophylactic agents. In some embodiments, the methods comprise administering to the subject a compound disclosed herein and a therapeutically effective amount of one or more additional therapeutic agents. In some embodiments, the compounds disclosed herein are combined with at least one other active therapeutic agent, wherein the combination is used for treating a viral infection in a subject in need thereof. In some embodiments, the combination can be used to treat multiple separate viral infections (e.g., RSV and HIV) in one subject. In some embodiments, the compounds disclosed herein are combined with at least one other active therapeutic agent to cover a broader spectrum of respiratory viruses in one treatment without need for a diagnostic.

In some embodiments, the combination can be used to treat the same virus (e.g., RSV) in one subject. Active therapeutic agents include, but are not limited to, approved drugs, therapeutic agents currently in clinical trials, therapeutic agents that have shown efficacy in an animal model, therapeutic agents that have shown potency in in vitro assays, or any of the above.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is an HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiments, the additional therapeutic agent is selected from the group consisting of cidofovir, adefovir, adefovir dipivoxil, tenofovir, TDF, and combinations thereof. In some embodiments, the additional therapeutic agent is selected from the group consisting of cidofovir, adefovir dipivoxil, TDF, and combinations thereof.

In some embodiments, the additional therapeutic agent is an HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picornavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is an agent for treatment of COVID-19 (coronavirus disease 2019, a disease caused by a virus named SARS-CoV-2). In some embodiments, the additional therapeutic agent is selected from a group consisting of IFX-1, FM-201, CYNK-001, DPP4-Fc, ranpirnase, nafamostat, LB-2, AM-1, anti-viroporins, remdesivir, VV116, GS-441524, GS-5245, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan),T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB 114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1

(Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is an HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMIDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV capsid inhibitor (e.g., lenacapavir).

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156,and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiments, the additional therapeutic agent is selected from the group consisting of raltegravir, elvitegravir, dolutegravir, abacavir, lamivudine, bictegravir and combinations thereof. In some embodiments, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMD1, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), room temperaturel1, MRTX-849 (G12C) and KRAS(G12D)-selective inhibitory peptides, including KRpep-2, KRpep-2d, and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. In some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein-based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vagta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccine (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a SARS-COV-2 vaccine.

In some embodiments, the additional therapeutic agent is an antibody, for example a monoclonal antibody. For example, the additional therapeutic agent is an antibody against SARS-COV-2 selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS CoV antibody CR-3022. In some embodiments, the additional therapeutic agent is aPD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASC09F, GC376, GC813, phenylisoserine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5]decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS or MERS. In some embodiments, the additional therapeutic agent is a of SARS-COV-2 virus antibody.

Formulations of the disclosure are also used in combination with other active ingredients. For the treatment of SARS-COV-2 virus infections, in some embodiments, the other active therapeutic agent is active against coronavirus infections, for example SARS-COV-2 virus infections. The compounds and formulations of the present disclosure are also intended for use with general care provided subjects with SARS-COV-2 viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immunomodulatory medications (e.g., interferon), other small molecule or biologics antiviral agents targeting SARS-COV-2 (such as but not limited to lopinavir/ritonavir, EIDD-1931, favipiravir, ribavirine, neutralizing antibodies, etc.), vaccines, pain medications, and medications for other common diseases in the subject population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine.

In some embodiments, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g., azithromycin, clarithromycin, and mycoplasmapneumoniae), fluoroquinolones (e.g., ciprofloxacin and levofloxacin), tetracyclines (e.g., doxycycline and tetracycline), or a combination thereof.

In some embodiments, the compounds disclosed herein are used in combination with pneumonia standard of care (see e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the subjects. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 subjects. In some embodiments, the compounds disclosed herein are used in combination with plasma transfusion. In some embodiments, the compounds disclosed herein are used in combination with stem cells.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some embodiments, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (rhizobium), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the disclosure with one or more additional active therapeutic agents in a unitary dosage form for simultaneous or sequential administration to a subject. The combination therapy can be administered as a simultaneous or sequential regimen. When administered sequentially, the combination can be administered in two or more administrations.

Co-administration of a compound of the disclosure with one or more other active therapeutic agents generally refers to simultaneous or sequential administration of a compound of the disclosure and one or more other active therapeutic agents, such that therapeutically effective amounts of the compound of the disclosure and one or more other active therapeutic agents are both present in the body of the subject.

Co-administration includes administration of unit dosages of the compounds of the disclosure before or after administration of unit dosages of one or more other active therapeutic agents, for example, administration of the compounds of the disclosure within seconds, minutes, or hours of the administration of one or more other active therapeutic agents. For example, a unit dose of a compound of the disclosure can be administered first, followed within seconds or minutes by administration of a unit dose of one or more other active therapeutic agents. Alternatively, a unit dose of one or more other therapeutic agents can be administered first, followed by administration of a unit dose of a compound of the disclosure within seconds or minutes. In some cases, it can be desirable to administer a unit dose of a compound of the disclosure first, followed, after a period of hours (e.g., 1-12 hours), by administration of a unit dose of one or more other active therapeutic agents. In other cases, it can be desirable to administer a unit dose of one or more other active therapeutic agents first, followed, after a period of hours (e.g., 1-12 hours), by administration of a unit dose of a compound of the disclosure.

The combination therapy can provide "synergy" and "synergistic," i.e., the effect achieved when the active ingredients used together is greater than the sum of the effects that results from using the compounds separately. A synergistic effect can be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect can be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect which is greater than the predicted purely additive effects of the individual compounds of the combination.

A. Combination Therapy for the Treatment of Pneumoviridae

The compounds and pharmaceutically acceptable salts thereof disclosed herein can be used in combination with any of the active therapeutic agents discussed in Section VIII herein and/or with other active therapeutic agents for the treatment of Pneumoviridae virus infections discussed specifically here in Section VIII.A. In some embodiments, the other active therapeutic agent is active against Pneumoviridae virus infections, particularly respiratory syncytial virus infections and/or metapneumovirus infections. As described more fully herein, compounds of the present disclosure can be administered with one or more additional therapeutic agent(s) to an subject (e.g., a human) infected with RSV. Further, in certain embodiments, when used to treat or prevent RSV, a compound of the present disclosure may be administered with one or more (e.g., one, two, three, four or more) additional therapeutic agent(s) selected from the group consisting of RSV combination drugs, RSV vaccines, RSV RNA polymerase inhibitors, immunomodulators toll-like receptor (TLR) modulators, interferon alpha receptor ligands, hyaluronidase inhibitors, respiratory syncytial surface antigen inhibitors, cytotoxic T-lymphocyte-associated protein 4 (ipi4) inhibitors, cyclophilin inhibitors, RSV viral entry inhibitors, antisense oligonucleotide targeting viral mRNA, short interfering RNAs (siRNA) and ddRNAi endonuclease modulators, ribonucelotide reductase inhibitors, farnesoid X receptor agonists, RSV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PD-1 inhibitors, PD-L1 inhibitors, recombinant thymosin alpha-1, bruton's tyrosine kinase (BTK) inhibitors, KDM inhibitors, RSV replication inhibitors, arginase inhibitors, and other RSV drugs.

Non-limiting examples of these other active therapeutic agents active against RSV include active monoclonal antibody and nanobody therapeutic agents, agents active against RSV infections, respiratory syncytial virus protein F inhibitors, viral replication inhibitors, RNA polymerase inhibitors, siRNA-based therapies, and combinations thereof. Non-limiting examples of active monoclonal antibody and nanobody therapeutic agents include palivizumab, RSV-IGIV (RESPIGAM®), MEDI-557 (motavizumab), MEDI8897 (nirsevimab), MK-1654, ALX-0171, A-60444 (also known as RSV604), anti-RSV G protein antibodies, and mixtures thereof. Other non-limiting examples of other active therapeutic agents active against respiratory syncytial virus infections include respiratory syncytial virus protein F inhibitors, such as MDT-637, BMS-433771, AK-0529, RV-521 (sisunatovir), JNJ-53718678 (rilematovir), BTA-585, and presatovir; RNA polymerase inhibitors, such as ribavirin, A-60444 (also known as RSV604), JNJ-64417184, ALS-8112 (JNJ-64041575; lumicitabine), and ALS-8112 (the parent nuc of lumicitabine); and viral replication inhibitors, such as EDP-938 and nitazoxanide; siRNA-based therapies, such as ALN-RSVO1; and combinations thereof.

In some embodiments, the other active therapeutic agent can be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent can be a vaccine for the treatment or prevention of metapneumovirus infections, including but not limited to mRNA-1653 and rHMPV-Pa vaccine.

B. Combination Therapy for the Treatment of Picornaviridae

The compounds and pharmaceutically acceptable salts thereof disclosed herein can be used in combination with any of the active therapeutic agents discussed in Section VIII herein and/or with other active therapeutic agents for the treatment of Picornaviridae virus infections discussed specifically here in Section VIII.B. In some embodiments, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent can be a vaccine for the treatment or prevention of Picornaviridae virus infections, including but not limited to EV71 vaccines, TAK-021, and EV-D68 adenovector-based vaccine.

C. Combination Therapy for the Treatment of Respiratory Infections

The compounds and pharmaceutically acceptable salts thereof disclosed herein can be used in combination with any of the active therapeutic agents discussed in Section VIII herein and/or with other active therapeutic agents discussed specifically here in Section VIII.C. Many of the infections of the Pneumoviridae and Picornaviridae viruses are respiratory infections. Therefore, additional active therapeutics used to treat respiratory symptoms and sequelae of infection can be used in combination with the compounds provided herein. The additional agents can be administered orally or by direct inhalation. For example, other additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that can be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AIS™), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's can be used to treat both the bronchoconstriction and the inflammation (SYMBICORT® and ADVAIR®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists include, but are not limited to, bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype), which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo[3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, and bencycloquidium bromide.

Mucolytic Agents

The compounds provided herein can also be combined with mucolytic agents to treat both the infection and symptoms of respiratory infections. A non-limiting example of a mucolytic agent is ambroxol. Similarly, the compounds can be combined with expectorants to treat both the infection and symptoms of respiratory infections. A non-limiting example of an expectorant is guaifenesin.

Nebulized hypertonic saline is used to improve immediate and long-term clearance of small airways in subjects with lung diseases (Kuzik, J. Pediatrics 2007, 266). Thus, the compounds provided herein can also be combined with nebulized hypertonic saline particularly when the virus infection is complicated with bronchiolitis. The combination of the compound provided herein with hypertonic saline can also comprise any of the additional agents discussed above. In some embodiments, 3% hypertonic saline is used.

D. Combination Therapy for the Treatment of COPD

The compounds and pharmaceutically acceptable salts thereof disclosed herein can be used in combination with any of the active therapeutic agents discussed in Section VIII herein and/or with other active therapeutic agents for the treatment of respiratory exacerbations of COPD discussed specifically here in Section VIII.D. In some embodiments, the other active therapeutic agents include other active agents against COPD. Non-limiting examples of these other active therapeutic agents include anti-IL5 antibodies, such as benralizumab, mepolizumab; dipeptidyl peptidase I (DPP1) inhibitors, such as AZD-7986 (INS-1007); DNA gyrase inhibitor/topoisomerase IV inhibitors, such as ciprofloxacin hydrochloride; MDR associated protein 4/phosphodiesterase (PDE) 3 and 4 inhibitors, such as RPL-554; CFTR stimulators, such as ivacaftor, QBW-251; MMP-9/MMP-12 inhibitors, such as RBx-10017609; Adenosine A1 receptor antagonists, such as PBF-680; GATA 3 transcription factor inhibitors, such as SB-010; muscarinic receptor modulator/nicotinic acetylcholine receptor agonists, such as ASM-024; MARCKS protein inhibitors, such as BIO-11006; kit tyrosine kinase/PDGF inhibitors such as masitinib; phosphodiesterase (PDE) 4 inhibitors, such as roflumilast, CHF-6001; phosphoinositide-3 kinase delta inhibitors, such as nemiralisib; 5-Lipoxygenase inhibitors, such as TA-270; muscarinic receptor antagonist/beta 2 adrenoceptor agonist, such as batefenterol succinate, AZD-887, ipratropium bromide; TRN-157; elastase inhibitors, such as erdosteine; metalloprotease-12 inhibitors such as FP-025; interleukin 18 ligand inhibitors, such as tadekinig alfa; skeletal muscle troponin activators, such as CK-2127107; p38 MAP kinase inhibitors, such as acumapimod; IL-17 receptor modulators, such as CNTO-6785; CXCR2 chemokine antagonists, such as danirixin; leukocyte elastase inhibitors, such as POL-6014; epoxide hydrolase inhibitors, such as GSK-2256294; HNE inhibitors, such as CHF-6333; VIP agonists, such as aviptadil; phosphoinositide-3 kinase delta/gamma inhibitors, such as RV-1729; complement C3 inhibitors, such as APL-1; and G-protein coupled receptor-44 antagonists, such as AM-211.

Other non-limiting examples of active therapeutic agents also include, but are not limited to, budesonide, adipocell, nitric oxide, PUR-1800, YLP-001, LT-4001, azithromycin, gamunex, QBKPN, sodium pyruvate, MUL-1867, mannitol, MV-130, MEDI-3506, BI-443651, VR-096, OPK-0018, TEV-48107, doxofylline, TEV-46017, OligoG-COPD-5/20, STEMPEUCEL®, ZP-051, and lysine acetylsalicylate.

In some embodiments, the other active therapeutic agent may be a vaccine that is active against COPD, including but not limited to MV-130 and GSK-2838497A.

E. Combination Therapy for the Treatment of Flaviviridae Virus Infections

The compounds and pharmaceutically acceptable salts thereof disclosed herein can be used in combination with any of the active therapeutic agents discussed in Section VIII herein and/or with other active therapeutic agents for the treatment of Flaviviridae virus infections discussed specifically here in Section VIII.E. In some embodiments, the other active therapeutic agent is active against Flaviviridae virus infections.

For treatment of the Flaviviridae virus infections, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent can be a vaccine for the treatment or prevention of dengue, including but not limited to TETRAVAX-DV, DENGVAXIA®, DPIV-001, TAK-003, live attenuated dengue vaccine, tetravalent dengue fever vaccine, tetravalent DNA vaccine, rDEN2delta30-7169; and DENV-1 PIV.

F. Combination Therapy for the Treatment of Filoviridae Virus Infections

The compounds and pharmaceutically acceptable salts thereof disclosed herein can be used in combination with any of the active therapeutic agents discussed in Section VIII herein and/or with other active therapeutic agents for the treatment of Filoviridae virus infections discussed specifically here in Section VIII.F. In some embodiments, the other active therapeutic agent is active against Filoviridae virus infections (e.g., marburg virus, ebola virus, Sudan virus, and cueva virus infections). Non-limiting examples of these other active therapeutic agents include:MR186-YTE, remdesivir, ribavirin, palivizumab, motavizumab, RSV-IGIV (RESPIGAM®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as INMAZEB (atoltivimab, maftivimab, and odesivimab), ZMapp, and mAb 114 (EBANGA).

Other non-limiting active therapeutic agents active against Ebola include, but are not limited to, an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent can be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds provided herein can also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to subjects with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the subject population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

G. Combination Therapy for the Treatment of Influenza

The compounds and pharmaceutically acceptable salts thereof disclosed herein can be used in combination with any of the active therapeutic agents discussed in Section VIII herein and/or with other active therapeutic agents for the treatment of influenza virus infections discussed specifically here in Section VIII.G. In some embodiments, the compounds provided herein are also used in combination with other active therapeutic agents for the treatment of influenza virus infections. The compounds and compositions provided herein are also used in combination with other active therapeutic agents. In some embodiments, the compounds provided herein can also be combined with influenza treatments. In some embodiments, the compounds provided herein are used with influenza treatments when treating influenza viruses. In some embodiments, the compounds provided herein are used with influenza treatments to treat a broader spectrum of respiratory viruses, such as those disclosed herein. In some embodiments, the influenza treatment is a neuraminidase (NA) inhibitor. In some embodiments, the influenza treatment is an M2 inhibitor. Examples of influenza treatments include, but are not limited to, AB-5080, ALS-1, amantadine (GOCOVRI®), AV-001, AV-5124, AVM-0703, baloxavir marboxil (XOFLUZA®), CB-012, CC-42344, CD-388, CT-P27, Codivir, DAS-181, DNK-651, ENOB-FL-01, ENOB-FL-11, favipiravir, GP-584, GP-681, H-015, HC-imAb, HEC-116094HCl $3H_2O$, HNC-042, histamine glutarimide, IFV-PA, Ingavirin, INI-2004, INNA-051, KYAH01-2019-121, laninamivir, molnupiravir, niclosamide, nitazoxanide, norketotifen, NX-2016, oseltamivir phosphate (TAMIFLU®), peramivir (RAPIVAB®), REVTx-99, rimantadine, S-416, SAB-176, STP-702, T-7051V, TG-1000, TJ-27, TSR-066, 7HP-349, VIR-2482, VIS-410, VIS-FLX, XC-221, zanamivir (RELENZA®), zanamivir-dinitrophenyl conjugate, ZSP-1273, and ZX-7101A.

IX. Compound Preparation

In some embodiments, the present disclosure provides processes and intermediates useful for preparing the compounds disclosed herein or pharmaceutically acceptable salts thereof.

Compounds disclosed herein can be purified by any of the means known in the art, including chromatographic means, including but not limited to high-performance liquid chromatography (HPLC), preparative thin layer chromatography, flash column chromatography, and ion exchange chromatography. Any suitable stationary phase can be used, including but not limited to, normal and reversed phases as well as ionic resins. In some embodiments, the disclosed compounds are purified via silica gel and/or alumina chromatography.

During any of the processes for preparation of the compounds provided herein, it can be necessary and/or desirable to protect sensitive or reactive groups on any of the molecules concerned. This can be achieved by means of conventional protecting groups as described in standard works, such as T. W. Greene and P. G. M. Wuts, Protective Groups in Organic Synthesis, $4^{th}$ ed., Wiley, New York 2006. The protecting groups can be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials can be suitably selected so that the ultimately desired substituents will be carried through the reaction scheme with or without protection as appropriate to yield the desired product. Alternatively, it can be necessary or desirable to employ, in the place of the ultimately desired substituent, a suitable group that can be carried through the reaction scheme and replaced as appropriate with the desired substituent. Furthermore, one of skill in the art will recognize that the transformations shown in the schemes below can be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in the schemes below, and the particular examples that follow.

Scheme 1

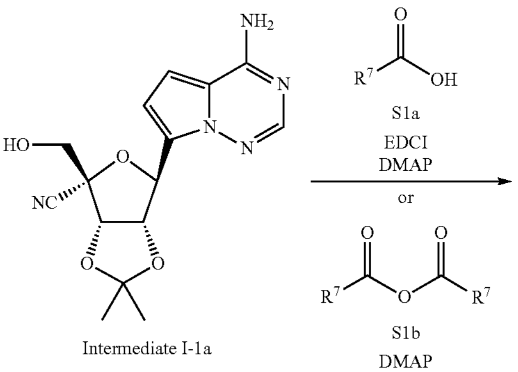

Intermediate I-1a

-continued

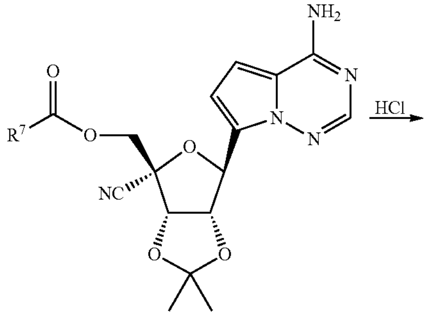

S1c

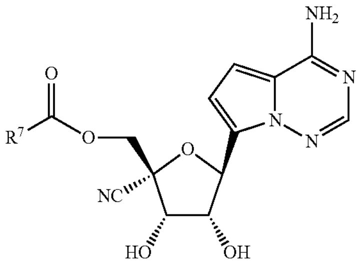

S1d

Scheme 1 shows the general synthesis of compounds starting with the reaction of Intermediate I-1a with carboxylic acid S1a in the presence of a coupling agent (e.g., EDCI) and base (e.g., DMAP) to afford S1c. Alternatively, the reaction of Intermediate I-1a with anhydride S1b in the presence of base (e.g., DMAP) affords Sic. Removal of the acetonide group under acidic conditions (e.g., HCl) affords the final compounds of the type S1d.

Scheme 2

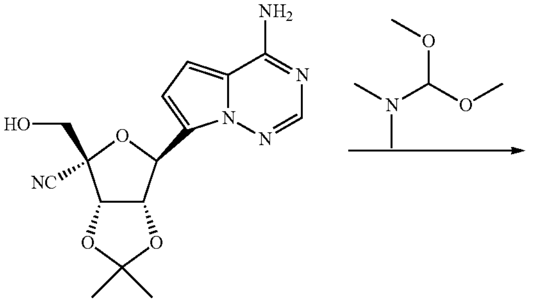

Intermediate I-1a

-continued

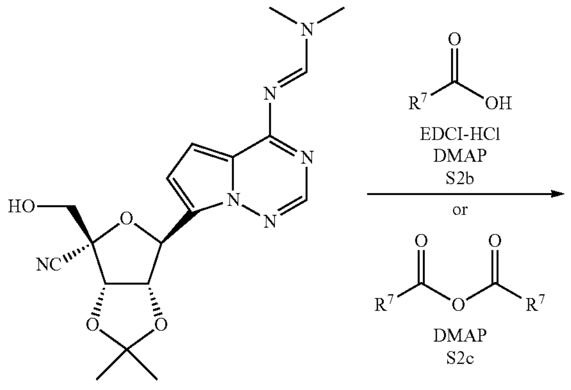

S2a

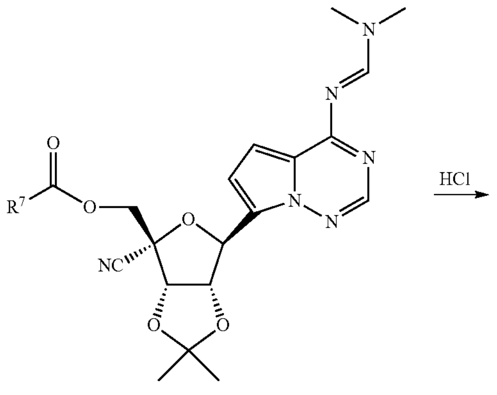

S2d

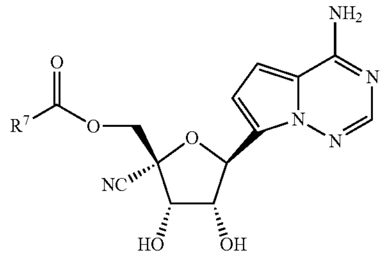

S2e

Scheme 2 shows the general synthesis of compounds starting with the reaction of Intermediate I-1a with 1,1-dimethoxy-N,N-dimethylmethanamine to afford the amidine protected base S2a. Coupling of S2a with the carboxylic acid S2b in the presence of a coupling agent (e.g., EDCI) and base (e.g., DMAP) can afford S2d. Alternatively, the reaction of S2a with anhydride S2c in the presence of base (e.g., DMAP) affords S2d. Removal of the acetonide group and the amidine group under acidic conditions (e.g., HCl) affords the final compounds of the type S2e.

Scheme 3

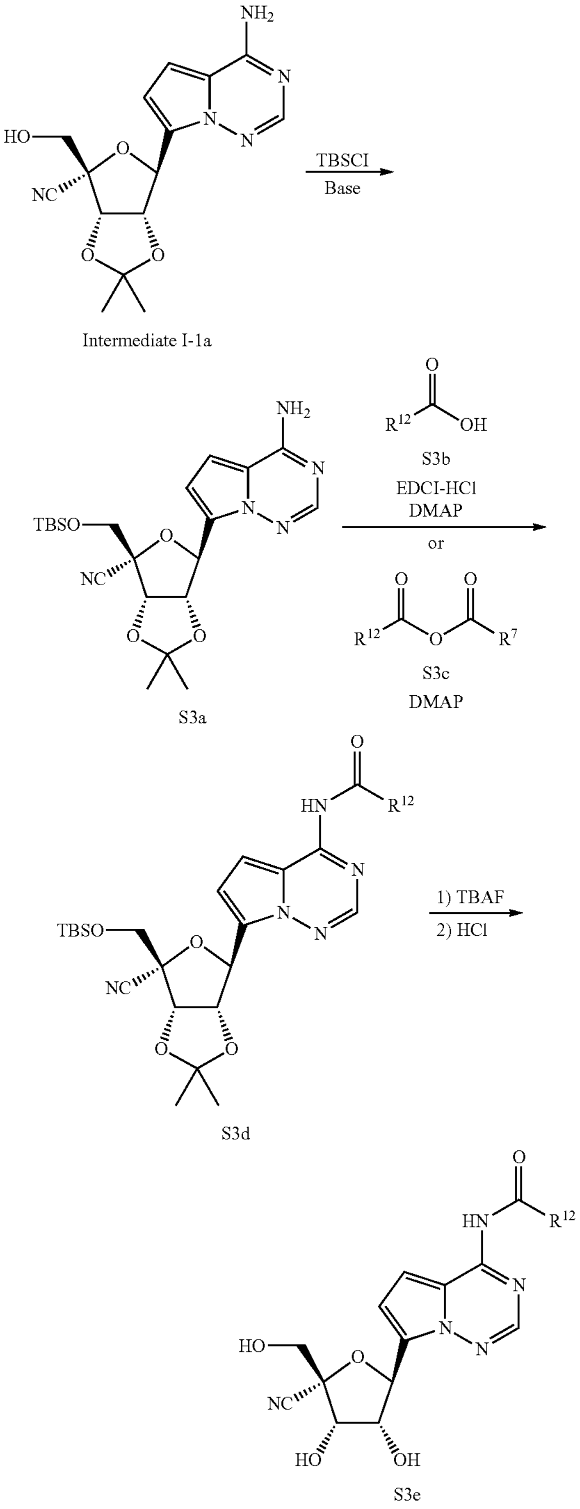

Intermediate I-1a

S3a

S3d

S3e

Scheme 3 shows the general synthesis of compounds starting with the reaction of Intermediate I-1a with a silyl protecting group reagent (e.g., TBSCl) under basic conditions (e.g., $Et_3N$) to afford S3a. Coupling of S3a with the carboxylic acid S3b in the presence of a coupling agent (e.g., EDCI) and base (e.g., DMAP) affords S3d. Alternatively, the reaction of S3a with anhydride S3c in the presence of base (e.g., DMAP) affords S3d. Removal of the TBS protecting group with fluoride (e.g., TBAF) and the acetonide group under acidic conditions (e.g., HCl) affords the final compounds of the type S3e.

Scheme 4

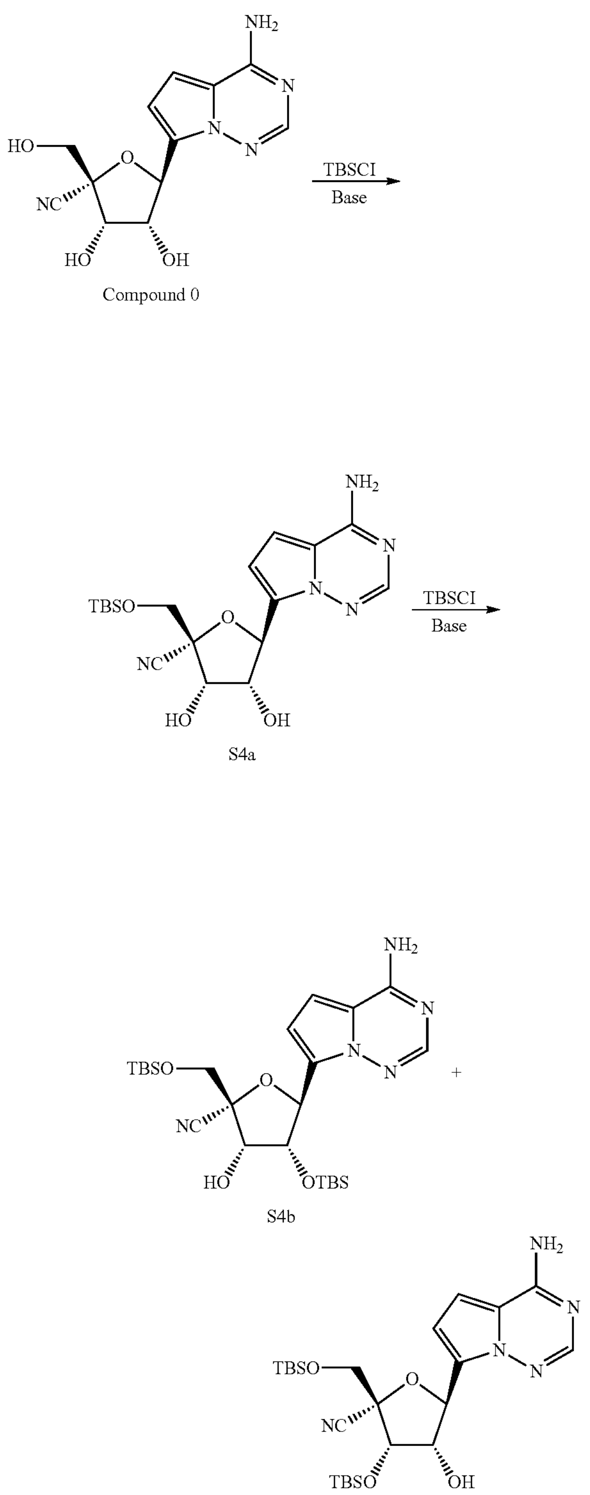

Compound 0

S4a

S4b

+

S4c

-continued

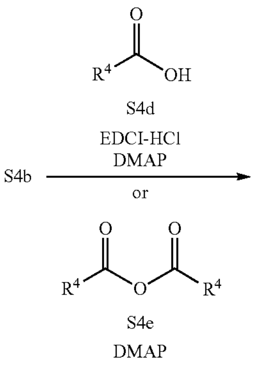

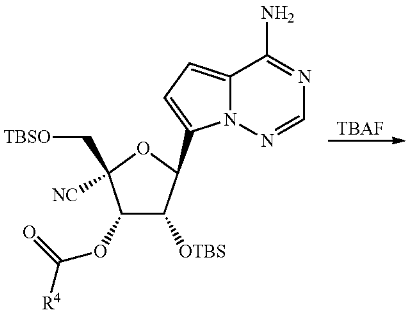

S4f

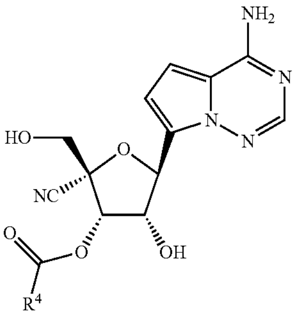

S4g

-continued

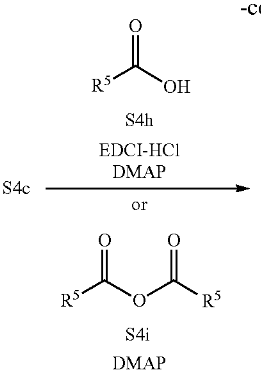

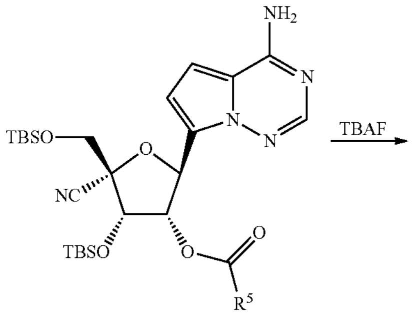

S4j

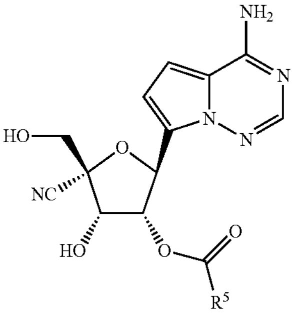

S4k

Scheme 4 shows the general synthesis of compounds starting with the reaction of Compound 0 with a silyl protecting group reagent (e.g., TBSCl) under basic conditions (e.g., $Et_3N$) to afford S4a. Reaction of S4a with another equivalent of silyl protecting group reagent (e.g., TBSCl) under basic conditions (e.g., $Et_3N$) affords a mixture of the bis-silyl protected intermediates S4b and S4c. The coupling of S4b with the carboxylic acid S4d in the presence of a coupling agent (e.g., EDCI) and base (e.g., DMAP) affords S4f. Alternatively, the reaction of S4b with anhydride S4e in the presence of base (e.g., DMAP) affords S4f. Removal of the TBS protecting groups with fluoride (e.g., TBAF) affords the final compounds of the type S4g. Furthermore, the coupling of S4c with the carboxylic acid S4h in the presence of a coupling agent (e.g., EDCI) and base (e.g., DMAP) affords S4j. Alternatively, the reaction of S4c with anhydride S4i in the presence of base (e.g., DMAP) affords S4j. Removal of the TBS protecting groups with fluoride (e.g., TBAF) affords the final compounds of the type S4k.

Scheme 5

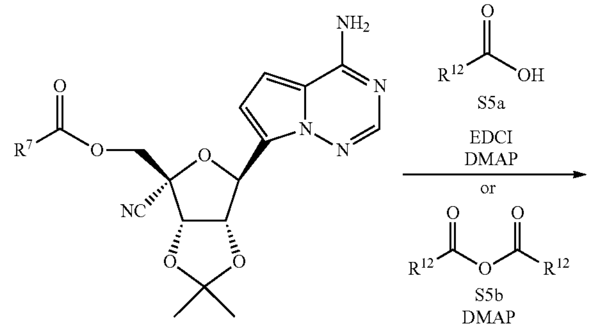

S1c

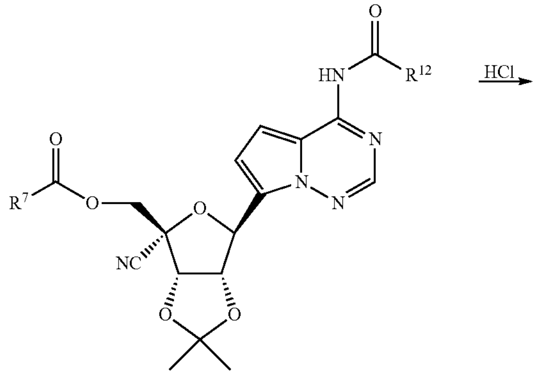

S5c

-continued

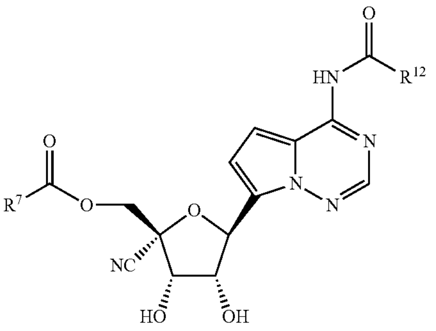

S5d

Scheme 5 shows the general synthesis of compounds starting with the reaction of intermediate S1c with the carboxylic acid S5a in the presence of a coupling agent (e.g., EDCI) and base (e.g., DMAP) which affords S5c. Alternatively, the reaction of S1c with anhydride S5b in the presence of base (e.g., DMAP) affords S5c. Removal of the acetonide group under acidic conditions (e.g., HCl) affords the final compounds of the type S5d.

Scheme 6

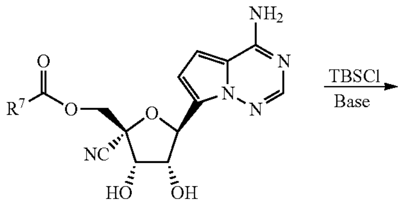

S1d

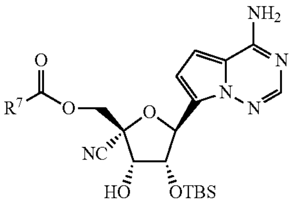

S6a

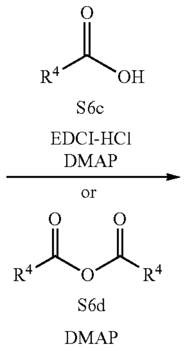

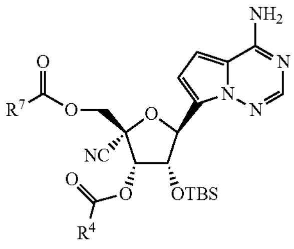

S6e

+

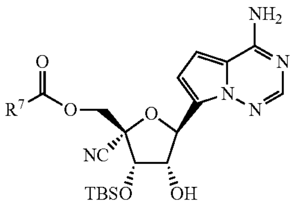

S6b

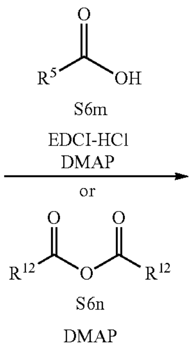

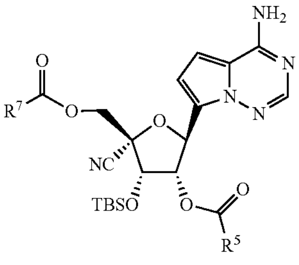

S6o

-continued
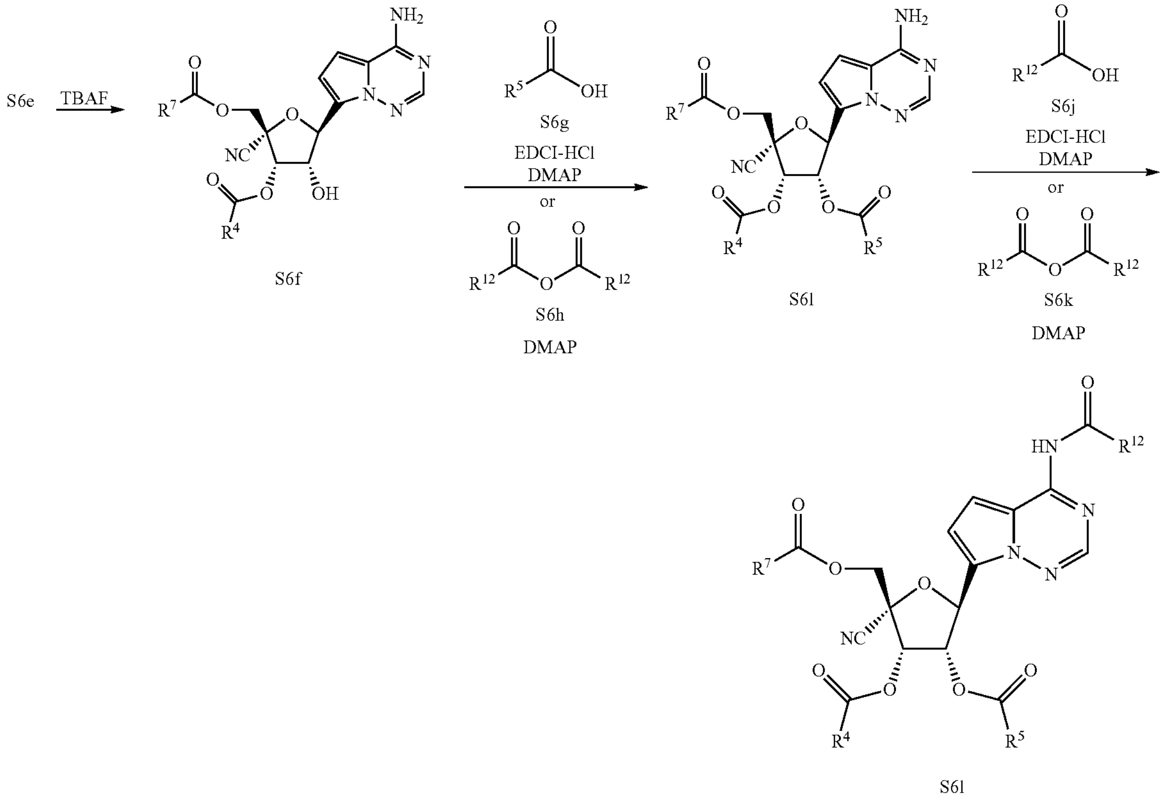
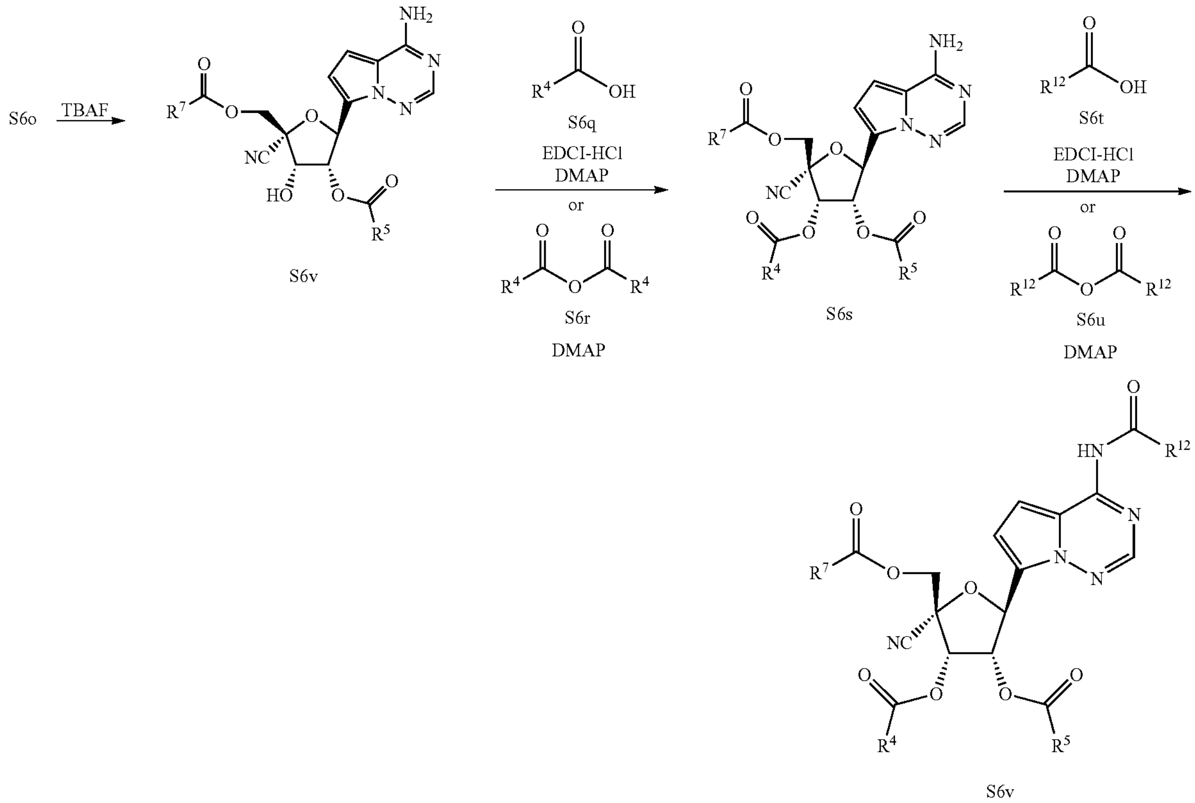

Scheme 6 shows the general synthesis of compounds starting with the reaction of intermediate S1d with a silyl protecting group reagent (e.g., TBSCl) under basic conditions (e.g., $Et_3N$) to afford a mixture of the silyl protected intermediates S6a and S6b. The coupling of S6a with the carboxylic acid S6c in the presence of a coupling agent (e.g., EDCI) and base (e.g., DMAP) affords S6e. Alternatively, the reaction of S6a with anhydride S6d in the presence of base (e.g., DMAP) affords S6e. Removal of the TBS protecting groups with fluoride (e.g., TBAF) affords the final compounds of the type S6f. The coupling of S6f with either the carboxylic acid S6g in the presence of a coupling agent (e.g., EDCI) and base (e.g., DMAP) or the anhydride S6h in the presence of base (e.g., DMAP) affords final compounds of the type S6i. The coupling of S6i with either the carboxylic acid S6j in the presence of a coupling agent (e.g., EDCI) and base (e.g., DMAP) or the anhydride S6k in the presence of base (e.g., DMAP) affords final compounds of the type S6l. Furthermore, the coupling of S6b with the carboxylic acid S6m in the presence of a coupling agent (e.g., EDCI) and base (e.g., DMAP) affords S6o. Alternatively, the reaction of S6b with anhydride S6n in the presence of base (e.g., DMAP) affords S6o. Removal of the TBS protecting groups with fluoride (e.g., TBAF) affords the final compounds of the type S6p. The coupling of S6p with either the carboxylic acid S6q in the presence of a coupling agent (e.g., EDCI) and base (e.g., DMAP) or the anhydride S6r in the presence of base (e.g., DMAP) affords final compounds of the type S6s. The coupling of S6s with either the carboxylic acid S6t in the presence of a coupling agent (e.g., EDCI) and base (e.g., DMAP) or the anhydride S6u in the presence of base (e.g., DMAP) affords final compounds of the type S6v.

Scheme 7

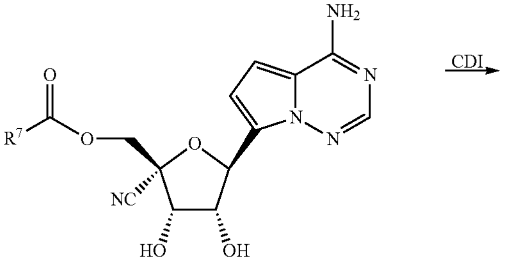

S1d

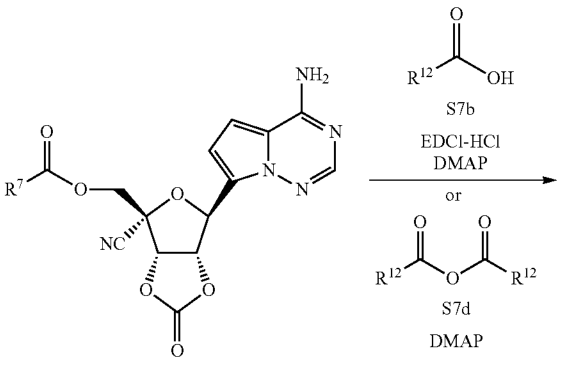

S7a

-continued

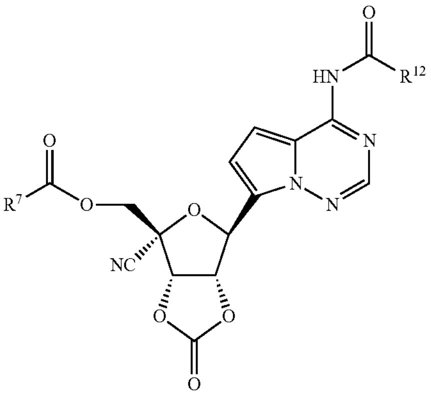

S7e

Scheme 7 shows the general synthesis of compounds starting with the reaction of S1d with CDI to afford final compound of the type S7a. The coupling of S7a with either the carboxylic acid S7b in the presence of a coupling agent (e.g., EDCI) and base (e.g., DMAP) or the anhydride S7d in the presence of base (e.g., DMAP) affords final compounds of the type S7e.

Scheme 8

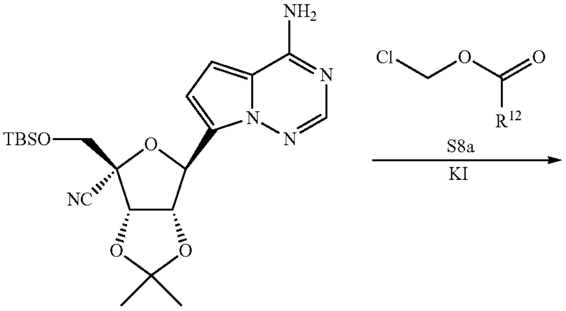

S3a

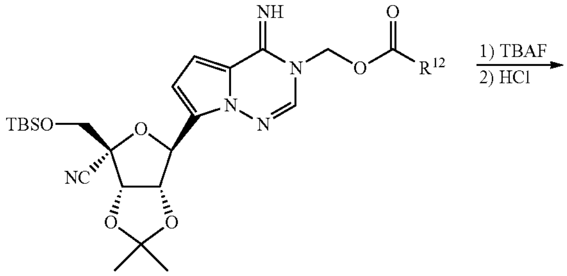

S8b

-continued

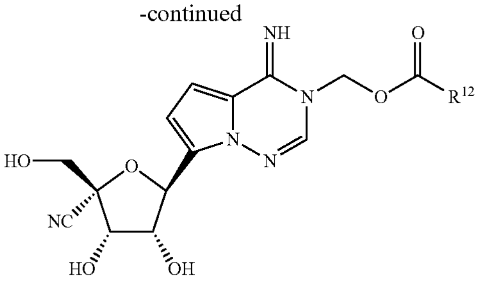

S8c

Scheme 8 shows the general synthesis of compounds starting with the reaction of S3a with the chloromethyl ester S8a in the presences if iodide ion (e.g., KI) to afford intermediate S8b. Cleavage of the TBS protecting group in the presence of fluoride (e.g., TBAF) followed by acetonide removal under acidic conditions (e.g., HCl) affords compounds of the type S8c.

Scheme 9

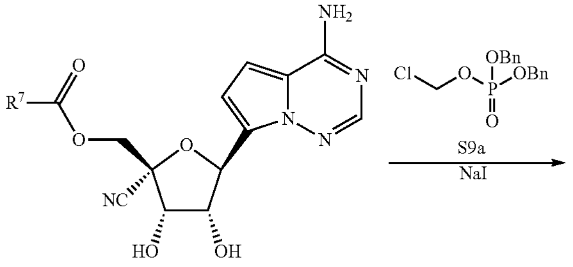

S1d

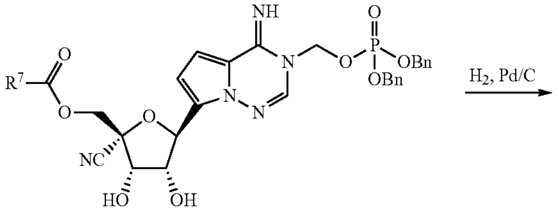

S9b

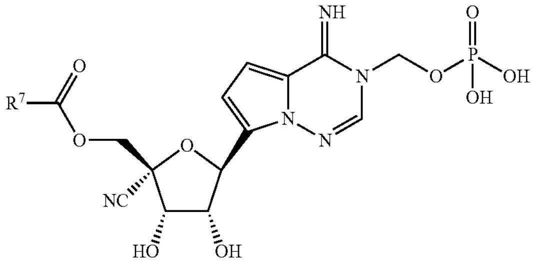

S9a

Scheme 9 shows the general synthesis of compounds starting with the reaction of S1d with the chloromethyl phosphate S9a in the presences of iodide ion (e.g., NaI) to afford intermediate S9b. Cleavage of the TBS protecting group in the presence of fluoride (e.g., TBAF) followed by benzyl removal with $H_2$ gas and Pd/C affords compounds of the type S9c.

Scheme 10

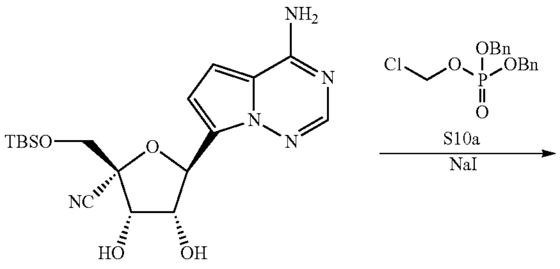

S4a

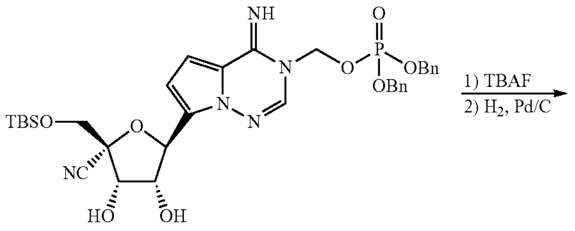

S10b

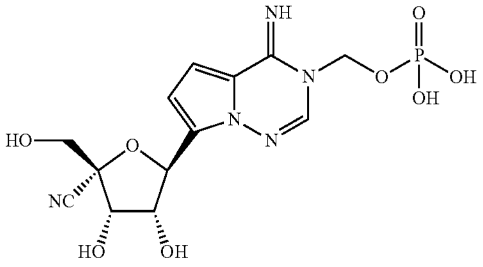

S10c

Scheme 10 shows the general synthesis of compounds starting with the reaction of S4a with the chloromethyl phosphate S10a in the presences of iodide ion (e.g., NaI) to afford intermediate S10b. Cleavage of the TBS protecting group in the presence of fluoride (e.g., TBAF) followed by benzyl removal with $H_2$ gas and Pd/C affords the compound S10c.

Scheme 11

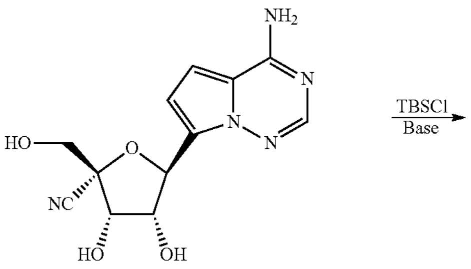

Compound 0

-continued

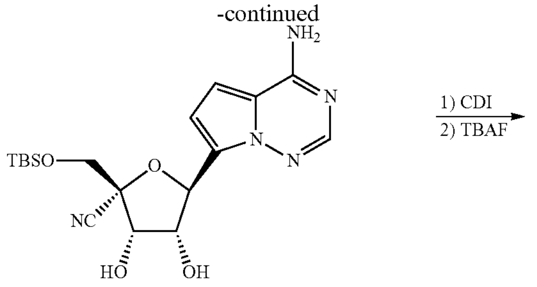

S11a

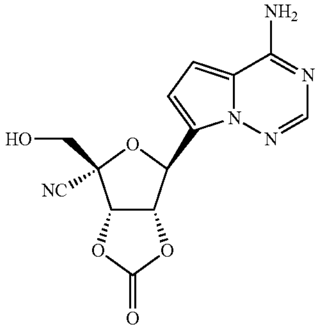

S11b

Scheme 11 shows the general synthesis of compounds starting with the reaction of Compound 0 with a silyl protecting group reagent (e.g., TBSCl) under basic conditions (e.g., $Et_3N$) to afford intermediate S11a. The reaction of S11a with CDI to afford the cyclic carbonate followed by TBS removal in the presence of fluoride (e.g., TBAF) generates the final compound S11b.

EXAMPLES

A. Abbreviations

Certain abbreviations and acronyms are used in describing the experimental details. Although most of these would be understood by one skilled in the art, Table 12 contains a list of many of these abbreviations and acronyms.

TABLE 12

List of abbreviations and acronyms.

| Abbreviation | Meaning |
|---|---|
| Ac | acetate |
| ACN | acetonitrile |
| AIBN | azobisisobutyronitrile |
| Bn | benzyl |
| Bu | butyl |
| Bz | benzoyl |
| BzCl | benzoyl chloride |
| CDI | 1,1'-carbonyldiimidazole |
| cHCl | concentrated HCl |
| DAST | diethylaminosulfur trifluoride |
| DCE | 1,2-dichloroethane |
| DCM | dichloromethane |
| DIPEA | N,N-diisopropylethylamine |
| DMAP | 4-dimethylamiopyridine |
| DMDO | dimethydioxirane |
| DMSO | dimethylsulfoxide |
| DMF | dimethylformamide |
| DMTrCl | 4,4'-dimethoxytritylchloride |
| DMTr | 4,4'-dimethoxytrityl |
| EDCI | N-(3-dimethylaminopropyl)-N'-ethylcarbodiimide hydrochloride |
| Et | ethyl |
| Imid | imidazole |
| KOtBu | potassium tert-butoxide |
| LC | liquid chromatography |
| MCPBA | meta-chloroperbenzoic acid |
| Me | methyl |
| m/z | mass to charge ratio |
| MS or ms | mass spectrum |
| NIS | N-iodosuccinimide |
| NMP | N-methyl-2-pyrrolidone |
| Ph | phenyl |
| $Ph_3P$ | triphenylphosphine |
| PMB | para-methoxybenzyl |
| PMBCl | para-methoxybenzyl chloride |
| PhOC(S)Cl | phenylchlorothionoformate |
| $(PhO)_3PMeI$ | methyltriphenoxyphosphonium iodide |
| Pyr | pyridine |
| RT | room temperature |
| SFC | supercritical fluid chromatography |
| TBAF | tetrabutylammonium fluoride |
| TBS | tert-butyldimethylsilyl |
| TBSCl | tert-Butyldimethylsilyl chloride |
| $TMSN_3$ | trimethylsilyl azide |
| TEA | triethylamine |
| TES | triethylsilane |
| TFA | trifluoroacetic acid |
| THF | tetrahydrofuran |
| TMS | trimethylsilyl |
| TMSCl | trimethylsilyl chloride |
| Ts | 4-toluenesulfonyl |
| TsOH | tosylic acid |
| δ | parts per million referenced to residual non-deuterated solvent peak |

B. Intermediates

Intermediate I-1a: (3aS,4R,6S,6aS)-6-(4-aminopyrrolo[2,1-f][1,2,4]triazin-7-yl)-4-(hydroxymethyl)-2,2-dimethyltetrahydrofuro[3,4-d][1,3]dioxole-4-carbonitrile Intermediate I-1a

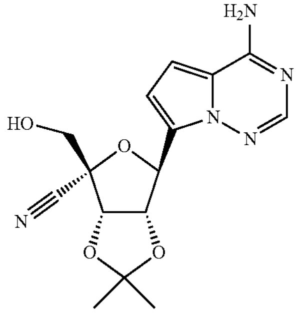

Took up Intermediate I-26 (18.87 mmol) in THE (100 mL). Added TBAF 1.0 M in THE (28.31 mmol) in one portion at ambient temperature. Allowed to stir at ambient temperature for 10 min. The reaction was determined to be complete by LCMS. The reaction mixture was quenched with water and the organics were removed under reduced pressure. The crude was partitioned between EtOAc and Water. The layers were separated and the aqueous was washed with EtOAc. The organics were combined and dried over sodium sulfate. The solids were filtered off and the solvent removed under reduced pressure. The crude was purified by silica gel chromatography 120 g column 0% to 10% $CH_3OH$ in $CH_2Cl_2$ to afford Intermediate I-1a. LC/MS: $t_R$=0.76 min, MS m/z=332.14 [M+1]; LC system: Thermo Accela 1250 UHPLC. MS system: Thermo LCQ Fleet; Column: Kinetex 2.6μ XB-C18 100A, 50×3.00 mm. Solvents: Acetonitrile with 0.1% formic acid, Water with 0.1% formic acid. Gradient: 0 min-2.4 min 2-100% ACN, 2.4 min-2.80 min 100% ACN, 2.8 min-2.85 min 100%-2% ACN, 2.85 min-3.0 min 2% ACN at 1.8 mL/min. $^1H$ NMR (400 MHz, DMSO-$d_6$) δ 7.87-7.80 (m, 3H), 6.85 (d, J=4.5 Hz, 1H), 6.82 (d, J=4.5 Hz, 1H), 5.74 (t, J=5.8 Hz, 1H), 5.52 (d, J=4.2 Hz, 1H), 5.24 (dd, J=6.8, 4.2 Hz, 1H), 4.92 (d, J=6.8 Hz, 1H), 3.65 (dd, J=6.1, 1.7 Hz, 2H), 1.61 (s, 3H), 1.33 (s, 3H).

Intermediate I-1: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl benzoate

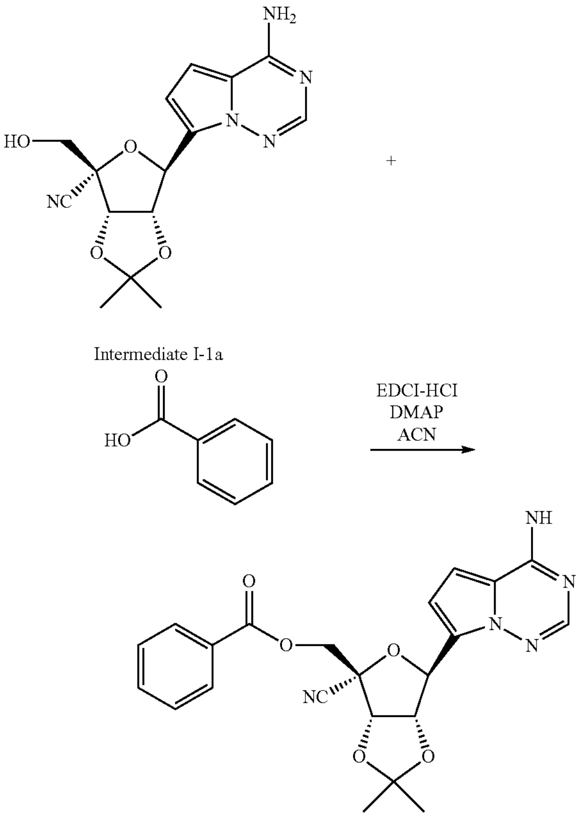

Intermediate I-1

To a mixture of Intermediate I-1a (1.51 mmol) and benzoic acid (2.26 mmol) in DMF (5 mL) were added DMAP (1.51 mmol) and then EDCI-HCl (2.26 mmol). The resulting mixture was stirred at room temperature for 2h, MeOH (0.5 mL) added, concentrated in vacuo, and purified by silica gel column chromatography (0% to 10% MeOH in DCM) to give Intermediate I-1. $^1H$ NMR (400 MHz, Acetonitrile-d3) δ 8.12-8.01 (m, 2H), 7.84 (s, 1H), 7.69 (m, 1H), 7.61-7.42 (m, 2H), 6.80 (d, J=4.5 Hz, 1H), 6.75 (d, J=4.5 Hz, 1H), 6.27 (s, 2H), 5.70 (d, J=3.4 Hz, 1H), 5.37 (dd, J=6.6, 3.4 Hz, 1H), 5.22 (d, J=6.7 Hz, 1H), 4.76 (d, J=11.6 Hz, 1H), 4.62 (d, J=11.6 Hz, 1H), 1.74 (s, 3H), 1.42-1.39 (s, 3H). MS m/z [M+1]=436.

Intermediates I-2 & I-3: Intermediate I-2 ((3aS,4R,6S,6aS)-4-cyano-6-(4-(2-ethylbutanamido)pyrrolo[2,1-f][1,2,4]triazin-7-yl)-2,2-dimethyltetrahydrofuro[3,4-d][1,3]dioxol-4-yl)methyl 2-ethylbutanoate and Intermediate I-3 ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 2-ethylbutanoate

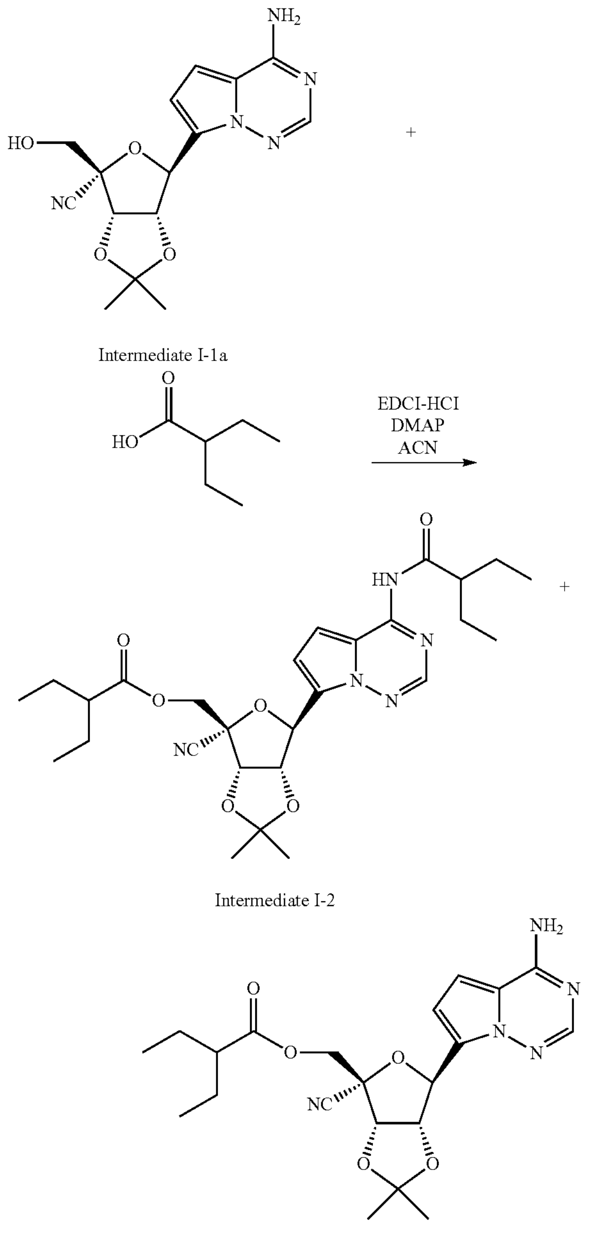

Intermediate I-3

To a mixture of Intermediate I-1a (0.362 mmol) and 2-ethylbutanoic acid (0.543 mmol) in DMF (2 mL) were added DMAP (0.543 mmol) and then EDCI-HCl (0.543 mmol). The resulting mixture was stirred at rt for 2h, MeOH (0.5 mL) added, concentrated in vacuo, and purified by silica gel column chromatography (0% to 5% MeOH in DCM) to give Intermediate 1-2 & Intermediate 1-3.

Intermediate I-2: $^{1}$H NMR (400 MHz, Acetonitrile-d3) δ 8.92 (s, 1H), 8.22 (s, 1H), 7.22 (d, J=4.7 Hz, 1H), 6.99 (d, J=4.7 Hz, 1H), 5.75 (d, J=3.4 Hz, 1H), 5.34 (dd, J=6.6, 3.4 Hz, 1H), 5.07 (d, J=6.6 Hz, 1H), 4.51 (d, J=11.7 Hz, 1H), 4.38 (d, J=11.7 Hz, 1H), 2.62 (m, 1H), 2.28 (m, 1H), 1.79-1.48 (m, 11H), 1.38 (s, 3H), 0.97 (t, J=7.4 Hz, 6H), 0.88 (q, J=7.6 Hz, 6H). MS m/z [M+1]=528.

Intermediate I-3: $^{1}$H NMR (400 MHz, Acetonitrile-d3) δ 7.91 (s, 1H), 6.81 (d, J=4.5 Hz, 1H), 6.77 (d, J=4.5 Hz, 1H), 6.26 (s, 2H), 5.67 (d, J=3.5 Hz, 1H), 5.33 (dd, J=6.6, 3.5 Hz, 1H), 5.06 (d, J=6.6 Hz, 1H), 4.51 (d, J=11.7 Hz, 1H), 4.36 (d, J=11.7 Hz, 1H), 2.29 (m, 1H), 1.71 (s, 3H), 1.66-1.48 (m, 4H), 1.39 (s, 3H), 0.88 (m, 6H). MS m/z [M+1]=430.

Intermediate I-4: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl pivalate

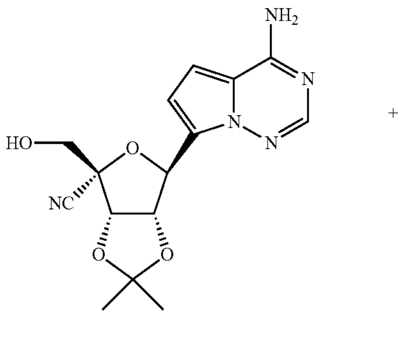

Intermediate I-1a

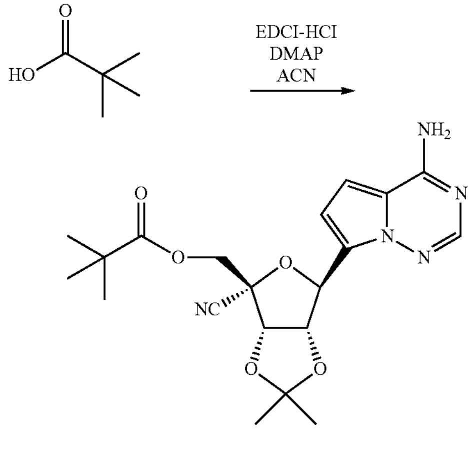

Intermediate I-4

To a mixture of Intermediate I-1a (0.637 mmol) and pivalic acid (0.955 mmol) in DMF (2 mL) were added DMAP (0.955 mmol) and then EDCI-HCl (0.955 mmol). The resulting mixture was stirred at room temperature for 3 h, MeOH (0.5 mL) added, concentrated in vacuo, and purified by silica gel column chromatography (0% to 5% MeOH in DCM) to give Intermediate I-4. $^{1}$H NMR (400 MHz, Acetonitrile-d3) δ 7.91 (s, 1H), 6.80 (d, J=4.5 Hz, 1H), 6.77 (d, J=4.5 Hz, 1H), 6.26 (s, 2H), 5.67 (d, J=3.5 Hz, 1H), 5.32 (dd, J=6.7, 3.5 Hz, 1H), 5.07 (d, J=6.6 Hz, 1H), 4.48 (d, J=11.6 Hz, 1H), 4.33 (d, J=11.6 Hz, 1H), 1.71 (s, 3H), 1.39 (s, 3H), 1.22 (s, 9H). MS m/z [M+1]=416.

Intermediate I-5: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (tert-butoxycarbonyl)-L-valinate

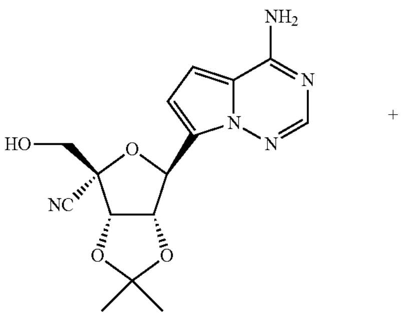

Intermediate I-1a

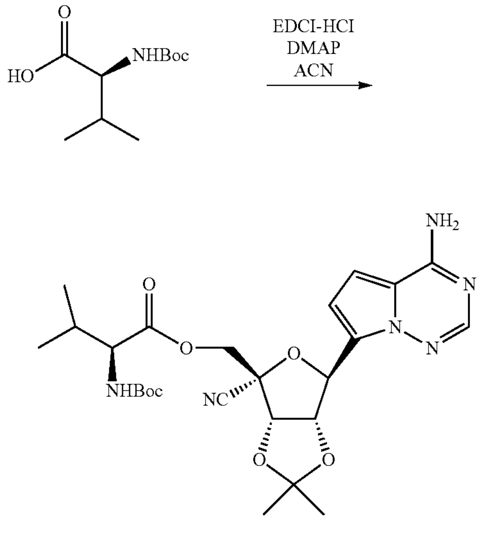

Intermediate I-5

To a mixture of Intermediate I-1a (0.634 mmol) and L-Boc-alanine (0.951 mmol) in DMF (2 mL) were added DMAP (0.951 mmol) and then EDCI-HCl (0.951 mmol). The resulting mixture was stirred at room temperature for 1 h, MeOH (0.5 mL) added, concentrated in vacuo, and purified by silica gel column chromatography (0% to 10% MeOH in DCM) to give Intermediate I-5. $^{1}$H NMR (400 MHz, Acetonitrile-d3) δ 7.92 (s, 1H), 6.80 (d, J=4.5 Hz, 1H), 6.77 (d, J=4.5 Hz, 1H), 6.27 (s, 2H), 5.67 (d, J=3.5 Hz, 1H), 5.55 (d, J=8.9 Hz, 1H), 5.33 (dd, J=6.6, 3.5 Hz, 1H), 5.08 (d, J=6.6 Hz, 1H), 4.48 (d, J=2.1 Hz, 2H), 4.10 (m, 1H), 2.17-2.02 (m, 1H), 1.72 (s, 3H), 1.44-1.24 (m, 12H), 0.92 (d, J=6.9 Hz, 3H), 0.86 (d, J=6.8 Hz, 3H). MS m/z [M+1]=531.

Intermediate I-6: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl3,3-dimethylbutanoate

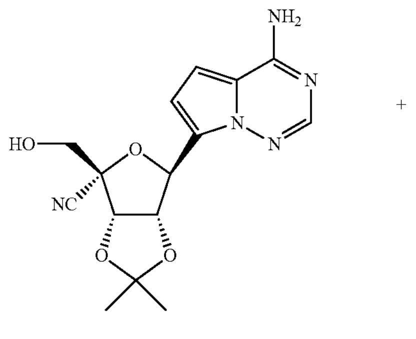

Intermediate I-1a

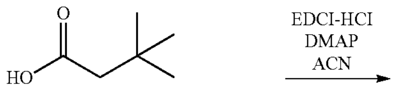

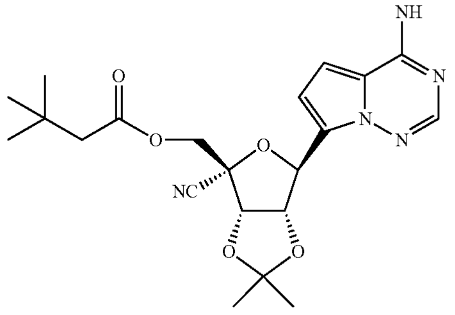

Intermediate I-6

To a mixture of Intermediate I-1a (0.356 mmol) and 3,3-dimethylbutanoic acid (0.534 mmol) in DMF (2 mL) were added DMAP (0.534 mmol) and then EDCI-HCl (0.534 mmol). The resulting mixture was stirred at rt for 2 h, water (0.5 mL) added, concentrated in vacuo, and purified by silica gel column chromatography (0% to 5% MeOH in DCM) to give Intermediate I-6. $^1$H NMR (400 MHz, Acetonitrile-d3) δ 7.91 (s, 1H), 6.80 (d, J=4.6 Hz, 1H), 6.77 (d, J=4.5 Hz, 1H), 6.26 (s, 2H), 5.67 (d, J=3.5 Hz, 1H), 5.33 (dd, J=6.6, 3.5 Hz, 1H), 5.06 (d, J=6.6 Hz, 1H), 4.47 (d, J=11.7 Hz, 1H), 4.34 (d, J=11.7 Hz, 1H), 2.27 (s, 2H), 1.77-1.67 (s, 3H), 1.39 (s, J=0.7 Hz, 3H), 1.02 (s, 9H). MS m/z [M+1]=430.

Intermediate I-7: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 4-methylbenzoate

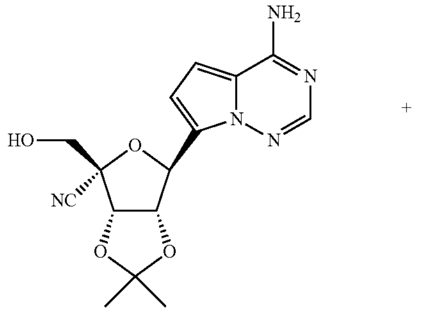

Intermediate I-1a

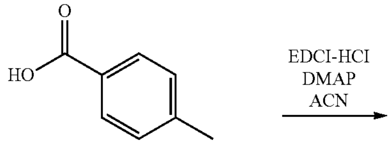

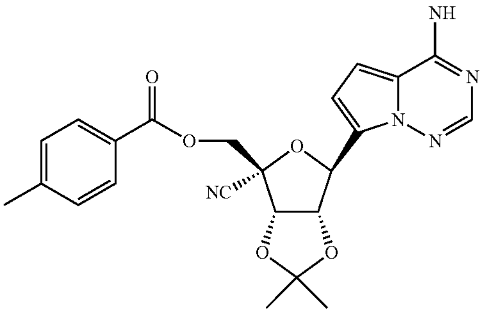

Intermediate I-7

To a mixture of Intermediate I-1a (0.326 mmol) and 4-methylbenzoic acid (0.453 mmol) in DMF (2 mL) were added DMAP (0.489 mmol) and then EDCI-HCl (0.489 mmol). The resulting mixture was stirred at room temperature for 2 h, water (1 mL) added, concentrated in vacuo, and purified by silica gel column chromatography (0 to 5% MeOH in DCM) to give Intermediate I-7. $^1$H NMR (400 MHz, Acetonitrile-d3) δ 7.99-7.89 (m, 2H), 7.85 (s, 1H), 7.39-7.32 (m, 2H), 6.80 (d, J=4.5 Hz, 1H), 6.75 (d, J=4.5 Hz, 1H), 6.25 (s, 2H), 5.69 (d, J=3.5 Hz, 1H), 5.36 (dd, J=6.7, 3.5 Hz, 1H), 5.21 (d, J=6.7 Hz, 1H), 4.73 (d, J=11.6 Hz, 1H), 4.59 (d, J=11.7 Hz, 1H), 2.44 (s, 3H), 1.74 (s, 3H), 1.41 (s, 3H). MS m/z [M+1]=450.

Intermediate I-8: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 1-methylcyclopropane-1-carboxylate

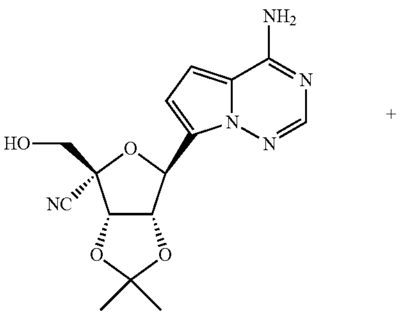

Intermediate I-1a

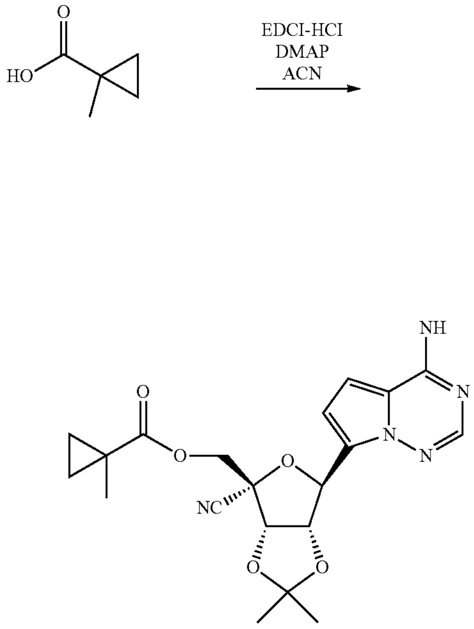

Intermediate I-8

To a mixture of Intermediate I-1a (0.323 mmol) and 1-methylcyclopropanecarboxylic acid (0.420 mmol) in DMF (2 mL) were added DMAP (51 mg, 0.420 mmol) and then EDCI-HCl (81 mg, 0.420 mmol). The resulting mixture was stirred at room temperature for 4 h, water (0.5 mL) added, concentrated in vacuo, and purified by silica gel column chromatography (0% to 5% MeOH in DCM) to give Intermediate I-8. $^1$H NMR (400 MHz, Acetonitrile-d3) δ 7.91 (s, 1H), 6.80 (d, J=4.5 Hz, 1H), 6.77 (d, J=4.5 Hz, 1H), 6.27 (s, 2H), 5.66 (d, J=3.4 Hz, 1H), 5.31 (dd, J=6.6, 3.5 Hz, 1H), 5.06 (d, J=6.6 Hz, 1H), 4.44 (d, J=11.6 Hz, 1H), 4.33 (d, J=11.6 Hz, 1H), 1.71 (s, 3H), 1.39 (s, 3H), 1.29 (s, 3H), 1.22 (m, 2H), 0.78 (m, 2H). MS m/z [M+1]=414.

Intermediate I-9: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 2-cyclobutylacetate

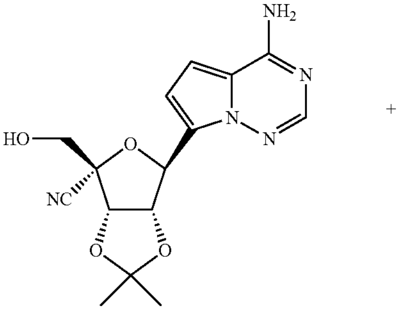

Intermediate I-1a

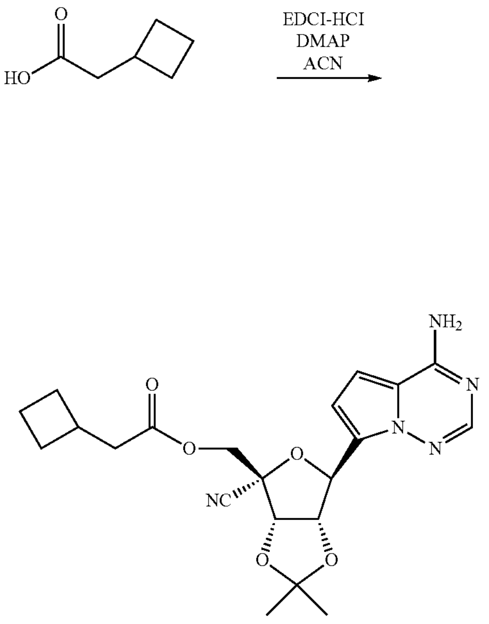

Intermediate I-9

To a mixture of Intermediate I-1a (0.664 mmol) and 2-cyclobutylacetic acid (0.863 mmol) in DMF (4 mL) were added DMAP (0.863 mmol) and then EDCI-HCl (0.863 mmol). The resulting mixture was stirred at rt for 1.5 h, water (0.5 mL) added, concentrated in vacuo, and purified by silica gel column chromatography (0% to 5% MeOH in DCM) to give Intermediate I-9. $^1$H NMR (400 MHz, Acetonitrile-$d_3$) δ 7.91 (s, 1H), 6.80 (d, J=4.5 Hz, 1H), 6.77 (d, J=4.5 Hz, 1H), 6.27 (s, 2H), 5.66 (d, J=3.5 Hz, 1H), 5.32 (dd, J=6.6, 3.5 Hz, 1H), 5.05 (d, J=6.6 Hz, 1H), 4.47 (d, J=11.7 Hz, 1H), 4.32 (d, J=11.7 Hz, 1H), 2.71-2.57 (m, 1H), 2.48 (d, J=7.6 Hz, 2H), 2.23-2.05 (m, 4H), 1.94-1.80 (m, 1H), 1.75-1.64 (m, 4H), 1.43-1.36 (m, 3H). MS m/z [M+1]= 428.

Intermediate I-10: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl3,3-dimethylcyclobutane-1-carboxylate

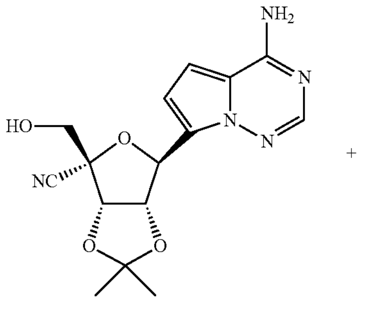

Intermediate I-1a

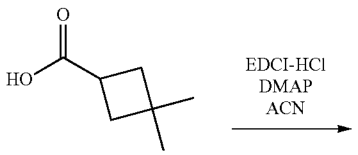

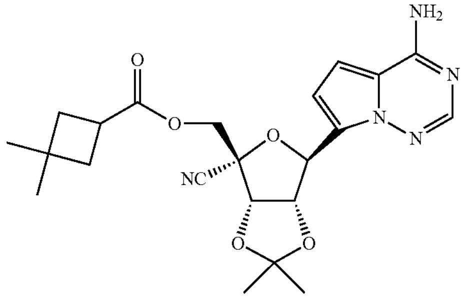

Intermediate I-10

To a mixture of Intermediate I-1a (0.326 mmol) and 3,3-dimethylcyclobutanecarboxylic acid (0.424 mmol) in DMF (2 mL) were added DMAP (0.424 mmol) and then EDCI-HCl (0.424 mmol). The resulting mixture was stirred at room temperature for 3.5 h, water (0.5 mL) added, concentrated in vacuo, and purified by silica gel column chromatography (0% to 5% MeOH in DCM) to give Intermediate I-10. $^1$H NMR (400 MHz, Acetonitrile-d3) δ 7.91 (s, 1H), 6.78 (m, 2H), 6.44 (s, 2H), 5.67 (d, J=3.5 Hz, 1H), 5.31 (dd, J=6.6, 3.4 Hz, 1H), 5.06 (d, J=6.6 Hz, 1H), 4.51 (d, J=11.7 Hz, 1H), 4.34 (d, J=11.6 Hz, 1H), 3.13 (m, 1H), 2.09-1.90 (m, 4H), 1.71 (s, 3H), 1.39 (s, 3H), 1.16 (s, 3H), 1.07 (s, 3H). MS m/z [M+1]=442.

Intermediates I-11 & I-12: ((2R,3S,4R,5S)-5-(4-aminopyrrolo[2,1-f][1,2,4]triazin-7-yl)-4-((tert-butyldimethylsilyl)oxy)-2-cyano-3-hydroxytetrahydrofuran-2-yl)methyl benzoate and ((2R,3S,4S,5S)-5-(4-aminopyrrolo[2,1-f][1,2,4]triazin-7-yl)-3-((tert-butyldimethylsilyl) oxy)-2-cyano-4-hydroxytetrahydrofuran-2-yl)methyl benzoate

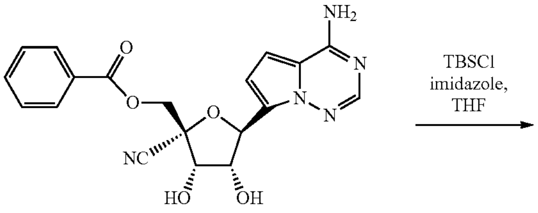

Compound 2

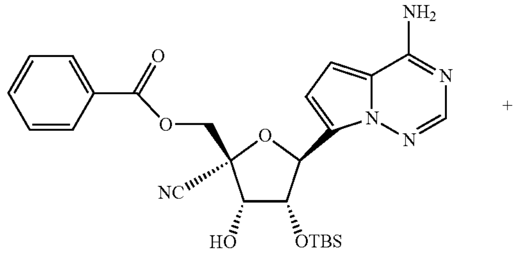

Intermediate I-11

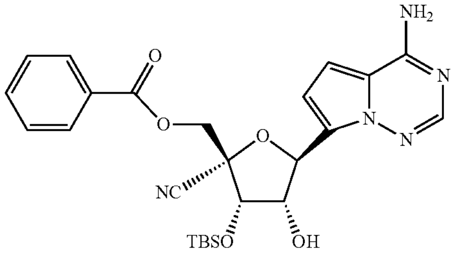

Intermediate I-12

To a mixture of Compound 2 (1.11 mmol) and TBSCl (3.84 mmol) in THE (5 mL) was added imidazole (4.38 mmol) at room temperature. The resulting mixture was stirred at rt for 1 h and the reaction quenched by adding methanol (1 mL). After dilution with EtOAc, it was washed with water, dried, concentrated in vacuo, and purified by silica gel (20% to 100% EtOAc in hexane) to give Intermediate I-11 and Intermediate I-12.

Intermediate I-11.: H NMR (400 MHz, Acetonitrile-d3) δ 8.08-8.02 (m, 2H), 7.81 (s, 1H), 7.68 (m, 1H), 7.55 (m, 2H), 6.77-6.71 (m, 2H), 6.24 (s, 2H), 5.50 (d, J=4.2 Hz, 1H), 4.86-4.78 (m, 2H), 4.66-4.59 (m, 2H), 3.76 (d, J=7.8 Hz, 1H), 0.91 (s, 9H), 0.04 (s, 3H), -0.04 (s, 3H). MS m/z [M+1]=510.

Intermediate I-12: $^1$H NMR (400 MHz, Acetonitrile-d3) δ 8.05-7.96 (m, 2H), 7.85 (s, 1H), 7.71-7.64 (m, 1H), 7.58-7.50 (m, 2H), 6.77-6.68 (m, 2H), 6.23 (s, 2H), 5.52 (d, J=5.3 Hz, 1H), 4.80-4.72 (m, 2H), 4.68 (q, J=5.2 Hz, 1H), 4.54 (d, J=11.9 Hz, 1H), 3.45 (d, J=5.2 Hz, 1H), 1.03 (s, 9H), 0.24 (s, 3H), 0.23 (s, 3H). MS m/z [M+1]=510.

Intermediates I-13 & I-14 (Mixture): ((2R,3S,4S,5S)-5-(4-aminopyrrolo[2,1-f][1,2,4]triazin-7-yl)-3-((tert-butyldimethylsilyl)oxy)-2-cyano-4-(isobutyryloxy)tetrahydrofuran-2-yl)methyl benzoate and ((2R,3S,4S,5S)-5-(4-aminopyrrolo[2,1-f][1,2,4]triazin-7-yl)-4-((tert-butyldimethylsilyl)oxy)-2-cyano-3-(isobutyryloxy)tetrahydrofuran-2-yl)methyl benzoate

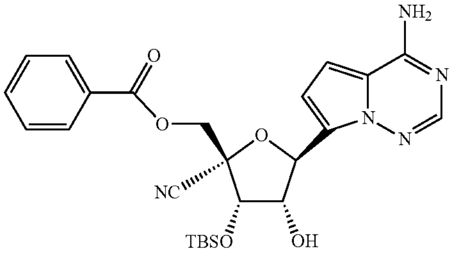

+

Intermediate I-12

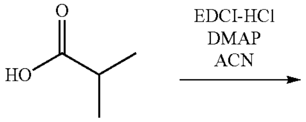

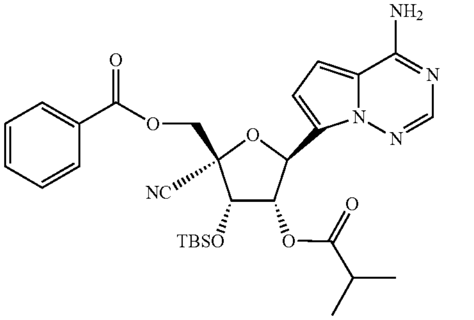

+

Intermediate I-13

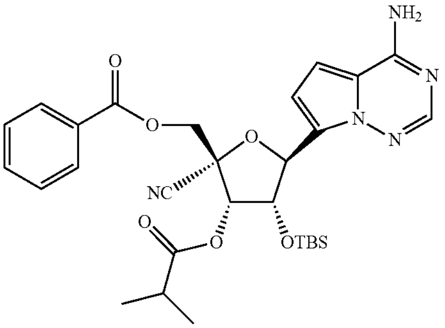

Intermediate I-14

To a mixture of Intermediate I-12 (0.135 mmol) and isobutyric acid (0.016 mL, 0.176 mmol) in DMF (1 mL) were added DMAP (0.203 mmol) and then EDCI-HCl (0.203 mmol). The resulting mixture was stirred at rt for 2 h, water (0.5 mL) added, concentrated in vacuo, and purified by silica gel column chromatography (0% to 5% MeOH in DCM) to give Intermediate I-13 and Intermediate I-14 as a mixture Mixture of Intermediates I-13 and I-14: $^1$H NMR (400 MHz, Acetonitrile-d3) δ 8.08-8.03 (m, 1H), 7.99-7.91 (m, 1H), 7.82 (s, 0.5H), 7.78 (s, 0.5H), 7.67 (m, 1H), 7.52 (m, 2H), 6.78 (s, 1H), 6.73 (s, 1H), 6.51 (bs, 2H), 5.81 (dd, J=5.5, 2.7 Hz, 0.5H), 5.65 (d, J=5.3 Hz, 0.5H), 5.59 (d, J=2.7 Hz, 0.5H), 5.52 (d, J=5.5 Hz, 0.5H), 5.19 (d, J=5.5 Hz, 0.5H), 5.06 (t, J=5.5 Hz, 0.5H), 4.91 (d, J=12.1 Hz, 0.5H), 4.86 (d, J=11.9 Hz, 0.5H), 4.69 (d, J=11.8 Hz, 0.5H), 4.52 (d, J=12.1 Hz, 0.5H), 2.70 (dq, J=26.1, 7.0 Hz, 0.5H), 2.54 (h, J=7.0 Hz, 0.5H), 1.30-1.20 (m, 3H), 1.16 (d, J=6.9 Hz, 3H), 0.98 (s, 4.5H), 0.82 (s, 4.5H), 0.22 (s, 1.5H), 0.17 (s, 1.5H), -0.05 (s, 1.5H), -0.19 (s, 1.5H). MS m/z [M+1]=580.

Intermediate I-15: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl isobutyrate

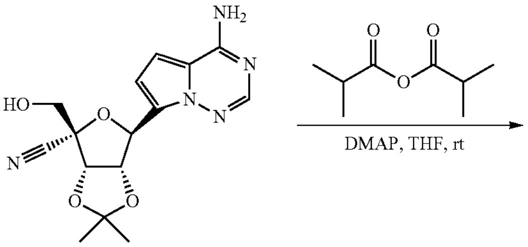

Intermediate I-1a

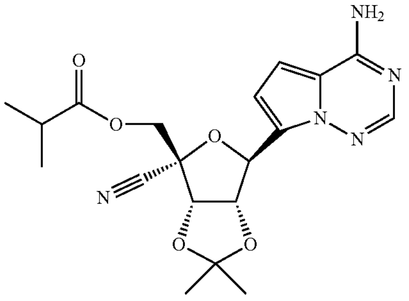

Intermediate I-15

To a solution of Intermediate I-1a (2.1 mmol, 1.0 equiv.) and 4-dimethylaminopyridine (0.23 mmol, 0.11 equiv.) in THF (7.0 mL) was added isobutyric anhydride (0.34 mL, 2.1 mmol, 1.0 equiv.) dropwise at room temperature. The solution was stirred for 30 min. The reaction mixture was concentrated in vacuo and the crude material was purified by silica gel (0% to 100% EtOAc in DCM) to afford the Intermediate I-15. $^1$H NMR (400 MHz, Methanol-d4) δ 7.84 (s, 1H), 6.86 (d, J=4.5 Hz, 1H), 6.77 (d, J=4.5 Hz, 1H), 5.63 (d, J=3.1 Hz, 1H), 5.32 (dd, J=6.6, 3.2 Hz, 1H), 5.10 (d, J=6.6 Hz, 1H), 4.50 (d, J=11.5 Hz, 1H), 4.35 (d, J=11.5 Hz, 1H), 2.69-2.57 (m, 1H), 1.71 (s, 3H), 1.39 (s, 3H), 1.20-1.15 (m, 6H). MS m/z [M+1]=402.1.

Intermediate I-16: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 3-methylbutanoate

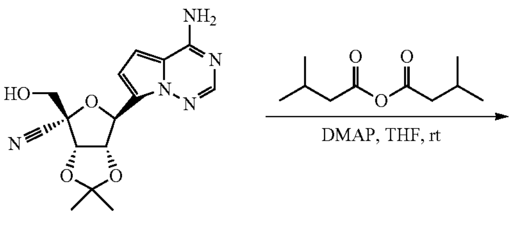

Intermediate I-1a

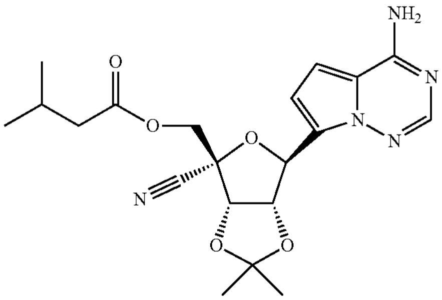

Intermediate I-16

To a solution of Intermediate I-1a (0.45 mmol, 1.0 equiv.) and 4-dimethylaminopyridine (0.11 mmol, 0.25 equiv.) in THF (2.0 mL) was added isovaleric anhydride (0.10 mL, 0.50 mmol, 1.1 equiv.) dropwise at room temperature. The solution was stirred for 30 min. The reaction mixture was concentrated in vacuo and the crude material was purified by silica gel (0% to 100% EtOAc in DCM) to afford Intermediate I-16. $^1$H NMR (400 MHz, Methanol-$d_4$) δ 7.84 (s, 1H), 6.86 (d, J=4.5 Hz, 1H), 6.77 (d, J=4.5 Hz, 1H), 5.63 (d, J=3.2 Hz, 1H), 5.33 (dd, J=6.6, 3.2 Hz, 1H), 5.10 (d, J=6.6 Hz, 1H), 4.49 (d, J=11.5 Hz, 1H), 4.36 (d, J=11.5 Hz, 1H), 2.28-2.24 (m, 2H), 2.13-2.02 (m, 1H), 1.71 (s, 3H), 1.39 (s, 3H), 0.98-0.92 (m, 6H). MS m/z [M+1]=416.1.

Intermediate I-17: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl acetate

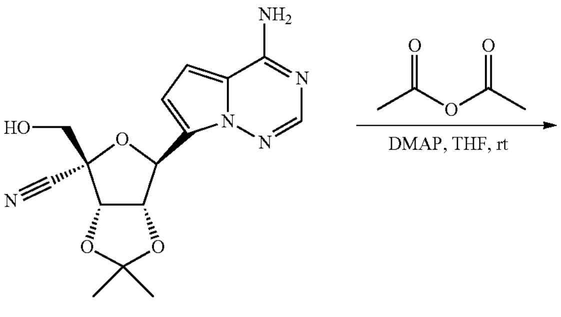

Intermediate I-1a

-continued

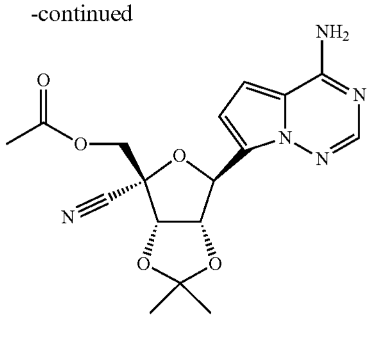

Intermediate I-17

To a solution of Intermediate I-1a (0.44 mmol, 1.0 equiv.) and 4-dimethylaminopyridine (0.19 mmol, 0.42 equiv.) in THF (2.0 mL) was added acetic anhydride (0.47 mmol, 1.1 equiv.) dropwise at room temperature. The solution was stirred for 20 min. The reaction mixture was concentrated in vacuo and the crude material was purified by silica gel (0% to 100% EtOAc in DCM) to afford Intermediate I-17. $^1$H NMR (400 MHz, Methanol-$d_4$) δ 7.83 (s, 1H), 6.85 (d, J=4.5 Hz, 1H), 6.77 (d, J=4.5 Hz, 1H), 5.62 (d, J=3.2 Hz, 1H), 5.32 (dd, J=6.6, 3.2 Hz, 1H), 5.10 (d, J=6.6 Hz, 1H), 4.49 (d, J=11.5 Hz, 1H), 4.35 (d, J=11.5 Hz, 1H), 2.10 (s, 3H), 1.71 (s, 3H), 1.39 (s, 3H). MS m/z [M+1]=374.1.

Intermediate I-18: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl propionate

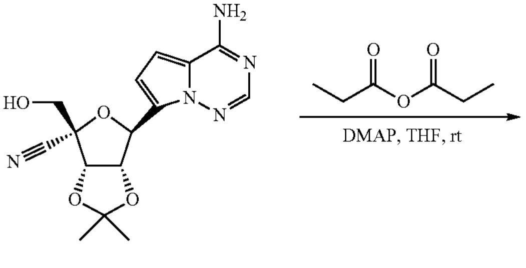

Intermediate I-1a

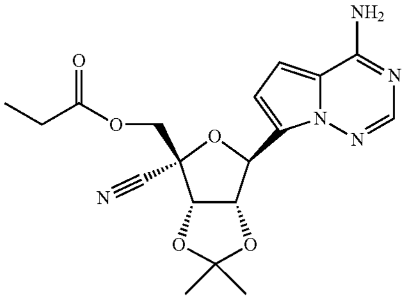

Intermediate I-18

To a solution of Intermediate I-1a (0.45 mmol, 1.0 equiv.) and 4-dimethylaminopyridine (0.14 mmol, 0.31 equiv.) in THF (2.0 mL) was added propionic anhydride (65 μL, 0.50 mmol, 1.1 equiv.) dropwise at room temperature. The solution was stirred for 1 h. The reaction mixture was concentrated in vacuo and the crude material was purified by silica gel (0% to 100% EtOAc in DCM) to afford the Intermediate I-18. MS m/z [M+1]=388.2.

Intermediate I-19: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl cyclopentanecarboxylate

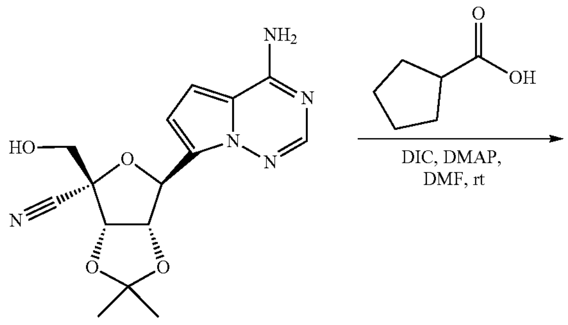

Intermediate I-1a

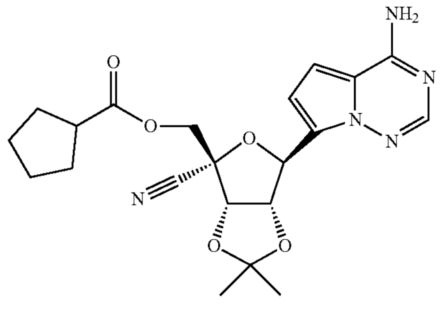

Intermediate I-19

To a solution of Intermediate I-1a (0.46 mmol, 1.0 equiv.) in DMF (2.0 mL) was added cyclopentanecarboxylic acid (55 μL, 0.51 mmol, 1.1 equiv.) followed by DIAD (0.09 mL, 0.46 mmol, 1.0 equiv.) and 4-dimethylaminopyridine (0.46 mmol, 1.0 equiv.). The solution was stirred at room temperature for 30 min prior to the addition of DIC (0.09 mL, 0.55 mmol, 1.2 equiv.). The solution was stirred for an additional 6 h before quenching with water (50 mL) and extracting with EtOAc (2×50 mL). The organic layers were combined, dried over $Na_2SO_4$, filtered, concentrated in vacuo and purified by silica gel chromatography (0%-10% MeOH in DCM) to afford Intermediate I-19. MS m/z [M+1]=428.1.

Intermediate I-20: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl cyclohexanecarboxylate

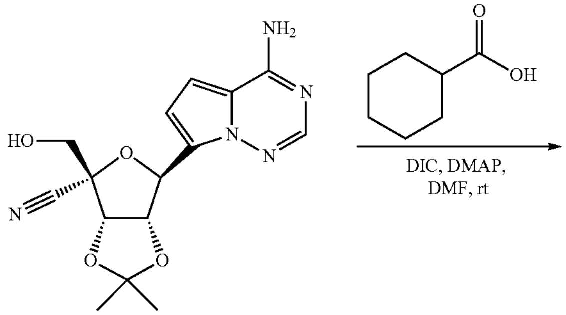

Intermediate I-1a

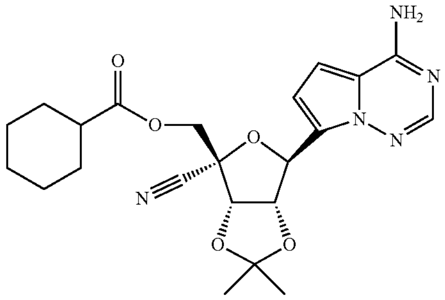

Intermediate I-20

To a solution of Intermediate I-1a (0.48 mmol, 1.0 equiv.) in DMF (2.0 mL) was added cyclohexanecarboxylic acid (65 μL, 0.53 mmol, 1.1 equiv.) and DIC (0.09 mL, 0.58 mmol, 1.2 equiv.) followed by 4-dimethylaminopyridine (0.48 mmol, 1.0 equiv.). The solution was stirred at room temperature overnight. The reaction was quenched with water (50 mL) and the aqueous layer was extracted with EtOAc (2×50 mL). The organic layers were combined, dried over $Na_2SO_4$, filtered, concentrated in vacuo and purified by silica gel chromatography (0%-20% MeOH in DCM) to afford Intermediate I-20. MS m/z [M+1]=442.1.

Intermediate I-21: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl cyclobutanecarboxylate

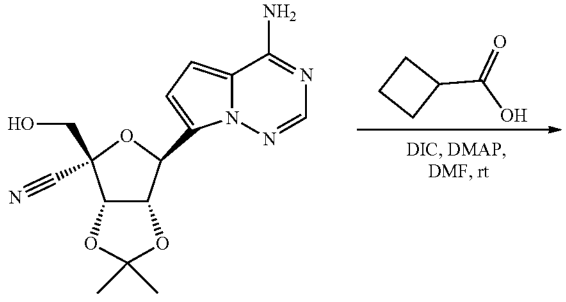

Intermediate I-1a

-continued

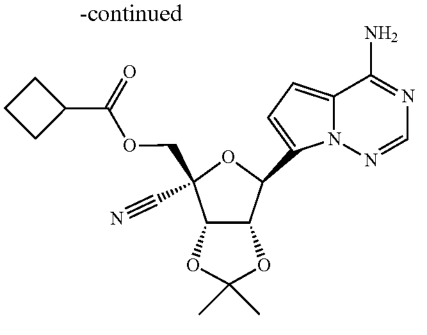

Intermediate I-21

To a solution of Intermediate I-1a (0.39 mmol), cyclobutanecarboxylic acid (0.47 mmol) in DMF (2 mL), was added N,N'-Diisopropylcarbodiimide (0.47 mmol) dropwise followed by 4-dimethylaminopyridine (0.39 mmol) and stirred 4 h at room temperature. The reaction mixture was diluted with ethyl acetate, washed once with water, once with brine solution, dried over $Na_2SO_4$, filtered and concentrated under reduced pressure (Temperature maintained <30° C.). The crude product was dissolved in 5% MeOH/DCM, load on 40 g silica gel column, and elute with Hexane 2 min, DCM for 1 min, and 0%-100% EtOAc/DCM 18 min. The pure fractions were combined, concentrated to afford Intermediate I-21. 1H NMR (400 MHz, Methanol-d4) δ 7.86 (s, 1H), 6.88 (d, J=4.5 Hz, 1H), 6.79 (d, J=4.5 Hz, 1H), 5.64 (d, J=3.1 Hz, 1H), 5.34 (dd, J=6.6, 3.2 Hz, 1H), 5.12 (d, J=6.6 Hz, 1H), 4.45 (dd, J=66.7, 11.5 Hz, 2H), 4.12 (q, J=7.1 Hz, 1H), 3.80 (p, J=6.5 Hz, 2H, DIPEA salt), 3.26 (p, J=8.4 Hz, 1H), 2.37-2.18 (m, 5H), 1.99-1.86 (m, 1H), 1.73 (s, 3H), 1.41 (s, 3H), 1.12 (d, J=6.5 Hz, 12H, DIPEA salt). MS m/z [M+1] =414.05.

Intermediate I-22: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl cyclopropanecarboxylate

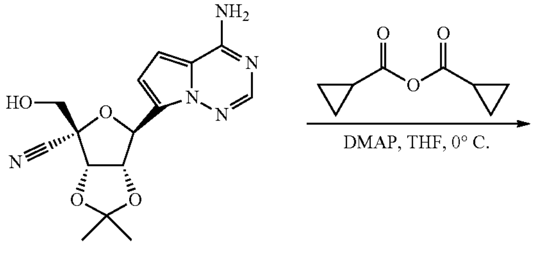

Intermediate I-1a

-continued

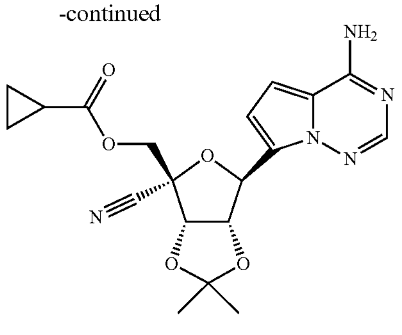

Intermediate I-22

To a solution of Intermediate I-1a (0.45 mmol), DMAP (0.068 mmol) in THF (4.5 mL) at 0° C. was added cyclopropanecarbonyl cyclopropanecarboxylate (0.45 mmol) and stirred 1 h at 0° C. The reaction mixture was warmed to room temperature and directly load on 40 g silica gel column, and elute with Hexane 3 min, with DCM 1 min, and 0%-100% EtOAc/DCM 18 min. The pure fractions were combined, concentrated to afford Intermediate I-22. MS m/z [M+1]=400.03.

Intermediate I-23: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl butyrate

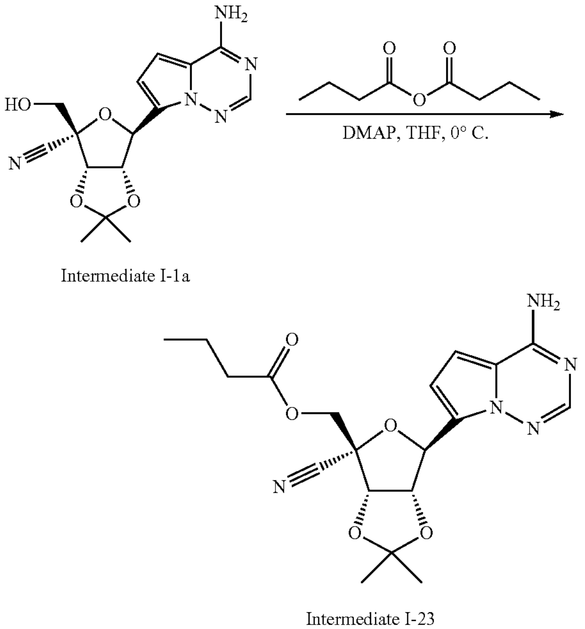

Intermediate I-1a

Intermediate I-23

To a solution of Intermediate I-1a (0.45 mmol), DMAP (0.068 mmol) in THF (4.5 mL) at 0° C. was added butanoyl butanoate (0.45 mmol) drop wise (5 min) and stirred 1 h at 0° C. The reaction mixture was warmed to room temperature and directly load on 40 g silica gel column, elute with Hexane 3 min, with DCM 1 min, and 0%-100% EtOAc/DCM 18 min. The pure fractions were combined, concentrated to afford Intermediate I-23. MS m/z [M+1]=402.07.

Intermediate I-24: Synthesis of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 2-(1-methylcyclobutyl)acetate

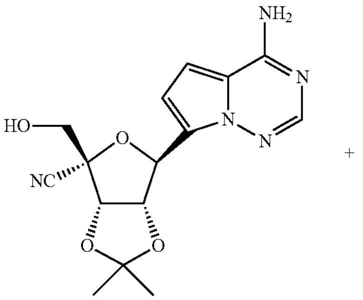

Intermediate I-1a

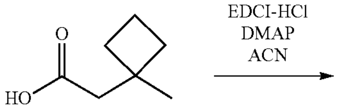

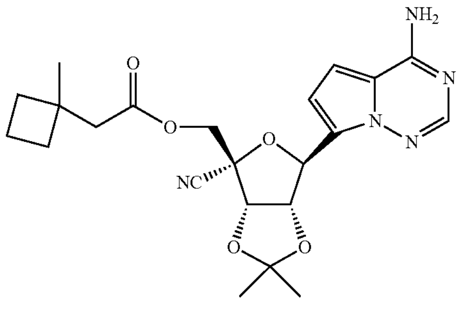

Intermediate I-24

To a mixture of Intermediate I-1a (0.302 mmol) and 2-(1-methylcyclobutyl)acetic acid (0.453 mmol) in ACN (2 mL) were added DMAP (0.453 mmol) and then EDCI-HCl (0.453 mmol). The resulting mixture was stirred at rt for 1 h, methanol (0.5 mL) added, concentrated in vacuo, and purified by silica gel column chromatography (0% to 5% MeOH in DCM) to give Intermediate I-24. $^1H$ NMR (400 MHz, Acetonitrile-d3) δ 7.91 (s, 1H), 6.80 (d, J=4.5 Hz, 1H), 6.78 (dd, J=4.5, 0.8 Hz, 1H), 6.39 (s, 2H), 5.67 (d, J=3.4 Hz, 1H), 5.36-5.27 (m, 1H), 5.06 (d, J=6.6 Hz, 1H), 4.47 (dd, J=11.7, 0.8 Hz, 1H), 4.34 (dd, J=11.7, 0.8 Hz, 1H), 2.47 (s, 2H), 2.07-1.73 (m, 6H), 1.71 (s, 3H), 1.39 (s, 3H), 1.19 (s, 3H). MS m/z [M+1]=441.9.

Intermediate I-25: Synthesis of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl spiro[3,3]heptane-2-carboxylate

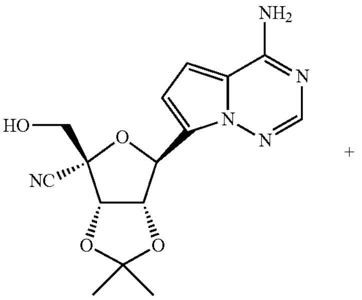

Intermediate I-1a

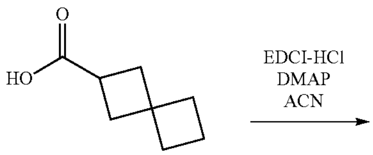

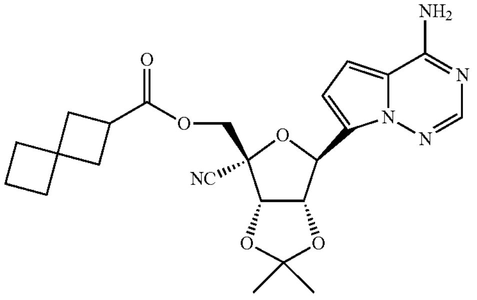

Intermediate I-25

To a mixture of Intermediate I-1a (0.302 mmol) and spiro[3.3]heptane-2-carboxylic acid (0.453 mmol) in ACN (2 mL) were added DMAP (0.453 mmol) and then EDCI-HCl (0.453 mmol). The resulting mixture was stirred at rt for 2 h, water (0.5 mL) added, concentrated in vacuo, and purified by silica gel column chromatography (0% to 5% MeOH in DCM) to give Intermediate I-25. $^1H$ NMR (400 MHz, Acetonitrile-d3) δ 7.91 (s, 1H), 6.79 (m, 2H), 6.38 (s, 2H), 5.66 (d, J=3.5 Hz, 1H), 5.31 (dd, J=6.7, 3.5 Hz, 1H), 5.05 (d, J=6.6 Hz, 1H), 4.49 (d, J=11.7 Hz, 1H), 4.32 (d, J=11.7 Hz, 1H), 3.10-2.90 (m, 1H), 2.22 (m, 4H), 2.09-2.00 (m, 2H), 1.97-1.88 (m, 2H), 1.85-1.74 (m, 2H), 1.71 (s, 3H), 1.39 (s, 3H). MS m/z [M+1]=453.8.

Intermediate I-26: (3aS,4R,6S,6aS)-6-(4-aminopyrrolo[2,1-f][1,2,4]triazin-7-yl)-4-(((tert-butyldimethylsilyl)oxy)methyl)-2,2-dimethyltetrahydrofuro[3,4-d][1,3]dioxole-4-carbonitrile

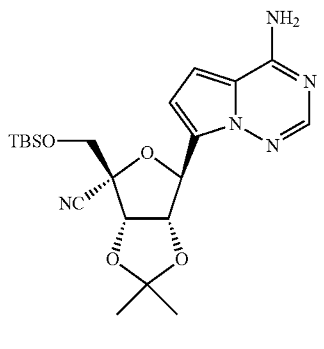

Intermediate I-26

Intermediate I-26 was prepared according to WO2015/069939. For example, pages 127-138 of WO2015/069939 provide a process for preparing this compound (identified as compound 14k in WO2015/069939).

Intermediate I-27: (7-((3aS,4S,6R,6aS)-6-(((tert-butyldimethylsilyl)oxy)methyl)-6-cyano-2,2-dimethyltetrahydrofuro[3,4-d][1,3]dioxol-4-yl)-4-iminopyrrolo[2,1-f][1,2,4]triazin-3(4H)-yl)methyl isobutyrate

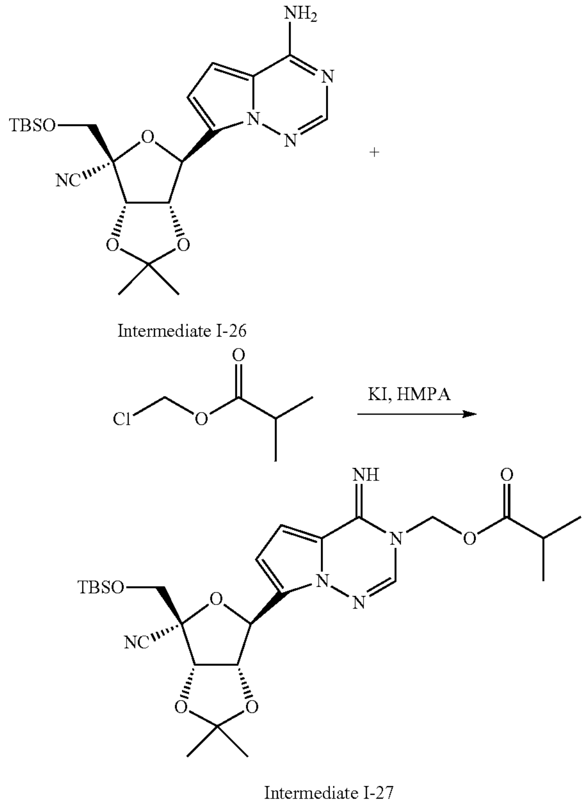

Intermediate I-27

To a mixture of Intermediate I-26 (0.180 mmol, 80% purity) and KI (0.898 mmol) in HMPA (1 mL) was added chloromethyl isobutyrate (0.449 mmol). The resulting mixture was stirred at rt for 15 h, diluted with EtOAc (30 mL), washed with brine (10 mL×3), dried with sodium sulfate, concentrated in vacuo, and purified by silica gel column chromatography (0% to 5% MeOH in DCM) to give Intermediate I-27. $^1$H NMR (400 MHz, Acetonitrile-d3) δ 7.91-7.66 (m, 2H), 6.82 (d, J=4.3 Hz, 1H), 6.52 (d, J=4.3 Hz, 1H), 5.86 (s, 2H), 5.47 (d, J=3.7 Hz, 1H), 5.18 (dd, J=3.88, 6.66 Hz, 1H), 4.92 (d, J=6.6 Hz, 1H), 4.02-3.78 (m, 2H), 2.59 (m, 1H), 1.69 (s, 3H), 1.39 (s, 3H), 1.14 (d, J=7.0 Hz, 6H), 0.92 (s, 9H), 0.09 (s, 6H). MS m/z [M+1]=545.9.

Intermediate I-28: ((3aS,4R,6S,6aS)-4-cyano-6-(4-(3,3-dimethylbutanamido)pyrrolo[2,1-f][1,2,4]triazin-7-yl)-2,2-dimethyltetrahydrofuro[3,4-d][1,3]dioxol-4-yl)methyl 3,3-dimethylbutanoate

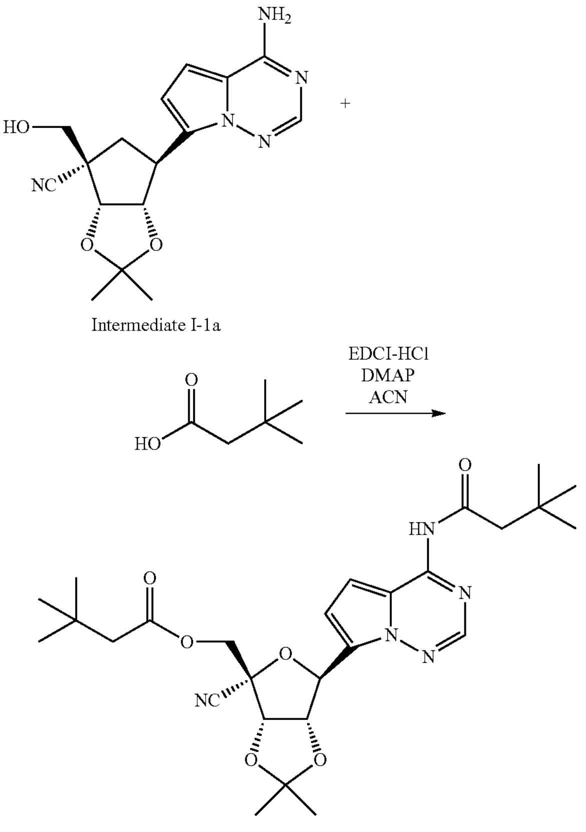

Intermediate I-28

To a mixture of Intermediate I-1a (2.32 mmol) and 3,3-dimethylbutanoic acid (0.36 mL, 2.79 mmol) in ACN (15 mL) were added DMAP (2.79 mmol) and then EDCI-HCl (2.79 mmol). The resulting mixture was stirred at rt for 1 h, water (5 mL) added, concentrated in vacuo, and purified by silica gel column chromatography (0 to 5% MeOH in DCM) to give Intermediate I-28. $^1$H NMR (400 MHz, Acetonitrile-d3) δ 8.80 (s, 1H), 8.22 (s, 1H), 7.21 (dd, J=4.7, 0.9 Hz, 1H), 6.99 (d, J=4.7 Hz, 1H), 5.75 (d, J=3.4 Hz, 1H), 5.34 (ddd, J=6.6, 3.4, 1.0 Hz, 1H), 5.07 (d, J=6.6 Hz, 1H), 4.49-4.41 (m, 1H), 4.38-4.30 (m, 1H), 2.52 (s, 2H), 2.27 (s, 2H), 1.72 (s, 3H), 1.40 (s, 3H), 1.13 (s, 9H), 1.02 (s, 9H). MS m/z [M+1]=528.0.

Intermediate I-29: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 1-methylcyclobutane-1-carboxylate

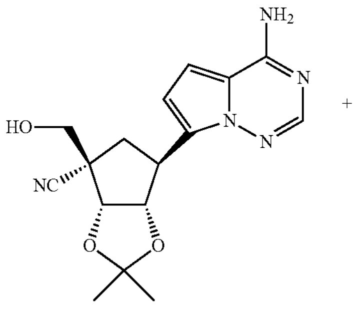

Intermediate I-1a

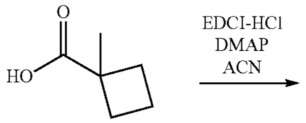

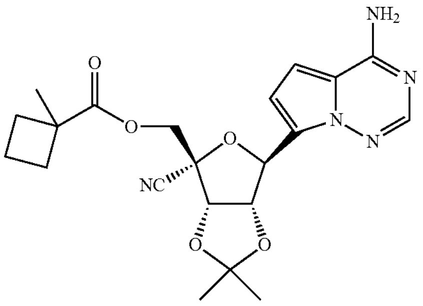

Intermediate I-29

To a mixture of Intermediate I-1a (0.302 mmol) and 1-methylcyclobutane-1-carboxylic acid (0.362 mmol) in ACN (2 mL) were added DMAP (0.362 mmol) and then EDCI-HCl (0.362 mmol). The resulting mixture was stirred at rt for 5 h, concentrated in vacuo, and purified by silica gel column chromatography (0% to 5% MeOH in DCM) to give Intermediate I-29. $^{1}$H NMR (400 MHz, Acetonitrile-d3) δ 7.92 (s, 1H), 6.78 (m, 2H), 6.37 (s, 2H), 5.68 (d, J=3.4 Hz, 1H), 5.32 (dd, J=6.6, 3.5 Hz, 1H), 5.08 (d, J=6.7 Hz, 1H), 4.53 (d, J=11.6 Hz, 1H), 4.36 (d, J=11.6 Hz, 1H), 2.60-2.35 (m, 2H), 1.98 (m, 2H), 1.92-1.80 (m, 2H), 1.71 (s, 3H), 1.43-1.34 (m, 6H). MS m/z [M+1]=428.2.

Intermediate I-30: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 3,3-dimethylpentanoate

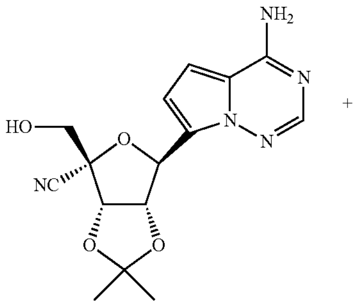

Intermediate I-1a

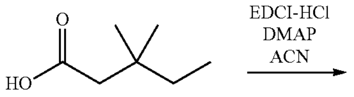

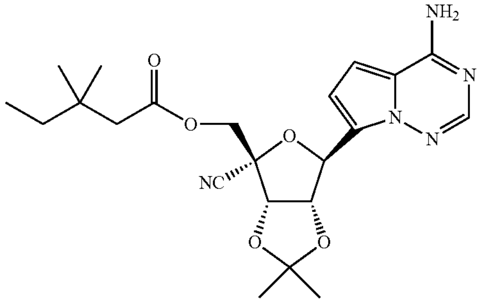

Intermediate I-30

To a mixture of Intermediate I-1a (0.302 mmol) and 3,3-dimethylpentanoic acid (0.362 mmol) in ACN (2 mL) were added DMAP (0.362 mmol) and then EDCI-HCl (0.362 mmol). The resulting mixture was stirred at rt for 5 h, concentrated in vacuo, and purified by silica gel column chromatography (0 to 5% MeOH in DCM) to give Intermediate I-30. $^{1}$H NMR (400 MHz, Acetonitrile-d3) δ 7.91 (s, 1H), 6.80 (d, J=4.5 Hz, 1H), 6.77 (d, J=4.5 Hz, 1H), 6.31 (s, 2H), 5.67 (d, J=3.5 Hz, 1H), 5.33 (dd, J=6.6, 3.5 Hz, 1H), 5.06 (d, J=6.6 Hz, 1H), 4.46 (d, J=11.7 Hz, 1H), 4.34 (d, J=11.7 Hz, 1H), 2.25 (s, 2H), 1.71 (s, 3H), 1.43-1.26 (m, 5H), 0.97 (s, 6H), 0.85 (t, J=7.5 Hz, 3H). MS m/z [M+1]=444.3.

Intermediate I-31: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 3-fluoro-2,2-dimethylpropanoate

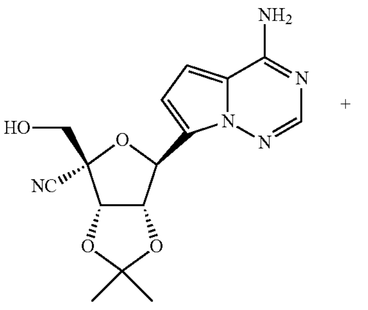

Intermediate I-1a

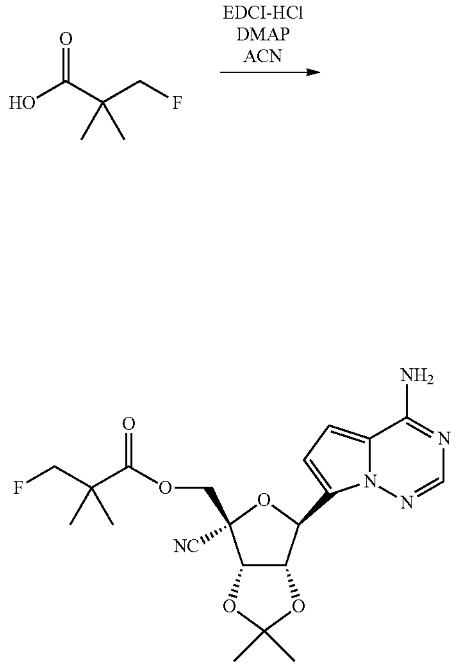

Intermediate I-31

To a mixture of Intermediate I-1a (0.302 mmol) and 3-fluoro-2,2-dimethyl-propanoic acid (0.362 mmol) in ACN (2 mL) were added DMAP (0.362 mmol) and then EDCI-HCl (0.362 mmol). The resulting mixture was stirred at rt for 5 h, concentrated in vacuo, and purified by silica gel column chromatography (0% to 5% MeOH in DCM) to give Intermediate I-31. $^1$H NMR (400 MHz, Acetonitrile-d3) δ 7.91 (s, 1H), 7.47-7.36 (m, 2H), 6.96 (s, 2H), 5.63 (m, 1H), 5.24 (m, 1H), 5.00 (m, 1H), 4.53-4.44 (m, 2H), 4.41-4.25 (m, 2H), 1.72 (s, 3H), 1.37 (s, 3H), 1.30-1.17 (m, 6H). MS m/z [M+1]=434.3.

Intermediate I-32: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (R)-5-oxotetrahydrofuran-2-carboxylate

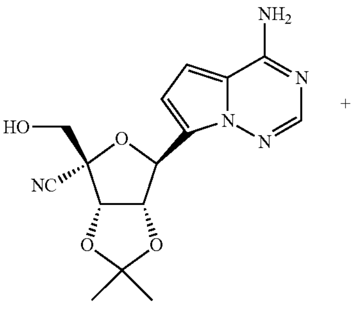

Intermediate I-1a

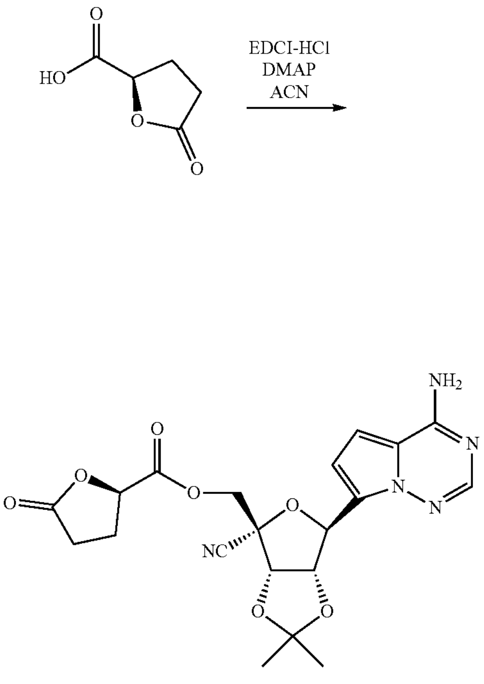

Intermediate I-32

To a mixture of Intermediate I-1a (0.302 mmol) and (2R)-5-oxotetrahydrofuran-2-carboxylic acid (0.362 mmol) in ACN (2 mL) were added DMAP (0.362 mmol) and then EDCI-HCl (0.362 mmol). The resulting mixture was stirred at rt for 15 h, concentrated in vacuo, and purified by silica gel column chromatography (0% to 5% MeOH in DCM) to give Intermediate I-32. $^1$H NMR (400 MHz, Acetonitrile-d3) δ 7.92 (s, 1H), 6.81 (d, J=4.5 Hz, 1H), 6.77 (d, J=4.5 Hz, 1H), 6.34 (s, 2H), 5.69 (d, J=3.3 Hz, 1H), 5.33 (dd, J=6.6, 3.3 Hz, 1H), 5.11 (d, J=6.6 Hz, 1H), 5.05 (m, 1H), 4.68 (d, J=11.7 Hz, 1H), 4.47 (d, J=11.7 Hz, 1H), 2.66-2.43 (m, 3H), 2.31 (m, 1H), 1.72 (s, 3H), 1.39 (s, 3H). MS m/z [M+1]=444.2.

Intermediate I-33: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 2,2-dimethylbutanoate

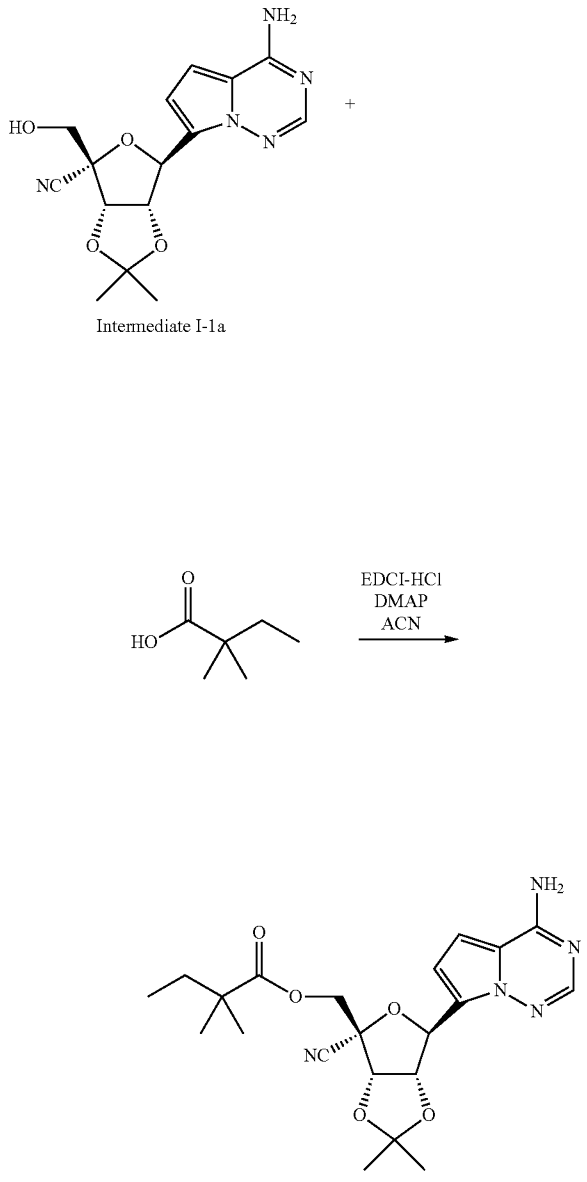

Intermediate I-33

To a mixture of Intermediate I-1a (0.302 mmol) and 2,2-dimethylbutanoic acid (0.362 mmol) in ACN (2 mL) were added DMAP (0.362 mmol) and then EDCI-HCl (0.362 mmol). The resulting mixture was stirred at rt for 5 h, concentrated in vacuo, and purified by silica gel column chromatography (0% to 5% MeOH in DCM) to give Intermediate I-33. $^1$H NMR (400 MHz, Methanol-d4) δ 7.85 (s, 1H), 6.85 (d, J=4.5 Hz, 1H), 6.78 (d, J=4.5 Hz, 1H), 5.65 (d, J=3.2 Hz, 1H), 5.34 (ddd, J=6.7, 3.3, 1.1 Hz, 1H), 5.08 (d, J=6.6 Hz, 1H), 4.47 (dd, J=11.5, 1.1 Hz, 1H), 4.36 (dd, J=11.5, 1.1 Hz, 1H), 1.72 (s, 3H), 1.65-1.52 (m, 2H), 1.40 (s, 3H), 1.19-1.17 (m, 3H), 1.15 (s, 3H), 0.89-0.74 (m, 3H). MS m/z [M+1]=430.0.

Intermediate I-34: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl4,4-dimethylpentanoate

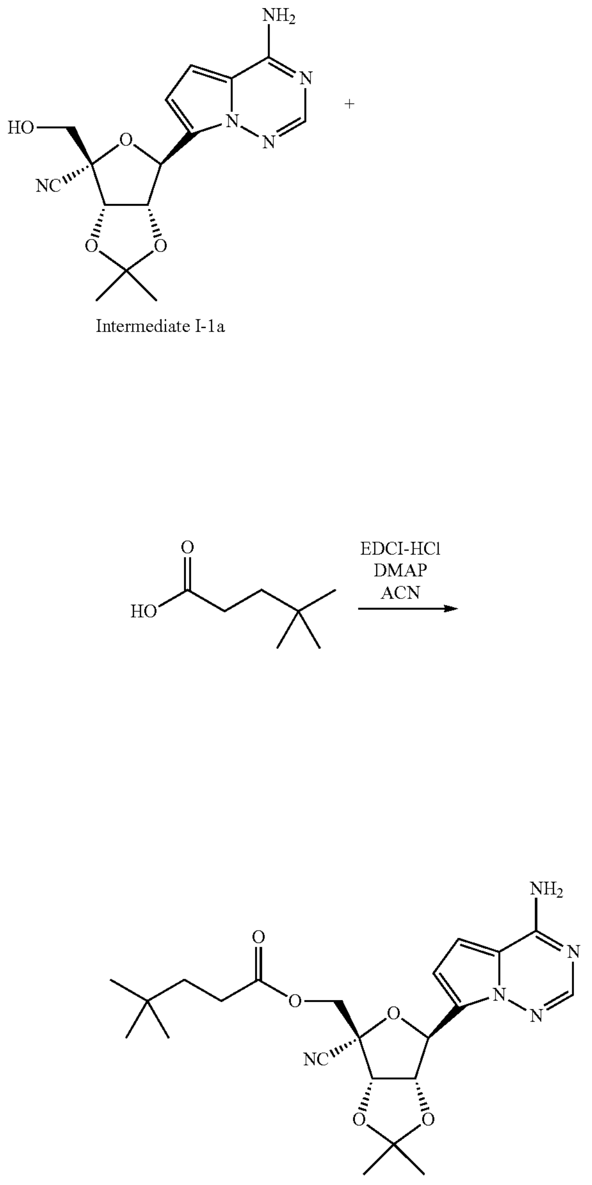

Intermediate I-34

To a mixture of Intermediate I-1a (0.453 mmol) and 4,4-dimethylpentanoic acid (0.543 mmol) in ACN (2 mL) were added DMAP (0.543 mmol) and then EDCI-HCl (0.543 mmol). The resulting mixture was stirred at rt for 5 h, concentrated in vacuo, and purified by silica gel column chromatography (0% to 5% MeOH in DCM) to give Intermediate I-34. $^1$H NMR (400 MHz, Acetonitrile-d3) δ 7.91 (s, 1H), 6.80 (d, J=4.5 Hz, 1H), 6.77 (d, J=4.5 Hz, 1H), 6.40 (s, 2H), 5.67 (d, J=3.5 Hz, 1H), 5.32 (dd, J=6.6, 3.5 Hz, 1H), 5.07 (d, J=6.6 Hz, 1H), 4.50 (d, J=11.7 Hz, 1H), 4.33 (d, J=11.7 Hz, 1H), 2.39-2.28 (m, 2H), 1.72 (s, 3H), 1.57-1.48 (m, 2H), 1.39 (s, 3H), 0.89 (s, 9H). MS m/z [M+1]=444.0.

Intermediate I-35: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl (R)-2-methylbutanoate

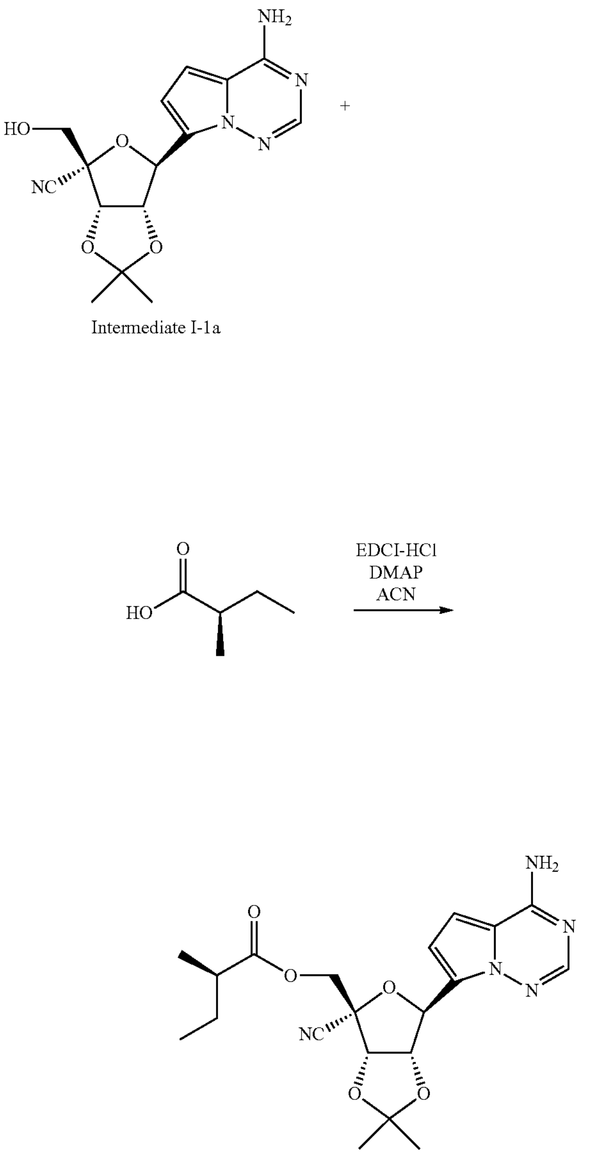

Intermediate I-1a

Intermediate I-35

To a mixture of Intermediate I-1a (0.302 mmol) and (R)-2-methylbutanoic acid (0.362 mmol) in ACN (2 mL) were added DMAP (0.362 mmol) and then EDCI-HCl (0.362 mmol). The resulting mixture was stirred at rt for 5 h, concentrated in vacuo, and purified by silica gel column chromatography (0% to 5% MeOH in DCM) to give Intermediate I-35. $^1$H NMR (400 MHz, Acetonitrile-d3) δ 7.92 (s, 1H), 6.80 (d, J=4.5 Hz, 1H), 6.77 (d, J=4.5 Hz, 1H), 6.35 (s, 2H), 5.67 (d, J=3.4 Hz, 1H), 5.32 (ddd, J=6.7, 3.4, 0.8 Hz, 1H), 5.07 (d, J=6.6 Hz, 1H), 4.52 (dd, J=11.7, 0.8 Hz, 1H), 4.34 (dd, J=11.7, 0.8 Hz, 1H), 2.45 (m, 1H), 1.76-1.60 (m, 4H), 1.51 (m, 1H), 1.39 (s, 3H), 1.14 (dd, J=6.9, 0.8 Hz, 3H), 0.91 (dd, J=7.9, 7.1 Hz, 3H). MS m/z [M+1]=416.1.

Intermediate I-36: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl 2-phenylacetate

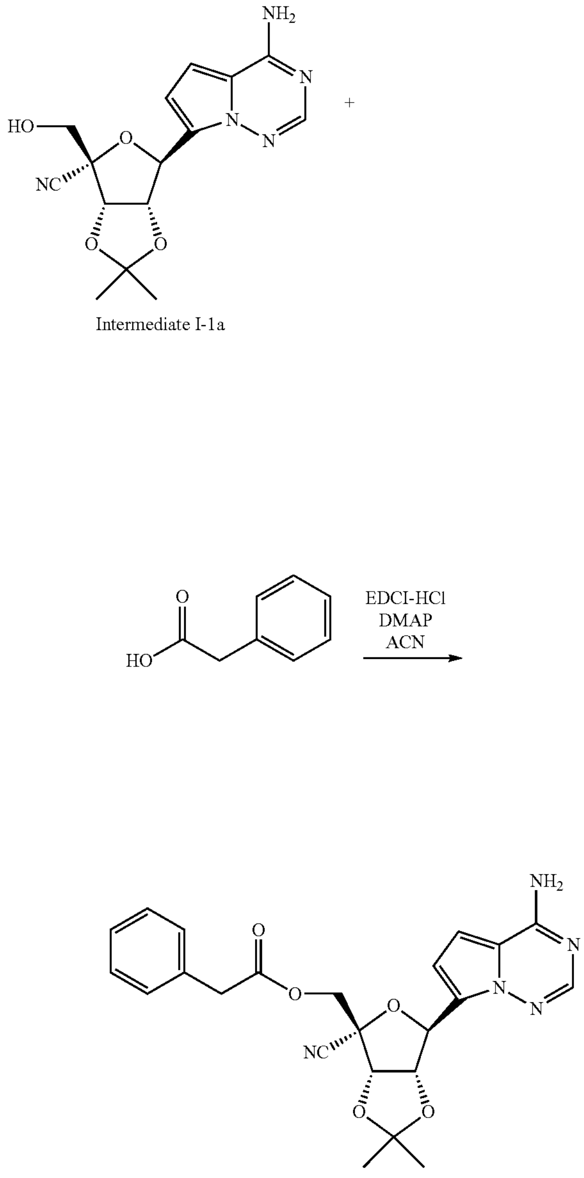

Intermediate I-1a

Intermediate I-36

To a mixture of Intermediate I-1a (0.302 mmol) and 2-phenylacetic acid (0.362 mmol) in ACN (2 mL) were added DMAP (0.362 mmol) and then EDCI-HCl (0.362 mmol). The resulting mixture was stirred at rt for 5 h, concentrated in vacuo, and purified by silica gel column chromatography (0 to 5% MeOH in DCM) to give Intermediate I-36. $^1$H NMR (400 MHz, Acetonitrile-d3) δ 7.91 (s, 1H), 7.38-7.19 (m, 5H), 6.80-6.74 (m, 2H), 6.32 (s, 2H), 5.66 (d, J=3.6 Hz, 1H), 5.28 (dd, J=6.6, 3.6 Hz, 1H), 5.05 (d, J=6.6 Hz, 1H), 4.53 (d, J=11.7 Hz, 1H), 4.38 (d, J=11.7 Hz, 1H), 3.72 (s, 2H), 1.72 (s, 3H), 1.39 (s, 3H). MS m/z [M+1]=450.0.

Intermediates I-37 and I-38: ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl) methyl acetate (Intermediate I-37), and ((3aS,4R,6S,6aS)-6-(4-acetamidopyrrolo[2,1-f][1,2,4]triazin-7-yl)-4-cyano-2,2-dimethyltetrahydrofuro[3,4-d][1,3]dioxol-4-yl)methyl acetate (Intermediate I-38)
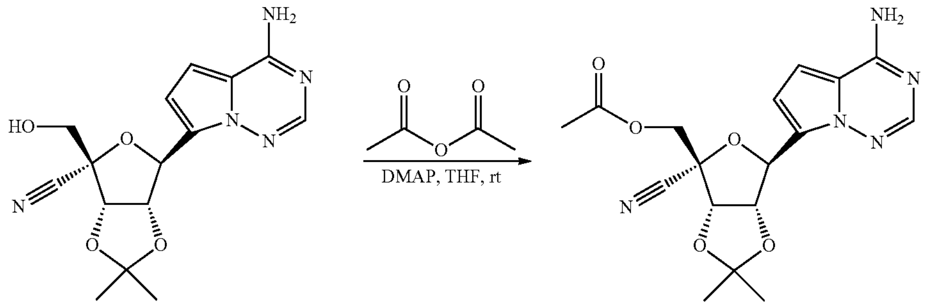
Intermediate I-1a Intermediate I-37
+
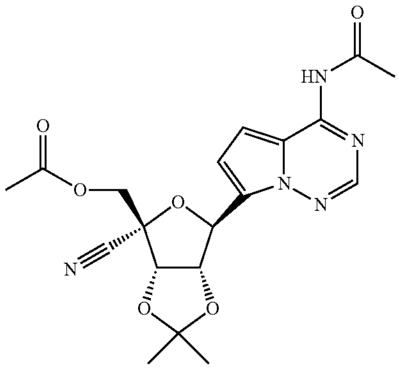
Intermediate I-38

To a solution of Intermediate I-1a (1.5 mmol) and 4-dimethylaminopyridine (0.17 mmol) in THF (8.0 mL) at 0° C. was added acetic anhydride (0.29 mL, 3 mmol) drop wise. The solution was stirred for 30 min at 0° C. and room temperature 30 min. The reaction mixture was concentrated in vacuo, dissolved in DCM load on 40 g silica gel column, eluted with hexane 3 minutes, DCM 1 minute, and 0%-100% EtOAc in DCM for 16 minutes to afford Intermediate I-37 (MS m/z [M+1]=374.0) and Intermediate I-38 (MS m/z [M+1]=416.0).

Intermediates 1-39 and 1-40: ((3aS,4R,6S,6aS)-4-cyano-6-(4-isobutyramidopyrrolo[2,1-f][1,2,4]triazin-7-yl)-2,2-dimethyltetrahydrofuro[3,4-d][1,3]dioxol-4-yl)methyl acetate (Intermediate I-39), and ((3aS,4R,6S,6aS)-6-(4-acetamidopyrrolo[2,1-f][1,2,4]triazin-7-yl)-4-cyano-2,2-dimethyltetrahydrofuro[3,4-d][1,3]dioxol-4-yl)methyl acetate (Intermediate I-40)

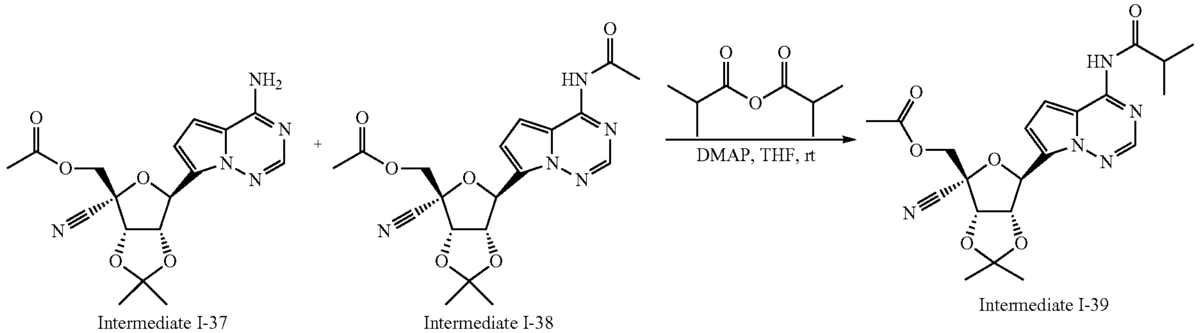

Intermediate I-37 + Intermediate I-38 → Intermediate I-39

+

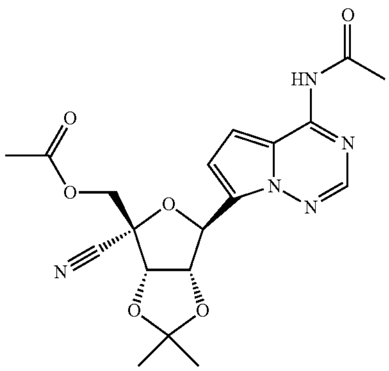

Intermediate I-40

To a mixture of ((3aS,4R,6S,6aS)-6-(4-aminopyrrolo[2,1-f][1,2,4]triazin-7-yl)-4-cyano-2,2-dimethyltetrahydrofuro[3,4-d][1,3]dioxol-4-yl)methyl acetate (120 mg, 0.32 mmol) and ((3aS,4R,6S,6aS)-6-(4-acetamidopyrrolo[2,1-f][1,2,4]triazin-7-yl)-4-cyano-2,2-dimethyltetrahydrofuro[3,4-d][1,3]dioxol-4-yl)methyl acetate (150 mg, 0.36 mmol), DMAP (0.07 mmol) in THF was added isobutyric anhydride (0.11 mL, 0.64 mmol) drop wise, and stirred 30 min at 0° C., and 30 min at room temperature. The reaction mixture was concentrated in vacuo and the crude material was purified by silica gel column chromatography (00% to 1000% EtOAc in DCM) to afford Intermediate I-39 and Intermediate I-40.

Intermediate I-39. 1H NMR (400 MHz, Acetonitrile-d3) δ 8.90 (s, 1H), 8.21 (s, 1H), 7.22 (d, J=4.7 Hz, 1H), 6.99 (d, J=4.7 Hz, 1H), 5.74 (d, J=3.3 Hz, 1H), 5.33 (dd, J=6.6, 3.4 Hz, 1H), 5.09 (d, J=6.6 Hz, 1H), 4.57-4.30 (m, 2H), 3.04-2.94 (m, 1H), 2.08 (s, 3H), 1.73 (s, 3H), 1.40 (s, 3H), 1.24 (d, J=6.8 Hz, 6H), MS m/z [M+1]=444.1.

Intermediate I-40. 1H NMR (400 MHz, Acetonitrile-d3) δ 8.85 (s, 1H), 8.22 (s, 1H), 7.17 (d, J=4.7 Hz, 1H), 6.98 (d, J=4.7 Hz, 1H), 5.74 (d, J=3.4 Hz, 1H), 5.33 (dd, J=6.6, 3.4 Hz, 1H), 5.09 (d, J=6.6 Hz, 1H), 4.54-4.28 (m, 2H), 2.40 (s, 3H), 2.08 (s, 3H), 1.73 (s, 3H), 1.40 (s, 3H). MS m/z [M+1]=416.1.

C. Compounds

Example 0. Compound 0 (2R,3S,4R,5S)-5-(4-aminopyrrolo[1,2-f][1,2,4]triazin-7-yl)-3,4-dihydroxy-2-(hydroxymethyl)tetrahydrofuran-2-carbonitrile Compound 0

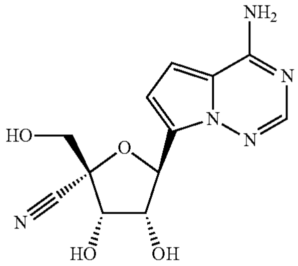

Compound 0 was prepared according to WO2015/069939. For example, pages 43-55 of WO2015/069939 provide a process for preparing this compound (identified as compound 1 in WO2015/069939).

Example 1: Compound 1 ((2R,3S,4R,5S)-5-(4-aminopyrrolo[2,1-f][1,2,4]triazin-7-yl)-2-cyano-3,4-dihydroxytetrahydrofuran-2-yl)methyl isobutyrate

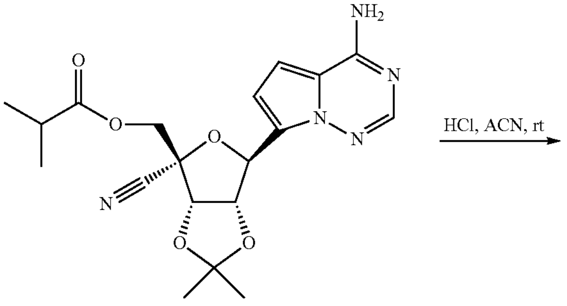

Intermediate I-15

-continued

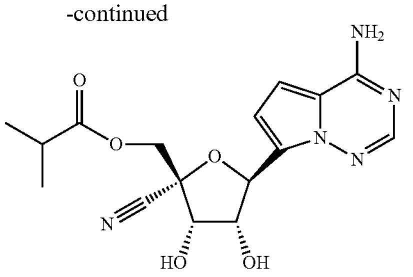

Compound 1

To a solution of Intermediate I-15 (1.9 mmol, 1.0 equiv.) in ACN (10.0 mL) was added concentrated HCl (0.80 mL, 12 M, 5.0 equiv.) at room temperature. The reaction mixture was stirred for 55 min prior to diluting with EtOAc (50 mL) and quenching with a saturated solution of $NaHCO_3$ (50 mL). The layers were separated, and the aqueous layer was extracted once more with EtOAc (50 mL). The organic fractions were combined, washed with brine (50 mL), dried over $Na_2SO_4$, filtered and concentrated in vacuo prior to purification by silica gel chromatography (0%-30% MeOH in DCM) to afford Compound 1. $^1$H NMR (400 MHz, Methanol-d4) δ 7.80 (s, 1H), 6.86 (d, J=4.5 Hz, 1H), 6.73 (d, J=4.5 Hz, 1H), 5.48 (d, J=4.8 Hz, 1H), 4.66-4.61 (m, 1H), 4.54 (d, J=11.8 Hz, 1H), 4.45 (d, J=5.6 Hz, 1H), 4.35 (d, J=11.7 Hz, 1H), 2.67-2.54 (m, 1H), 1.18-1.13 (m, 6H). MS m/z [M+1]=362.1.

Example 2: Compound 2 ((2R,3S,4R,5S)-5-(4-aminopyrrolo[2,1-f][1,2,4]triazin-7-yl)-2-cyano-3,4-dihydroxytetrahydrofuran-2-yl)methyl benzoate

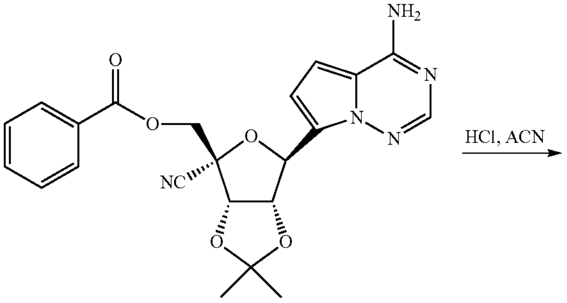

Intermediate I-1

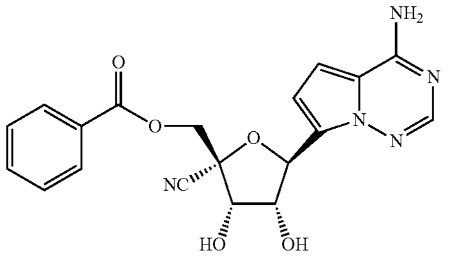

Compound 2

To a solution of Intermediate I-1 (1.49 mmol) in ACN (3 mL) was added cHCl (1 mL) at room temperature. The mixture was stirred for 1 h, diluted with EtOAc, and $aqNaHCO_3$ added slowly. After stirring for 5 min, the phases were separated, and aqueous phase extracted with EtOAc three times. The combined organic layer was dried over sodium sulfate, concentrated in vacuo, and purified by silica gel column chromatography (0% to 10% MeOH in DCM) to give Compound 2. $^{1}$H NMR (400 MHz, Acetonitrile-d3) δ 8.11-7.92 (m, 2H), 7.84 (s, 1H), 7.75-7.63 (m, 1H), 7.63-7.44 (m, 2H), 6.74 (s, 2H), 6.21 (s, 2H), 5.50 (d, J=4.7 Hz, 1H), 4.77 (d, J=11.8 Hz, 1H), 4.67 (m, 1H), 4.64-4.53 (m, 2H), 4.25 (d, J=6.5 Hz, 1H), 3.97 (d, J=4.9 Hz, 1H). MS m/z [M+1]=396.

Example 3: Compound 3 ((2R,3S,4R,5S)-5-(4-aminopyrrolo[2,1-f][1,2,4]triazin-7-yl)-2-cyano-3,4-dihydroxytetrahydrofuran-2-yl)methyl 3-methylbutanoate

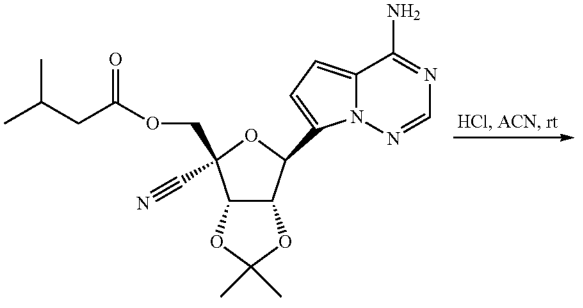

Intermediate I-16

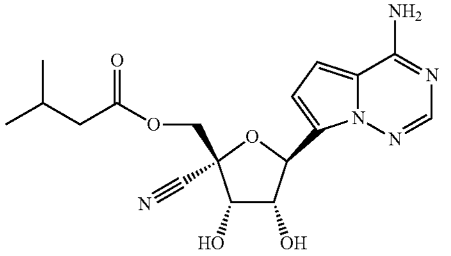

Compound 3

To a solution of Intermediate I-16 (0.33 mmol, 1.0 equiv.) in ACN (5.0 mL) was added concentrated HCl (0.14 mL, 12 M, 5.0 equiv.) at room temperature. The reaction mixture was stirred for 1 h and 20 min prior to diluting with EtOAc (30 mL) and quenching with a 1:1 solution of water and saturated $NaHCO_3$ (30 mL). The layers were separated, and the aqueous layer extracted once more with EtOAc (30 mL). The organic fractions were combined, washed with 1:1 water:brine (20 mL), dried over $Na_2SO_4$, filtered and concentrated in vacuo prior to purification by silica gel chromatography (0%-20% MeOH in DCM) to afford Compound 3. $^{1}$H NMR (400 MHz, DMSO-d$_6$) δ 7.86 (s, 1H), 7.76 (br s, 2H), 6.86 (d, J=4.6 Hz, 1H), 6.73 (d, J=4.4 Hz, 1H), 6.10 (d, J=5.9 Hz, 1H), 5.49 (d, J=5.4 Hz, 1H), 5.38 (d, J=5.5 Hz, 1H), 4.54-4.44 (m, 2H), 4.31-4.19 (m, 2H), 2.25-2.17 (m, 2H), 2.03-1.90 (m, 1H), 0.91-0.85 (m, 6H). MS m/z [M+1]=376.2.

Example 4: Compound 4 ((2R,3S,4R,5S)-5-(4-aminopyrrolo[2,1-f][1,2,4]triazin-7-yl)-2-cyano-3,4-dihydroxytetrahydrofuran-2-yl)methyl acetate

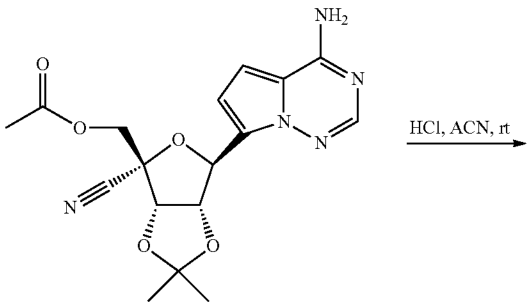

Intermediate I-17

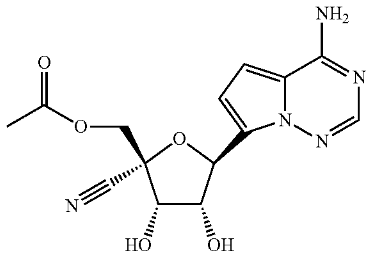

Compound 4

To a solution of Intermediate I-17 (0.40 mmol, 1.0 equiv.) in ACN (5.0 mL) was added concentrated HCl (0.17 mL, 12 M, 5.0 equiv.) at room temperature. The reaction mixture was stirred for 1 h prior to diluting with EtOAc (30 mL) and quenching with a 1:1 solution of water:saturated $NaHCO_3$ (30 mL). The layers were separated, and the aqueous layer extracted once more with EtOAc (30 mL). The organic fractions were combined, washed with 1:1 water:brine (20 mL), dried over $Na_2SO_4$, filtered and concentrated in vacuo prior to purification by silica gel chromatography (0%-20% MeOH in DCM) to afford Compound 4. $^{1}$H NMR (400 MHz, DMSO-d$_6$) δ 7.86 (s, 1H), 7.76 (br s, 2H), 6.86 (d, J=4.5 Hz, 1H), 6.73 (d, J=4.5 Hz, 1H), 6.11 (d, J=6.0 Hz, 1H), 5.49 (d, J=5.5 Hz, 1H), 5.38 (d, J=5.5 Hz, 1H), 4.50-4.43 (m, 2H), 4.31-4.18 (m, 2H), 2.06 (s, 3H). MS m/z [M+1]=334.2.

Example 5: Compound 5 ((2R,3S,4R,5S)-5-(4-aminopyrrolo[2,1-f][1,2,4]triazin-7-yl)-2-cyano-3,4-dihydroxytetrahydrofuran-2-yl)methyl propionate

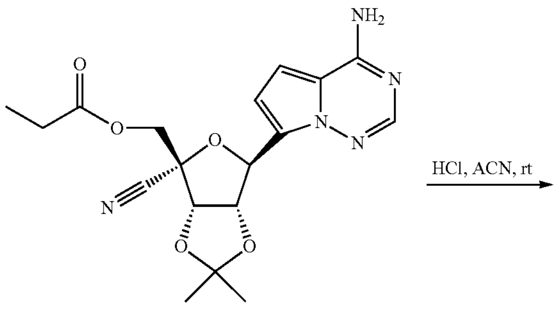

Intermediate I-18

-continued

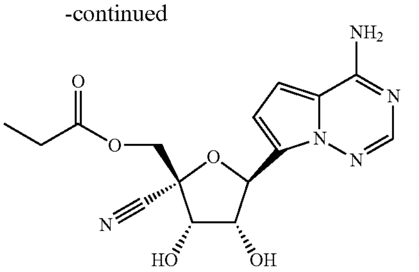

Compound 5

To a solution of Intermediate I-18 (0.34 mmol, 1.0 equiv.) in ACN (5.0 mL) was added concentrated HCl acid (0.14 mL, 12 M, 5.0 equiv.) at room temperature. The reaction mixture was stirred for 4 h and 45 min prior to diluting with EtOAc (30 mL) and quenching with a 1:1 solution of water:saturated $NaHCO_3$ (30 mL). The layers were separated and the aqueous layer was extracted once more with EtOAc (30 mL). The organic fractions were combined, washed with 1:1 water:brine (30 mL), dried over $Na_2SO_4$, filtered and concentrated in vacuo prior to purification by silica gel chromatography (0%-20% MeOH in DCM) to afford Compound 5. $^1$H NMR (400 MHz, Methanol-$d_4$) δ 7.80 (s, 1H), 6.86 (d, J=4.5 Hz, 1H), 6.72 (d, J=4.5 Hz, 1H), 5.49 (d, J=4.7 Hz, 1H), 4.65-4.60 (m, 1H), 4.55 (d, J=11.8 Hz, 1H), 4.45 (d, J=5.6 Hz, 1H), 4.35 (d, J=11.7 Hz, 1H), 2.46-2.31 (m, 2H), 1.14-1.08 (m, 3H). MS m/z [M+1]=348.2.

Example 6: Compound 6 ((2R,3S,4R,5S)-5-(4-aminopyrrolo[2,1-f][1,2,4]triazin-7-yl)-2-cyano-3,4-dihydroxytetrahydrofuran-2-yl)methyl butyrate

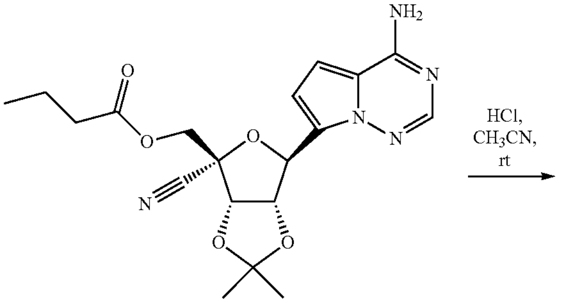

Intermediate I-23

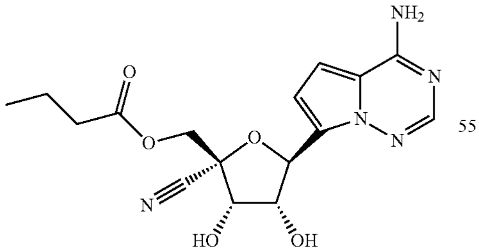

Compound 6

To well stirring mixture of Intermediate I-23 (0.34 mmol), in $CH_3CN$ (2.0 mL), at room temperature was added concentrated HCl (100 uL, 1.2 mmol) drop wish (2 min), and stirred 4 h. The reaction mixture was diluted with EtOAc, followed by saturated sodium bicarbonate. (Keep diluting with EtOAc (100 mL) and $NaHCO_3$ (50 mL) until solid dissolute and form clear solution). The aqueous layer was extracted with EtOAc (50 mL×2), and organic layer separated, washed once with brine solution (70 mL), dried over sodium sulfate, filtered and concentrated under reduced pressure (Temperature maintained <30° C.). The crude product was dissolved in 10% MeOH/DCM, load on 40 g silica gel column, and elute with Hexane 3 min, DCM 1 min, and 0%-25% MeOH/DCM 18 min. The pure fractions were combined, concentrated to afford Compound 6. 1H NMR (400 MHz, Methanol-d4) δ 7.82 (s, 1H), 6.88 (d, J=4.5 Hz, 1H), 6.74 (d, J=4.5 Hz, 1H), 5.50 (d, J=4.7 Hz, 1H), 4.65 (t, J=5.1 Hz, 1H), 4.57 (d, J=11.8 Hz, 1H), 4.47 (d, J=5.6 Hz, 1H), 4.37 (d, J=11.8 Hz, 1H), 2.36 (td, J=7.3, 3.0 Hz, 2H), 1.65 (h, J=7.3 Hz, 2H), 0.95 (t, J=7.4 Hz, 3H). MS m/z [M+1]=362.17.

Example 7: Compound 7 ((2R,3S,4R,5S)-5-(4-aminopyrrolo[2,1-f][1,2,4]triazin-7-yl)-2-cyano-3,4-dihydroxytetrahydrofuran-2-yl)methyl cyclopropanecarboxylate

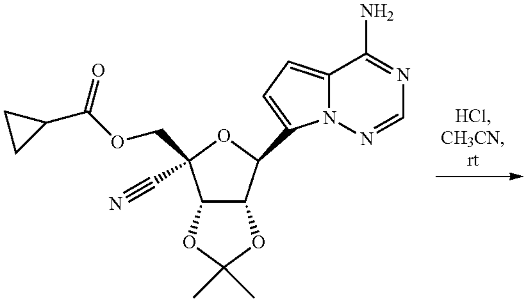

Intermediate I-22

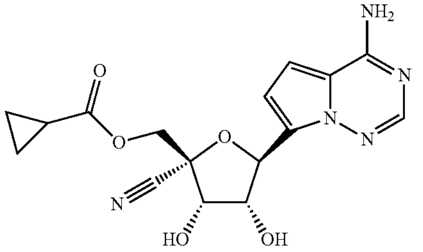

Compound 7

To well stirring mixture of Intermediate I-22 (0.34 mmol), in $CH_3CN$ (2.5 mL), at room temperature was added concentrated HCl (140 uL, 1.7 mmol) drop wish (2 min), and stirred 70 min. The reaction mixture was diluted with EtOAc, followed by saturated sodium bicarbonate (Keep diluting with EtOAc (100 mL) and $NaHCO_3$ (50 mL) until solid dissolute and form clear solution). The aqueous layer extracted with EtOAc (100 mL×2), and organic layer separated, washed once with brine solution (70 mL), dried over sodium sulfate, filtered and concentrated under reduced pressure (Temperature maintained <30° C.). The crude product was dissolved in 15% MeOH/DCM, load on 40 g silica gel column, elute with Hexane 3 min, DCM 1 min, and 0%-25% MeOH/DCM 20 min. The pure fractions were combined, concentrated to afford Compound 7. $^1$H NMR (400 MHz, Methanol-d4) δ 7.82 (s, 1H), 6.88 (d, J=4.5 Hz, 1H), 6.75 (d, J=4.5 Hz, 1H), 5.51 (d, J=4.7 Hz, 1H), 4.64 (t, J=5.2 Hz, 1H), 4.57 (d, J=11.7 Hz, 1H), 4.48 (d, J=5.5 Hz, 1H), 4.36 (d, J=11.8 Hz, 1H), 1.79-1.58 (m, 1H), 0.97 (dtd, J=12.6, 7.2, 3.7 Hz, 4H). MS m/z [M+1]=360.02.

Example 8: Compound 8 ((2R,3S,4R,5S)-5-(4-aminopyrrolo[2,1-f][1,2,4]triazin-7-yl)-2-cyano-3,4-dihydroxytetrahydrofuran-2-yl)methyl cyclobutanecarboxylate

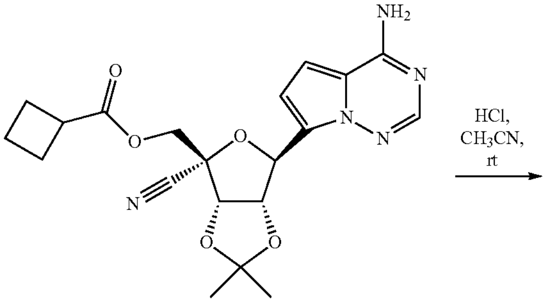

Intermediate I-21

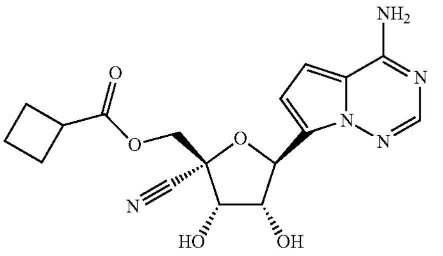

Compound 8

To well stirring mixture of Intermediate I-21 (0.31 mmol), in $CH_3CN$ (3 mL), at room temperature was added concentrated HCl (130 uL, 1.6 mmol) drop wish (2 min). The reaction mixture goes from opaque solid to clear solution in few minutes and stirred 2 h. The reaction mixture was diluted with EtOAc, followed by saturated sodium bicarbonate. (Keep diluting with EtOAc (50 mL) and $NaHCO_3$ (40 mL) until solid dissolute and form clear solution). The aqueous layer extracted with EtOAc (50 mL×2), and organic layer separated, washed once with brine solution (70 mL), dried over sodium sulfate, filtered and concentrated under reduced pressure (Temperature maintained <30° C.). The crude product was dissolved in 10% MeOH/DCM, load on 40 g silica gel column, and elute with Hexane 3 min, DCM for 1 min, and eluted 0%-25% MeOH/DCM 15 min. The pure fractions were combined, concentrated to afford Compound 8. $^1$H NMR (400 MHz, Methanol-d4) δ 7.82 (s, 1H), 6.88 (d, J=4.5 Hz, 1H), 6.74 (d, J=4.5 Hz, 1H), 5.50 (d, J=4.8 Hz, 1H), 4.64 (t, J=5.2 Hz, 1H), 4.57 (d, J=11.8 Hz, 1H), 4.46 (d, J=5.5 Hz, 1H), 4.37 (d, J=11.8 Hz, 1H), 3.24 (p, J=8.8 Hz, 1H), 2.37-2.16 (m, 4H), 2.08-1.85 (m, 2H). MS m/z [M+1]=374.11.

Example 9: Compound 9: ((2R,3S,4R,5S)-5-(4-aminopyrrolo[2,1-f][1,2,4]triazin-7-yl)-2-cyano-3,4-dihydroxytetrahydrofuran-2-yl)methyl 2-ethylbutanoate

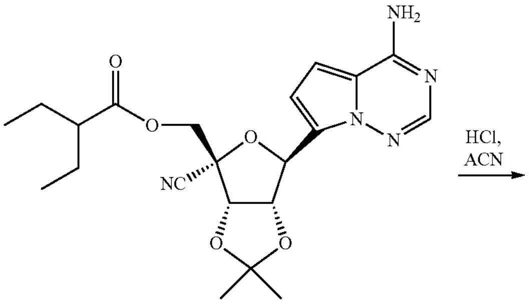

Intermediate I-3

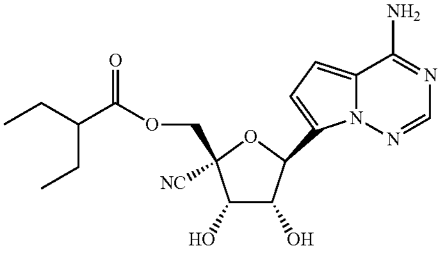

Compound 9

To a solution of Intermediate I-3 (0.263 mmol) in ACN (1 mL) was added cHCl (1 mL) at room temperature. The mixture was stirred at room temperature for 1 h, diluted with EtOAc, and aq$NaHCO_3$ added slowly. After stirring for 5 min, the phases were separated, and aqueous phase extracted with EtOAc three times. The combined organic phase was dried under sodium sulfate, concentrated in vacuo, and purified by silica gel column chromatography (0% to 10% MeOH in DCM) to give Compound 9. $^1$H NMR (400 MHz, Acetonitrile-d3) δ 7.89 (s, 1H), 6.79 (d, J=4.6 Hz, 1H), 6.76 (d, J=4.6 Hz, 1H), 6.36 (s, 2H), 5.48 (d, J=5.0 Hz, 1H), 4.63 (t, J=5.4 Hz, 1H), 4.52 (d, J=11.9 Hz, 1H), 4.45 (d, J=5.8 Hz, 1H), 4.36 (d, J=11.9 Hz, 1H), 2.29 (m, 1H), 1.68-1.47 (m, 4H), 0.88 (m, 6H). MS m/z [M+1]=390.

Example 10: Compound 10 ((2R,3S,4R,5S)-5-(4-aminopyrrolo[2,1-f][1,2,4]triazin-7-yl)-2-cyano-3,4-dihydroxytetrahydrofuran-2-yl)methyl pivalate

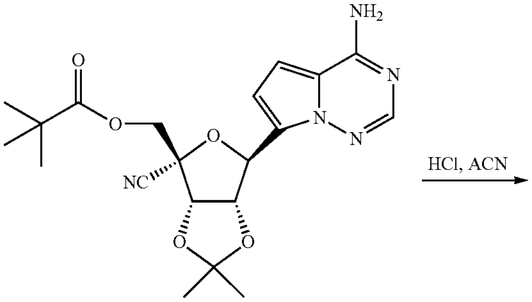

Intermediate I-4

-continued

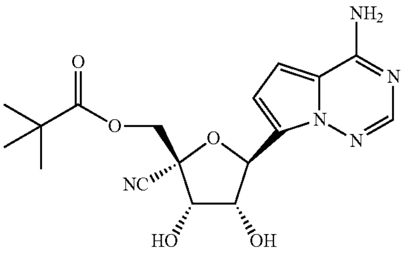

Compound 10

To a solution of Intermediate I-4 (0.481 mmol) in ACN (4 mL), THE (2 mL) was added cHCl (0.7 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried over sodium sulfate, concentrated in vacuo, and purified by silica gel column chromatography (0 to 10% MeOH in DCM) to give Compound 10. $^1$H NMR (400 MHz, DMSO-d6) δ 7.87 (s, 1H), 7.72 (s, 2H), 6.88 (d, J=4.5 Hz, 1H), 6.74 (d, J=4.4 Hz, 1H), 6.07 (m, 1H), 5.48 (m, 1H), 5.41 (d, J=5.6 Hz, 1H), 4.55-4.39 (m, 2H), 4.30 (t, J=5.7 Hz, 1H), 4.25 (d, J=11.8 Hz, 1H), 1.18 (s, 9H). MS m/z [M+1]=376.

Example 11: Compound 11 ((2R,3S,4R,5S)-2-cyano-5-(4-(2-ethylbutanamido)pyrrolo[2,1-f][1,2,4]triazin-7-yl)-3,4-dihydroxytetrahydrofuran-2-yl)methyl 2-ethylbutanoate

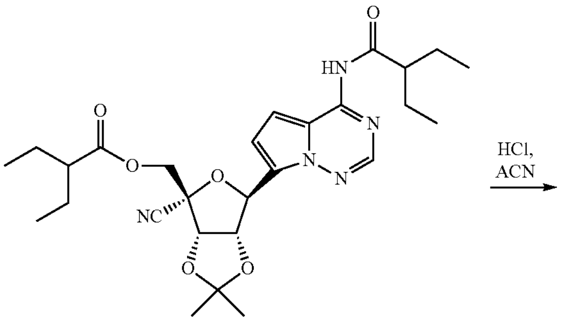

Intermediate I-2

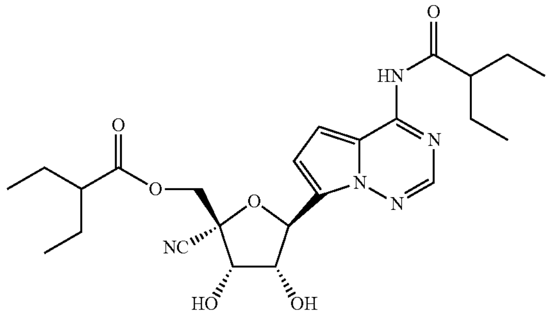

Compound 11

To a solution of Intermediate I-2 (0.0417 mmol) in ACN (1 mL) was added cHCl (0.2 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried over sodium sulfate, concentrated in vacuo, and purified by silica gel column chromatography (0% to 10% MeOH in DCM) to give Compound 11. $^1$H NMR (400 MHz, DMSO-d6) δ 10.97 (s, 1H), 8.34 (s, 1H), 7.24 (d, J=4.7 Hz, 1H), 7.04 (d, J=4.7 Hz, 1H), 5.51 (d, J=5.4 Hz, 1H), 4.59-4.35 (m, 2H), 4.35-4.14 (m, 2H), 2.78 (td, J=8.7, 4.4 Hz, 1H), 2.24 (tt, J=8.1, 5.7 Hz, 1H), 1.72-1.40 (m, 8H), 0.90 (t, J=7.4 Hz, 6H), 0.81 (td, J=7.4, 4.6 Hz, 6H). MS m/z [M+1]=488.

Example 12: Compound 12 ((2R,3S,4R,5S)-5-(4-aminopyrrolo[2,1-f][1,2,4]triazin-7-yl)-2-cyano-3,4-dihydroxytetrahydrofuran-2-yl)methyl L-valinate

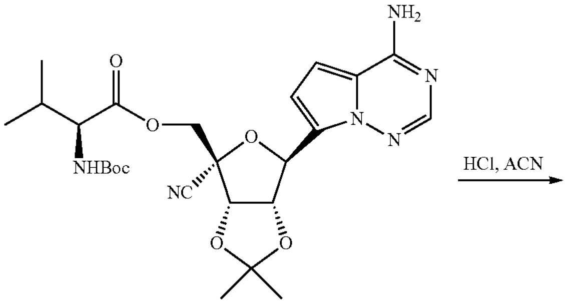

Intermediate I-5

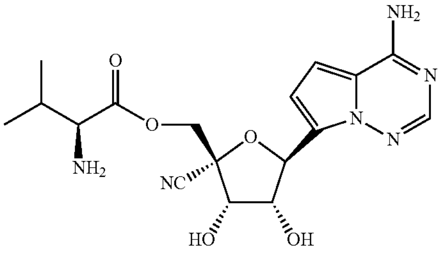

Compound 12

To a solution of Intermediate I-5 (0.477 mmol) in ACN (2 mL) was added cHCl (0.3 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried over sodium sulfate, concentrated in vacuo, and lyophilized in ACN to give a crude product, which was dissolved in water (5 mL) and purified by prep HPLC (10% to 50% ACN w/0.1% TFA in water w/0.1% TFA) to give Compound 12 as a TFA salt. $^1$H NMR (400 MHz, Methanol-d4) δ 8.08 (s, 1H), 7.43 (d, J=4.7 Hz, 1H), 6.99 (d, J=4.7 Hz, 1H), 5.58 (d, J=4.8 Hz, 1H), 4.82 (s, 1H), 4.61-4.50 (m, 2H), 4.40 (d, J=5.5 Hz, 1H), 4.07 (d, J=4.3 Hz, 1H), 2.34 (m, 1H), 1.08 (m, 6H). MS m/z [M+1]=391.

Example 13: Compound 13 ((2R,3S,4R,5S)-5-(4-aminopyrrolo[2,1-f][1,2,4]triazin-7-yl)-2-cyano-3,4-dihydroxytetrahydrofuran-2-yl)methyl 3,3-dimethylbutanoate

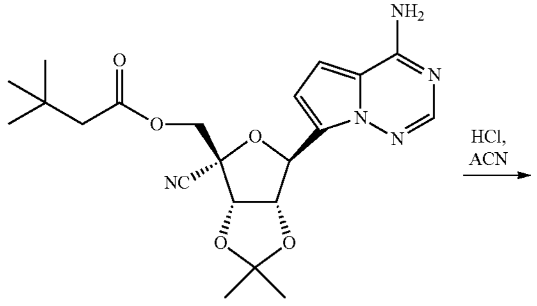

Intermediate I-6

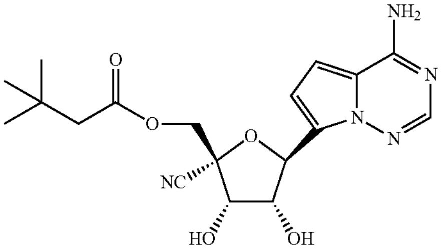

Compound 13

To a solution of Intermediate I-6 (0.270 mmol) in ACN (1 mL) was added cHCl (1 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried under sodium sulfate, concentrated in vacuo, and purified by silica gel column chromatography (0% to 10% to MeOH in DCM to give Compound 13. $^1$H NMR (400 MHz, Methanol-d4) δ 7.82 (s, 1H), 6.87 (d, J=4.5 Hz, 1H), 6.74 (d, J=4.5 Hz, 1H), 5.51 (d, J=4.8 Hz, 1H), 4.67 (t, J=5.2 Hz, 1H), 4.51 (d, J=11.8 Hz, 1H), 4.46 (d, J=5.5 Hz, 1H), 4.39 (d, J=11.8 Hz, 1H), 2.25 (m, 2H), 1.02 (s, 9H). MS m/z [M+1]=390.

Example 14: Compound 14 ((2R,3S,4R,5S)-5-(4-aminopyrrolo[2,1-f][1,2,4]triazin-7-yl)-2-cyano-3,4-dihydroxytetrahydrofuran-2-yl)methyl 4-methylbenzoate

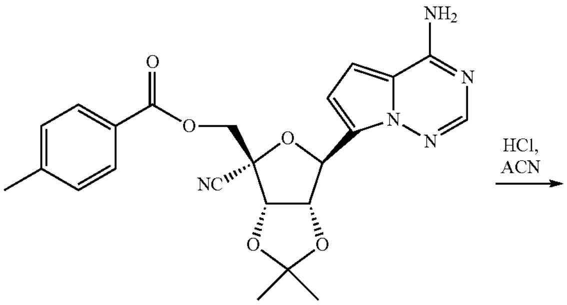

Intermediate I-7

-continued

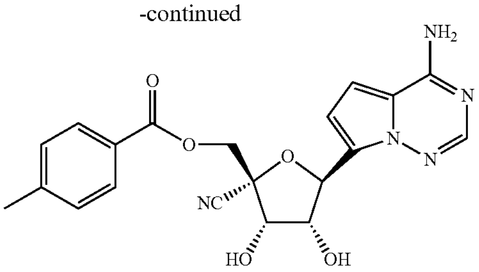

Compound 14

To a solution of Intermediate I-7 (0.267 mmol) in ACN (1 mL) was added cHCl (1 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried over sodium sulfate, concentrated in vacuo, and purified by silica gel column chromatography (0% to 10% MeOH in DCM) to give Compound 14. $^1$H NMR (400 MHz, Methanol-d4) δ 7.96-7.87 (m, 2H), 7.73 (s, 1H), 7.31 (d, J=8.0 Hz, 2H), 6.82 (d, J=4.5 Hz, 1H), 6.71 (d, J=4.5 Hz, 1H), 5.53 (d, J=4.6 Hz, 1H), 4.80 (d, J=11.8 Hz, 1H), 4.71 (dd, J=5.6, 4.6 Hz, 1H), 4.65-4.55 (m, 2H), 2.43 (s, 3H). MS m/z [M+1]=410.

Example 15: Compound 15 ((2R,3S,4R,5S)-5-(4-aminopyrrolo[2,1-f][1,2,4]triazin-7-yl)-2-cyano-3,4-dihydroxytetrahydrofuran-2-yl)methyl 1-methylcyclopropane-1-carboxylate

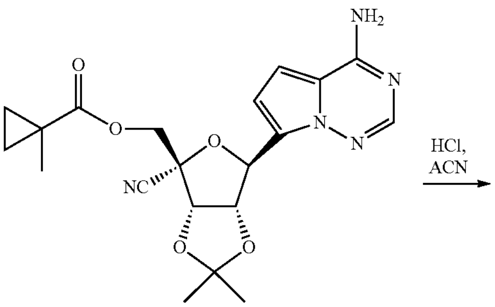

Intermediate I-8

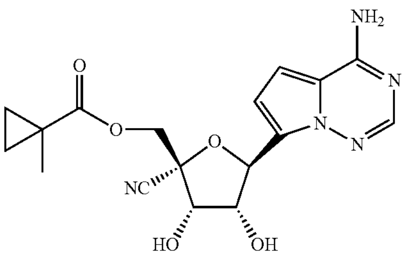

Compound 15

To a solution of Intermediate I-8 (0.235 mmol) in ACN (2 mL) was added cHCl (1 mL) at rt. The mixture was stirred for 1 h, diluted with EtOAc, and aq$NaHCO_3$ added slowly. After stirring for 5 min, the phases were separated, and aqueous phase extracted with EtOAc three times. The combined organic phase was dried over sodium sulfate, concentrated in vacuo, and purified by silica gel column chromatography (0% to 10% MeOH in DCM) to give Compound 15. $^1H$ NMR (400 MHz, Methanol-d4) δ 7.82 (d, J=0.9 Hz, 1H), 6.88 (dd, J=4.5, 0.9 Hz, 1H), 6.73 (d, J=4.5 Hz, 1H), 5.49 (d, J=4.8 Hz, 1H), 4.65 (td, J=5.2, 4.8, 1.0 Hz, 1H), 4.52 (dd, J=11.7, 0.9 Hz, 1H), 4.45 (d, J=5.6 Hz, 1H), 4.35 (dd, J=11.8, 0.9 Hz, 1H), 1.31 (s, 3H), 1.27 (m, 2H), 0.76 (m, 2H). MS m/z [M+1]=374.

Example 16: Compound 16 ((2R,3S,4R,5S)-5-(4-aminopyrrolo[2,1-f][1,2,4]triazin-7-yl)-2-cyano-3,4-dihydroxytetrahydrofuran-2-yl)methyl 2-cyclobutylacetate

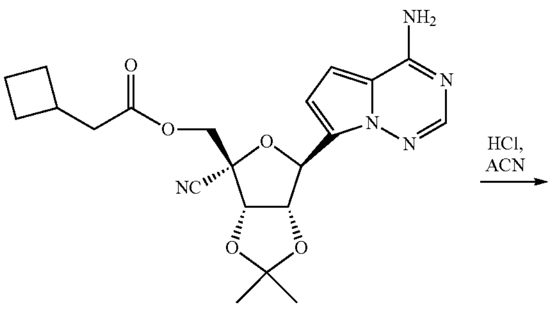

Intermediate I-9

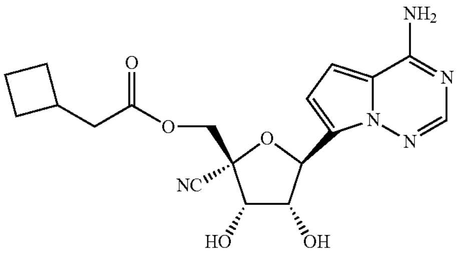

Compound 16

To a solution of Intermediate I-9 (0.503 mmol) in ACN (4 mL) was added cHCl (2 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried over sodium sulfate, concentrated in vacuo, and purified by silica gel column chromatography (0% to 10% MeOH in DCM) to give Compound 16. $^1H$ NMR (400 MHz, Methanol-d4) δ 7.82 (s, 1H), 6.88 (d, J=4.5 Hz, 1H), 6.74 (d, J=4.5 Hz, 1H), 5.50 (d, J=4.7 Hz, 1H), 4.66 (t, J=5.1 Hz, 1H), 4.54 (d, J=11.8 Hz, 1H), 4.47 (d, J=5.5 Hz, 1H), 4.35 (d, J=11.8 Hz, 1H), 2.66 (m, 1H), 2.47 (m, 2H), 2.11 (m, 2H), 1.95-1.79 (m, 2H), 1.71 (m, 2H). MS m/z [M+1]=388.

Example 17: Compound 17 ((2R,3S,4R,5S)-5-(4-aminopyrrolo[2,1-f][1,2,4]triazin-7-yl)-2-cyano-3,4-dihydroxytetrahydrofuran-2-yl)methyl 3,3-dimethylcyclobutane-1-carboxylate

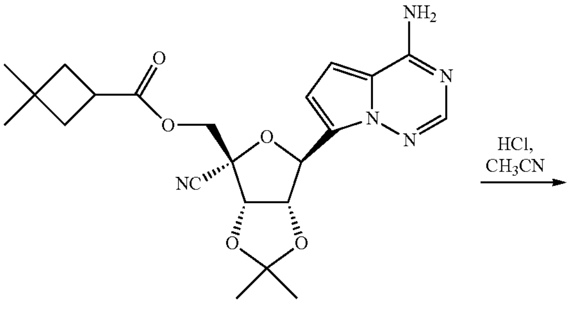

Intermediate I-10

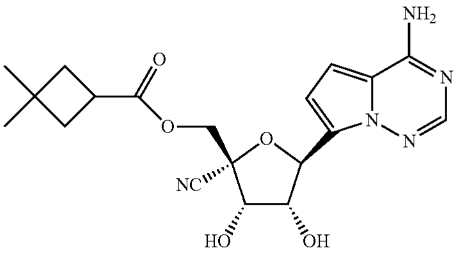

Compound 17

To a solution of Intermediate I-10 (0.256 mmol) in ACN (2 mL) was added cHCl (1 mL) at room temperature. The mixture was stirred for 1 h, diluted with EtOAc, and aq$NaHCO_3$ added slowly. After stirring for 5 min, the phases were separated, and aqueous phase extracted with EtOAc three times. The combined organic phase was dried under sodium sulfate, concentrated in vacuo, and purified by silica gel column chromatography (0% to 5% MeOH in DCM) to give Compound 17. $^1H$ NMR (400 MHz, Methanol-d4) δ 7.82 (s, 1H), 6.88 (d, J=4.5 Hz, 1H), 6.74 (d, J=4.5 Hz, 1H), 5.51 (d, J=4.7 Hz, 1H), 4.64 (t, J=5.1 Hz, 1H), 4.57 (d, J=11.7 Hz, 1H), 4.46 (d, J=5.5 Hz, 1H), 4.37 (d, J=11.7 Hz, 1H), 3.13 (p, J=8.8 Hz, 1H), 2.15-1.91 (m, 4H), 1.18 (s, 3H), 1.08 (s, 3H). MS m/z [M+1]=402.

Example 18: Compound 18 ((2R,3S,4R,5S)-5-(4-aminopyrrolo[2,1-f][1,2,4]triazin-7-yl)-2-cyano-3,4-dihydroxytetrahydrofuran-2-yl)methyl cyclopentanecarboxylate

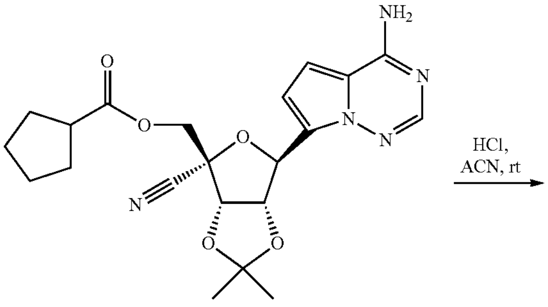

Intermediate I-19

-continued

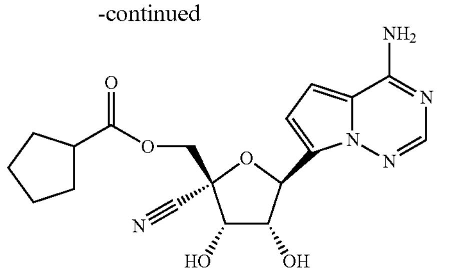

Compound 18

To a solution of Intermediate I-19 (0.30 mmol, 1.0 equiv.) in ACN (5.0 mL) was added concentrated HCl (0.12 mL, 12 M, 5.0 equiv.) at room temperature. The reaction mixture was stirred for 1 h prior to diluting with EtOAc (30 mL) and quenching with saturated $NaHCO_3$ (30 mL). The layers were separated, and the aqueous layer extracted once more with EtOAc (30 mL). The organic fractions were combined, washed with 1:1 water:brine (20 mL), dried over $Na_2SO_4$, filtered and concentrated in vacuo prior to purification by silica gel chromatography (0% to 20% EtOAc in hexanes then 0-20% MeOH in DCM) to afford Compound 18. $^1H$ NMR (400 MHz, Methanol-$d_4$) δ 7.80 (s, 1H), 6.86 (d, J=4.5 Hz, 1H), 6.72 (d, J=4.5 Hz, 1H), 5.49 (d, J=4.8 Hz, 1H), 4.66-4.61 (m, 1H), 4.54 (d, J=11.7 Hz, 1H), 4.45 (d, J=5.6 Hz, 1H), 4.35 (d, J=11.8 Hz, 1H), 2.85-2.75 (m, 1H), 1.94-1.74 (m, 4H), 1.74-1.52 (m, 4H). MS m/z [M+1]=388.1.

Example 19: Compound 19 ((2R,3S,4R,5S)-5-(4-aminopyrrolo[2,1-f][1,2,4]triazin-7-yl)-2-cyano-3,4-dihydroxytetrahydrofuran-2-yl)methyl cyclohexanecarboxylate

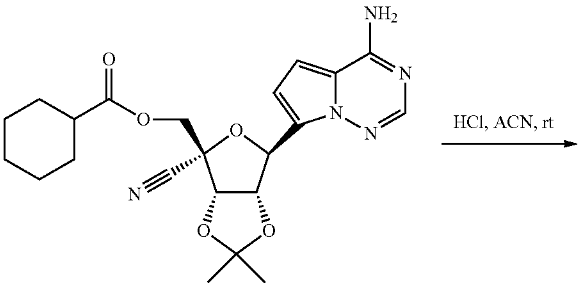

Intermediate I-20

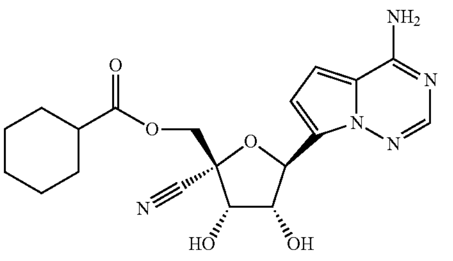

Compound 19

Intermediate I-20 Compound 19

To a solution of Intermediate I-20 (0.39 mmol, 1.0 equiv.) in ACN (5.0 mL) was added concentrated HCl (0.16 mL, 12 M, 5.0 equiv.) at room temperature. The reaction mixture was stirred for 8 h prior to diluting with EtOAc (30 mL) and quenching with a 1:1 solution of water:saturated $NaHCO_3$ (30 mL). The layers were separated, and the aqueous layer extracted once more with EtOAc (30 mL). The organic fractions were combined, washed with 1:1 water:brine (20 mL), dried over $Na_2SO_4$, filtered and concentrated in vacuo prior to purification by silica gel chromatography (0%-15% MeOH in DCM) to afford Compound 19. $^1H$ NMR (400 MHz, Methanol-$d_4$) δ 7.80 (s, 1H), 6.86 (d, J=4.5 Hz, 1H), 6.72 (d, J=4.5 Hz, 1H), 5.48 (d, J=4.6 Hz, 1H), 4.67-4.62 (m, 1H), 4.53 (d, J=11.8 Hz, 1H), 4.46 (d, J=5.5 Hz, 1H), 4.33 (d, J=11.8 Hz, 1H), 2.39-2.28 (m, 1H), 1.94-1.13 (m, 10H). MS m/z [M+1]=402.1.

Example 20 and 21: Compound 20 (2R,3S,4S,5S)-5-(4-aminopyrrolo[2,1-f][1,2,4]triazin-7-yl)-2-cyano-2-((isobutyryloxy)methyl)tetrahydrofuran-3,4-diyl bis(2-methylpropanoate) and Compound 21 (2R,3S,4S,5S)-2-cyano-5-(4-isobutyramidopyrrolo[2,1-f][1,2,4]triazin-7-yl)-2-((isobutyryloxy)methyl)tetrahydrofuran-3,4-diyl bis(2-methylpropanoate)

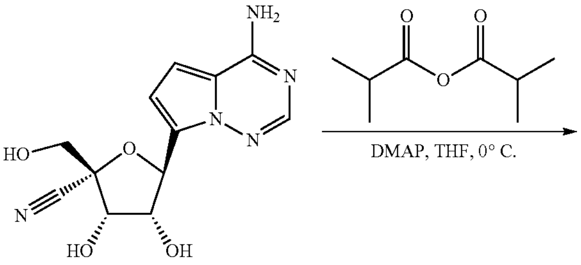

Compound 0

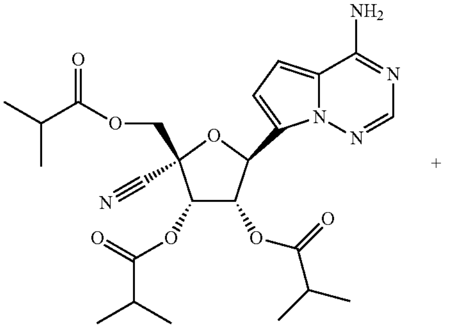

Compound 20

+

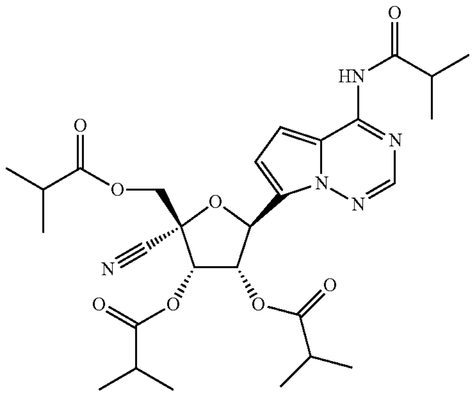

Compound 21

To a solution of Compound 0 (0.34 mmol), DMAP (0.069 mmol) in THF (3 mL) at 0° C. was added 2-methylpropanoyl 2-methylpropanoate (0.11 uL, 0.69 mmol) drop wise and stirred 30 min at 0° C. The reaction mixture was warmed to room temperature and directly load on 12 silica gel cartridge and used 40 g silica gel column, elute with Hexane 3 min, with DCM 1 min, and 0%-100% EtOAc/DCM 18 min. The pure fractions were combined, concentrated to afford Compound 20 and Compound 21.

Compound 20: 1H NMR (400 MHz, Acetonitrile-d3) δ 7.92 (s, 1H), 6.79 (q, J=4.6 Hz, 2H), 6.38 (s, 2H), 5.94-5.80 (m, 2H), 5.68 (d, J=3.8 Hz, 1H), 4.48 (dd, J=68.6, 12.0 Hz, 2H), 2.65 (ddq, J=35.6, 14.1, 7.0 Hz, 3H), 1.26-1.10 (m, 18H). MS m/z [M+1]=502.08.

Compound 21: 1H NMR (400 MHz, Acetonitrile-d3) δ 8.83 (s, 1H), 8.22 (s, 1H), 7.22 (d, J=4.8 Hz, 1H), 6.98 (d, J=4.7 Hz, 1H), 5.88-5.80 (m, 2H), 5.76 (d, J=4.1 Hz, 1H), 4.66-4.28 (m, 2H), 2.99 (h, J=7.0 Hz, 1H), 2.76-2.53 (m, 3H), 1.28-1.09 (m, 24H). MS m/z [M+1]=572.11.

Example 22: Compound 22 ((2R,3S,4R,5S)-5-(4-aminopyrrolo[2,1-f][1,2,4]triazin-7-yl)-2-cyano-3-hydroxy-4-(isobutyryloxy)tetrahydrofuran-2-yl) methyl benzoate

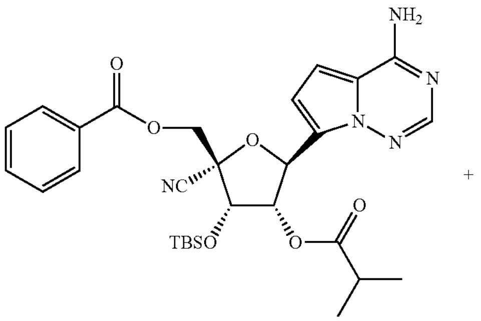

Intermediate I-13

+

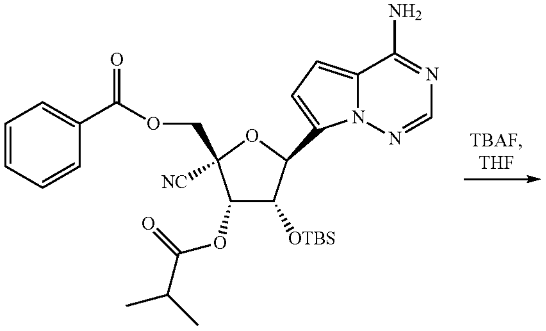

Intermediate I-14

-continued

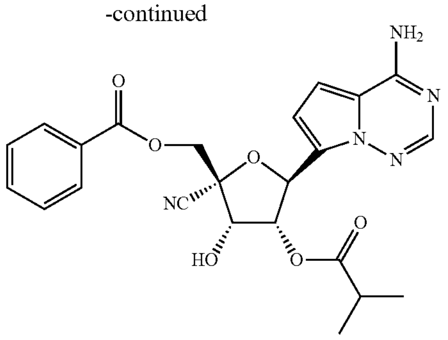

Compound 22

To a solution of mixture of Intermediate I-13 and Intermediate I-14 (0.0811 mmol) in THE (1 mL) was added TBAF (0.24 mL) at room temperature and stirred for 20 min, diluted with EtOAc, washed with brine, dried with sodium sulfate, concentrated in vacuo, and purified by silica gel column chromatography (0% to 5% MeOH in DCM) to give Compound 22. $^{1}$H NMR (400 MHz, Acetonitrile-d3) δ 8.02-7.98 (m, 2H), 7.81 (s, 1H), 7.70-7.64 (m, 1H), 7.52 (m, 2H), 6.75 (d, J=4.5 Hz, 1H), 6.72 (d, J=4.6 Hz, 1H), 6.33 (s, 2H), 5.72 (dd, J=5.9, 3.7 Hz, 1H), 5.64 (d, J=3.7 Hz, 1H), 4.99 (d, J=5.9 Hz, 1H), 4.84 (d, J=12.0 Hz, 1H), 4.61 (d, J=12.0 Hz, 1H), 4.46 (bs, 1H), 2.69 (m, 1H), 1.23 (d, J=7.0 Hz, 3H), 1.20 (d, J=7.0 Hz, 3H). MS m/z [M+1]=466.

Example 23: Compound 23 ((2R,3S,4R,5S)-2-cyano-3,4-dihydroxy-5-(4-isobutyramidopyrrolo[2,1-f][1,2,4]triazin-7-yl)tetrahydrofuran-2-yl)methyl acetate

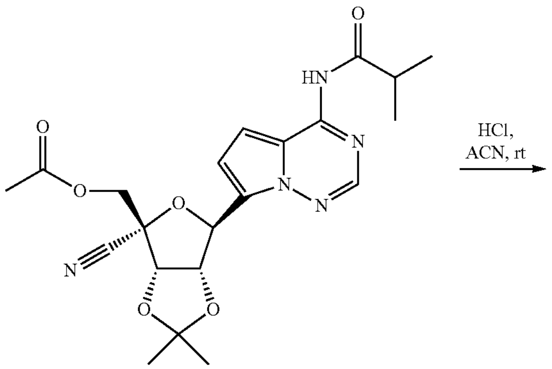

Intermediate I-39

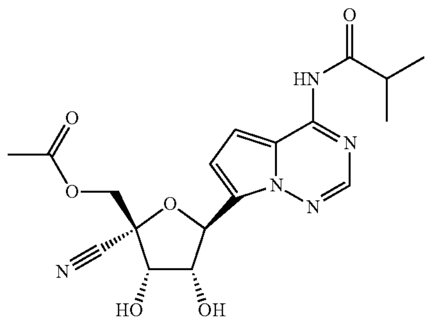

Compound 23

To well stirring mixture of Intermediate 1-39 (0.25 mmol) in $CH_3CN$ (4.0 mL), at 0° C. was added concentrated HCl (100 uL) drop wise (2 min). The reaction warmed to room temperature stirred 3 h. The reaction mixture was diluted with EtOAc, followed by saturated sodium bicarbonate. Keep diluting with EtOAc (30 mL) and saturated $NaHCO_3$ solution (30 mL) until solid dissolute and form clear solution. The aqueous layer was extracted with EtOAc (50 mL×2), and organic layer separated, washed once with brine solution (50 mL), dried over sodium sulfate, filtered and concentrated under reduced pressure. The crude product was dissolved in 10% MeOH/DCM, load on 40 g silica gel column, and elute with Hexane 3 min, DCM 1 min, and 0-25% MeOH/DCM 18 min. The pure fractions were combined, concentrated to afford Compound 23. 1H NMR (400 MHz, Acetonitrile-d3) δ 8.80 (s, 1H), 8.20 (s, 1H), 7.21 (d, J=4.7 Hz, 1H), 6.94 (d, J=4.7 Hz, 1H), 5.57 (d, J=4.6 Hz, 1H), 4.62-4.459 (m, 1H), 4.53 (d, J=11.9 Hz, 1H), 4.46 (d, J=5.7 Hz, 1H), 4.33 (d, J=11.9 Hz, 1H), 4.25 (s, 1H), 4.03 (s, 1H), 3.03-2.96 (m, 1H), 2.09 (s, 3H), 1.24 (d, J=6.8 Hz, 6H). MS m/z [M+1]=404.0.

Example 24: Compound 24 ((2R,3S,4R,5S)-5-(4-aminopyrrolo[2,1-f][1,2,4]triazin-7-yl)-2-cyano-3,4-dihydroxytetrahydrofuran-2-yl)methyl 1-methylcyclobutane-1-carboxylate

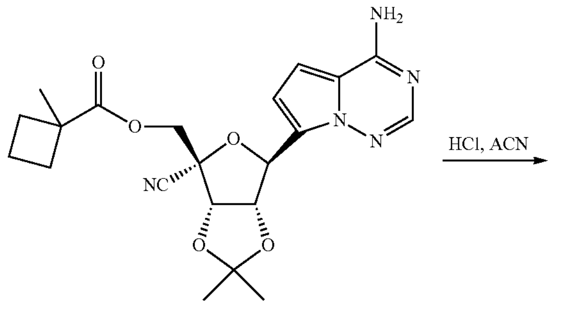

Intermediate I-29

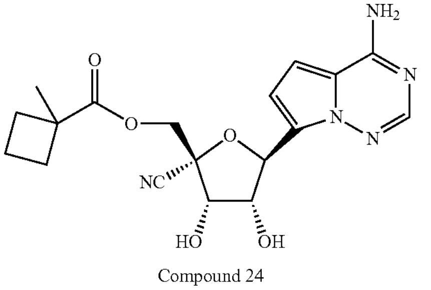

Compound 24

To a solution of Intermediate 1-29 (0.257 mmol) in ACN (1 mL) was added 25% HCl (0.2 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 24. $^1$H NMR (400 MHz, Methanol-d4) δ 7.82 (s, 1H), 6.87 (d, J=4.5 Hz, 1H), 6.74 (d, J=4.5 Hz, 1H), 5.51 (d, J=4.8 Hz, 1H), 4.66 (dd, J=5.6, 4.8 Hz, 1H), 4.57 (d, J=11.7 Hz, 1H), 4.46 (d, J=5.6 Hz, 1H), 4.40 (d, J=11.8 Hz, 1H), 2.63-2.40 (m, 2H), 2.13-1.76 (m, 4H), 1.42 (s, 3H). MS m/z [M+1]=388.2.

Example 25: Compound 25 ((2R,3S,4R,5S)-5-(4-aminopyrrolo[2,1-f][1,2,4]triazin-7-yl)-2-cyano-3,4-dihydroxytetrahydrofuran-2-yl)methyl (R)-5-oxotetrahydrofuran-2-carboxylate

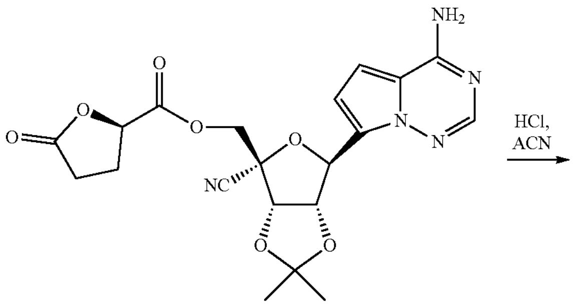

Intermediate I-32

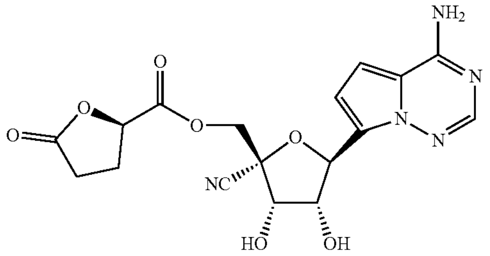

Compound 25

To a solution of Intermediate 1-32 (0.226 mmol) in ACN (1 mL) was added 25% HCl (0.2 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 25. $^1$H NMR (400 MHz, Methanol-d4) δ 7.83 (s, 1H), 6.87 (d, J=4.5 Hz, 1H), 6.76 (d, J=4.5 Hz, 1H), 5.52 (d, J=4.5 Hz, 1H), 5.15-5.09 (m, 1H), 4.76 (d, J=11.7 Hz, 1H), 4.66 (dd, J=5.6, 4.6 Hz, 1H), 4.54-4.47 (m, 2H), 2.67-2.44 (m, 3H), 2.41-2.28 (m, 1H). MS m/z [M+1]=404.0.

Example 26: Compound 26 ((2R,3S,4R,5S)-2-cyano-5-(4-(3,3-dimethylbutanamido) pyrrolo[2,1-f][1,2,4]triazin-7-yl)-3,4-dihydroxytetrahydrofuran-2-yl)methyl 3,3-dimethylbutanoate

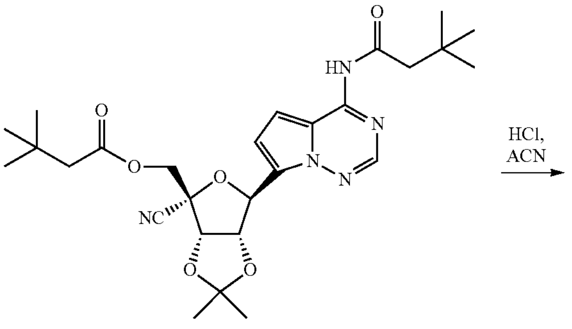

Intermediate I-28

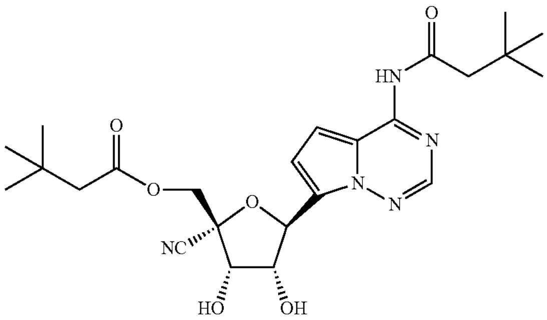

Compound 26

To a solution of Intermediate I-28 (0.0512 mmol) in ACN (1 mL) was added 25% HCl (0.1 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 26. $^1$H NMR (400 MHz, Methanol-d4) δ 8.21 (s, 1H), 7.20 (d, J=4.7 Hz, 1H), 6.98 (d, J=4.7 Hz, 1H), 5.60 (d, J=4.8 Hz, 1H), 4.66 (t, J=5.2 Hz, 1H), 4.51 (d, J=11.8 Hz, 1H), 4.46-4.36 (m, 2H), 2.51 (s, 2H), 2.33-2.18 (m, 2H), 1.14 (s, 9H), 1.02 (s, 9H). MS m/z [M+1]=487.9.

Example 27: Compound 27 ((2R,3S,4R,5S)-5-(4-aminopyrrolo[2,1-f][1,2,4]triazin-7-yl)-2-cyano-3,4-dihydroxytetrahydrofuran-2-yl)methyl 3,3-dimethylpentanoate

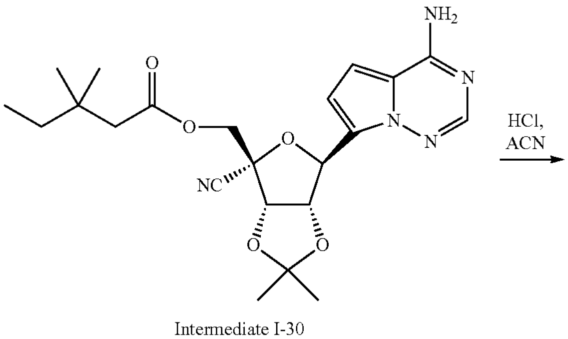

Intermediate I-30

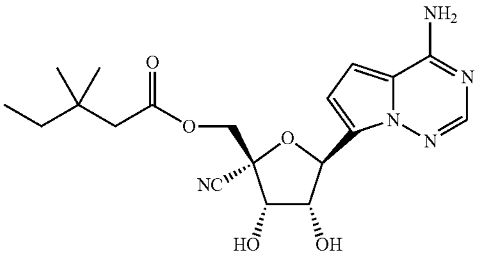

Compound 27

To a solution of Intermediate I-30 (0.248 mmol) in ACN (1 mL) was added 25% HCl (0.2 mL) at rt. The mixture was stirred for 2 h, diluted with EtOAc (20 mL) and aqNaHCO3 (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 27. $^1$H NMR (400 MHz, Methanol-d4) δ 7.82 (s, 1H), 6.87 (d, J=4.5 Hz, 1H), 6.74 (d, J=4.5 Hz, 1H), 5.54-5.44 (m, 1H), 4.72-4.61 (m, 1H), 4.50 (d, J=11.8 Hz, 1H), 4.46 (d, J=5.5 Hz, 1H), 4.39 (d, J=11.8 Hz, 1H), 2.30-2.15 (m, 2H), 1.35 (m, 2H), 0.97 (s, 6H), 0.85 (t, J=7.5 Hz, 3H). MS m/z [M+1]=404.3.

Example 28: Compound 28 (2R,3S,4S,5S)-2-(acetoxymethyl)-5-(4-aminopyrrolo[2,1-f][1,2,4]triazin-7-yl)-2-cyanotetrahydrofuran-3,4-diyl diacetate

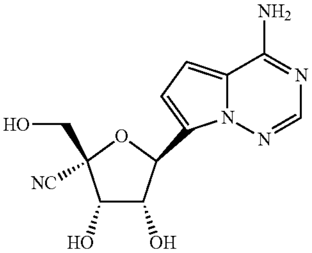

Compound 0

+

-continued

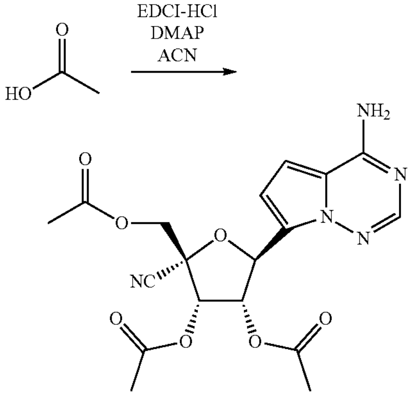

Compound 28

To a mixture of Compound 0 (0.604 mmol) and acetic acid (0.17 mL, 2.79 mmol) in DMF (2 mL) were added DMAP (2.79 mmol) and then EDCI-HCl (302 mmol). The resulting mixture was stirred at rt for 1 h, water (5 mL) added, concentrated in vacuo, and purified by silica gel column chromatography (0% to 5% MeOH in DCM) to give Compound 28. $^1$H NMR (400 MHz, Acetonitrile-d3) δ 7.93 (s, 1H), 6.88-6.70 (m, 2H), 6.33 (s, 2H), 5.85-5.79 (m, 2H), 5.71-5.65 (m, 1H), 4.61 (d, J=12.0 Hz, 1H), 4.36 (d, J=12.0 Hz, 1H), 2.17 (s, 3H), 2.09 (s, 3H), 2.06 (s, 3H). MS m/z [M+1]=418.2.

Example 29: Compound 29 ((2R,3S,4R,5S)-5-(4-aminopyrrolo[2,1-f][1,2,4]triazin-7-yl)-2-cyano-3,4-dihydroxytetrahydrofuran-2-yl)methyl 3-fluoro-2,2-dimethylpropanoate

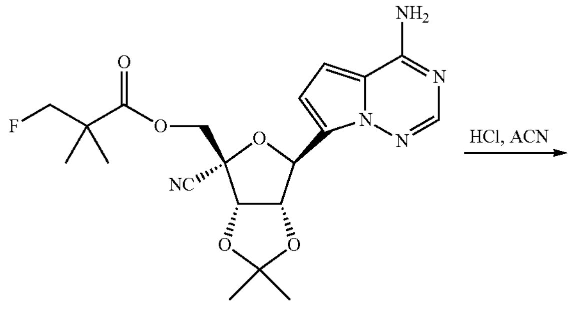

Intermediate I-31

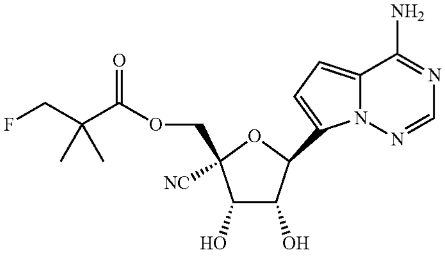

Compound 29

To a solution of Intermediate 1-31 (0.254 mmol) in ACN (1 mL) was added 25% HCl (0.2 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 29. $^1$H NMR (400 MHz, Methanol-d4) δ 7.82 (s, 1H), 6.87 (d, J=4.5 Hz, 1H), 6.74 (d, J=4.6 Hz, 1H), 5.51 (d, J=4.9 Hz, 1H), 4.70-4.64 (m, 1H), 4.57 (d, J=11.7 Hz, 1H), 4.48 (s, 1H), 4.46 (d, J=5.7 Hz, 1H), 4.43 (d, J=11.7 Hz, 1H), 4.36 (s, 1H), 1.27-1.21 (m, 6H). $^{19}$F NMR (376 MHz, Methanol-d4) δ 17.31. MS m/z [M+1]=394.3.

Example 30: Compound 30 & Compound 34, N-(7-((2S,3R,4S,5R)-5-cyano-3,4-dihydroxy-5-(hydroxymethyl)tetrahydrofuran-2-yl)pyrrolo[2,1-f][1,2,4]triazin-4-yl)isobutyramide (Compound 30); and (7-((2S,3R,4S,5R)-5-cyano-3,4-dihydroxy-5-(hydroxymethyl)tetrahydrofuran-2-yl)-4-iminopyrrolo[2,1-f][1,2,4]triazin-3(4H)-yl)methyl isobutyrate (Compound 34)

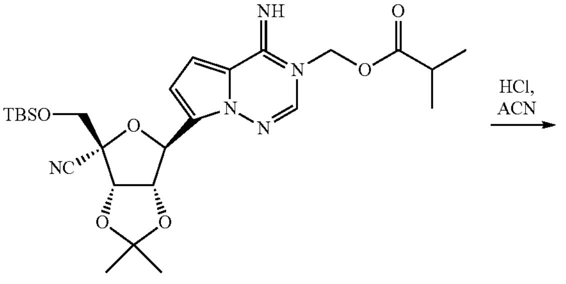

Intermediate I-27

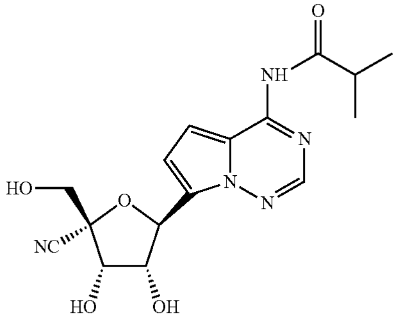

Compound 30

+

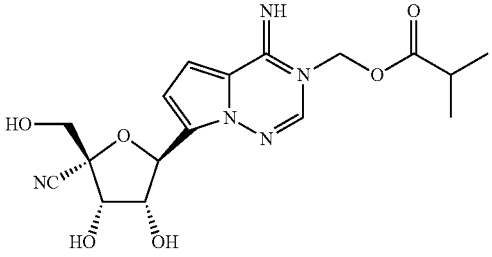

Compound 34

To a solution of Intermediate I-27 (0.123 mmol) in ACN (1 mL) was added 25% HCl (1.0 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (20 mL×3). The combined organic phase was dried under sodium sulfate, concentrated in vacuo, and purified by silica gel column chromatography (0% to 5% MeOH in DCM) to give Compound 30 and Compound 34.

Compound 30: $^{1}$H NMR (400 MHz, Acetonitrile-d3) δ 8.79 (s, 1H), 8.19 (s, 1H), 7.20 (d, J=4.7 Hz, 1H), 6.96 (d, J=4.7 Hz, 1H), 5.50 (d, J=5.7 Hz, 1H), 4.65-4.54 (m, 1H), 4.42 (d, J=5.6 Hz, 1H), 4.15 (s, 1H), 3.97-3.73 (m, 4H), 2.99 (m, 1H), 1.24 (d, J=6.8 Hz, 6H). MS m/z [M+1]=362.0.

Compound 34: $^{1}$H NMR (400 MHz, Acetonitrile-d3) δ 7.76 (s, 1H), 6.83 (d, J=4.3 Hz, 1H), 6.51 (d, J=4.3 Hz, 1H), 5.85 (s, 2H), 5.24 (d, J=6.0 Hz, 1H), 4.52-4.43 (m, 1H), 4.35 (d, J=5.7 Hz, 1H), 4.12 (s, 1H), 3.96-3.60 (m, 4H), 2.59 (m, 1H), 1.14 (d, J=7.0 Hz, 6H). MS m/z [M+1]=391.9.

Example 32: Compound 32 ((2R,3S,4R,5S)-5-(4-aminopyrrolo[2,1-f][1,2,4]triazin-7-yl)-2-cyano-3,4-dihydroxytetrahydrofuran-2-yl)methyl spiro[3.3] heptane-2-carboxylate

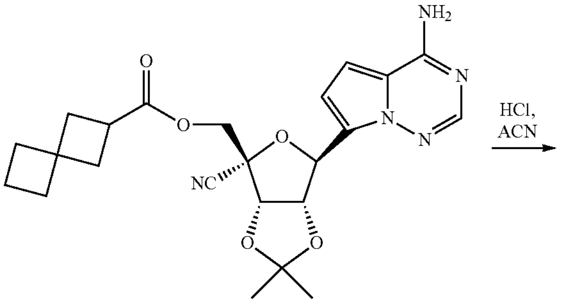

Intermediate I-25

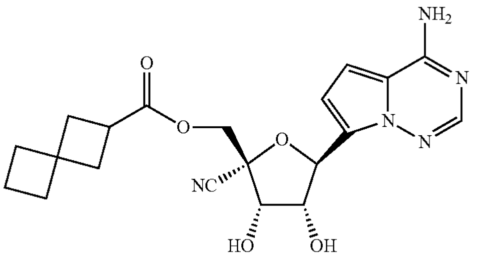

Compound 32

To a solution of Intermediate 1-25 (0.221 mmol) in ACN (2 mL) was added 25% HCl (0.2 mL) at rt. The mixture was stirred for 2 h, diluted with EtOAc (30 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0% to 5% MeOH in DCM) to give Compound 32. $^{1}$H NMR (400 MHz, Methanol-d4) δ 7.82 (s, 1H), 6.88 (d, J=4.5 Hz, 1H), 6.73 (d, J=4.5 Hz, 1H), 5.63-5.45 (m, 1H), 4.66-4.62 (m, 1H), 4.56 (d, J=11.8 Hz, 1H), 4.45 (d, J=5.5 Hz, 1H), 4.36 (d, J=11.8 Hz, 1H), 3.03 (p, J=8.43 Hz, 1H), 2.02-2.02 (m, 4H), 2.10-2.01 (m, 2H), 2.00-1.86 (m, 2H), 1.86-1.73 (m, 2H). MS m/z [M+1]=413.9.

Example 33: Compound 33 ((2R,3S,4R,5S)-5-(4-aminopyrrolo[2,1-f][1,2,4]triazin-7-yl)-2-cyano-3,4-dihydroxytetrahydrofuran-2-yl)methyl 2-(1-methylcyclobutyl)acetate

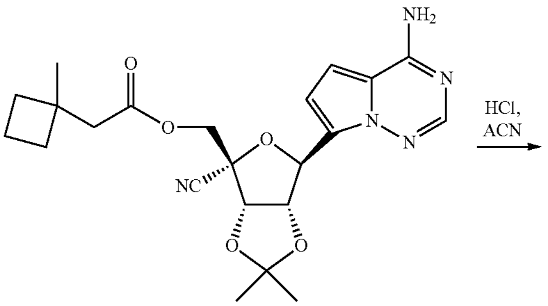

Intermediate I-24

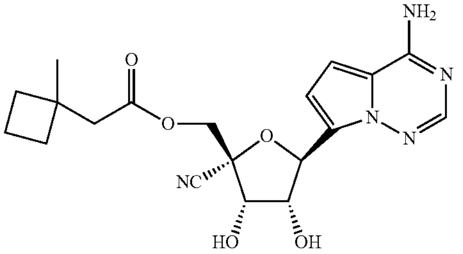

Compound 33

To a solution of Intermediate 1-24 (0.256 mmol) in ACN (2 mL) was added 25% HCl (0.2 mL) at rt. The mixture was stirred for 2 h, diluted with EtOAc (30 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 33. $^{1}$H NMR (400 MHz, Methanol-d4) δ 7.81 (s, 1H), 6.86 (d, J=4.5 Hz, 1H), 6.73 (d, J=4.5 Hz, 1H), 5.52 (d, J=4.8 Hz, 1H), 4.73-4.59 (m, 1H), 4.53 (d, J=11.8 Hz, 1H), 4.47 (d, J=5.6 Hz, 1H), 4.39 (d, J=11.8 Hz, 1H), 2.52-2.27 (m, 2H), 2.08-1.61 (m, 6H), 1.17 (s, 3H). MS m/z [M+1]=401.9.

Example 34: Compound 34 (7-((2S,3R,4S,5R)-5-cyano-3,4-dihydroxy-5-(hydroxymethyl) tetrahydrofuran-2-yl)-4-iminopyrrolo[2,1-f][1,2,4]triazin-3 (4H)-yl)methyl isobutyrate

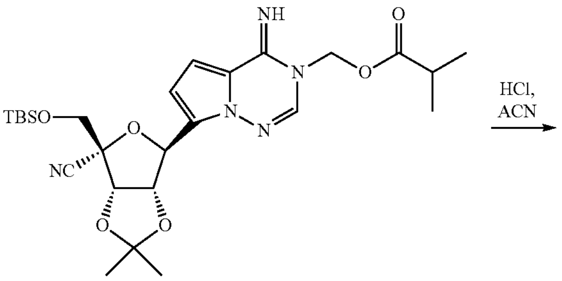

Intermediate I-27

-continued

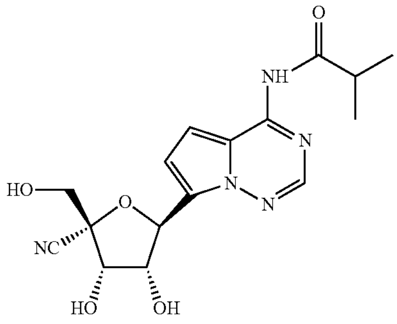

Compound 30

+

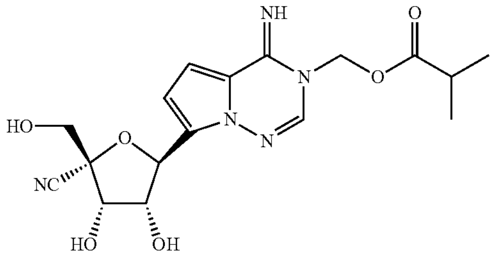

Compound 34

The method for preparing Compound 34 and its related characterization data is described above in Example 30.

Example 35: Compound 35 ((2R,3S,4R,5S)-5-(4-aminopyrrolo[2,1-f][1,2,4]triazin-7-yl)-2-cyano-3,4-dihydroxytetrahydrofuran-2-yl)methyl 2,2-dimethylbutanoate

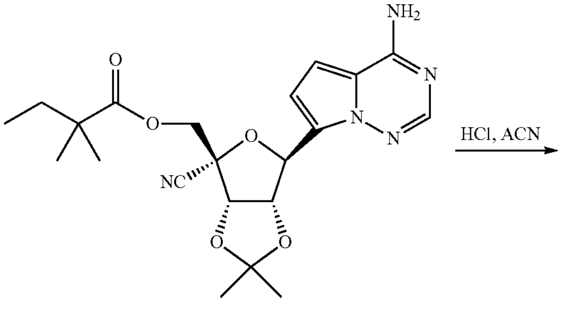

Intermediate I-33

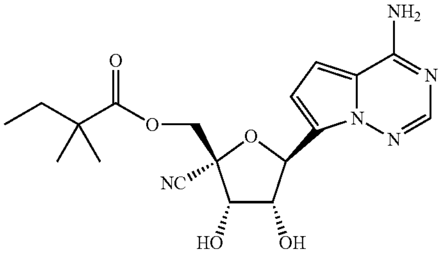

Compound 35

To a solution of Intermediate I-33 (0.275 mmol) in ACN (1 mL) was added 25% HCl (0.2 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 35. $^1$H NMR (400 MHz, Methanol-d4) δ 7.82 (s, 1H), 6.88 (d, J=4.5 Hz, 1H), 6.75 (d, J=4.5 Hz, 1H), 5.50 (d, J=4.9 Hz, 1H), 4.67 (dd, J=5.6, 4.9 Hz, 1H), 4.50 (d, J=11.7 Hz, 1H), 4.45 (d, J=5.6 Hz, 1H), 4.39 (d, J=11.8 Hz, 1H), 1.60 (m, 2H), 1.19 (s, 6H), 0.84 (t, J=7.5 Hz, 3H). MS m/z [M+1]=390.0.

Example 36: Compound 36 ((2R,3S,4R,5S)-5-(4-aminopyrrolo[2,1-f][1,2,4]triazin-7-yl)-2-cyano-3,4-dihydroxytetrahydrofuran-2-yl)methyl 4,4-dimethylpentanoate

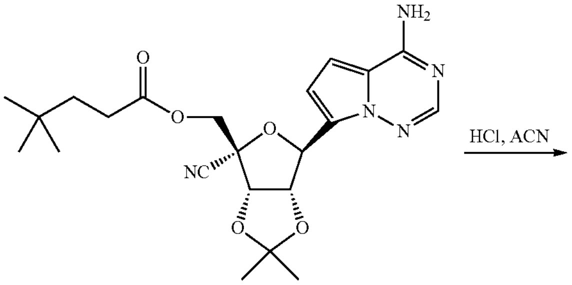

Intermediate I-34

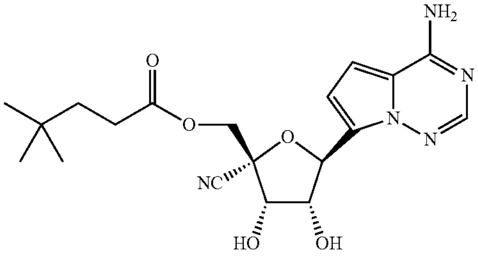

Compound 36

To a solution of Intermediate I-34 (0.361 mmol) in ACN (1 mL) was added 25% HCl (0.2 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0% to 5% MeOH in DCM) to give Compound 36. $^1$H NMR (400 MHz, Methanol-d4) δ 7.82 (s, 1H), 6.87 (d, J=4.5 Hz, 1H), 6.74 (d, J=4.5 Hz, 1H), 5.52 (d, J=4.6 Hz, 1H), 4.65 (dd, J=5.5, 4.6 Hz, 1H), 4.56 (d, J=11.8 Hz, 1H), 4.49 (d, J=5.5 Hz, 1H), 4.37 (d, J=11.7 Hz, 1H), 2.34 (m, 2H), 1.61-1.50 (m, 2H), 0.90 (s, 9H). MS m/z [M+1]=404.0.

Example 37: Compound 37 ((2R,3S,4R,5S)-5-(4-aminopyrrolo[2,1-f][1,2,4]triazin-7-yl)-2-cyano-3,4-dihydroxytetrahydrofuran-2-yl)methyl (R)-2-methylbutanoate

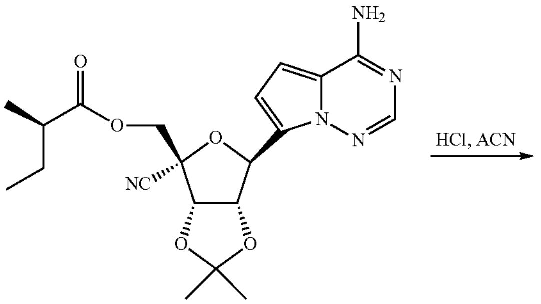

Intermediate I-35

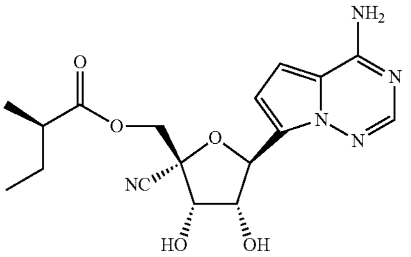

Compound 37

To a solution of Intermediate 1-35 (0.193 mmol) in ACN (1 mL) was added 25% HCl (0.2 mL) at rt. The mixture was stirred for 2 h, diluted with EtOAc (20 mL), and aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0% to 5% MeOH in DCM) to give Compound 37. $^1$H NMR (400 MHz, Methanol-d4) δ 7.82 (s, 1H), 6.87 (d, J=4.5 Hz, 1H), 6.74 (d, J=4.5 Hz, 1H), 5.62-5.34 (m, 1H), 4.66 (dd, J=5.6, 4.8 Hz, 1H), 4.55 (d, J=11.7 Hz, 1H), 4.47 (d, J=5.5 Hz, 1H), 4.39 (d, J=11.8 Hz, 1H), 2.45 (m, 1H), 1.68 (m, 1H), 1.49 (m, 1H), 1.21-1.07 (m, 3H), 0.90 (t, J=7.4 Hz, 3H). MS m/z [M+1]=376.0.

Example 38: Compound 38 ((2R,3S,4R,5S)-5-(4-aminopyrrolo[2,1-f][1,2,4]triazin-7-yl)-2-cyano-3,4-dihydroxytetrahydrofuran-2-yl)methyl 2-phenylacetate

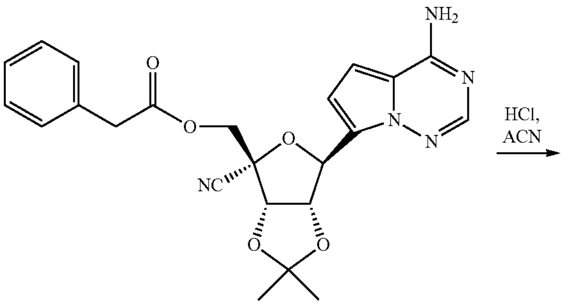

Intermediate I-36

-continued

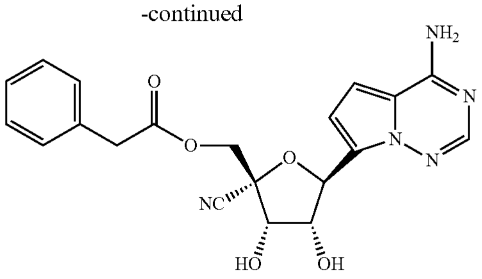

Compound 38

To a solution of Intermediate I-36 (0.218 mmol) in ACN (1 mL) was added 25% HCl (0.2 mL) at rt. The mixture was stirred for 2 h, diluted with EtOAc (20 mL), aq$NaHCO_3$ (10 mL) added slowly. The mixture was stirred for 10 min, the phases separated, and the aqueous phase extracted with EtOAc (10 mL×3). The combined organic phase was dried under sodium sulfate, concentrated in vacuo, and purified by silica gel column chromatography (0 to 5% MeOH in DCM) to give Compound 38. $^1$H NMR (400 MHz, Methanol-d4) δ 7.81 (s, 1H), 7.33-7.18 (m, 5H), 6.87 (d, J=4.5 Hz, 1H), 6.70 (d, J=4.5 Hz, 1H), 5.57-5.42 (m, 1H), 4.64-4.53 (m, 2H), 4.49-4.31 (m, 2H), 3.74-3.65 (m, 2H). MS m/z [M+1]=410.0.

D. Biological Examples

Example A. DENV-2 moDC $EC_{50}$

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and suspended in serum-free RPMI. moDCs were infected with Vero-derived Dengue 2, New Guinea strain (NGC) at a MOI=0.1 for two hours in serum-free RPMI with gentle agitation at 37° C. Cells were washed and resuspended in 10% serum-containing RPMI (Gibco, supplemented with sodium pyruvate, NEAA, Penicillin-Streptomycin). 10≡cells were plated in triplicate in 96-well plates with compounds dispensed at graded doses (Hewlett-Packard D300 Digital Dispenser). All wells were normalized to 0.25% DMSO. At 48 hours, cells were washed with 1×PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example B. moDC $CC_{50}$

Human monocyte-derived dendritic cells (moDCs) were derived from CD14+ monocytes (AllCells) cultured in Human Mo-DC Differentiation medium containing GM-CSF and IL-4 (Miltenyi Biotec). On day 7, moDCs were harvested by mechanical disruption, washed and cultured in triplicate at 1×10—5×10—4 cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example C. DENV-2 Huh-7 $EC_{50}$

Huh7 (Human hepatocarcinoma 7) cells were maintained in 10% FCS-containing DMEM complete media. On the day of the assay, cells were trypsinized (0.1% Trypsin-EDTA), washed and infected for 2 hours in serum-free DMEM with Dengue serotype 2 New Guinea C (NGC) strain at MOI=0.1 with gentle agitation at 37° C. After 2 hours, cells were washed with serum-free media and suspended in 10% FCS-containing DMEM (Gibco, supplemented with sodium pyruvate, NEAA, Penicillin-Streptomycin). 10≡cells were plated in triplicate in 96-well plates with compounds dispensed at graded doses (Hewlett-Packard D300 Digital Dispenser). All wells were normalized to 0.25% DMSO. At 48 hours, cells were washed with 1× PBS and all supernatants removed. Total RNA was extracted using RNEasy 96 plates (Qiagen) and used to generate first-strand cDNA using XLT cDNA 5× Supermix (QuantaBio). cDNA was used as a template in a Taqman qPCR duplex reaction specific to DENV2 viral and GAPDH gene expression. $EC_{50}$ values were determined using Prism Graphpad software, with normalization to a positive control and no compound negative control wells.

Example D. Huh-7 $CC_{50}$

Human hepatocarcinoma 7 (Huh7) cells were maintained in 10% FCS-containing complete DMEM. On day of assay, cells were trypsinized with 0.1% Trypsin-EDTA, washed and cultured in triplicate at 1-2×10—4 cells/well in 96-well plates with compounds dispensed at graded doses (Hewlett-Packard D300 Digital Dispenser). All wells were normalized to 0.25% DMSO. After 48 hours, CellTiter Glo (Promega) was added and incubated for 10 minutes at room temp before reading on a luminometer. % viability curves were calculated against no compound and no cell control wells. $CC_{50}$ values were determined using Prism Graphpad software.

Example E. RSV HEp-2 $EC_{50}$

Antiviral activity against RSV is determined using an infectious cytopathic cell protection assay in HEp-2 cells. In this assay, compounds inhibiting viral infection and/or replication produce a cytoprotective effect against the virus-induced cell killing that can be quantified using a cell viability reagent. The techniques used here are novel adaptations of methods described in published literature (Chapman et al., ANTIMICROB AGENTS CHEMOTHER. 2007, 51(9):3346-53).

HEp-2 cells are obtained from ATCC (Manassas, VI) and maintained in MEM media supplemented with 10% fetal bovine serum and penicillin/streptomycin. Cells are passaged twice a week and kept at subconfluent stage. Commercial stock of RSV strain A2 (Advanced Biotechnologies, Columbia, MD) is titered before compound testing to determine the appropriate dilution of the virus stock that generates desirable cytopathic effect in HEp-2 cells.

For antiviral tests, HEp-2 cells are grown in large cell culture flasks to near confluency but not fully so. The compounds to be tested are prediluted in DMSO in 384-well compound dilution plates, either in an 8 or 40 sample per plate standardized dose response format. 3-fold serial dilution increments of each test compound are prepared in the plates and test samples are transferred via acoustic transfer apparatus (Echo, Labcyte) at 100 nL per well into cell culture assay 384-well plates. Each compound dilution is transferred in single or quadruplicate samples into dry assay plates, which are stored until assay is ready to go. The positive and negative controls are laid out in opposite on ends of the plate in vertical blocks (1 column).

Subsequently, an infectious mixture is prepared using an appropriate dilution of virus stock previously determined by titration with cells at a density of 50,000/ml and 20 Q QL/well is added to test plates w/compounds via automation (uFlow, Biotek). Each plate includes negative and positive controls (16 replicates each) to create 0% and 100% virus inhibition standards, respectively. Following the infection with RSV, testing plates are incubated for 4 days in a 37° C. cell culture incubator. After the incubation, a cell viability reagent, Cell TiterGlo (Promega, Madison, WI) is added to the assay plates, which are incubated briefly, and a luminescent readout is measured (Envision, Perkin Elmer) in all the assay plates. The RSV-induced cytopathic effect, percentage inhibition, is determined from the levels of remaining cell viability. These numbers are calculated for each tested concentration relative to the 0% and 100% inhibition controls, and the $EC_{50}$ value for each compound is determined by non-linear regression as a concentration inhibiting the RSV-induced cytopathic effect by 50%. Various potent anti-RSV tool compounds are used as positive controls for antiviral activity.

Example F. HEp-2 $CC_{50}$

Cytotoxicity of tested compounds is determined in uninfected HEp-2 cells in parallel with the antiviral activity using the cell viability reagent in a similar fashion as described before for other cell types (Cihlar et al., ANTIMICROB AGENTS CHEMOTHER. 2008,52(2):655-65). The same protocol as for the determination of antiviral activity is used for the measurement of compound cytotoxicity except that the cells are not infected with RSV. Instead, an uninfected cell mixture at the same density is added at 20 ul/well to plates containing prediluted compounds, also at 100 nL/sample. Assay plates are then incubated for 4 days followed by a cell viability test using the same CellTiter Glo reagent addition and measurement of luminescent readouts. Untreated cell and cells treated at 2 μM puromycin (Sigma, St. Louis, MO) serve as 100% and 0% cell viability control, respectively. The percent of cell viability is calculated for each tested compound concentration relative to the 0% and 100% controls and the $CC_{50}$ value is determined by non-linear regression as a compound concentration reducing the cell viability by 50%.

Example G. HEp-2 and MT4 $CC_{50}$

Cytotoxicity of the compounds was determined in uninfected cells using the cell viability reagent in a similar fashion as described before for other cell types (Cihlar et al., ANTIMICROB AGENTS CHEMOTHER. 2008,52(2):655-65). HEp-2 (1.5×103 cells/well) and MT-4 (2×103 cells/well) cells were plated in 384-well plates and incubated with the appropriate medium containing 3-fold serially diluted compound ranging from 15 nM to 100,000 nM. Cells were cultured for 4-5 days at 37° C. Following the incubation, the cells were allowed to equilibrate to 25° C., and cell viability was determined by adding Cell-Titer Glo viability reagent. The mixture was incubated for 10 min, and the luminescence signal was quantified using an Envision plate reader. Untreated cell and cells treated at 2 μM puromycin (Sigma, St. Louis, MO) serve as 100% and 0% cell viability control, respectively. The percent of cell viability was calculated for each tested compound concentration relative to the 0% and 100% controls and the $CC_{50}$ value was determined by non-linear regression as a compound concentration reducing the cell viability by 50%.

Example H. RSV NHBE $EC_{50}$

Normal human bronchial epithelial (NHBE) cells were purchased from Lonza (Walkersville, MD, Cat #CC-2540) and cultured in Bronchial Epithelial Growth Media (BEGM) (Lonza, Walkersville, MD, Cat #CC-3170). The cells were passaged 1-2 times per week to maintain <80% confluency. The NHBE cells were discarded after 6 passages in culture.

To conduct the RSV A2 antiviral assay, NHBE cells were plated in 96-well plates at a density of 7,500 cells per well in BEGM and allowed to attach overnight at 37° C. Following attachment, 100 μL of cell culture media was removed and 3-fold serially diluted compound was added using a Hewlett-Packard D300 Digital Dispenser. The final concentration of DMSO was normalized to 0.05%. Following compound addition, the NHBE cells were infected by the addition of 100 μL of RSV A2 at a titer of $1\times10^{4.5}$ tissue culture infectious doses/mL in BEGM and then incubated at 37° C. for 4 days. The NHBE cells were then allowed to equilibrate to 25° C. and cell viability was determined by removing 100 μL of culture medium and adding 100 μL of Cell-Titer Glo viability reagent. The mixtures were incubated for 10 minutes at 25° C., and the luminescence signal was quantified on an Envision luminescence plate reader.

Example L RSV NHBE FLuc $EC_{50}$

Normal human bronchial epithelial (NHBE) cells are purchased from Lonza (Walkersville, MD Cat #CC-2540) and maintained in Bronchial Epithelial Cell Growth Medium (BEGM) (Lonza, Walkersville, MD, Cat #CC-3170) with all provided supplements in the BulletKit. Cells are passaged 2-3 times per week to maintain sub-confluent densities and are used for experiments at passages 2-4.

Recombinant Respiratory Syncytial virus strain A2 containing the firefly luciferase reporter between the P and M genes (RSV-Fluc, $6.3\times10^6$ $TCID_{50}$/mL) is purchased from Viratree (Durham, NC, Cat #R145).

NHBE cells ($5\times10^3$/well) are seeded in 100 μL white wall/clear bottom 96-well plates (Corning) with culture medium and are incubated for 24 hours at 37° C. with 5% $CO_2$. On the following day, three-fold serial dilutions of compounds prepared in DMSO are added to the wells using the HP D300e digital dispenser with normalization to the highest concentration of DMSO in all wells. The cells are then infected with RSV-Fluc diluted with BEGM media at an MOI of 0.1 for a final volume of 200 μL media/well. Uninfected and untreated wells are included as controls to determine compound efficacy against RSV-Fluc. Following incubation with compound and virus for three days at 37° C. with 5% $CO_2$, 100 μL of culture supernatant is removed from each well and replaced with 100 μL of ONE-Glo luciferase reagent (Promega, Madison, WI, Cat #E6110). The plates are gently mixed by rocking for 10 minutes at 21° C. and luminescence signal is measured using an Envision plate reader (PerkinElmer). Values are normalized to the uninfected and infected DMSO controls (0% and 100% infection, respectively). Non-linear regression analysis is applied to determine the compound concentration at which 50% luminescence signal is reduced ($EC_{50}$) using the XLfit4 add-in for MICROSOFT® EXCEL®. All experiments are performed in duplicate with two technical repeats each.

Example J. RSV NHBE $CC_{50}$

NHBE cells were seeded in black 384-TC-treated plates (Corning) at $2\times10^3$ cells/well in a final volume of 20 μL BEBM+supplements (Lonza). The next day, add 0.1 μL of compound was added to the assay plates using an Echo acoustic dispenser. Plates were incubated for 3 additional days at 37° C. and 5% $CO_2$. On day 3 of treatment, 20 μL of CellTiter Glo (Promega) was added to each well using a Biotek dispenser. After a 10-minute incubation, luminescence signal was measured with 0.1 sec integration time using an EnVision (Perkin-Elmer) plate reader. Values were normalized to the DMSO- and puromycin- treated controls (0% and 100% cell death, respectively). Data was fit using non-linear regression analysis and $CC_{50}$ values were then determined as the concentration reducing the luciferase signal by 50%. The compiled data was generated based on least two independent experimental replicates, each containing technical quadruplicates for each concentration.

Example K. RSV HAE $EC_{50}$

HAE cells are cultured at the air-liquid interface and have an apical side that is exposed to the air and a basal side that is in contact with the medium. Prior to experimentation, HAE were removed from their agar-based shipping packaging and were acclimated to 37° C./5% $CO_2$ overnight in 1 ml of HAE Assay medium (AIR-100-MM, Mattek Corp). HAE were prepared for infection by washing the apical surface twice with 400 μL of PBS (either utilizing direct pipetting methods or by running each transwell through a trough containing PBS) to remove the mucus layer. Apical chambers were drained of PBS and tapped gently onto absorbent material to remove as much PBS as possible. After washing, the cells were transferred to fresh HAE maintenance media containing 4-fold serially diluted compound, delivered to the basal side of the cell monolayer, and apically infected with 100 μL of a 1:600 dilution of RSV A strain A2 1000× stock (ABI, Columbia, MD, cat #10-124-000) in HAE assay medium for 3 hours at 37° C. in 5% $CO_2$. The virus inoculum was removed and the apical surface of the cells was washed 3 times with PBS using either method previously described. The cells were then cultured in the presence of compound for 3 days at 37° C. Following the incubation, total RNA was extracted from the HAE cells using a MagMAX-96 Viral RNA isolation kit (Applied Biosystems, Foster City, CA, Cat #AM1836) and intracellular RSV RNA was quantified by real-time PCR. Approximately 25 ng of purified RNA was added to a PCR reaction mixture that contained 0.9 μM RSV N Forward and RSV N Reverse primers, 0.2 μM RSV N Probe and 1× Taqman RNA-to-Ct 1-Step Kit (Applied Biosystems, Foster City, CA, Cat #4392938). RNA levels were normalized using a Taqman GAPDH control primer set (Applied Biosystems, Foster City, CA, Cat #402869). Real-Time PCR Primers and Probe Used in the RSV A2 HAE Antiviral Assay:

```
RSV N Forward
                                        (SEQ ID NO: 1)
CATCCAGCAAATACACCATCCA,

RSV N Reverse
                                        (SEQ ID NO: 2)
TTCTGCACATCATAATTAGGAGTATCAA,

RSV N Probe
                                        (SEQ ID NO: 3)
FAM-CGGAGCACAGGAGAT-BHQ
```

Example L. HRV16 HELA $EC_{50}$

H1-HeLa cells, cultured in complete DMEM medium containing 10% heat-inactivated FBS and 1% Penicillin/Streptomycin, were seeded in 96 well plates at 3000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and the appropriate dilution of virus stock, previously determined by titration and prepared in cell culture media, was added to test plates containing cells and serially diluted compounds. Each plate included 6 wells of infected untreated cells and 6 wells of uninfected cells that served as 0% and 100% virus inhibition control, respectively. Following the infection, test plates were incubated for 96 h in a tissue culture incubator set to 33° C./5% $CO_2$. Following incubation, the H1-HeLa cells were removed from incubation and allowed to equilibrate to 25° C. Cell viability was determined by removing 100 μL of culture medium and adding 100 μL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example M. HRV1A HELA $EC_{50}$

H1-HeLa cells, cultured in complete RPMI 1640 medium containing 10% heat-inactivated FBS and 1% Penicillin/Streptomycin, were seeded in 96 well plates at 5000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and 100 μL of 1/4000 dilution of HRV1a virus stock was added to each well containing cells and serially diluted compounds. Each plate included 6 wells of infected untreated cells and 6 wells of cells containing 5 M Rupintrivir that served as 0% and 100% virus inhibition control, respectively. Following the infection, test plates were incubated for 96 h in a tissue culture incubator set to 37° C./5% $CO_2$. Following incubation, the H1-HeLa cells were removed from incubation and allowed to equilibrate to 25° C. Cell viability was determined by removing 100 μL of culture medium and adding 100 μL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example N. HRV14 HELA $EC_{50}$

H1-HeLa cells, cultured in complete RPMI 1640 medium containing 10% heat-inactivated FBS and 1% Penicillin/Streptomycin, were seeded in 96 well plates at 5000 cells/well one day prior to compound dosing and infection. The antiviral activity of each compound was measured in triplicate. Compounds were added directly to the cell cultures in serial 3-fold dilutions using the HP300 digital dispenser (Hewlett Packard, Palo Alto, CA) immediately prior to infection. The plates were transferred to BSL-2 containment and 100 μL of 1/4000 dilution of HRV14 virus stock was added to each well containing cells and serially diluted compounds. Each plate included 6 wells of infected untreated cells and 6 wells of cells containing 5 M Rupintrivir that served as 0% and 100% virus inhibition control, respectively. Following the infection, test plates were incubated for 96 h in a tissue culture incubator set to 37° C./5% $CO_2$. Following incubation, the H1-HeLa cells were removed from incubation and allowed to equilibrate to 25° C. Cell viability was determined by removing 100 μL of culture medium and adding 100 μL of Cell-Titer Glo viability reagent. The mixtures were incubated on a shaker for 10 minutes at 25° C., and the luminescence signal was quantified on an Envision luminescence plate reader. The percentage inhibition of virus infection was calculated for each tested concentration relative to the 0% and 100% inhibition controls and the $EC_{50}$ value for each compound was determined by 4-parametric non-linear regression as the effective concentration of compound that inhibited cytopathic effect by 50%.

Example O. HRVc15 and HRVc25 $EC_{50}$

First, HRV replicon RNA is prepared. 5ug of DNA Template (HRVc15 or HRVc25) is linearized with 2 μL of MluI enzyme in NEB buffer-3 in a final volume of 25 μL for 3 hours at 37° C. Following incubation, linearized DNA is purified on a PCR purification column and the following in vitro transcription is performed using the following conditions: 10 μL of RiboMAX Express T7 2× buffer, 1-8 μL of linear DNA template (1 μg), 0-7 μL nuclease free water, 2 μL enzyme mix T7 express. The final volume of 20 μL is mixed and incubated at 37° C. for 30 min. Following incubation, 1 μL of RQ1 RNase free DNase is added and the mixture is incubated at 37° C. for 15 min. The resulting RNA is then purified with the MegaClear Kit (Gibco Life Technologies cat #11835-030) and is eluted two times with 50 μL of elution buffer at 95° C. H1-HeLa cells cultured in complete RPMI 1640 media containing 10% heat-inactivated FBS and 1% Penicillin/Streptomycin are seeded into T-225 flasks at a concentration of 2E6 cells/flask a day prior to transfection and are incubated at 37° C./5% $CO_2$ overnight. On the day of transfection, cells are trypsinized following standard cell culture protocols and are washed two times with PBS. Following washes, cells are resuspended at a concentration of 1E7 cells/mL in PBS and the suspension is stored on wet ice. Electroporation is used to introduce replicon RNA into the H1-HeLa cells. A final volume of 10 μL containing 10 μg of replicon c15 or 1 μg of c25 replicon RNA, respectively, are pipetted into a 4 mm electroporation cuvette. The H1-HeLa cell stock is mixed by gently swirling and 0.5 mL of the cell stock previously prepared is transferred into the cuvette containing the replicon RNA. The combined solution is flicked to mix. Following mixing, cells are immediately electroporated using the following settings: 900V, 25 uF, infinite resistance, 1 pulse. Cuvettes are rested on ice for 10 min. Following the 10 min incubation, add 19 mL of ambient temperature, phenol red-free and antibiotic-free RPMI 1640 containing 10% heat-inactivated FBS per electroporation. 150 μL (4E4 cells) of the electroporated cell suspension are seeded per well into a 96well clear-bottom, white cell culture plate, and are incubated at 25° C. for 30 min. Compounds were added directly to the cell cultures in serial 3-fold dilutions using the HP300 digital dispenser (Hewlett Packard, Palo Alto, CA) and were tested in triplicate. Following the addition of compounds, plates are incubated at 33° C. for 48 hrs. Replicon activity is then measured by a Renilla-Glo Luciferase Assay system. Prior to signal quantification, plates are removed from incubators and are allowed to equilibrate to 25° C. after 50 uL is removed from each well. Following manufacturer's protocol, a 1:100 dilution of Renilla-Glo substrate to buffer is prepared and 100 uL of the Renill-Glo luciferase mix is added to each well. Plates are then incubated for 20 min at 25° C. under gentle agitation and luciferase signal are determined with a 0.1 second detection setting using an EnVision luciferase quantification reader. The percentage inhibition of replicon inhibition was calculated for each tested concentration relative to the 0% and 100% inhibition controls included in the experiments and the $EC_{50}$ value for each compound was determined by 4-parametric non-linear regression as the effective concentration of compound that inhibited luciferase signal by 50%.

Example P. DENV-2 Huh-7 Rep $EC_{50}$

In 384 well plates (Greiner, Cat #781091), compounds were acoustically transferred at 200 nl per well in a 8 compound (4 replicates) or 40 compound dose response format (3 replicates). For all plates tested, Balapiravir, GS-5734 and NITD008 were included as positive inhibition controls alongside 0% inhibition, DMSO-only negative control wells. Following compound addition, Huh-7 cells containing the DENV2 replicon construct were harvested following standard cell culture procedures and were adjusted to a concentration of 1.25E5 cells/mL in cell culture media composed of cDMEM without genticin. 40 μL of the cell stock was then added to each well for a final cell density of 5,000 cells/well. Cell and compound mixtures were incubated at 37° C./5% $CO_2$ for 48 hours. Prior to harvesting cells, EnduRen Live Cell Substrate (Promega, Cat #E6481) was prepared by suspending 3.4 mg into 100 uL of DMSO to generate a 60 mM stock solution. The stock solution was then diluted 1:200 in pre-warmed cDMEM and 10 uL of this diluted solution was added to each well of the 384 well plates. Plates were then centrifuged at 500 rpm briefly and were placed on a plate shaker for 2 min. Following mixing, plates were incubated at 7° C./5% $CO_2$ for 1.5 hours prior to measuring luminescence on an Envision luminometer. The percentage inhibition of replicon signal was calculated for each tested concentration relative to the 0% and 100% inhibition controls and the $EC_{50}$ value for each compound was determined by 4-parametric non-linear regression as the effective concentration of compound that inhibited replicon signal by 50%.

Example Q. HCV Rep 1B and 2A $EC_{50}$

Compounds were serially diluted in ten steps of 1:3 dilutions in 384-well plates. All serial dilutions were performed in four replicates per compound within the same 384-well plate. An HCV protease inhibitor ITMN-191 at 100 μM was added as a control of 100% inhibition of HCV replication while puromycin at 10 mM was included as a control of 100% cytotoxicity. To each well of a black polystyrene 384-well plate (Greiner Bio-one, Monroe, NC), 90 μL of cell culture medium (without Geneticin) containing 2000 suspended HCV replicon cells was added with a Biotek Flow workstation. For compound transfer into cell culture plates, 0.4 μL of compound solution from the compound serial dilution plate was transferred to the cell culture plate on a Biomek FX workstation. The DMSO concentration in the final assay wells was 0.44%. The plates were incubated for 3 days at 37° C. with 5% $CO_2$ and 85% humidity. The HCV replicon assay was a multiplex assay, able to assess both cytotoxicity and antireplicon activity from the same well. The $CC_{50}$ assay was performed first. The media in the 384-well cell culture plate was aspirated, and the wells were washed four times with 100 μL of PBS each, using a Biotek ELX405 plate washer. A volume of 50 μL of a solution containing 400 nM calcein AM (Anaspec, Fremont, CA) in 1× PBS was added to each well of the plate with a Biotek Flow workstation. The plate was incubated for 30 min at room temperature before the fluorescence signal (excitation 490 nm, emission 520 nm) was measured with a Perkin-Elmer Envision plate reader. The $EC_{50}$ assay was performed in the same wells as the $CC_{50}$ assay. The calcein-PBS solution in the 384-well cell culture plate was aspirated with a Biotek ELX405 plate washer. A volume of 20 μL of Dual-Glo luciferase buffer (Promega, Madison, WI) was added to each well of the plate with a Biotek μFlow Workstation. The plate was incubated for 10 min at room temperature. A volume of 20 μL of a solution containing a 1:100 mixture of Dual-Glo Stop & Glo substrate (Promega, Madison, WI) and Dual-Glo Stop & Glo buffer (Promega, Madison, WI) was added to each well of the plate with a Biotek Flow Workstation. The plate was then incubated at room temperature for 10 min before the luminescence signal was measured with a Perkin-Elmer Envision Plate Reader.

Example R. HEp-2 RSV-Luc5 384-well Assay ($EC_{50}$ RSVFLUC Hep2-384)

HEp-2 cell line was purchased from ATCC (Manassas, VA Cat #CCL-23) and maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus recombinant with luciferase (RSV-Luc5) direct pelleted virus (≥1×107 TCID50/ml) was purchased from Microbiologics (Saint Cloud, MN). Viral replication was determined in HEp-2 cells in the following manner.

Compounds are prepared in 384-well polypropylene plates (Greiner, Monroe, NC, Cat #784201) with 8 compounds per plate in grouped replicates of 4 at 10 serially diluted concentrations (1:3).

HEp-2 cells were suspended in DMEM (supplemented with 10% FBS and 1× Penicillin-Streptomycin-L-Glutamine) and 60 uL of 4,000 cells per well were seeded into 384-well plates (Greiner, Monroe, NC, Cat #781080) using Biotek MultiFlo dispenser. After overnight incubation at 37° C. and 5% $CO_2$, 0.4 uL of three-fold serial dilutions of compound was added to each well using a Biomek FX pipette station. RSV-Luc5 viruses were diluted in DMEM (supplemented with 10% FBS and 1× Penicillin-Streptomycin-L-Glutamine) at an MOI=0.5. Virus suspension was added to each 384-well compound plate at 20 uL per well using a Biotek MultiFlo dispenser. The assay plates were incubated for 3 days at 37° C. and 5% $CO_2$. At the end of incubation, One-Glo reagent (Promega, Madison, WI, Cat #E6120) was prepared. The assay plate and the reagent were equilibrated to room temperature for 30 minutes. 50 uL per well of medium was removed from assay plate and 40 uL per well of One-Glo reagent was added to each plate by Biomek FX. The plates were sat at room temp for 15 minutes. Viral replication was then assessed by measuring luminescence signal using and Envision plate reader. Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was then determined as the concentration reducing the viral replication by 50%.

Example S. HEp-2 and MT4 $CC_{50}$

Cytotoxicity of the compounds was determined in uninfected cells using the cell viability reagent in a similar fashion as described before for other cell types (Cihlar et al., Antimicrob Agents Chemother. 2008,52(2):655-65). HEp-2 (1.5×103 cells/well) and MT-4 (2×103 cells/well) cells were plated in 384-well plates and incubated with the appropriate medium containing 3-fold serially diluted compound ranging from 15 nM to 100,000 nM. Cells were cultured for 4-5 days at 37° C. Following the incubation, the cells were allowed to equilibrate to 25° C., and cell viability was determined by adding Cell-Titer Glo viability reagent. The mixture was incubated for 10 min, and the luminescence signal was quantified using an Envision plate reader. Untreated cell and cells treated at 2 μM puromycin (Sigma, St. Louis, MO) serve as 100% and 0% cell viability control, respectively. The percent of cell viability was calculated for each tested compound concentration relative to the 0% and 100% controls and the $CC_{50}$ value was determined by non-linear regression as a compound concentration reducing the cell viability by 50%.

Example T. H1-Hela Anti-HRV Assay

Both H1-HeLa cells and human rhinovirus 16 (HRV-16) are purchased from ATCC.

H1-HeLa maintenance media is composed of DMEM supplemented with 10% FBS and 1% Penn/Strep. Virus infection medium (VIM) is composed of DMEM+2% FBS.

H1-HeLa cells are seeded into 96-well black/clear bottom plates with 5,000 cells/well in 100 μL/well in H1-HeLa maintenance medium and incubated for 24 hours at 37° C. and 5% $CO_2$. On the following day medium is aspirated and replaced with 100 μL VIM, next three-fold serial dilutions of compounds prepared in DMSO are added to the wells using the HP D300e digital dispenser with normalization to the highest concentration of DMSO in all wells. HRV-16 is diluted with the VIM to an MOI=0.05 and added to the cells in 100 μL/well. On each plate, uninfected and infected DMSO controls are included to determine compound efficacy against HRV. When extensive cytopathic effect is observed in the positive control (usually 3-6 days post infection) following the incubation at 37° C. and 5% $CO_2$, the culture plates are cooled to room temperature. The culture medium is removed and 200 μL of CellTiter Glo (1:2 dilution in PBS) is added to each well. The plates are agitated for 10 minutes on a shaker at room temperature and luminescence signal is measured using an EnVision plate reader (PerkinElmer). Values are normalized to the uninfected and infected DMSO controls (0% and 100% infection, respectively). Non-linear regression analysis is applied to determine the compound concentration at which 50% luminescence signal is reduced ($EC_{50}$) using the XLfit4 add-in for MICROSOFT® EXCEL®. All experiments are performed in duplicate with two technical repeats.

Example U. NHBE RSV-Luc5 384-well Assay ($EC_{50}$ RSVFLUC NHBE-384)

Normal Human Bronchial Epithelial (NHBE) cells were purchased from Lonza (Walkersville, MD Cat #CC2540) and maintained in BEGM Bronchial Epithelial Cell Growth Medium BulletKit (Lonza CC-3170).

Cells were thawed, expanded, and were used for experiments at passage 2. Respiratory syncytial virus recombinant with luciferase (RSV-Luc5) (≥1×$10^7$ Infectious Units/ml (IU/ml) determined by $TCID_{50}$) was purchased from Microbiologics (Saint Cloud, MN). Viral replication was determined in NHBE cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well. NHBE cells were harvested and suspended in BEGM Bronchial Epithelial Cell Growth Medium BulletKit and seeded to the pre-spotted assay plates at 5,000 cells per well in 30 μL. RSV-Luc5 virus was diluted in BEGM Bronchial Epithelial Cell Growth Medium BulletKit at 500,000 Infectious Units (IU) per mL and 10 μL per well was added to the assay plates containing cells and compounds, for an MOI of 1. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 40 μL per well of One-Glo reagent was added and the plates were incubated at room temperature for 15 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing the viral replication by 50%.

Example V: HEp-2 RSV-Luc5 384-well Assay (EC50 RSVFLUC Hep2-384 v2)

HEp-2 cell line was purchased from ATCC (Manassas, VA Cat #CCL-23) and maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03) and 1× Penicillin-Streptomycin-L-Glutamine (Corning, New York, NY, Cat #30-009-CI). Cells were passaged 2 times per week to maintain sub-confluent densities and were used for experiments at passage 5-20. Respiratory syncytial virus recombinant with luciferase (RSV-Luc5) (≥1×107 TCID50/ml) was purchased from Microbiologics (Saint Cloud, MN). Viral replication was determined in HEp-2 cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well. HEp-2 cells were harvested and suspended in DMEM (supplemented with 10% FBS and 1× Penicillin-Streptomycin-L-Glutamine) and seeded to the pre-spotted assay plates at 4,000 cells per well in 30 μL. RSV-Luc5 viruses were diluted in DMEM (supplemented with 10% FBS and 1× Penicillin-Streptomycin-L-Glutamine) at 200,000 Infectious Units (IU) per mL and 10 μL per well was added to the assay plates containing cells and compounds, for an MOI=0.5. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 40 μL per well of One-Glo reagent was added and the plates were incubated at room temp for 15 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was then determined as the concentration reducing the viral replication by 50%.

Example W: NHBE RSV-Luc5 384-well Assay (EC50 RSVFLUC NHBE-384)

Normal Human Bronchial Epithelial (NHBE) cells were purchased from Lonza (Walkersville, MD Cat #CC2540) and maintained in BEGM Bronchial Epithelial Cell Growth Medium BulletKit (Lonza CC-3170).

Cells were thawed, expanded, and were used for experiments at passage 2. Respiratory syncytial virus recombinant with luciferase (RSV-Luc5) (≥1×$10^7$ Infectious Units/mL (IU/mL) determined by $TCID_{50}$) was purchased from Microbiologics (Saint Cloud, MN). Viral replication was determined in NHBE cells in the following manner.

Compounds are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well using an Echo acoustic dispenser (Labcyte, Sunnyvale, CA). NHBE cells were harvested and suspended in BEGM Bronchial Epithelial Cell Growth Medium BulletKit and seeded to the pre-spotted assay plates at 5,000 cells per well in 30 μL. RSV-Luc5 virus was diluted in BEGM Bronchial Epithelial Cell Growth Medium BulletKit at 500,000 Infectious Units (IU) per mL and 10 μL per well was added to the assay plates containing cells and compounds, for an MOI of 1. The assay plates were incubated for 3 days at 37° C. and 5% $CO_2$. At the end of incubation, One-Glo reagent (Promega, Madison, WI, Cat #E6120) was prepared. The assay plates and One-Glo reagent were equilibrated to room temperature for at least 15 minutes. 40 μL per well of One-Glo reagent was added and the plates were incubated at room temperature for 15 minutes before reading the luminescence signal on an EnVision multimode plate reader (Perkin Elmer, Waltham, MA). Remdesivir was used as positive control and DMSO was used as negative control. Values were normalized to the positive and negative controls (as 0% and 100% replication, respectively) and data was fitted using non-linear regression analysis by Gilead's dose response tool. The $EC_{50}$ value for each compound was defined as the concentration reducing the viral replication by 50%.

Example Y: H1-HeLa HRV-CTG 384-well Assay

H1-Hela cell line (ATCC, Manassas, VA, Cat #CRL-1958) was maintained in Dulbecco's Minimum Essential Medium (DMEM) (Corning, New York, NY, Cat #15-018CM) supplemented with 10% fetal bovine serum (FBS) (Hyclone, Logan, UT, Cat #SH30071-03), and 1× Penicillin-Streptomycin-L-Glutamine (Corning, New York, NY, Cat #30-009-CI). Cells were passaged 2 times per week to maintain sub-confluent densities and were used for experiments at passage 5-30. The Human Rhinovirus 1B (HRV1B) (ATCC, Manassas, VA, Cat #VR-1645), Human Rhinovirus 14 (HRV14) (ATCC, Manassas, VA, Cat #VR-284), and Human Rhinovirus 16 (HRV16) (ATCC, Manassas, VA, Cat #BR-283) was obtained through ATCC. Viral infection was monitored by determining viability of H1-HeLa cells as described below.

Test molecules are prepared in 100% DMSO in 384-well polypropylene plates (Greiner, Monroe, NC, Cat #784201) with 8 compounds per plate in grouped replicates of 4 at 10 serially diluted concentrations (1:3). The serially diluted compounds were transferred to low dead volume Echo plates (Labcyte, Sunnyvale, CA, Cat #LP-0200).

The test compounds were spotted to 384-well assay plates (Greiner, Monroe, NC, Cat #781091) at 200 nL per well using an Echo acoustic dispenser (Labcyte, Sunnyvale, CA). H1-HeLa cells were harvested and suspended in DMEM (supplemented with 2% FBS and 1× Penicillin-Streptomycin-L-Glutamine) and seeded to the pre-spotted assay plates at 5,000 cells per well in 30 μL. HRV1B, HRV14, and HRV16 was diluted in DMEM (supplemented with 2% FBS and 1× Penicillin-Streptomycin-L-Glutamine) at 97.1 million Infectious Units (IU) per mL, 151 million IU per mL and 221 million IU per mL respectively. 10 μL of virus per well was added to the assay plates containing cells and compounds, for an MOI of 0.5, 1.0, and 0.25 respectively. The assay plates were incubated for 4 days at 37° C. and 5% $CO_2$. At the end of incubation, Celltiter-Glo (Promega, Madison, WI, Cat #(Ga7573) was prepared. The assay plates and Celltiter-Glo reagent were equilibrated to room temperature for at least 15 minutes. 40 μL per well of Celltiter-Glo reagent was added and the plates were incubated at room temperature for 15 minutes before reading the luminescence signal on an EnVision multimode plate reader (Perkin Elmer, Waltham, MA). Rupintrivir was used as positive control and DMSO was used as negative control.

Values were normalized to the positive and negative controls (as 0% and 100% replication, respectively) and data was fitted using non-linear regression analysis by Gilead's dose response tool. The $EC_{50}$ value for each compound was defined as the concentration reducing viral replication by 50%.

Example Z: GI S9 Stability Data

Reagents

Stock solutions of test compounds in dimethyl sulfoxide (DMSO) having a final concentration of 10 mM were prepared and used in all experiments. Sekisui XenoTech (Kansas City, KS) provided pooled intestinal S9 fractions. All other chemicals were purchased from Sigma-Aldrich (St. Louis, MO) or VWR (West Chester, PA). Internal Standard/Quench (IS/Q) used to stop reactions was 100 nM labetalol in (by volume) methanol (10%) and acetonitrile (90%).

Assay

Stability in Intestinal S9 Fractions: Duplicate aliquots of test compound or positive control substrate were added to S9 stock diluted with phosphate buffered saline (137 mM NaCl, 2.7 mM KCl, 10 mM phosphate buffer), pH 7.4, to obtain a protein concentration of 1.0 mg/mL. The metabolic reactions were initiated by the addition of the substrates to the S9 reaction mixture to a final concentration of 2 μM. At 0, 10, 20, 30, 60 and 120 min, 25 μL aliquots of the reaction mixture were transferred to plates containing 225 μl of IS/Q solution. After quenching, the plates were centrifuged at 3000×g for 30 minutes. 150 μL aliquots of each supernatant were dried down then reconstituted with 300 μL water. Aliquots (10 μL) of the prepared samples were analyzed on a Thermo Q-Exactive mass spectrometer as described below.

Liquid Chromatography—Mass Spectrometry: Quantification of test compounds and control substrate was performed by analyte/internal standard peak area ratio (PAR) values measured on a Thermo Q-Exactive mass spectrometer coupled to a Dionex UltiMate 3000 HPLC with a Leap Technologies HTC PAL autosampler. The column used for analysis was a Waters Acquity BEH C18 (1.7 μm particle size, 2.1×50 mm). Mobile phase A consisted of 0.1% (v/v) formic acid in water. Mobile phase B consisted of 0.1% (v/v) formic acid in acetonitrile. Elution of analytes was achieved by a series of linear gradients varying the proportions of A and B. The mass spectrometer was calibrated on a weekly basis and mass tolerance of 5 ppm was used.

Data Analysis

Metabolic stabilities in S9 fractions were determined by measuring the rates of disappearance of test compound and positive control substrate.

Data (% of substrate remaining) were plotted on a semi-log scale and fitted using an exponential decline model:

$$C_t = C_0 \times e^{ln2/T1/2 \times t}$$

Where $C_t$—% of substrate remaining at time=t; $C_0$—% of substrate remaining at time=0; t—time; T½—half-life The Half-life (T½) is determined by the following equation:

$$T½ = -\ln 0.5/k = 0.693/k$$

Assuming a first-order reaction, the slope (k) is extrapolated from the aforementioned plotted data.

TABLE 13

T½ (half-life) data of some compounds disclosed herein

| Example | GIS9 Rat T½ (per Ex. Z) min | GIS9 DOG T½ (per Ex. Z) min | GIS9 Cyno T½ (per Ex. Z) min | GIS9 Human T½ (per Ex. Z) min |
|---|---|---|---|---|
| 1 | 11 | 121 | 25 | 38 |
| 2 | 8 | 789 | 32 | 27 |
| 3 | 12 | 497 | 17 | 42 |
| 4 | 9 | 41 | 9 | 23 |
| 5 | 10 | 114 | 6 | 29 |
| 6 | 4 | 38 | 8 | 8 |
| 7 | 26 | 633 | 100 | 292 |
| 8 | 2 | 10 | 4 | 4 |
| 9 | 23 | 510 | 57 | 55 |
| 10 | 53 | 269 | 123 | 124 |
| 11 | 37 | 95 | 19 | 56 |
| 12 | 9 | 5 | 2 | 2 |
| 13 | 185 | 755 | 408 | 789 |
| 14 | 6 | 426 | 22 | 25 |
| 15 | 23 | 789 | 123 | 104 |
| 16 | 4 | 89 | 3 | 14 |
| 17 | 3 | 48 | 0 | 13 |
| 18 | 3 | 26 | 3 | 8 |
| 19 | 4 | 48 | 2 | 13 |
| 20 | 2 | 3 | | 3 |
| 21 | 1 | 5 | 4 | 0 |
| 25 | 5 | | | 3 |
| 28 | 5 | | | 5 |
| 30 | 789 | | | 789 |
| 32 | 2 | | | 12 |
| 33 | 31 | | | 154 |
| 35 | 124 | | | 273 |
| 36 | 3 | | | 11 |
| 38 | 12 | | | 28 |

Example A1: Rat Pharmacokinetics Assay

Reference Compound 0, Compound 1 and all compounds were dosed orally by gavage to male Sprague-Dawley rats (n=3/group); Compound 0 was dosed at 10 mg/kg in 50 Ethanol; 5500 Polyethylene glycol 400 and 40 water+1 equiv HC, pH 3.4; All other compounds were dosed at 10 mg/kg in 2.5% Dimethyl sulfoxide; AUC KolliphornHS-15; f. Labrasol; 2.5 Propylene glycol and 750% water. Blood samples were collected into pre-chilled collection tubes containing $K_2EDTA$ and processed to plasma at 10-11 timepoints over a span of predose to 24 h post-administration. Plasma samples were subject to protein precipitation with 8-fold volume of acetonitrile, vortexed and centrifuged. Supernatants were transferred and diluted by water. Separation was achieved on a Phenomenex Polar-RP column, a mobile phase A of 0.1% formic acid in acetonitrile: water (1:99) and a mobile phase B of 0.1% formic acid in acetonitrile: water (95:5) with a stepwise linear gradient from 1 to 99% mobile phase B. An LCMS/MS method was used to measure the concentrations of the Reference compound 0 and the corresponding compound in plasma. Data for Reference Compound 0 following oral administration of Compound 0, and all other compounds is tabulated below.

TABLE 14

| Rat pharmacokinetics of some compounds disclosed herein | | | | |
|---|---|---|---|---|
| Compound | Oral dose (mg/kg) | Reference compound 0 Cmax (nM) | Reference compound 0 AUCinf. (nM · h) | Reference Compound Oral Bioavailability F % |
| 0 | 10 | 5870 | 39200 | 46 |
| 1 | 10 | 7850 | 45400 | 54 |
| 2 | 10 | 6620 | 28500 | 43 |
| 4 | 10 | 8030 | 41900 | 50 |
| 7 | 10 | 9050 | 44200 | 64 |
| 9 | 10 | 10900 | 43700 | 69 |
| 10 | 10 | 10100 | 55700 | 85 |
| 13 | 10 | 9300 | 40800 | 65 |
| 15 | 10 | 6200 | 49400 | 75 |

Example A2: Dog Pharmacokinetics Assay

Reference Compound 0, Compound 1 and Compound 13 were dosed orally by gavage to male beagle dogs (n=3/group); Compound 0 at 5 mg/kg in 2.5% Dimethyl sulfoxide; 10% Kolliphor HS-15; 10% Labrasol; 2.5% Propylene glycol and 75% water, pH 3.5; Compound 1 at 5 mg/kg in 2.5% DMSO; 10% Kolliphor HS-15; 10% Labrasol; 2.5% Propylene glycol and 75% water, pH 7.1; Compound 13 at 5 mg/kg in 2.5% Dimethyl sulfoxide; 10% Kolliphor HS-15; 10% Labrasol; 2.5% Propylene glycol and 75% water, pH 6.0. Blood samples were collected into pre-chilled collection tubes containing $K_2EDTA$ and processed to plasma at 10-11 timepoints over a span of predose to 24 h post-administration. Plasma samples were subject to protein precipitation with 8-fold volume of acetonitrile, vortexed and centrifuged. Supernatants were transferred and diluted by water. Separation was achieved on a Phenomenex Polar-RP column, a mobile phase A of 0.1% formic acid in acetonitrile: water (1:99) and a mobile phase B of 0.1% formic acid in acetonitrile: water (95:5) with a stepwise linear gradient from 1 to 99% mobile phase B. An LCMS/MS method was used to measure the concentrations of the Reference compound 0 and either Compound 1 or Compound 13 in plasma. Data for Reference Compound 0 following oral administration of Compound 0, Compound 1 or Compound 13 is tabulated below.

TABLE 15

| Dog pharmacokinetics of some compounds disclosed herein | | | | |
|---|---|---|---|---|
| Compound | Oral dose (mg/kg) | Reference compound 0 Cmax (nM) | Reference compound 0 AUCinf. (nM · h) | Reference Compound Oral Bioavailability F % |
| 0 | 5 | 8360 | 40600 | 46 |
| 1 | 5 | 9900 | 49500 | 55 |
| 13 | 5 | 5760 | 49300 | 73 |

Example A3 Monkey Pharmacokinetics Assay

Reference Compound 0, Compound 1 and Compound 13 were dosed orally by gavage to male cynomolgus monkeys (n=3/group) using the following formulations. Compound 0 at 5 mg/kg in 2.5% Dimethyl sulfoxide; 10% Kolliphor HS-15; 10% Labrasol; 2.5% Propylene glycol and 75% water, pH 3.5; Compound 1 at 5 mg/kg in 2.5% Dimethyl sulfoxide; 10% Kolliphor HS-15; 10% Labrasol; 2.5% Propylene glycol and 75% water, pH 7.1; Compound 13 at 5 mg/kg in 2.5% DMSO; 10% Kolliphor HS-15; 10% Labrasol; 2.5% Propylene glycol and 75% water, pH 6.0. Blood samples were collected into pre-chilled collection tubes containing $K_2EDTA$ and processed to plasma at 10-11 timepoints over a span of predose to 24 h post-administration. Plasma samples were subject to protein precipitation with 8-fold volume of acetonitrile, vortexed and centrifuged. Supernatants were transferred and diluted by water. Separation was achieved on a Phenomenex Polar-RP column, a mobile phase A of 0.1% formic acid in acetonitrile: water (1:99) and a mobile phase B of 0.1% formic acid in acetonitrile: water (95:5) with a stepwise linear gradient from 1 to 99% mobile phase B. An LCMS/MS method was used to measure the concentrations of the Reference compound 0 and either Compound 1 or Compound 13 in plasma. Data for Reference Compound 0 following oral administration of Compound 0, Compound 1 or Compound 13 is tabulated below.

TABLE 16

| Monkey pharmacokinetics of some compounds disclosed herein | | | | |
|---|---|---|---|---|
| Compound | Oral dose (mg/kg) | Reference compound 0 Cmax (nM) | Reference compound 0 AUCinf. (nM · h) | Reference Compound Oral Bioavailability F % |
| 0 | 5 | 1270 | 7900 | 30 |
| 1 | 5 | 2330 | 15500 | 59 |
| 13 | 5 | 3590 | 14400 | 73 |

Biological Data

Provided below in Tables 39 and 40 is biological data related to some compounds disclosed herein.

TABLE 39

| Biological Data for Some Compounds Disclosed Herein | | | | |
|---|---|---|---|---|
| CMPD | $EC_{50}$ RSV FLUC NHBE 384 (per Ex. U) nM | $EC_{50}$ RSV FLUC NHBE 384 V2 (per Ex. W) nM | RSV Hep-2 FLuc $EC_{50}$ (per Ex. R) nM | $EC_{50}$ RSV FLuc Hep-2 384 V2 (per Ex. V) nM |
| 1 | 22124 | 14360 | 10433 | 14991 |
| 2 | 7469 | 9313 | | 36810 |
| 3 | 8068 | 8554 | | 26414 |
| 4 | 11012 | 10741 | | 15660 |
| 5 | 8890 | 7784 | | 20010 |
| 6 | 7712 | 7693 | | 16795 |
| 7 | 9654 | 10681 | | 50000 |
| 8 | 8795 | 10088 | | 14857 |
| 9 | 8686 | 9468 | | 28857 |
| 10 | 8077 | 7874 | | 21764 |
| 11 | 25246 | 24603 | | 41482 |
| 12 | 11485 | 10687 | | 19191 |
| 13 | 10944 | 8588 | | 50000 |
| 14 | 8819 | 9603 | | 22032 |
| 15 | 8805 | 8772 | | 31636 |
| 16 | 9526 | 8357 | | 18283 |
| 17 | 8087 | 8700 | | 19706 |
| 18 | 8993 | 8714 | | 23253 |
| 19 | | 10935 | | 17996 |
| 20 | 31686 | 10444 | | 29864 |
| 21 | | 9077 | | |
| 22 | | 11330 | | 32135 |
| 23 | | 14941 | | 33129 |
| 24 | | 10832 | | 11988 |
| 25 | | 11698 | | 10300 |
| 26 | | 26584 | | 46822 |
| 27 | | 12180 | | 12303 |
| 28 | | 24587 | | 15947 |

TABLE 39-continued

Biological Data for Some Compounds Disclosed Herein

| CMPD | $EC_{50}$ RSV FLUC NHBE 384 (per Ex. U) nM | $EC_{50}$ RSV FLUC NHBE 384 V2 (per Ex. W) nM | RSV Hep-2 FLuc $EC_{50}$ (per Ex. R) nM | $EC_{50}$ RSV FLuc Hep-2 384 V2 (per Ex. V) nM |
|---|---|---|---|---|
| 29 | | 12989 | | 28782 |
| 30 | | 38534 | | >50000 |
| 31 | | 50000 | | 50000 |
| 32 | | 6704 | | 16403 |
| 33 | | 50000 | | 23417 |
| 34 | | 39085 | | >50000 |
| 35 | | 9604 | | 24427 |
| 36 | | 10784 | | 11806 |
| 37 | | 9925 | | 14790 |
| 38 | | 10645 | | 18908 |

TABLE 40

Biological Data for Some Compounds (CMPD) Disclosed Herein

| CMPD # | EC50 H1-HeLa_HRV14_HRV-CTG 384-well Assay (per Ex Y) nM | EC50 H1-HeLa_HRV16_HRV-CTG 384-well Assay (per Ex. Y) nM | EC50 H1-HeLa_HRV1B_HRV-CTG 384-well Assay (per Ex. Y) nM |
|---|---|---|---|
| 1 | 5134 | 9306 | 3050 |
| 2 | 23886 | 28316 | 9596 |
| 3 | 9331 | 13221 | 8842 |
| 4 | 4609 | 10102 | 6381 |
| 5 | 10474 | 9837 | 8487 |
| 6 | 7860 | 8235 | 4109 |
| 7 | 27069 | 30690 | 11419 |
| 8 | 5664 | 7739 | 3337 |
| 9 | 15472 | 35083 | 21613 |
| 10 | 10930 | 14253 | 9767 |
| 11 | 50000 | 50000 | 50000 |
| 12 | 6003 | 8819 | 6496 |
| 13 | 50000 | 50000 | 50000 |
| 14 | 8165 | 23794 | 9803 |
| 15 | 50000 | 31123 | 22826 |
| 16 | 6986 | 7148 | 3141 |
| 17 | 7831 | 7573 | 3199 |
| 18 | 6934 | 8006 | 3032 |
| 19 | 6838 | 9230 | 4108 |
| 20 | 12762 | 50000 | 9628 |
| 22 | 15922 | 33138 | 12762 |
| 23 | 49795 | 50000 | 33518 |
| 24 | 6344 | 8898 | 3428 |
| 25 | 6008 | 8306 | 3134 |
| 26 | 50000 | 50000 | 50000 |
| 27 | 50000 | 50000 | 50000 |
| 28 | 19767 | 23945 | 9450 |
| 29 | 16888 | 22742 | 9371 |
| 30 | 36233 | 50000 | 27515 |
| 32 | 5144 | 4556 | 3181 |
| 33 | 20825 | 50000 | 35108 |
| 34 | 50000 | 50000 | 28700 |
| 35 | 24553 | 48186 | 19152 |
| 36 | 6511 | 8026 | 3104 |
| 37 | 11929 | 9779 | 5711 |
| 38 | 6250 | 8435 | 3115 |

The present disclosure provides reference to various embodiments and techniques. However, it should be understood that many variations and modifications can be made while remaining within the spirit and scope of the present disclosure. The description is made with the understanding that it is to be considered an exemplification of the claimed subject matter, and is not intended to limit the appended claims to the specific embodiments illustrated.

The invention claimed is:

1. A compound of Formula I:

Formula I

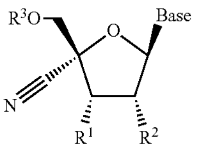

or a pharmaceutically acceptable salt thereof, wherein:

$R^1$ is OH;

$R^2$ is OH;

$R^3$ is $C(O)R^7$;

$R^7$ is $C_1$-$C_8$alkyl, $C_3$-$C_8$ carbocyclyl, $C_6$-$C_{10}$ aryl, 4 to 6 membered heterocyclyl containing 1, 2, or 3 O, or 5 to 6 membered heteroaryl containing 1, 2, or 3 heteroatoms selected from N, O, and S;

wherein the alkyl, carbocyclyl, aryl, heterocyclyl, and heteroaryl of $R^7$ are each, independently, optionally substituted with one, two or three substituents independently selected from the group consisting of halo, oxo, cyano, —$N_3$, —$OR^8$, $C_1$-$C_8$ alkyl, —$NR^9R^{10}$, $C_3$-$C_8$ carbocyclyl optionally substituted with $C_1$-$C_6$ alkyl, and phenyl optionally substituted with one, two, or three substituents independently selected from halo, cyano, and $C_1$-$C_6$ alkyl; and each $R^8$ is independently H, $C_1$-$C_6$ alkyl, $C_1$-$C_6$ haloalkyl, and $C_3$-$C_6$ cycloalkyl;

each $R^9$ is independently H, $C_1$-$C_6$ alkyl, $C_1$-$C_6$ haloalkyl, and $C_3$-$C_6$ cycloalkyl;

each $R^{10}$ is independently H, $C_1$-$C_6$ alkyl, $C_1$-$C_6$ haloalkyl, and $C_3$-$C_6$ cycloalkyl; and Base is

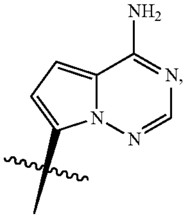 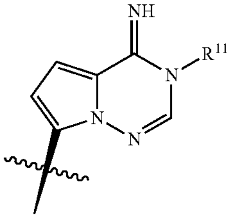,

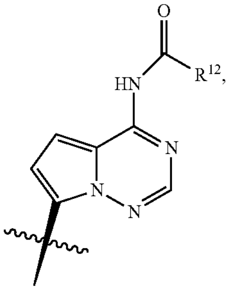 or 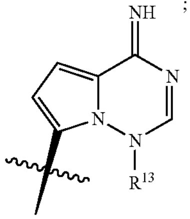;

wherein $R^{11}$ is $C_1$-$C_6$ alkyl substituted with —$OP(O)(OH)_2$ or —$OC(O)R^{12}$;

$R^{12}$ is $C_1$-$C_8$ alkyl; and $R^{13}$ is $C_1$-$C_6$ alkyl substituted with —$OP(O)(OH)_2$ or —$OC(O)R^{12}$.

2. The compound of claim 1, or the pharmaceutically acceptable salt thereof, wherein $R^3$ is

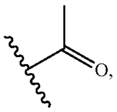, 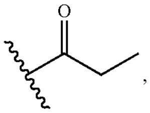, 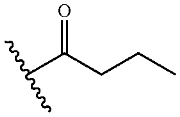,

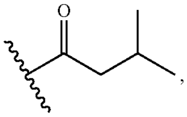, 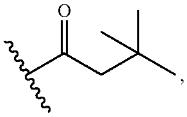,

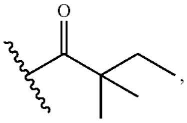, 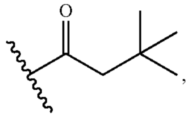,

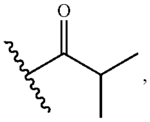, 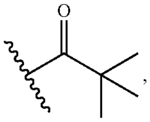,

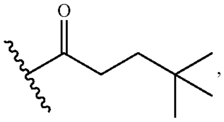, 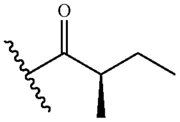,

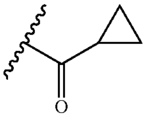, 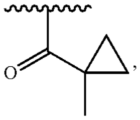, 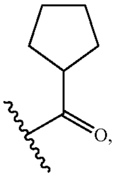,

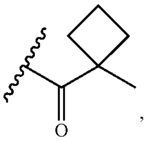, 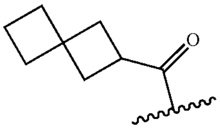,

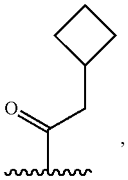, 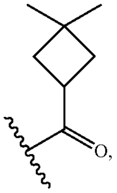, 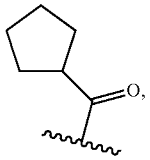,

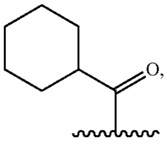, 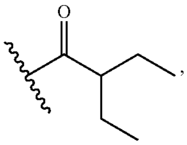,

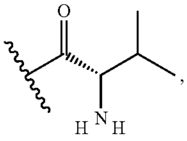, 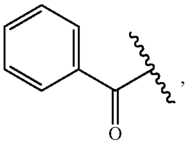,

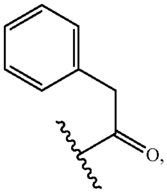, 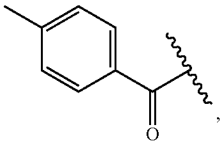,

-continued

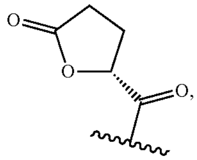, or 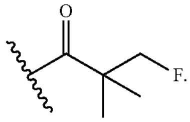.

3. The compound of claim 1, or the pharmaceutically acceptable salt thereof, wherein $R^7$ is $C_1$-$C_8$ alkyl.

4. The compound of claim 1, or the pharmaceutically acceptable salt thereof, wherein $R^7$ is $C_1$-$C_6$ alkyl.

5. The compound of claim 1, or the pharmaceutically acceptable salt thereof, wherein $R^7$ is $C_3$-$C_8$ carbocyclyl.

6. The compound of claim 1, or the pharmaceutically acceptable salt thereof, wherein Base is

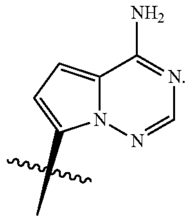.

7. The compound of claim 1, or the pharmaceutically acceptable salt thereof, wherein Base is

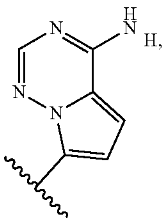, 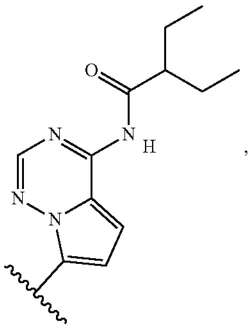,

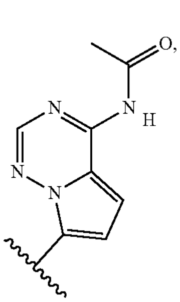, 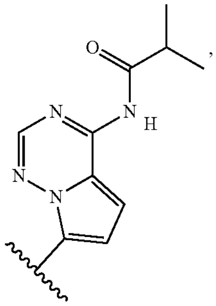,

-continued

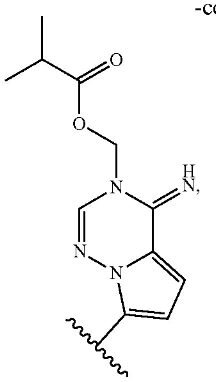

or

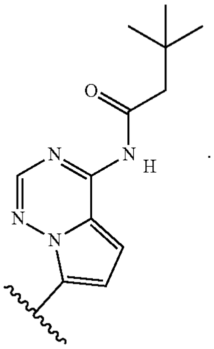

.

8. The compound of claim 1, or the pharmaceutically acceptable salt thereof, wherein the compound is

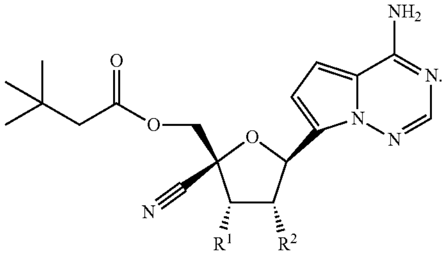

9. The compound of claim 1, or the pharmaceutically acceptable salt thereof, wherein the compound is

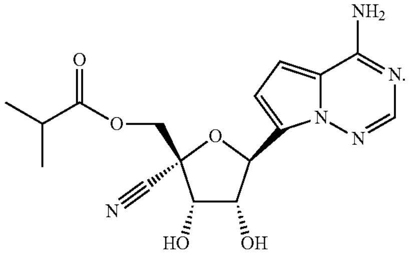 [SMILES: CC(C)C(=O)OC[C@@]1(C#N)O[C@@H](c2ccc3c(N)ncnn23)[C@H](O)[C@@H]1O]

10. The compound of claim 1, or the pharmaceutically acceptable salt thereof, wherein the compound is

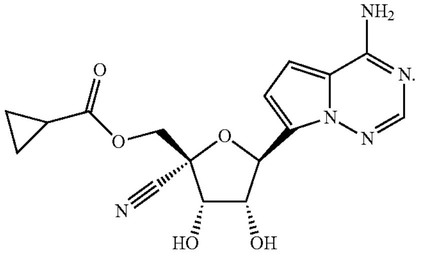 [SMILES: N#C[C@]1(COC(=O)C2CC2)O[C@@H](c2ccc3c(N)ncnn23)[C@H](O)[C@@H]1O]

11. The compound of claim 1, or the pharmaceutically acceptable salt thereof, wherein the compound is

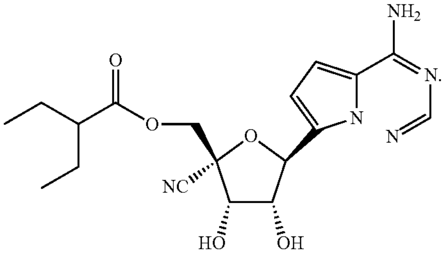 [SMILES: CCC(CC)C(=O)OC[C@@]1(C#N)O[C@@H](c2ccc(/C(N)=N\C=N)[nH]2)[C@H](O)[C@@H]1O]

12. The compound of claim 1, or the pharmaceutically acceptable salt thereof, wherein the compound is

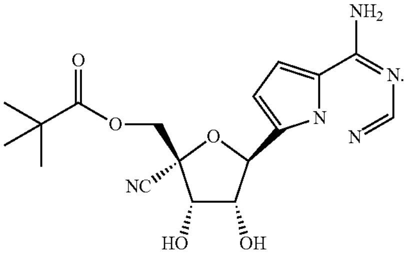 [SMILES: CC(C)(C)C(=O)OC[C@@]1(C#N)O[C@@H](c2ccc(/C(N)=N\C=N)[nH]2)[C@H](O)[C@@H]1O]

13. The compound of claim 1, or the pharmaceutically acceptable salt thereof, wherein the compound is

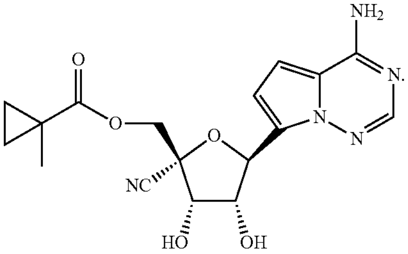 [SMILES: CC1(C(=O)OC[C@@]2(C#N)O[C@@H](c3ccc4c(N)ncnn34)[C@H](O)[C@@H]2O)CC1]

14. A pharmaceutical composition comprising a pharmaceutically effective amount of a compound of claim 1, or a pharmaceutically acceptable salt thereof, and a pharmaceutically acceptable carrier or excipient.

15. A method of treating a viral infection in a human in need thereof, wherein the method comprises administering to the human a therapeutically effective amount of a pharmaceutical composition of claim 14.

16. The method of claim 15, wherein the viral infection is a pneumoviridae virus infection.

17. The method of claim 16, wherein the pneumoviridae virus infection is respiratory syncytial virus infection.

18. The method of claim 16, wherein the pneumoviridae virus infection is human metapneumovirus infection.

19. The method of claim 15, wherein the viral infection is a picornaviridae virus infection.

20. The method of claim 19, wherein the picornaviridae virus infection is human rhinovirus infection.

* * * * *